US011903580B2

(12) United States Patent
Shelton, IV et al.

(10) Patent No.: US 11,903,580 B2
(45) Date of Patent: Feb. 20, 2024

(54) SURGICAL END EFFECTORS WITH POSITIVE JAW OPENING ARRANGEMENTS

(71) Applicant: Cilag GmbH International, Zug (CH)

(72) Inventors: Frederick E. Shelton, IV, Hillsboro, OH (US); Jerome R. Morgan, Cincinnati, OH (US); Gregory J. Bakos, Mason, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 23 days.

(21) Appl. No.: 17/023,892

(22) Filed: Sep. 17, 2020

(65) Prior Publication Data

US 2021/0059664 A1 Mar. 4, 2021

Related U.S. Application Data

(63) Continuation of application No. 16/157,729, filed on Oct. 11, 2018, now Pat. No. 11,576,669, which is a (Continued)

(51) Int. Cl.
*A61B 17/068* (2006.01)
*A61B 17/072* (2006.01)
(Continued)

(52) U.S. Cl.
CPC .......... *A61B 17/068* (2013.01); *A61B 17/072* (2013.01); *A61B 17/07207* (2013.01); (Continued)

(58) Field of Classification Search
CPC ............... A61B 17/068; A61B 17/072; A61B 17/07207; A61B 17/105; A61B 34/71;
(Continued)

(56) References Cited

U.S. PATENT DOCUMENTS 4,473,989 A * 10/1984 Tsutsumi ............... B65B 51/146
198/465.1
4,510,736 A * 4/1985 Muller ..................... B65B 1/02
53/284.7
(Continued)

FOREIGN PATENT DOCUMENTS

CN 2764312 Y 3/2006
CN 203736251 U 7/2014
(Continued)

*Primary Examiner* — Gloria R Weeks
*Assistant Examiner* — Mobeen Ahmed

(57) ABSTRACT

A surgical instrument comprising a surgical end effector that comprises a first jaw and a second jaw that is movably supported relative to the first jaw for selective movement between an open position and closed positions. The surgical instrument further comprises a closure member that is axially movable in response to closing and opening motions. The closure member comprises at least one opening cam that protrudes therefrom to movably engage a corresponding cam surface on the second jaw such that upon application of the opening motion, the at least one opening cam movably engages the corresponding cam surface to move the second jaw to an open position, even when the jaws are under a load.

20 Claims, 79 Drawing Sheets

Related U.S. Application Data continuation of application No. 14/742,925, filed on Jun. 18, 2015, now Pat. No. 10,182,818.

(51) Int. Cl.
| | | |
|---|---|---|
| *A61B 17/10* | (2006.01) | |
| *A61B 90/00* | (2016.01) | |
| *A61B 17/00* | (2006.01) | |
| *A61B 17/29* | (2006.01) | |
| *A61B 34/00* | (2016.01) | |

(52) U.S. Cl.
CPC ........... *A61B 17/105* (2013.01); *A61B 34/71* (2016.02); *A61B 2017/0046* (2013.01); *A61B 2017/00323* (2013.01); *A61B 2017/00327* (2013.01); *A61B 2017/00398* (2013.01); *A61B 2017/00734* (2013.01); *A61B 2017/07214* (2013.01); *A61B 2017/07271* (2013.01); *A61B 2017/07278* (2013.01); *A61B 2017/07285* (2013.01); *A61B 2017/2902* (2013.01); *A61B 2017/2927* (2013.01); *A61B 2017/2933* (2013.01); *A61B 2017/2939* (2013.01); *A61B 2017/2943* (2013.01); *A61B 2017/2946* (2013.01); *A61B 2090/0818* (2016.02)

(58) Field of Classification Search
CPC ........... A61B 2017/00323; A61B 2017/00327; A61B 2017/00398; A61B 2017/0046; A61B 2017/00734; A61B 2017/07214; A61B 2017/07271; A61B 2017/07278; A61B 2017/07285; A61B 2017/2902; A61B 2017/2927; A61B 2017/2933; A61B 2017/2939; A61B 2017/2943; A61B 2017/2946; A61B 2090/0818; A61B 34/30; A61B 90/30; A61B 2017/2929; A61B 2017/2936; A61B 18/12

See application file for complete search history.

(56) References Cited

U.S. PATENT DOCUMENTS

| | | | | |
|---|---|---|---|---|
| 4,628,665 | A | * | 12/1986 | Herrington ............. B65B 43/42 53/53 |
| 4,873,815 | A | * | 10/1989 | Tetenborg ................. B65B 1/22 53/284.7 |
| 5,129,570 | A | | 7/1992 | Schulze et al. |
| 5,312,023 | A | | 5/1994 | Green et al. |
| 5,318,221 | A | | 6/1994 | Green et al. |
| 5,326,013 | A | | 7/1994 | Green et al. |
| 5,383,880 | A | | 1/1995 | Hooven |
| 5,403,312 | A | | 4/1995 | Yates et al. |
| 5,471,992 | A | | 12/1995 | Banik et al. |
| 5,478,003 | A | | 12/1995 | Green et al. |
| 5,485,952 | A | | 1/1996 | Fontayne |
| 5,489,290 | A | | 2/1996 | Furnish |
| 5,501,846 | A | | 3/1996 | Pavelle et al. |
| 5,632,432 | A | | 5/1997 | Schulze et al. |
| 5,662,667 | A | | 9/1997 | Knodel |
| 5,702,408 | A | * | 12/1997 | Wales ............... A61B 17/07207 606/205 |
| 5,704,534 | A | * | 1/1998 | Huitema .......... A61B 17/07207 227/176.1 |
| 5,704,535 | A | | 1/1998 | Thompson, Sr. |
| 5,749,893 | A | | 5/1998 | Vidal et al. |
| 5,797,537 | A | | 8/1998 | Oberlin et al. |
| 5,814,055 | A | | 9/1998 | Knodel et al. |
| 5,826,776 | A | | 10/1998 | Schulze et al. |
| 5,865,361 | A | | 2/1999 | Milliman et al. |
| 6,250,532 | B1 | * | 6/2001 | Green ............... A61B 17/07207 227/19 |
| 6,401,439 | B1 | * | 6/2002 | Tetenborg ............. B65B 43/465 53/567 |
| 6,460,317 | B1 | * | 10/2002 | Voss ....................... B65B 43/12 53/567 |
| 6,474,050 | B1 | * | 11/2002 | Tetenborg ................ B65B 1/22 53/567 |
| 6,716,232 | B1 | | 4/2004 | Vidal et al. |
| 6,722,552 | B2 | | 4/2004 | Fenton, Jr. |
| 6,786,382 | B1 | | 9/2004 | Hoffman |
| 6,964,363 | B2 | | 11/2005 | Wales et al. |
| 6,988,649 | B2 | | 1/2006 | Shelton, IV et al. |
| 7,000,818 | B2 | | 2/2006 | Shelton, IV et al. |
| 7,044,352 | B2 | | 5/2006 | Shelton, IV et al. |
| 7,213,736 | B2 | | 5/2007 | Wales et al. |
| 7,328,828 | B2 | | 2/2008 | Ortiz et al. |
| 7,380,695 | B2 | | 6/2008 | Doll et al. |
| 7,380,696 | B2 | | 6/2008 | Shelton, IV et al. |
| 7,395,842 | B2 | * | 7/2008 | Dyer ....................... B65B 67/12 211/85.15 |
| 7,422,139 | B2 | | 9/2008 | Shelton, IV et al. |
| 7,431,188 | B1 | | 10/2008 | Marczyk |
| 7,455,208 | B2 | | 11/2008 | Wales et al. |
| 7,461,767 | B2 | | 12/2008 | Viola et al. |
| 7,464,849 | B2 | | 12/2008 | Shelton, IV et al. |
| 7,494,501 | B2 | | 2/2009 | Ahlberg et al. |
| 7,513,407 | B1 | | 4/2009 | Chang |
| 7,543,730 | B1 | | 6/2009 | Marczyk |
| 7,588,177 | B2 | | 9/2009 | Racenet |
| 7,611,102 | B2 | * | 11/2009 | Murray ................. B65B 43/465 248/101 |
| 7,615,067 | B2 | | 11/2009 | Lee et al. |
| 7,617,961 | B2 | | 11/2009 | Viola |
| 7,641,093 | B2 | | 1/2010 | Doll et al. |
| 7,641,095 | B2 | | 1/2010 | Viola |
| 7,651,017 | B2 | | 1/2010 | Ortiz et al. |
| 7,670,334 | B2 | * | 3/2010 | Hueil ............... A61B 17/07207 606/1 |
| 7,682,367 | B2 | | 3/2010 | Shah et al. |
| 7,703,653 | B2 | | 4/2010 | Shah et al. |
| 7,753,245 | B2 | | 7/2010 | Boudreaux et al. |
| 7,776,065 | B2 | | 8/2010 | Griffiths et al. |
| 7,845,537 | B2 | | 12/2010 | Shelton, IV et al. |
| 7,857,183 | B2 | | 12/2010 | Shelton, IV |
| 7,877,966 | B2 | * | 2/2011 | Knoke ....................... B65B 1/36 53/469 |
| 7,980,443 | B2 | | 7/2011 | Scheib et al. |
| 8,011,555 | B2 | | 9/2011 | Tarinelli et al. |
| 8,187,290 | B2 | | 5/2012 | Buckman et al. |
| 8,210,411 | B2 | | 7/2012 | Yates et al. |
| 8,220,688 | B2 | | 7/2012 | Laurent et al. |
| 8,308,040 | B2 | | 11/2012 | Huang et al. |
| 8,308,725 | B2 | | 11/2012 | Bell et al. |
| 8,322,455 | B2 | | 12/2012 | Shelton, IV et al. |
| 8,382,792 | B2 | | 2/2013 | Chojin |
| 8,393,514 | B2 | | 3/2013 | Shelton, IV et al. |
| 8,393,516 | B2 | | 3/2013 | Kostrzewski |
| 8,403,945 | B2 | | 3/2013 | Whitfield et al. |
| 8,408,439 | B2 | | 4/2013 | Huang et al. |
| 8,469,991 | B2 | | 6/2013 | Kerr |
| 8,475,453 | B2 | | 7/2013 | Marczyk et al. |
| 8,485,412 | B2 | | 7/2013 | Shelton, IV et al. |
| 8,485,413 | B2 | | 7/2013 | Scheib et al. |
| 8,561,870 | B2 | | 10/2013 | Baxter, III et al. |
| 8,579,176 | B2 | | 11/2013 | Smith et al. |
| 8,608,043 | B2 | | 12/2013 | Scirica |
| 8,608,045 | B2 | | 12/2013 | Smith et al. |
| 8,628,544 | B2 | | 1/2014 | Farascioni |
| 8,657,177 | B2 | | 2/2014 | Scirica et al. |
| 8,672,206 | B2 | | 3/2014 | Aranyi et al. |
| 8,684,253 | B2 | | 4/2014 | Giordano et al. |
| 8,733,613 | B2 | | 5/2014 | Huitema et al. |
| 8,747,238 | B2 | | 6/2014 | Shelton, IV et al. |
| 8,757,465 | B2 | | 6/2014 | Woodard, Jr. et al. |
| 8,795,327 | B2 | | 8/2014 | Dietz et al. |
| 8,800,841 | B2 | | 8/2014 | Ellerhorst et al. |
| 8,834,518 | B2 | | 9/2014 | Faller et al. |
| 8,870,867 | B2 | | 10/2014 | Walberg et al. |
| 8,893,949 | B2 | | 11/2014 | Shelton, IV et al. |
| 8,931,682 | B2 | | 1/2015 | Timm et al. |

(56) References Cited

U.S. PATENT DOCUMENTS

| | | | |
|---|---|---|---|
| 9,072,535 B2 | 7/2015 | Shelton, IV et al. | |
| 9,078,653 B2 | 7/2015 | Leimbach et al. | |
| 9,101,358 B2 | 8/2015 | Kerr et al. | |
| 9,123,652 B2 | 9/2015 | Desplats et al. | |
| 9,179,912 B2 | 11/2015 | Yates et al. | |
| 9,186,142 B2* | 11/2015 | Fanelli | A61B 17/07207 |
| 9,204,923 B2 | 12/2015 | Manzo et al. | |
| 9,216,020 B2 | 12/2015 | Zhang et al. | |
| 9,232,941 B2 | 1/2016 | Mandakolathur Vasudevan et al. | |
| 9,282,962 B2 | 3/2016 | Schmid et al. | |
| 9,289,211 B2 | 3/2016 | Williams et al. | |
| 9,307,986 B2 | 4/2016 | Hall et al. | |
| 9,326,767 B2 | 5/2016 | Koch et al. | |
| 9,332,987 B2 | 5/2016 | Leimbach et al. | |
| 9,345,481 B2 | 5/2016 | Hall et al. | |
| 9,351,726 B2 | 5/2016 | Leimbach et al. | |
| 9,351,727 B2 | 5/2016 | Leimbach et al. | |
| 9,351,751 B2 | 5/2016 | Malkowski | |
| 9,358,003 B2 | 6/2016 | Hall et al. | |
| 9,398,911 B2 | 7/2016 | Auld | |
| 9,402,682 B2 | 8/2016 | Worrell et al. | |
| 9,468,438 B2 | 10/2016 | Baber et al. | |
| 9,480,492 B2 | 11/2016 | Aranyi et al. | |
| 9,526,497 B2 | 12/2016 | Cappola et al. | |
| 9,554,794 B2 | 1/2017 | Baber et al. | |
| 9,566,048 B1 | 2/2017 | Knodel et al. | |
| 9,566,062 B2 | 2/2017 | Boudreaux | |
| 9,573,716 B2* | 2/2017 | Murray | B65B 3/02 |
| 9,629,623 B2 | 4/2017 | Lytle, IV et al. | |
| 9,629,629 B2 | 4/2017 | Leimbach et al. | |
| 9,642,620 B2 | 5/2017 | Baxter, III et al. | |
| 9,649,110 B2 | 5/2017 | Parihar et al. | |
| 9,675,351 B2 | 6/2017 | Hodgkinson et al. | |
| 9,687,230 B2 | 6/2017 | Leimbach et al. | |
| 9,690,362 B2 | 6/2017 | Leimbach et al. | |
| 9,700,309 B2 | 7/2017 | Jaworek et al. | |
| 9,707,003 B2 | 7/2017 | Hoell, Jr. et al. | |
| 9,724,094 B2 | 8/2017 | Baber et al. | |
| 9,724,096 B2 | 8/2017 | Thompson et al. | |
| 9,730,753 B2 | 8/2017 | Worrell et al. | |
| 9,733,663 B2 | 8/2017 | Leimbach et al. | |
| 9,737,301 B2 | 8/2017 | Baber et al. | |
| 9,743,929 B2 | 8/2017 | Leimbach et al. | |
| 9,750,499 B2 | 9/2017 | Leimbach et al. | |
| 9,757,128 B2 | 9/2017 | Baber et al. | |
| 9,782,169 B2 | 10/2017 | Kimsey et al. | |
| 9,788,836 B2 | 10/2017 | Overmyer et al. | |
| 9,795,379 B2 | 10/2017 | Leimbach et al. | |
| 9,801,626 B2 | 10/2017 | Parihar et al. | |
| 9,804,618 B2 | 10/2017 | Leimbach et al. | |
| 9,808,244 B2 | 11/2017 | Leimbach et al. | |
| 9,808,246 B2 | 11/2017 | Shelton, IV et al. | |
| 9,814,460 B2 | 11/2017 | Kimsey et al. | |
| 9,820,738 B2 | 11/2017 | Lytle, IV et al. | |
| 9,826,976 B2 | 11/2017 | Parihar et al. | |
| 9,826,977 B2 | 11/2017 | Leimbach et al. | |
| 9,826,978 B2 | 11/2017 | Shelton, IV et al. | |
| 9,839,421 B2 | 12/2017 | Zerkle et al. | |
| 9,844,368 B2 | 12/2017 | Boudreaux et al. | |
| 9,844,374 B2 | 12/2017 | Lytle, IV et al. | |
| 9,844,375 B2 | 12/2017 | Overmyer et al. | |
| 9,867,612 B2 | 1/2018 | Parihar et al. | |
| 9,873,532 B2* | 1/2018 | Canestri | B65B 1/32 |
| 9,883,860 B2 | 2/2018 | Leimbach | |
| 9,888,919 B2 | 2/2018 | Leimbach et al. | |
| 9,895,148 B2 | 2/2018 | Shelton, IV et al. | |
| 9,901,341 B2 | 2/2018 | Kostrzewski | |
| 9,901,342 B2 | 2/2018 | Shelton, IV et al. | |
| 9,924,961 B2 | 3/2018 | Shelton, IV et al. | |
| 9,931,118 B2 | 4/2018 | Shelton, IV et al. | |
| 9,943,309 B2 | 4/2018 | Shelton, IV et al. | |
| 9,944,037 B2* | 4/2018 | Murray | B65B 1/02 |
| 9,968,355 B2 | 5/2018 | Shelton, IV et al. | |
| 9,987,000 B2 | 6/2018 | Shelton, IV et al. | |
| 9,993,248 B2 | 6/2018 | Shelton, IV et al. | |
| 9,993,258 B2 | 6/2018 | Shelton, IV et al. | |
| 10,004,497 B2 | 6/2018 | Overmyer et al. | |
| 10,004,501 B2 | 6/2018 | Shelton, IV et al. | |
| 10,013,049 B2 | 7/2018 | Leimbach et al. | |
| 10,016,199 B2 | 7/2018 | Baber et al. | |
| 10,028,761 B2 | 7/2018 | Leimbach et al. | |
| 10,039,532 B2 | 8/2018 | Srinivas et al. | |
| 10,045,776 B2 | 8/2018 | Shelton, IV et al. | |
| 10,045,779 B2 | 8/2018 | Savage et al. | |
| 10,052,044 B2 | 8/2018 | Shelton, IV et al. | |
| 10,052,102 B2 | 8/2018 | Baxter, III et al. | |
| 10,064,620 B2 | 9/2018 | Gettinger et al. | |
| 10,080,565 B2 | 9/2018 | Pastorelli et al. | |
| 10,085,748 B2 | 10/2018 | Morgan et al. | |
| 10,111,679 B2 | 10/2018 | Baber et al. | |
| 10,117,649 B2 | 11/2018 | Baxter et al. | |
| 10,117,650 B2 | 11/2018 | Nicholas et al. | |
| 10,135,242 B2 | 11/2018 | Baber et al. | |
| 10,136,887 B2 | 11/2018 | Shelton, IV et al. | |
| 10,149,680 B2 | 12/2018 | Parihar et al. | |
| 10,154,841 B2 | 12/2018 | Weaner et al. | |
| 10,159,483 B2 | 12/2018 | Beckman et al. | |
| 10,178,992 B2 | 1/2019 | Wise et al. | |
| 10,180,463 B2 | 1/2019 | Beckman et al. | |
| 10,182,816 B2 | 1/2019 | Shelton, IV et al. | |
| 10,182,818 B2 | 1/2019 | Hensel et al. | |
| 10,188,385 B2 | 1/2019 | Kerr et al. | |
| 10,201,364 B2 | 2/2019 | Leimbach et al. | |
| 10,226,250 B2 | 3/2019 | Beckman et al. | |
| 10,245,027 B2 | 4/2019 | Shelton, IV et al. | |
| 10,245,028 B2 | 4/2019 | Shelton, IV et al. | |
| 10,245,033 B2 | 4/2019 | Overmyer et al. | |
| 10,321,907 B2 | 6/2019 | Shelton, IV et al. | |
| 10,327,765 B2 | 6/2019 | Timm et al. | |
| 10,335,149 B2 | 7/2019 | Baxter, III et al. | |
| 10,368,861 B2 | 8/2019 | Baxter, III et al. | |
| 10,405,857 B2 | 9/2019 | Shelton, IV et al. | |
| 10,405,863 B2 | 9/2019 | Wise et al. | |
| 10,441,279 B2 | 10/2019 | Shelton, IV et al. | |
| 10,470,762 B2 | 11/2019 | Leimbach et al. | |
| 10,542,978 B2 | 1/2020 | Chowaniec et al. | |
| 10,548,504 B2 | 2/2020 | Shelton, IV et al. | |
| 10,588,623 B2 | 3/2020 | Schmid et al. | |
| 10,617,412 B2 | 4/2020 | Shelton, IV et al. | |
| 10,687,806 B2 | 6/2020 | Shelton, IV et al. | |
| 10,934,039 B2* | 3/2021 | Black | B65B 3/06 |
| 11,267,599 B2* | 3/2022 | Concetti | B65B 51/32 |
| 11,331,095 B2 | 5/2022 | Wise et al. | |
| 2001/0030219 A1 | 10/2001 | Green et al. | |
| 2002/0050304 A1* | 5/2002 | Hiramoto | B65B 43/465 |
| | | | 53/384.1 |
| 2002/0117533 A1 | 8/2002 | Milliman et al. | |
| 2002/0156497 A1 | 10/2002 | Nagase et al. | |
| 2004/0182469 A1* | 9/2004 | Concetti | B65B 1/34 |
| | | | 53/502 |
| 2004/0232201 A1 | 11/2004 | Wenchell et al. | |
| 2004/0243151 A1 | 12/2004 | Demmy et al. | |
| 2005/0006430 A1 | 1/2005 | Wales | |
| 2005/0006432 A1* | 1/2005 | Racenet | A61B 17/105 |
| | | | 227/176.1 |
| 2005/0229550 A1* | 10/2005 | Eder | B65B 39/145 |
| | | | 53/284.7 |
| 2006/0025809 A1 | 2/2006 | Shelton | |
| 2006/0025810 A1 | 2/2006 | Shelton | |
| 2006/0025812 A1 | 2/2006 | Shelton | |
| 2006/0229665 A1 | 10/2006 | Wales et al. | |
| 2006/0289602 A1 | 12/2006 | Wales et al. | |
| 2007/0027468 A1 | 2/2007 | Wales et al. | |
| 2007/0084897 A1* | 4/2007 | Shelton, IV | A61B 34/30 |
| | | | 227/176.1 |
| 2007/0102474 A1 | 5/2007 | Shelton et al. | |
| 2007/0106317 A1 | 5/2007 | Shelton et al. | |
| 2007/0152014 A1 | 7/2007 | Gillum et al. | |
| 2007/0175950 A1 | 8/2007 | Shelton et al. | |
| 2007/0175955 A1 | 8/2007 | Shelton et al. | |
| 2007/0241151 A1* | 10/2007 | Murray | B65B 43/465 |
| | | | 224/407 |
| 2008/0035701 A1* | 2/2008 | Racenet | A61B 17/07207 |
| | | | 227/176.1 |

(56) References Cited

U.S. PATENT DOCUMENTS

| | | | |
|---|---|---|---|
| 2008/0046003 A1 | 2/2008 | Renger et al. | |
| 2008/0083807 A1 | 4/2008 | Beardsley et al. | |
| 2008/0132919 A1 | 6/2008 | Chui et al. | |
| 2008/0169333 A1 | 7/2008 | Shelton et al. | |
| 2008/0223903 A1 | 9/2008 | Marczyk | |
| 2008/0300579 A1 | 12/2008 | Broehl et al. | |
| 2008/0300580 A1 | 12/2008 | Shelton, IV et al. | |
| 2008/0308603 A1* | 12/2008 | Shelton | A61B 17/07207 227/175.1 |
| 2008/0308605 A1 | 12/2008 | Scirica | |
| 2009/0090763 A1 | 4/2009 | Zemlok et al. | |
| 2009/0177041 A1* | 7/2009 | Stefanchik | A61B 17/29 600/146 |
| 2009/0188965 A1 | 7/2009 | Levin et al. | |
| 2009/0206130 A1* | 8/2009 | Hall | A61B 50/30 227/175.2 |
| 2009/0206131 A1 | 8/2009 | Weisenburgh et al. | |
| 2009/0206133 A1 | 8/2009 | Morgan et al. | |
| 2010/0041945 A1 | 2/2010 | Isbell, Jr. | |
| 2010/0193566 A1 | 8/2010 | Scheib et al. | |
| 2010/0193568 A1 | 8/2010 | Scheib et al. | |
| 2010/0206424 A1* | 8/2010 | Gustafsson | B65B 43/465 141/37 |
| 2011/0089220 A1 | 4/2011 | Ingmanson et al. | |
| 2011/0107730 A1* | 5/2011 | Scott | B65B 3/04 53/570 |
| 2011/0112517 A1 | 5/2011 | Peine et al. | |
| 2011/0118709 A1 | 5/2011 | Burbank | |
| 2011/0184459 A1 | 7/2011 | Malkowski et al. | |
| 2011/0276057 A1 | 11/2011 | Conlon et al. | |
| 2011/0290853 A1* | 12/2011 | Shelton, IV | A61B 17/068 227/177.1 |
| 2011/0295270 A1* | 12/2011 | Giordano | A61B 17/320092 606/130 |
| 2012/0051971 A1* | 3/2012 | Giribona | B65B 3/003 422/63 |
| 2012/0074200 A1 | 3/2012 | Schmid et al. | |
| 2012/0078243 A1* | 3/2012 | Worrell | A61B 17/07207 606/130 |
| 2012/0080344 A1 | 4/2012 | Shelton, IV | |
| 2012/0197190 A1 | 8/2012 | Suon et al. | |
| 2012/0234893 A1* | 9/2012 | Schuckmann | A61B 17/07207 227/175.2 |
| 2012/0239009 A1* | 9/2012 | Mollere | A61B 17/07207 606/1 |
| 2012/0286019 A1* | 11/2012 | Hueil | A61B 17/068 227/175.1 |
| 2012/0289391 A1* | 11/2012 | Murray | B65B 1/02 493/227 |
| 2012/0292367 A1 | 11/2012 | Morgan et al. | |
| 2012/0310220 A1 | 12/2012 | Malkowski et al. | |
| 2012/0318844 A1 | 12/2012 | Shelton, IV et al. | |
| 2013/0012958 A1 | 1/2013 | Marczyk et al. | |
| 2013/0126586 A1* | 5/2013 | Zhang | A61B 17/068 227/176.1 |
| 2013/0172929 A1 | 7/2013 | Hess et al. | |
| 2013/0248577 A1* | 9/2013 | Leimbach | A61B 17/105 227/176.1 |
| 2013/0253480 A1 | 9/2013 | Kimball et al. | |
| 2013/0270322 A1 | 10/2013 | Scheib et al. | |
| 2013/0274722 A1* | 10/2013 | Kostrzewski | A61B 17/00234 606/1 |
| 2013/0334281 A1* | 12/2013 | Williams | A61B 17/07207 227/176.1 |
| 2014/0005702 A1 | 1/2014 | Timm et al. | |
| 2014/0005718 A1 | 1/2014 | Shelton, IV et al. | |
| 2014/0025046 A1* | 1/2014 | Williams | A61B 17/07207 606/1 |
| 2014/0114334 A1* | 4/2014 | Olson | A61B 34/37 606/169 |
| 2014/0236174 A1 | 8/2014 | Williams et al. | |
| 2014/0243801 A1* | 8/2014 | Fanelli | A61B 17/07207 606/1 |
| 2014/0246475 A1 | 9/2014 | Hall et al. | |
| 2014/0249557 A1 | 9/2014 | Koch et al. | |
| 2014/0252064 A1 | 9/2014 | Mozdzierz et al. | |
| 2014/0263541 A1 | 9/2014 | Leimbach et al. | |
| 2014/0263552 A1 | 9/2014 | Hall et al. | |
| 2014/0276730 A1 | 9/2014 | Boudreaux et al. | |
| 2014/0276776 A1* | 9/2014 | Parihar | A61B 17/2816 606/1 |
| 2014/0303668 A1* | 10/2014 | Nicholas | A61B 17/07207 606/207 |
| 2014/0331603 A1* | 11/2014 | Takahashi | B65B 65/003 53/110 |
| 2014/0331619 A1* | 11/2014 | Takahashi | B65B 43/16 53/525 |
| 2014/0373652 A1 | 12/2014 | Zergiebel et al. | |
| 2015/0073439 A1* | 3/2015 | Dannaher | A61B 17/1285 606/142 |
| 2015/0173756 A1 | 6/2015 | Baxter, III et al. | |
| 2015/0183537 A1* | 7/2015 | Canestri | B65B 1/36 53/436 |
| 2015/0231409 A1 | 8/2015 | Racenet et al. | |
| 2015/0272557 A1 | 10/2015 | Overmyer et al. | |
| 2015/0272571 A1 | 10/2015 | Leimbach et al. | |
| 2015/0272580 A1 | 10/2015 | Leimbach et al. | |
| 2015/0272582 A1 | 10/2015 | Leimbach et al. | |
| 2015/0284122 A1* | 10/2015 | Murray | B65B 43/60 248/99 |
| 2016/0066913 A1 | 3/2016 | Swayze et al. | |
| 2016/0122057 A1* | 5/2016 | Takahashi | B65B 51/10 53/284.7 |
| 2016/0249910 A1 | 9/2016 | Shelton, IV et al. | |
| 2017/0205530 A1* | 7/2017 | Fujitomi | G01V 8/20 |
| 2017/0348043 A1 | 12/2017 | Wang et al. | |
| 2018/0086617 A1* | 3/2018 | Lindberg | B65B 57/145 |
| 2018/0148199 A1* | 5/2018 | Katsuyama | B65B 5/067 |
| 2018/0215489 A1* | 8/2018 | Gallaun | B65B 39/10 |
| 2019/0105048 A1 | 4/2019 | Hensel et al. | |
| 2019/0183504 A1 | 6/2019 | Shelton, IV et al. | |
| 2019/0350581 A1 | 11/2019 | Baxter, III et al. | |
| 2020/0130877 A1* | 4/2020 | Concetti | B65B 39/10 |
| 2020/0130944 A1* | 4/2020 | Guggenberger | B65H 29/047 |
| 2020/0189779 A1* | 6/2020 | Canalicchio | B65B 61/207 |
| 2020/0289110 A1 | 9/2020 | Hensel et al. | |
| 2020/0315611 A1 | 10/2020 | Hensel et al. | |
| 2020/0315613 A1 | 10/2020 | Hensel et al. | |
| 2020/0315614 A1 | 10/2020 | Hensel et al. | |
| 2021/0059663 A1 | 3/2021 | Hensel et al. | |
| 2021/0059665 A1 | 3/2021 | Hensel et al. | |
| 2021/0068819 A1 | 3/2021 | Hensel et al. | |
| 2021/0290226 A1 | 9/2021 | Mandakolathur Vasudevan et al. | |
| 2022/0218335 A1 | 7/2022 | Baxter, III et al. | |
| 2022/0340320 A1* | 10/2022 | Nakamoto | B65B 31/041 |

FOREIGN PATENT DOCUMENTS

| | | |
|---|---|---|
| EP | 0625335 B1 | 11/1997 |
| EP | 2743042 A2 | 6/2014 |
| EP | 2687164 B1 | 5/2017 |
| JP | H06067357 A | 1/1994 |
| JP | H06327684 A | 11/1994 |
| WO | WO-2013022325 A2 | 2/2013 |

* cited by examiner

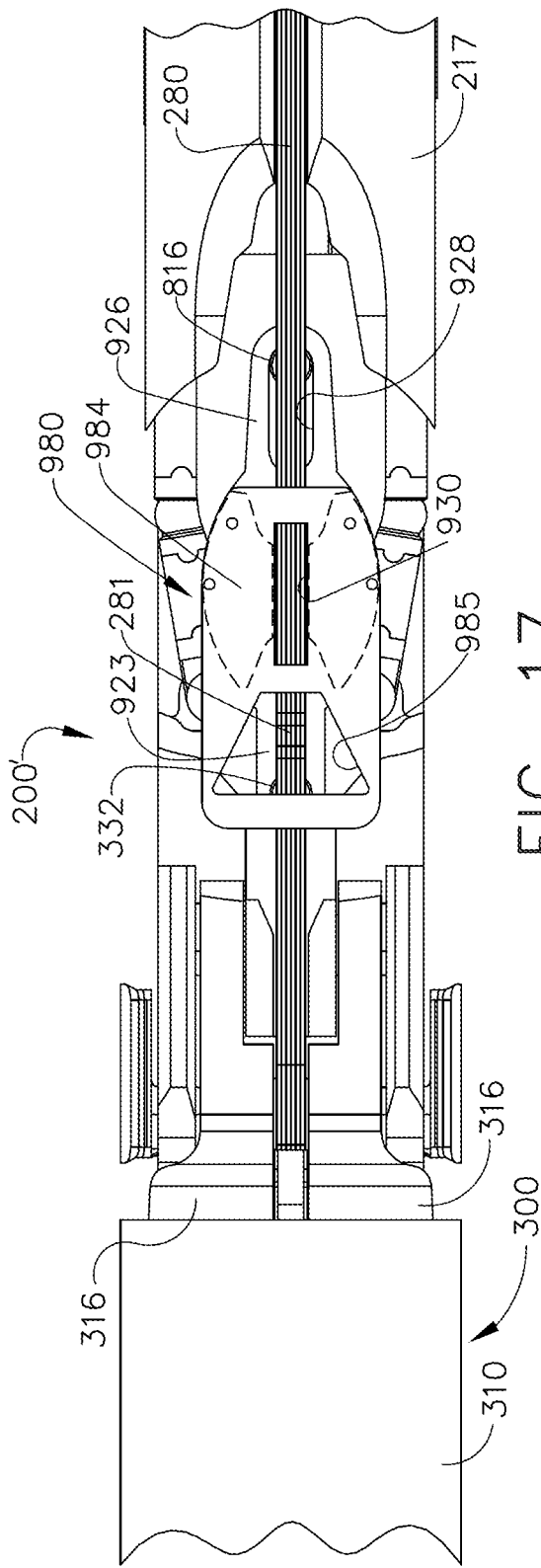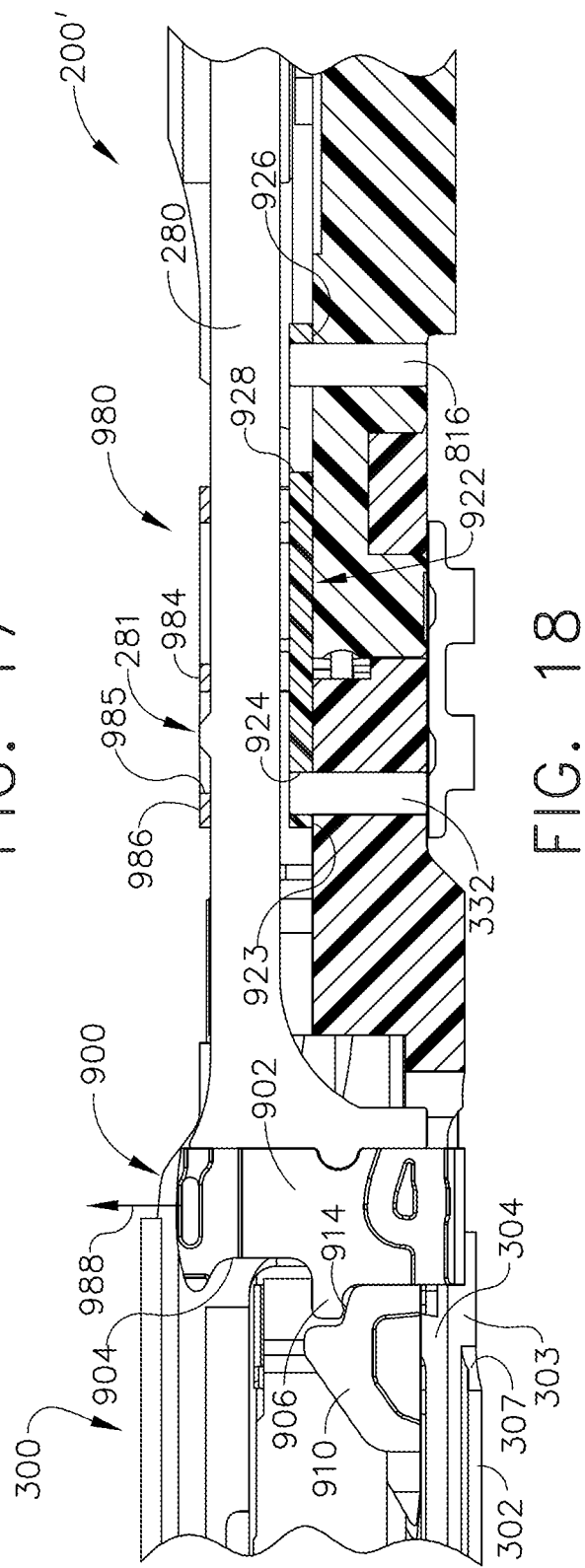

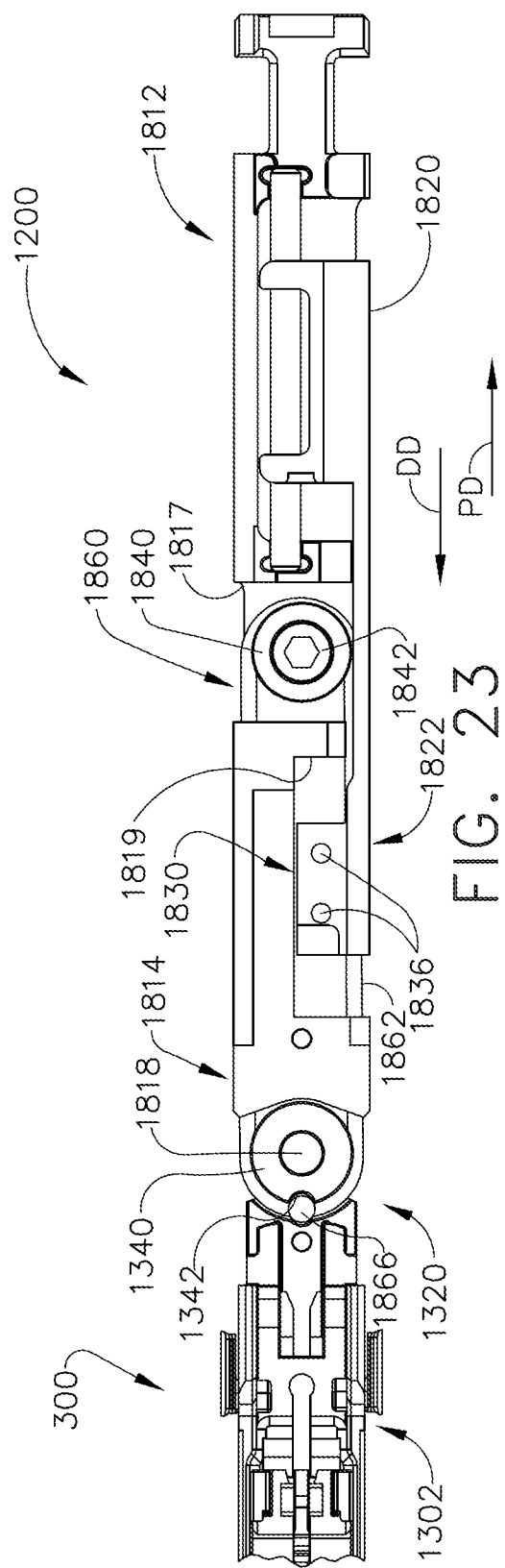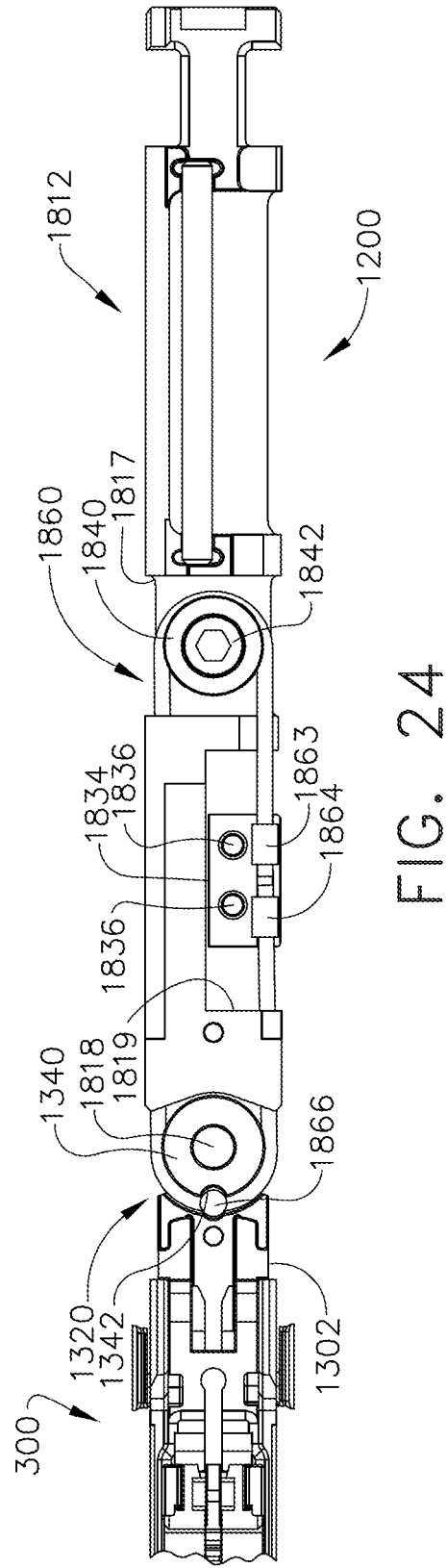

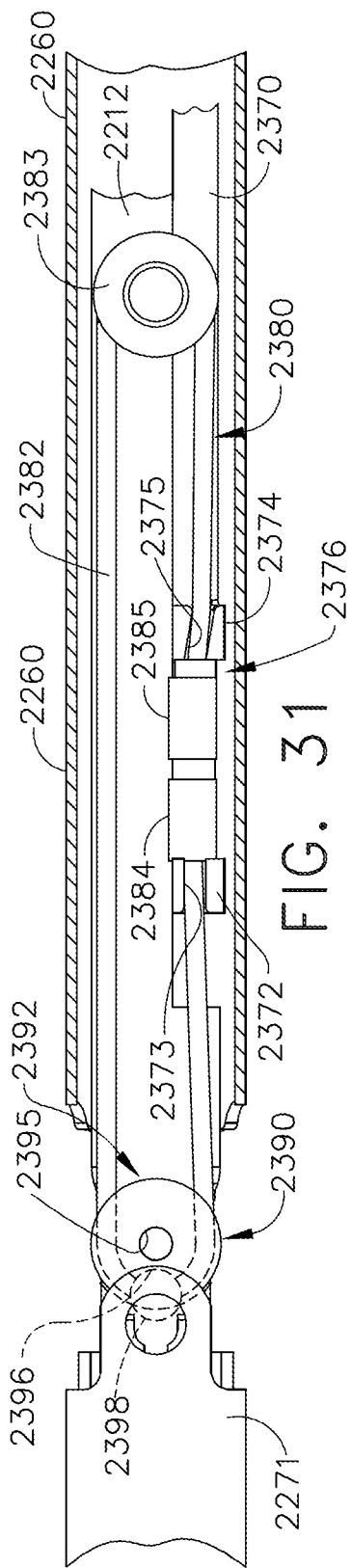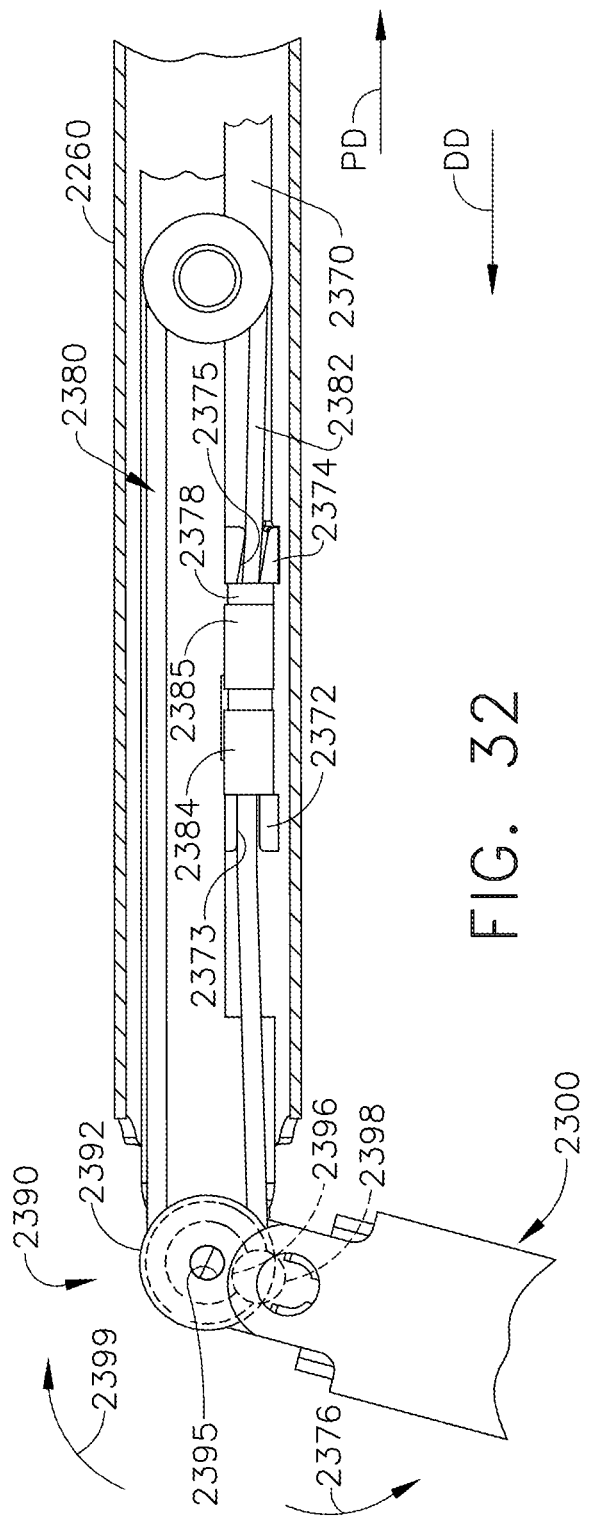

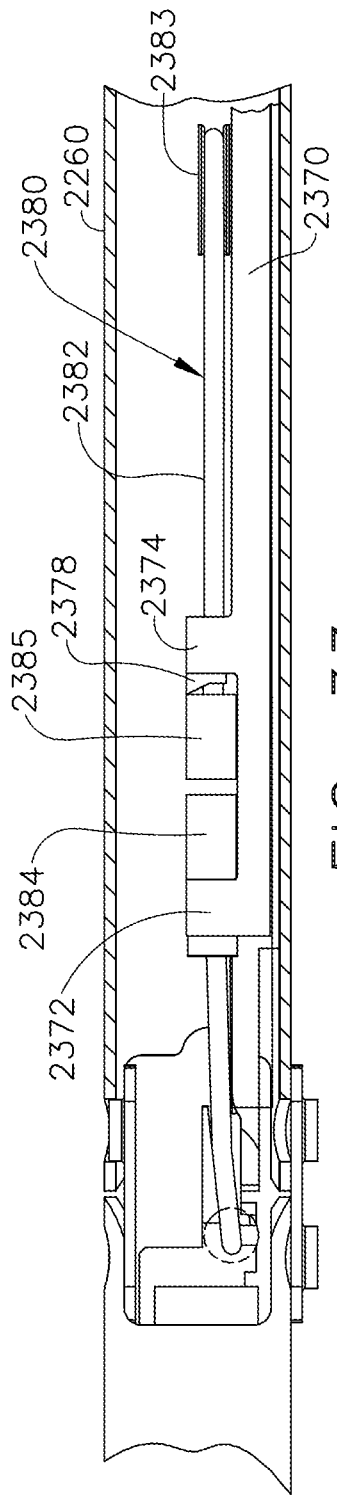
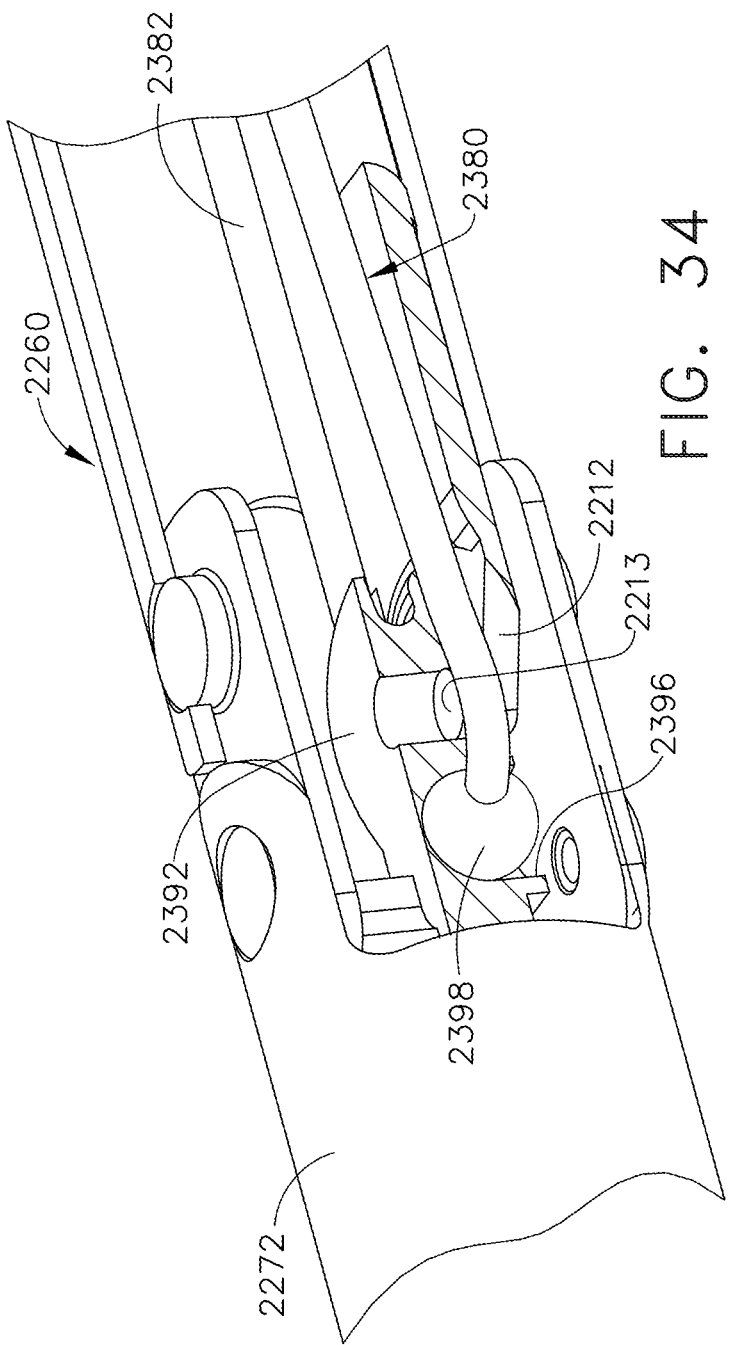

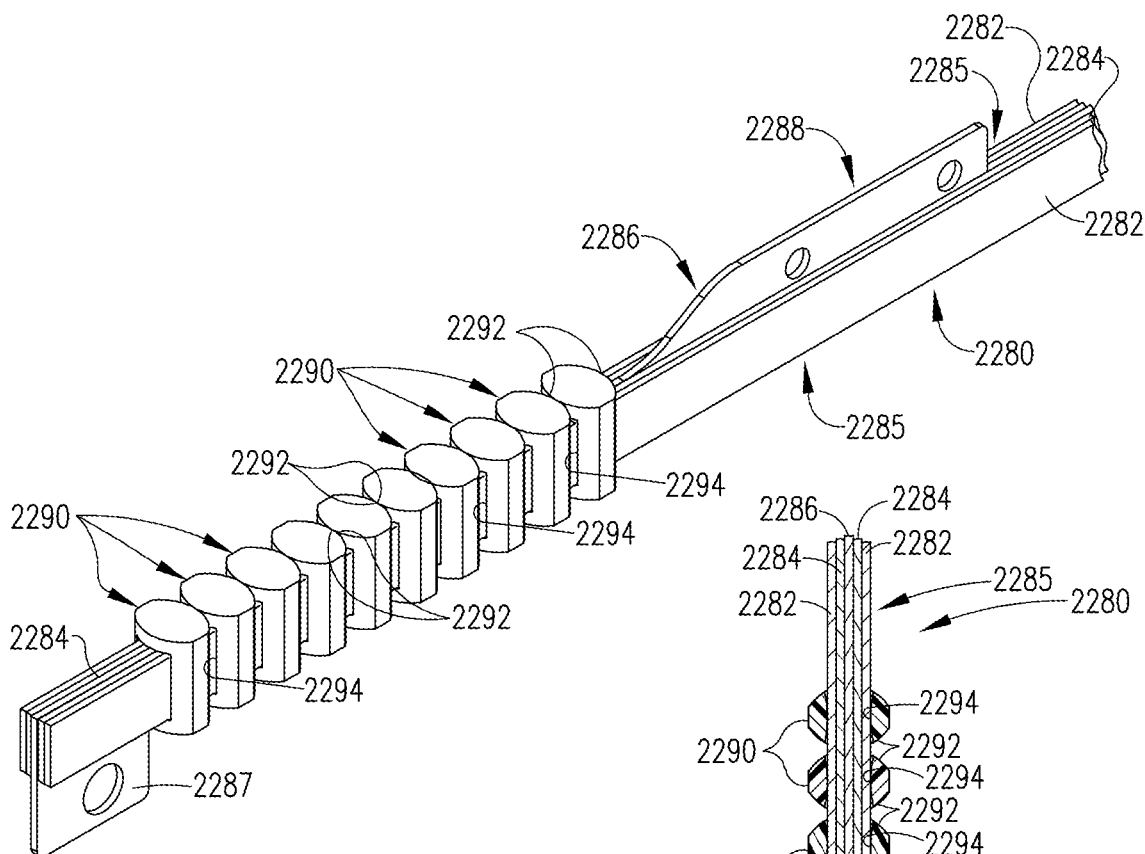
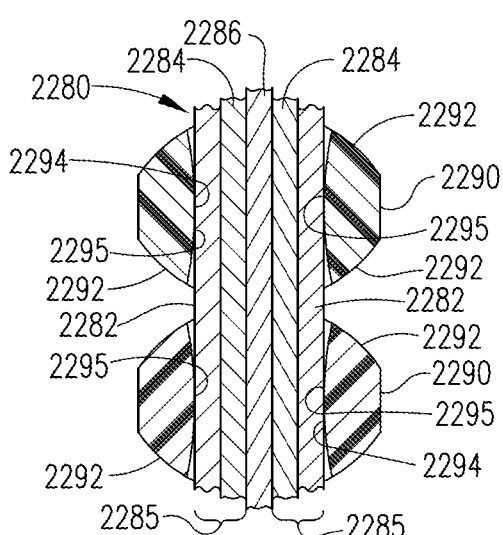
FIG. 37
FIG. 38
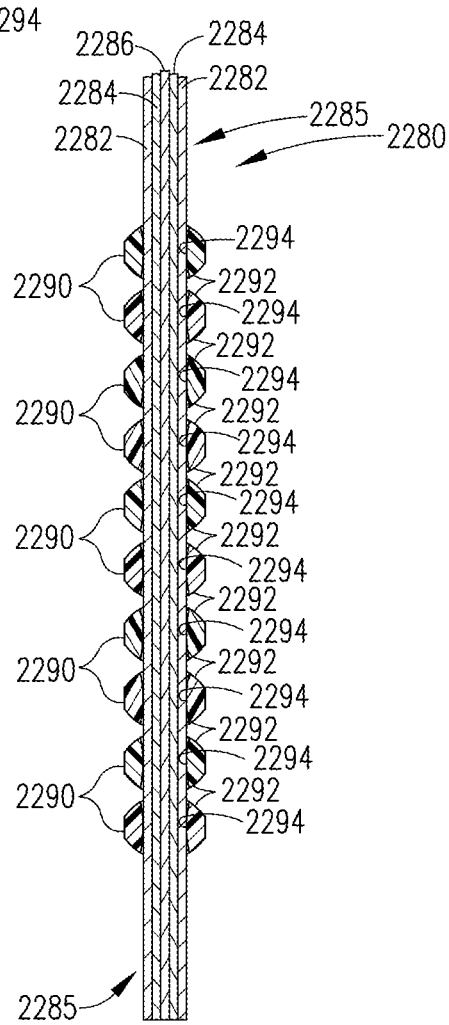
FIG. 39

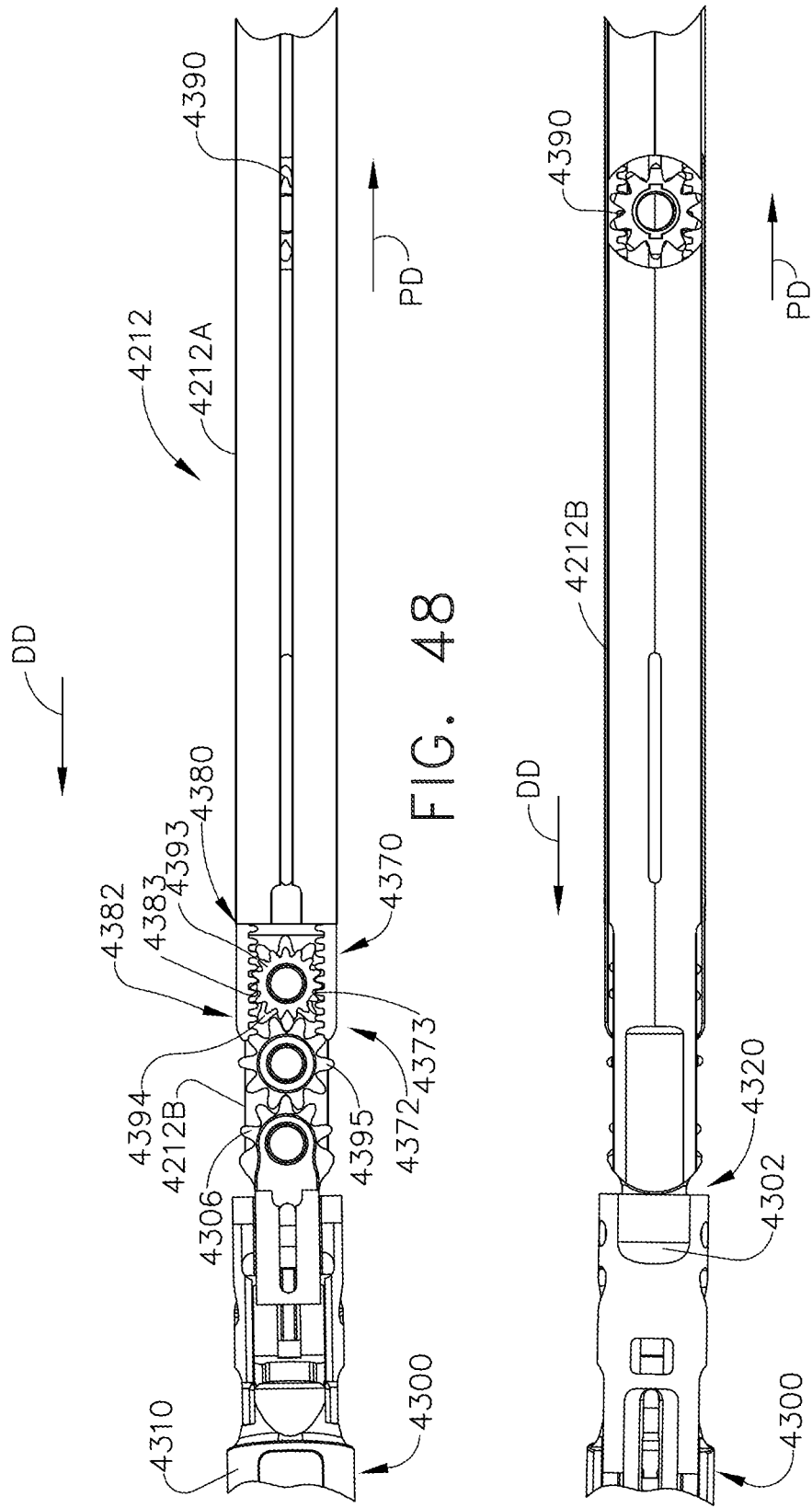

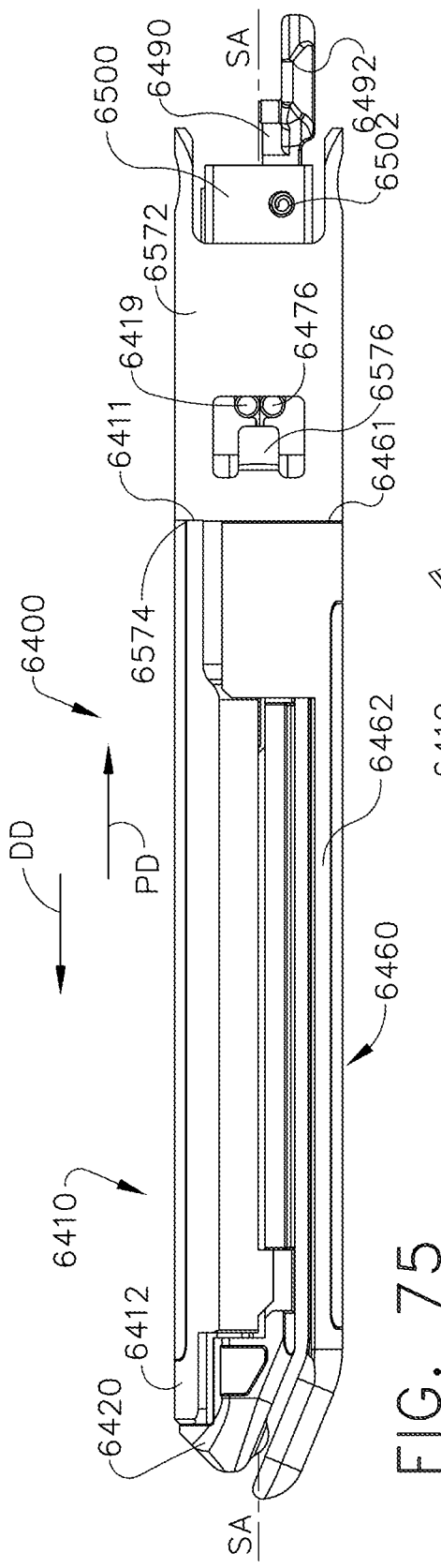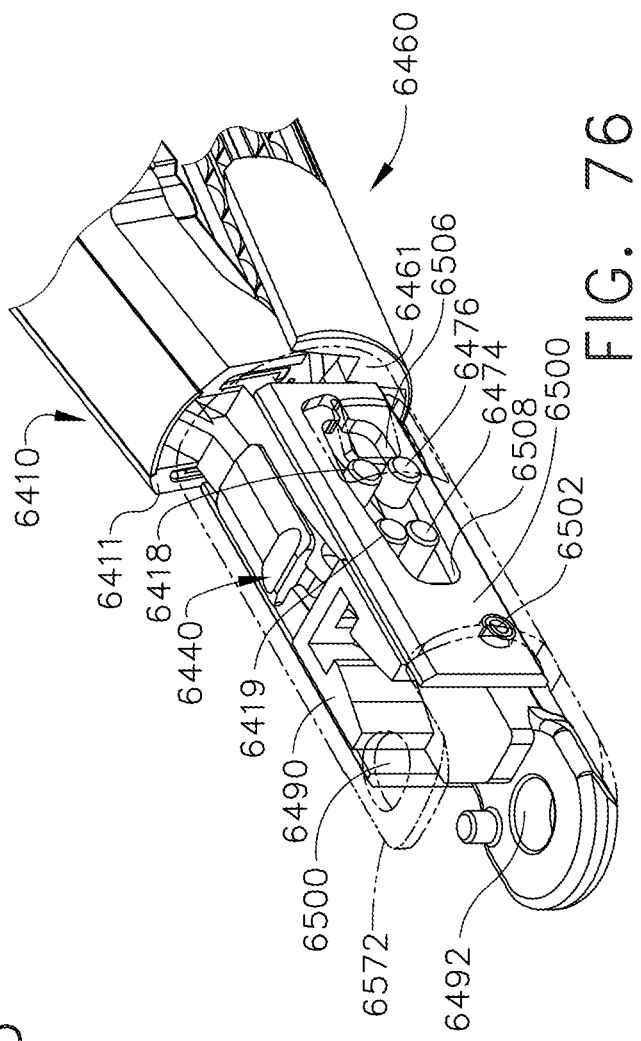

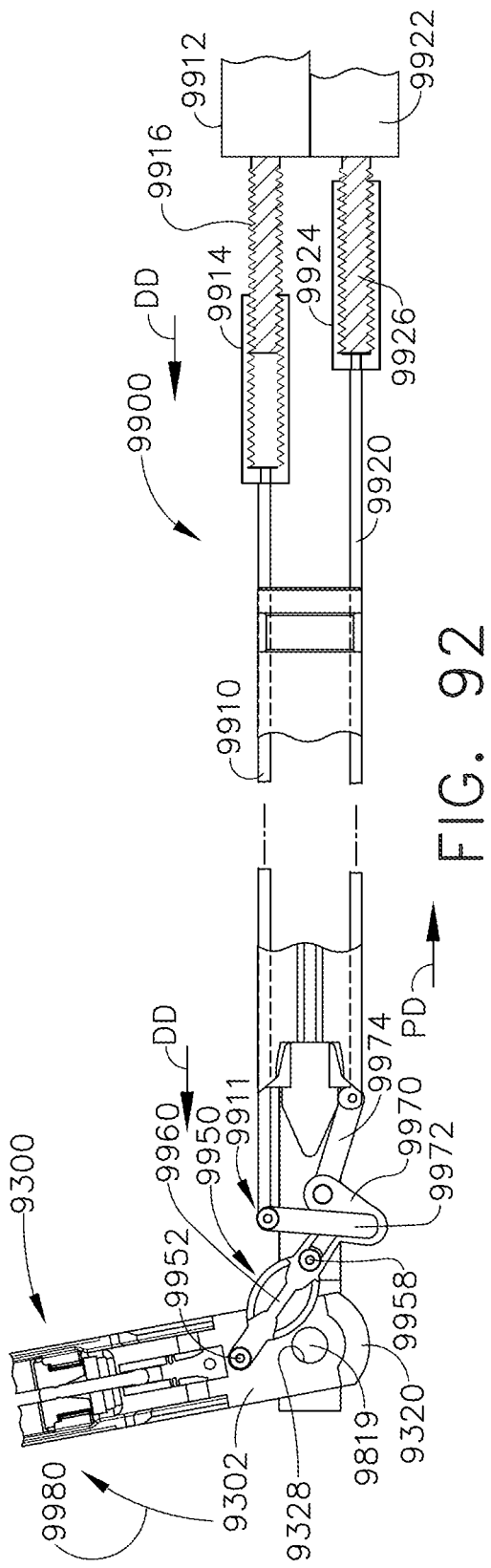
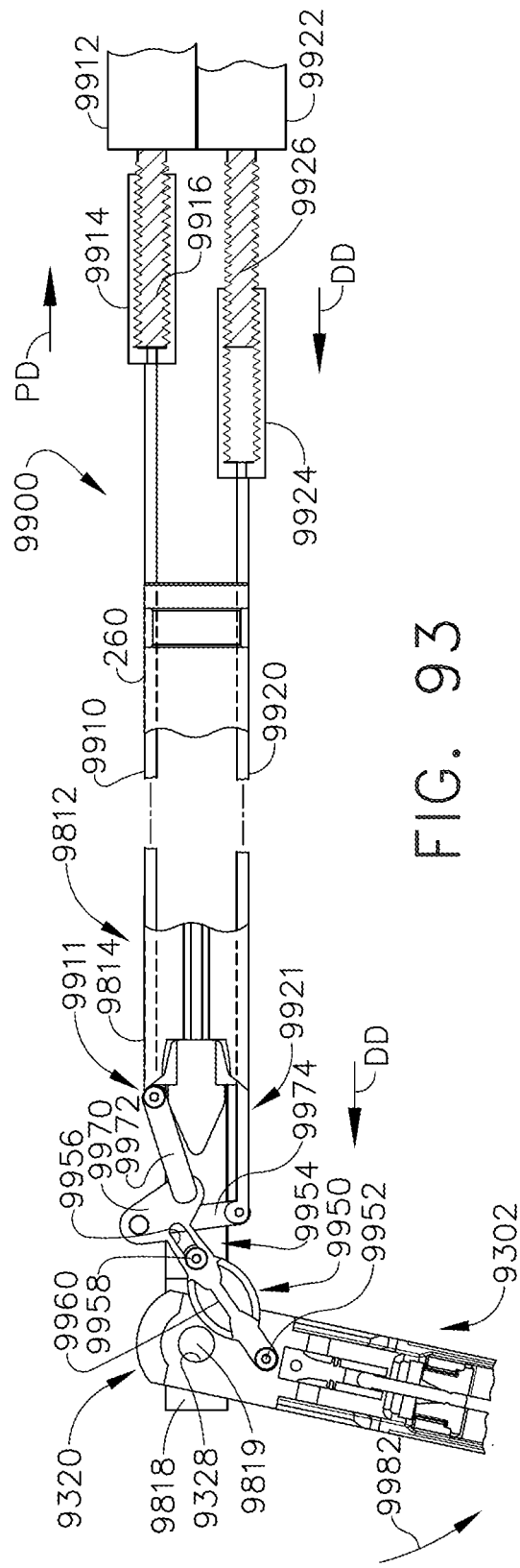

SURGICAL END EFFECTORS WITH POSITIVE JAW OPENING ARRANGEMENTS

CROSS-REFERENCE TO RELATED APPLICATIONS

This application is a continuation application claiming priority under 35 U.S.C. § 120 to U.S. patent application Ser. No. 16/157,729, entitled SURGICAL END EFFECTORS WITH POSITIVE JAW OPENING ARRANGEMENTS, filed Oct. 11, 2018, which issued on Feb. 14, 2023 as U.S. Pat. No. 11,576,669, which is a continuation application claiming priority under 35 U.S.C. § 120 to U.S. patent application Ser. No. 14/742,925, entitled SURGICAL END EFFECTORS WITH POSITIVE JAW OPENING ARRANGEMENTS, filed Jun. 18, 2015, which issued on Jan. 22, 2019 as U.S. Pat. No. 10,182,818, the entire disclosures of which are hereby incorporated by reference herein.

BACKGROUND

The present invention relates to surgical instruments and, in various embodiments, to surgical stapling and cutting instruments and staple cartridges for use therewith.

A stapling instrument can include a pair of cooperating elongate jaw members, wherein each jaw member can be adapted to be inserted into a patient and positioned relative to tissue that is to be stapled and/or incised. In various embodiments, one of the jaw members can support a staple cartridge with at least two laterally spaced rows of staples contained therein, and the other jaw member can support an anvil with staple-forming pockets aligned with the rows of staples in the staple cartridge. Generally, the stapling instrument can further include a pusher bar and a knife blade which are slidable relative to the jaw members to sequentially eject the staples from the staple cartridge via camming surfaces on the pusher bar and/or camming surfaces on a wedge sled that is pushed by the pusher bar. In at least one embodiment, the camming surfaces can be configured to activate a plurality of staple drivers carried by the cartridge and associated with the staples in order to push the staples against the anvil and form laterally spaced rows of deformed staples in the tissue gripped between the jaw members. In at least one embodiment, the knife blade can trail the camming surfaces and cut the tissue along a line between the staple rows.

The foregoing discussion is intended only to illustrate various aspects of the related art in the field of the invention at the time, and should not be taken as a disavowal of claim scope.

BRIEF DESCRIPTION OF THE DRAWINGS

Various features of the embodiments described herein, together with advantages thereof, may be understood in accordance with the following description taken in conjunction with the accompanying drawings as follows:

FIG. 17 is a top view of portions of the elongate shaft assembly embodiment of FIGS. 15 and 16;

FIG. 18 is a cross-sectional side elevational view of the elongate shaft assembly embodiment of FIGS. 15-17 with a surgical staple cartridge mounted in the surgical end effector portion;

FIG. 23 is a top view of portions of the surgical end effector and elongate shaft assembly embodiment of FIGS. 21 and 22;

FIG. 24 is another top view of the portions of the surgical end effector and elongate shaft assembly embodiment of FIGS. 21-23 with portions thereof omitted for clarity;

FIG. 31 is a top view of portions of the surgical end effector and elongate shaft assembly embodiment of FIGS. 27-30 with portions thereof omitted for clarity;

FIG. 32 is another top view of portions of the surgical end effector and elongate shaft assembly embodiment of FIGS. 27-31 with portions thereof omitted for clarity and with the surgical end effector in an articulated position or configuration;

FIG. 33 is a side elevational view of portions of the surgical end effector and elongate shaft assembly embodiment of FIGS. 27-32 with portions thereof omitted for clarity;

FIG. 34 is a perspective view of portions of the surgical end effector and elongate shaft assembly embodiment of FIGS. 27-33 with portions thereof omitted for clarity;

FIG. 37 is a perspective view of the distal firing beam assembly and lateral load carrying members of FIG. 36;

FIG. 38 is an enlarged cross-sectional view of portions of the distal firing beam assembly and lateral load carrying members of FIGS. 36 and 37;

FIG. 39 is another cross-sectional view of the distal firing beam assembly and lateral load carrying members of FIGS. 36-38;

FIG. 48 is a top view of portions of the surgical end effector embodiment and elongate shaft assembly embodiment of FIG. 47 with portions thereof omitted for clarity;

FIG. 49 is another top view of the surgical end effector embodiment and elongate shaft assembly embodiment of FIG. 48;

FIG. 75 is a side elevational view of the surgical end effector and closure sleeve embodiment of FIGS. 72-74 with the jaws thereof in a closed position or configuration;

FIG. 76 is a rear perspective view of the surgical end effector embodiment of FIGS. 72-75 with the closure sleeve embodiment thereof shown in phantom lines for clarity;

FIG. 92 is a top view of the elongate shaft assembly of FIGS. 88-91 with some components omitted for clarity and the surgical end effector thereof articulated in one direction;

FIG. 93 is another top view of the elongate shaft assembly of FIGS. 88-92 with some components thereof omitted for clarity and with the surgical end effector articulated in another direction;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
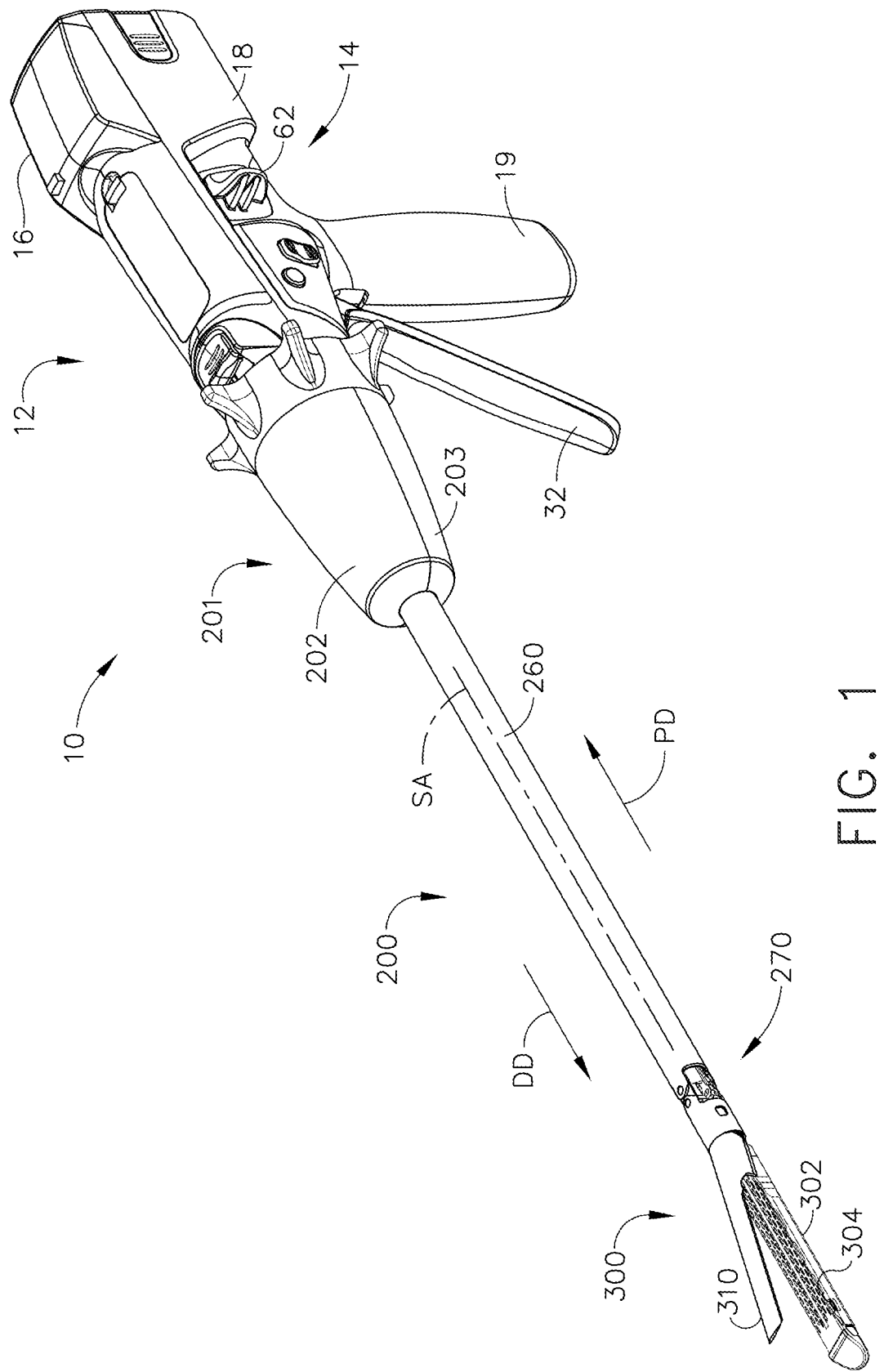
FIG. 1 is a perspective view of a surgical instrument and an elongate shaft assembly embodiment.

Applicant of the present application owns the following patent applications that were filed on Jun. 18, 2015 and which are each herein incorporated by reference in their respective entireties:

U.S. patent application Ser. No. 14/742,941, entitled SURGICAL END EFFECTORS WITH DUAL CAM ACTUATED JAW CLOSING FEATURES, now U.S. Pat. No. 10,052,102;

U.S. patent application Ser. No. 14/742,933, entitled SURGICAL STAPLING INSTRUMENTS WITH LOCKOUT ARRANGEMENTS FOR PREVENTING FIRING SYSTEM ACTUATION WHEN A CARTRIDGE IS SPENT OR MISSING; now U.S. Pat. No. 10,154,841;

U.S. patent application Ser. No. 14/742,914, entitled MOVABLE FIRING BEAM SUPPORT ARRANGEMENTS FOR ARTICULATABLE SURGICAL INSTRUMENTS, now U.S. Pat. No. 10,405,863;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Pat. No. 10,335,149;

U.S. patent application Ser. No. 14/742,885, entitled DUAL ARTICULATION DRIVE SYSTEM ARRANGEMENTS FOR ARTICULATABLE SURGICAL INSTRUMENTS, now U.S. Pat. No. 10,368,861; and U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015 and which are each herein incorporated by reference in their respective entireties:

U.S. patent application Ser. No. 14/640,746, entitled POWERED SURGICAL INSTRUMENT, now U.S. Pat. No. 9,808,246;

U.S. patent application Ser. No. 14/640,795, entitled MULTIPLE LEVEL THRESHOLDS TO MODIFY OPERATION OF POWERED SURGICAL INSTRUMENTS, now U.S. Pat. No. 10,441,279;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Pat. No. 10,687,806;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;

U.S. patent application Ser. No. 14/640,817, entitled INTERACTIVE FEEDBACK SYSTEM FOR POWERED SURGICAL INSTRUMENTS, now U.S. Pat. No. 9,924,961;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;

U.S. patent application Ser. No. 14/640,837, entitled SMART SENSORS WITH LOCAL SIGNAL PROCESSING, now U.S. Pat. No. 9,993,248;

U.S. patent application Ser. No. 14/640,765, entitled SYSTEM FOR DETECTING THE MIS-INSERTION OF A STAPLE CARTRIDGE INTO A SURGICAL STAPLER, now U.S. Pat. No. 10,617,412;

U.S. patent application Ser. No. 14/640,799, entitled SIGNAL AND POWER COMMUNICATION SYSTEM POSITIONED ON A ROTATABLE SHAFT, now U.S. Pat. No. 9,901,342; and U.S. patent application Ser. No. 14/640,780, entitled SURGICAL INSTRUMENT COMPRISING A LOCKABLE BATTERY HOUSING, now U.S. Pat. No. 10,245,033.

Applicant of the present application owns the following patent applications that were filed on Feb. 27, 2015, and which are each herein incorporated by reference in their respective entireties:

U.S. patent application Ser. No. 14/633,576, entitled SURGICAL INSTRUMENT SYSTEM COMPRISING AN INSPECTION STATION, now U.S. Pat. No. 10,045,779;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;

U.S. patent application Ser. No. 14/633,555, entitled SYSTEM FOR MONITORING WHETHER A SURGICAL INSTRUMENT NEEDS TO BE SERVICED, now U.S. Pat. No. 10,321,907;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Pat. No. 10,245,028;

U.S. patent application Ser. No. 14/633,526, entitled ADAPTABLE SURGICAL INSTRUMENT HANDLE, now U.S. Pat. No. 9,993,258;

U.S. patent application Ser. No. 14/633,541, entitled MODULAR STAPLING ASSEMBLY, now U.S. Pat. No. 10,226,250; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entireties:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Pat. No. 10,188,385;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWREEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Pat. No. 10,470,762;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled USE OF POLARITY OF HALL MAGNET DETECTION TO DETECT MISLOADED CARTRIDGE, now U.S. Pat. No. 10,016,199;

U.S. patent application Ser. No. 14/479,098, entitled SMART CARTRIDGE WAKE UP OPERATION AND DATA RETENTION, now U.S. Patent Application Publication No. 2016/0066911;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Pat. No. 10,135,242.

Applicant of the present application also owns the following patent applications that were filed on Apr. 9, 2014 and which are each herein incorporated by reference in their respective entireties:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Pat. No. 9,844,368;

U.S. patent application Ser. No. 14/248,588, entitled POWERED LINEAR SURGICAL STAPLER, now U.S. Pat. No. 10,405,857;

U.S. patent application Ser. No. 14/248,591, entitled TRANSMISSION ARRANGEMENT FOR A SURGICAL INSTRUMENT, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entireties:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIGS. 1-4 depict a motor-driven surgical cutting and fastening instrument 10 that may or may not be reused. In the illustrated embodiment, the instrument 10 includes a housing 12 that comprises a handle 14 that is configured to be grasped, manipulated and actuated by the clinician. The housing 12 is configured for operable attachment to an elongate shaft assembly 200 that has a surgical end effector 300 operably coupled thereto that is configured to perform one or more surgical tasks or procedures. The elongate shaft assembly 200 may be interchangeable with other shaft assemblies in the various manners disclosed, for example, in U.S. patent application Ser. No. 14/226,075, entitled MODULAR POWERED SURGICAL INSTRUMENT WITH DETACHABLE SHAFT ASSEMBLIES, now U.S. Pat. No. 9,743,929, the entire disclosure of which is hereby incorporated by reference herein. In other arrangements, the elongate shaft assembly may not be interchangeable with other shaft assemblies and essentially comprise a dedicated non-removable portion of the instrument.

As the present Detailed Description proceeds, it will be understood that the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the elongate shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. For example, the shaft assemblies disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, which is hereby incorporated by reference herein in its entirety.

The housing 12 depicted in FIG. 1 is shown in connection with the elongate shaft assembly 200 that includes a surgical end effector 300 that comprises a surgical cutting and fastening device that is configured to operably support a surgical staple cartridge 304 therein. The housing 12 may be configured for use in connection with shaft assemblies that include end effectors that are adapted to support different sizes and types of staple cartridges, have different shaft lengths, sizes, and types, etc. In addition, the housing 12 may also be effectively employed with a variety of other shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

FIG. 1 illustrates the housing 12 or handle 14 of the surgical instrument 10 with an interchangeable elongate shaft assembly 200 operably coupled thereto. As can be seen in FIG. 1, the handle 14 may comprise a pair of interconnectable handle housing segments 16 and 18 that may be interconnected by screws, snap features, adhesive, etc. In the illustrated arrangement, the handle housing segments 16, 18 cooperate to form a pistol grip portion 19 that can be gripped and manipulated by the clinician. As will be discussed in further detail below, the handle 14 operably supports a plurality of drive systems therein that are configured to generate and apply various control motions to corresponding portions of the interchangeable shaft assembly that is operably attached thereto.

Figure 2:
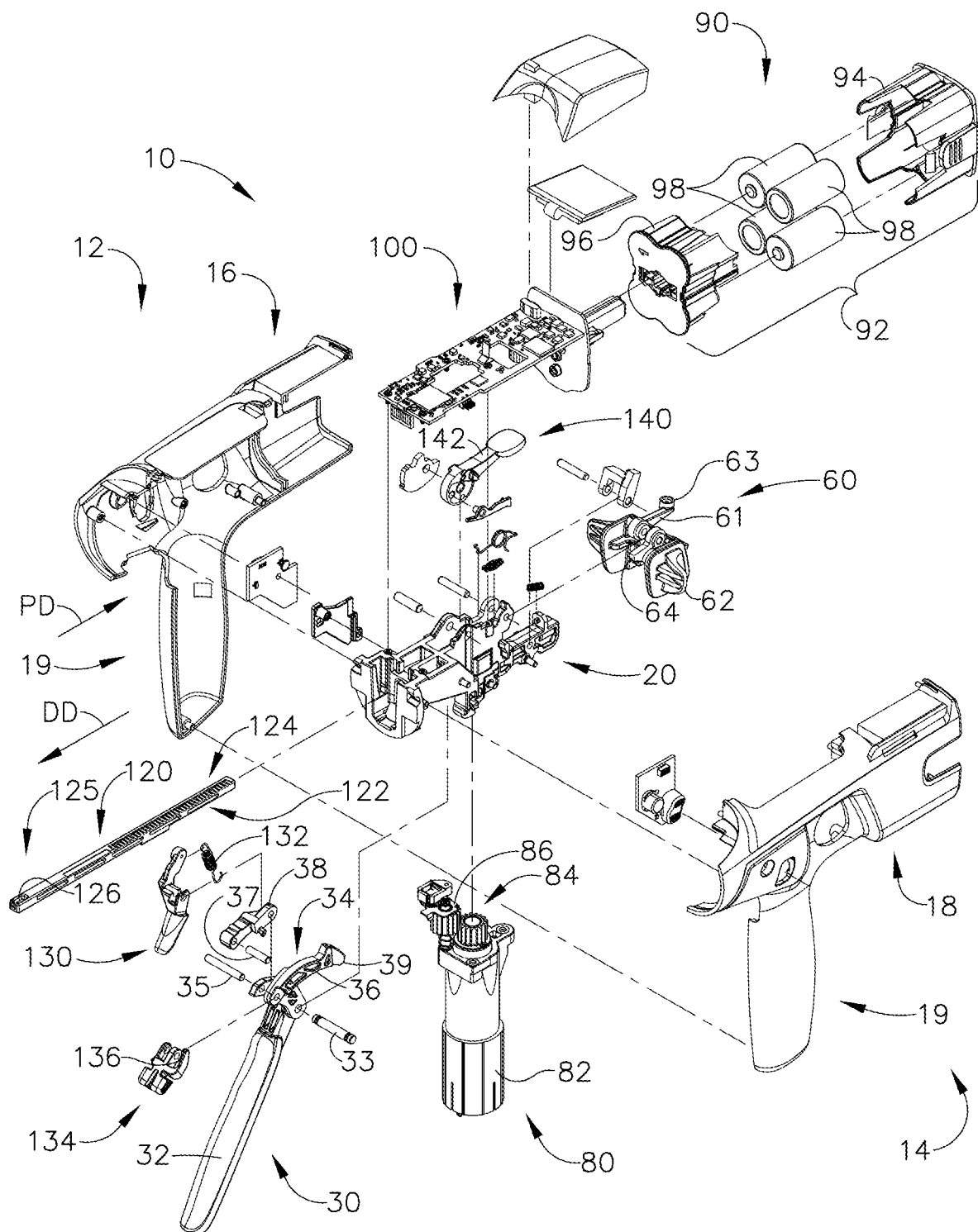
FIG. 2 is an exploded assembly view of the handle or housing portion of the surgical instrument of FIG. 1.

Referring now to FIG. 2, the handle 14 may further include a frame 20 that operably supports a plurality of drive systems. For example, the frame 20 can operably support a "first" or closure drive system, generally designated as 30, which may be employed to apply closing and opening motions to the elongate shaft assembly 200 that is operably attached or coupled thereto. In at least one form, the closure drive system 30 may include an actuator in the form of a closure trigger 32 that is pivotally supported by the frame 20. More specifically, as illustrated in FIG. 2, the closure trigger 32 is pivotally coupled to the housing 14 by a pin 33. Such arrangement enables the closure trigger 32 to be manipulated by a clinician such that when the clinician grips the pistol grip portion 19 of the handle 14, the closure trigger 32 may be easily pivoted from a starting or "unactuated" position to an "actuated" position and more particularly to a fully compressed or fully actuated position. The closure trigger 32 may be biased into the unactuated position by spring or other biasing arrangement (not shown). In various forms, the closure drive system 30 further includes a closure linkage assembly 34 that is pivotally coupled to the closure trigger 32. As can be seen in FIG. 2, the closure linkage assembly 34 may include a first closure link 36 and a second closure link 38 that are pivotally coupled to the closure trigger 32 by a pin 35. The second closure link 38 may also be referred to herein as an "attachment member" and include a transverse attachment pin 37.

Still referring to FIG. 2, it can be observed that the first closure link 36 may have a locking wall or end 39 thereon that is configured to cooperate with a closure release assembly 60 that is pivotally coupled to the frame 20. In at least one form, the closure release assembly 60 may comprise a release button assembly 62 that has a distally protruding locking pawl 64 formed thereon. The release button assembly 62 may be pivoted in a counterclockwise direction by a release spring (not shown). As the clinician depresses the closure trigger 32 from its unactuated position towards the pistol grip portion 19 of the handle 14, the first closure link 36 pivots upward to a point wherein the locking pawl 64 drops into retaining engagement with the locking wall 39 on the first closure link 36 thereby preventing the closure trigger 32 from returning to the unactuated position. Thus, the closure release assembly 60 serves to lock the closure trigger 32 in the fully actuated position. When the clinician desires to unlock the closure trigger 32 to permit it to be biased to the unactuated position, the clinician simply pivots the closure release button assembly 62 such that the locking pawl 64 is moved out of engagement with the locking wall 39 on the first closure link 36. When the locking pawl 64 has been moved out of engagement with the first closure link 36, the closure trigger 32 may pivot back to the unactuated position. Other closure trigger locking and release arrangements may also be employed.

When the closure trigger 32 is moved from its unactuated position to its actuated position, the closure release button 62 is pivoted between a first position and a second position. The rotation of the closure release button 62 can be referred to as being an upward rotation; however, at least a portion of the closure release button 62 is being rotated toward the circuit board 100. Still referring to FIG. 2, the closure release button 62 can include an arm 61 extending therefrom and a magnetic element 63, such as a permanent magnet, for example, mounted to the arm 61. When the closure release button 62 is rotated from its first position to its second position, the magnetic element 63 can move toward the circuit board 100. The circuit board 100 can include at least one sensor that is configured to detect the movement of the magnetic element 63. In at least one embodiment, a "Hall effect" sensor can be mounted to the bottom surface of the circuit board 100. The Hall effect sensor can be configured to detect changes in a magnetic field surrounding the Hall effect sensor that are caused by the movement of the magnetic element 63. The Hall effect sensor can be in signal communication with a microcontroller, for example, which can determine whether the closure release button 62 is in its first position, which is associated with the unactuated position of the closure trigger 32 and the open configuration of the end effector, its second position, which is associated with the actuated position of the closure trigger 32 and the closed configuration of the end effector, and/or any position between the first position and the second position.

Also in the illustrated arrangement, the handle 14 and the frame 20 operably support another drive system referred to herein as a firing drive system 80 that is configured to apply firing motions to corresponding portions of the interchangeable shaft assembly attached thereto. The firing drive system may 80 also be referred to herein as a "second drive system". The firing drive system 80 may employ an electric motor 82, located in the pistol grip portion 19 of the handle 14. In various forms, the motor 82 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 82 may be powered by a power source 90 that in one form may comprise a removable power pack 92. As can be seen in FIG. 2, for example, the power pack 92 may comprise a proximal housing portion 94 that is configured for attachment to a distal housing portion 96. The proximal housing portion 94 and the distal housing portion 96 are configured to operably support a plurality of batteries 98 therein. Batteries 98 may each comprise, for example, a Lithium Ion ("LI") or other suitable battery. The distal housing portion 96 is configured for removable operable attachment to a control circuit board assembly 100 which is also operably coupled to the motor 82. A number of batteries 98 may be connected in series may be used as the power source for the surgical instrument 10. In addition, the power source 90 may be replaceable and/or rechargeable.

As outlined above with respect to other various forms, the electric motor 82 includes a rotatable shaft (not shown) that operably interfaces with a gear reducer assembly 84 that is mounted in meshing engagement with a with a set, or rack, of drive teeth 122 on a longitudinally-movable drive member 120. In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the drive member 120 will be axially driven in the distal direction "DD". When the motor 82 is driven in the opposite rotary direction, the drive member 120 will be axially driven in a proximal direction "PD". The handle 14 can include a switch which can be configured to reverse the polarity applied to the electric motor 82 by the power source 90. As with the other forms described herein, the handle 14 can also include a sensor that is configured to detect the position of the drive member 120 and/or the direction in which the drive member 120 is being moved.

Actuation of the motor 82 is controlled by a firing trigger 130 that is pivotally supported on the handle 14. The firing trigger 130 may be pivoted between an unactuated position and an actuated position. The firing trigger 130 may be biased into the unactuated position by a spring 132 or other biasing arrangement such that when the clinician releases the firing trigger 130, it may be pivoted or otherwise returned to the unactuated position by the spring 132 or biasing arrangement. In at least one form, the firing trigger 130 can be positioned "outboard" of the closure trigger 32 as was discussed above. In at least one form, a firing trigger safety button 134 may be pivotally mounted to the closure trigger 32 by pin 35. The safety button 134 may be positioned between the firing trigger 130 and the closure trigger 32 and have a pivot arm 136 protruding therefrom. See FIG. 2. When the closure trigger 32 is in the unactuated position, the safety button 134 is contained in the handle 14 where the clinician cannot readily access it and move it between a safety position preventing actuation of the firing trigger 130 and a firing position wherein the firing trigger 130 may be fired. As the clinician depresses the closure trigger 32, the safety button 134 and the firing trigger 130 pivot down wherein they can then be manipulated by the clinician.

As discussed above, the handle 14 includes a closure trigger 32 and a firing trigger 130. The firing trigger 130 can be pivotably mounted to the closure trigger 32. When the closure trigger 32 is moved from its unactuated position to its actuated position, the firing trigger 130 can descend downwardly, as outlined above. After the safety button 134 has been moved to its firing position, the firing trigger 130 can be depressed to operate the motor of the surgical instrument firing system. In various instances, the handle 14 can include a tracking system configured to determine the position of the closure trigger 32 and/or the position of the firing trigger 130.

As indicated above, in at least one form, the longitudinally movable drive member 120 has a rack of drive teeth 122 formed thereon for meshing engagement with a corresponding drive gear 86 of the gear reducer assembly 84. At least one form also includes a manually-actuatable "bailout" assembly 140 that is configured to enable the clinician to manually retract the longitudinally movable drive member 120 should the motor 82 become disabled. The bailout assembly 140 may include a lever or bailout handle assembly 142 that is configured to be manually pivoted into ratcheting engagement with teeth 124 also provided in the drive member 120. Thus, the clinician can manually retract the drive member 120 by using the bailout handle assembly 142 to ratchet the drive member 120 in the proximal direction "PD". U.S. Patent Application Publication No. 2010/0089970, now U.S. Pat. No. 8,608,045, discloses bailout arrangements and other components, arrangements and systems that may also be employed with the various instruments disclosed herein. U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045, is hereby incorporated by reference in its entirety.

Figure 3:
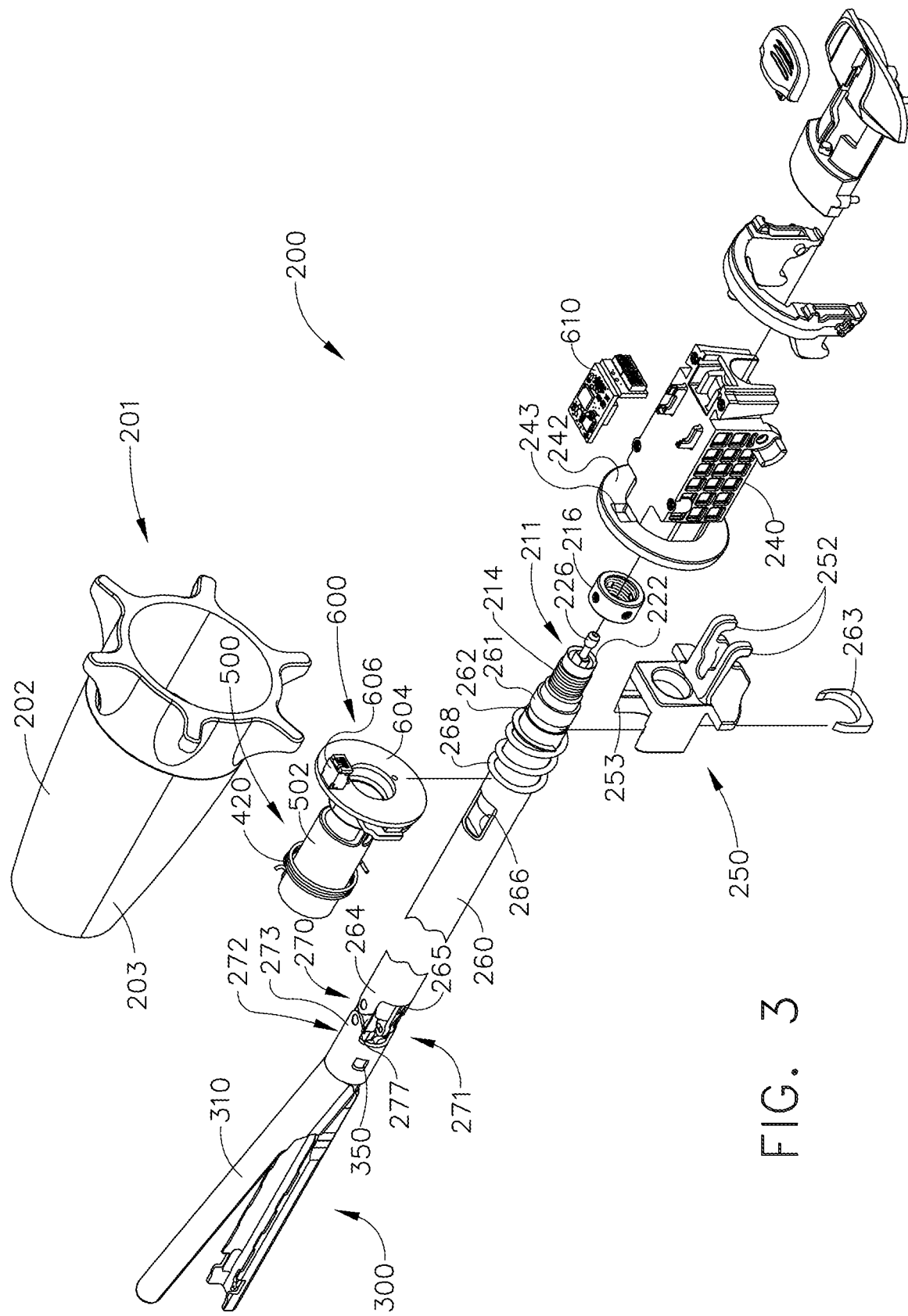
FIG. 3 is an exploded assembly view of a portion of an elongate shaft assembly.
Figure 4:
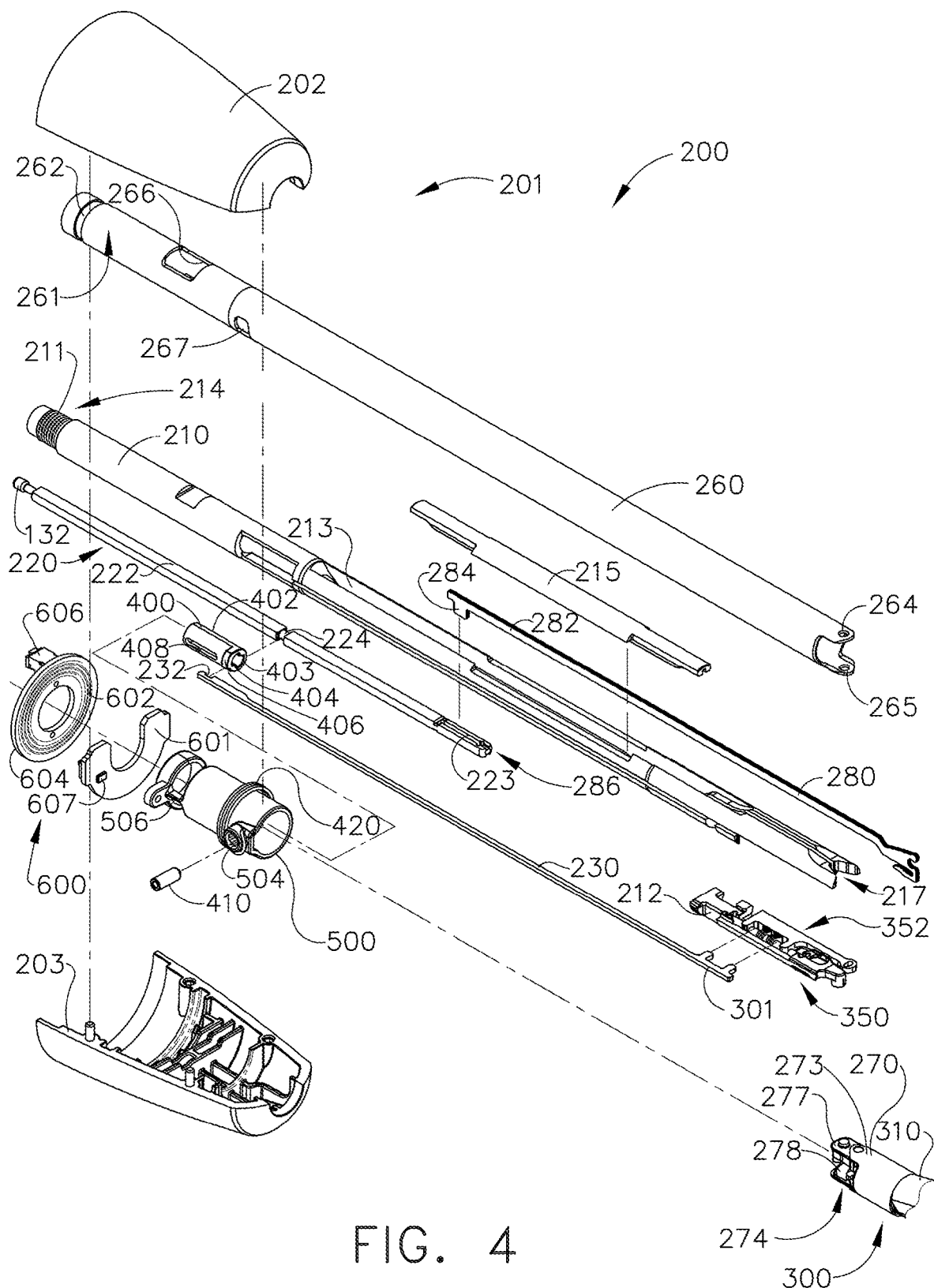
FIG. 4 is another exploded assembly view of another portion of the elongate shaft assembly of FIG. 3.

Turning now to FIGS. 1 and 3, the elongate shaft assembly 200 includes a surgical end effector 300 that comprises an elongate channel 302 that is configured to operably support a staple cartridge 304 therein. The end effector 300 may further include an anvil 310 that is pivotally supported relative to the elongate channel 302. As will be discussed in further detail below, the surgical end effector 300 may be articulated relative to the elongate shaft assembly about an articulation joint 270. As can be seen in FIGS. 3 and 4, the shaft assembly 200 can further include a proximal housing or nozzle 201 comprised of nozzle portions 202 and 203. The shaft assembly 200 further includes a closure tube 260 which can be utilized to close and/or open an anvil 310 of the end effector 300. As can be seen in FIG. 4, the shaft assembly 200 includes a spine 210 which can be configured to fixably support a shaft frame portion 212 of and articulation lock 350. Details regarding the construction and operation of the articulation lock 350 are set forth in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the disclosure of which is hereby incorporated by reference herein in its entirety. The spine 210 is configured to, one, slidably support a firing member 220 therein and, two, slidably support the closure tube 260 which extends around the spine 210. The spine 210 also slidably supports a proximal articulation driver 230. The proximal articulation driver 230 has a distal end 231 that is configured to operably engage the articulation lock 350. In one arrangement, the articulation lock 350 interfaces with an articulation frame 352 that is adapted to operably engage a drive pin (not shown) on the end effector frame (not shown).

In the illustrated arrangement, the spine 210 comprises a proximal end 211 which is rotatably supported in a chassis 240. In one arrangement, for example, the proximal end 211 of the spine 210 has a thread 214 formed thereon for threaded attachment to a spine bearing 216 configured to be supported within the chassis 240. See FIG. 3. Such arrangement facilitates rotatable attachment of the spine 210 to the chassis 240 such that the spine 210 may be selectively rotated about a shaft axis SA-SA relative to the chassis 240. The shaft assembly 200 also includes a closure shuttle 250 that is slidably supported within the chassis 240 such that it may be axially moved relative thereto. As can be seen in FIG. 3, the closure shuttle 250 includes a pair of proximally-protruding hooks 252 that are configured for attachment to the attachment pin 37 that is attached to the second closure link 38 as will be discussed in further detail below. See FIG. 2. A proximal end 261 of the closure tube 260 is coupled to the closure shuttle 250 for relative rotation thereto. For example, a U-shaped connector 263 is inserted into an annular slot 262 in the proximal end 261 of the closure tube 260 and is retained within vertical slots 253 in the closure shuttle 250. See FIG. 3. Such arrangement serves to attach the closure tube 260 to the closure shuttle 250 for axial travel therewith while enabling the closure tube 260 to rotate relative to the closure shuttle 250 about the shaft axis SA-SA. A closure spring 268 is journaled on the closure tube 260 and serves to bias the closure tube 260 in the proximal direction "PD" which can serve to pivot the closure trigger into the unactuated position when the shaft assembly 200 is operably coupled to the handle 14.

As was also indicated above, the elongate shaft assembly 200 further includes a firing member 220 that is supported for axial travel within the shaft spine 210. The firing member 220 includes an intermediate firing shaft portion 222 that is configured for attachment to a distal cutting portion or firing beam 280. The firing member 220 may also be referred to herein as a "second shaft" and/or a "second shaft assembly". As can be seen in FIG. 4, the intermediate firing shaft portion 222 may include a longitudinal slot 223 in the distal end thereof which can be configured to receive a tab 284 on the proximal end 282 of the distal firing beam 280. The longitudinal slot 223 and the proximal end 282 can be sized and configured to permit relative movement therebetween and can comprise a slip joint 286. The slip joint 286 can permit the intermediate firing shaft portion 222 of the firing drive 220 to be moved to articulate the surgical end effector 300 without moving, or at least substantially moving, the firing beam 280. Once the surgical end effector 300 has been suitably oriented, the intermediate firing shaft portion 222 can be advanced distally until a proximal sidewall of the longitudinal slot 223 comes into contact with the tab 284 in order to advance the firing beam 280 and fire a staple cartridge that may be supported in the end effector 300. As can be further seen in FIG. 4, the shaft spine 210 has an elongate opening or window 213 therein to facilitate assembly and insertion of the intermediate firing shaft portion 222 into the shaft frame 210. Once the intermediate firing shaft portion 222 has been inserted therein, a top frame segment 215 may be engaged with the shaft frame 212 to enclose the intermediate firing shaft portion 222 and firing beam 280 therein. Further description of the operation of the firing member 220 may be found in U.S. patent application Ser. No. 13/803,086, now U.S. Patent Application Publication No. 2014/0263541.

Further to the above, the illustrated shaft assembly 200 includes a clutch assembly 400 which can be configured to selectively and releasably couple the articulation driver 230 to the firing member 220. In one form, the clutch assembly 400 includes a lock collar, or sleeve 402, positioned around the firing member 220 wherein the lock sleeve 402 can be rotated between an engaged position in which the lock sleeve 402 couples the articulation driver 360 to the firing member 220 and a disengaged position in which the articulation driver 360 is not operably coupled to the firing member 200. When lock sleeve 402 is in its engaged position, distal movement of the firing member 220 can move the articulation driver 360 distally and, correspondingly, proximal movement of the firing member 220 can move the proximal articulation driver 230 proximally. When lock sleeve 402 is in its disengaged position, movement of the firing member 220 is not transmitted to the proximal articulation driver 230 and, as a result, the firing member 220 can move independently of the proximal articulation driver 230. In various circumstances, the proximal articulation driver 230 can be held in position by the articulation lock 350 when the proximal articulation driver 230 is not being moved in the proximal or distal directions by the firing member 220.

As can be further seen in FIG. 4, the lock sleeve 402 can comprise a cylindrical, or an at least substantially cylindrical, body including a longitudinal aperture 403 defined therein configured to receive the firing member 220. The lock sleeve 402 can comprise diametrically-opposed, inwardly-facing lock protrusions 404 and an outwardly-facing lock member 406. The lock protrusions 404 can be configured to be selectively engaged with the firing member 220. More particularly, when the lock sleeve 402 is in its engaged position, the lock protrusions 404 are positioned within a drive notch 224 defined in the firing member 220 such that a distal pushing force and/or a proximal pulling force can be transmitted from the firing member 220 to the lock sleeve 402. When the lock sleeve 402 is in its engaged position, a second lock member 406 is received within a drive notch 232 defined in the proximal articulation driver 230 such that the distal pushing force and/or the proximal pulling force applied to the lock sleeve 402 can be transmitted to the proximal articulation driver 230. In effect, the firing member 220, the lock sleeve 402, and the proximal articulation driver 230 will move together when the lock sleeve 402 is in its engaged position. On the other hand, when the lock sleeve 402 is in its disengaged position, the lock protrusions 404 may not be positioned within the drive notch 224 of the firing member 220 and, as a result, a distal pushing force and/or a proximal pulling force may not be transmitted from the firing member 220 to the lock sleeve 402. Correspondingly, the distal pushing force and/or the proximal pulling force may not be transmitted to the proximal articulation driver 230. In such circumstances, the firing member 220 can be slid proximally and/or distally relative to the lock sleeve 402 and the proximal articulation driver 230.

As can also be seen in FIG. 4, the elongate shaft assembly 200 further includes a switch drum 500 that is rotatably received on the closure tube 260. The switch drum 500 comprises a hollow shaft segment 502 that has a shaft boss 504 formed thereon for receive an outwardly protruding actuation pin 410 therein. In various circumstances, the actuation pin 410 extends through a slot 267 into a longitudinal slot 408 provided in the lock sleeve 402 to facilitate axial movement of the lock sleeve 402 when it is engaged with the proximal articulation driver 230. A rotary torsion spring 420 is configured to engage the shaft boss 504 on the switch drum 500 and a portion of the nozzle housing 203 to apply a biasing force to the switch drum 500. The switch drum 500 can further comprise at least partially circumferential openings 506 defined therein which, referring to FIGS. 5 and 6, can be configured to receive circumferential mounts extending from the nozzle portions 202, 203 and permit relative rotation, but not translation, between the switch drum 500 and the proximal nozzle 201. The mounts also extend through openings 266 in the closure tube 260 to be seated in recesses n the shaft spine 210. However, rotation of the nozzle 201 to a point where the mounts reach the end of their respective slots 506 in the switch drum 500 will result in rotation of the switch drum 500 about the shaft axis SA-SA. Rotation of the switch drum 500 will ultimately result in the rotation of the actuation pin 410 and the lock sleeve 402 between its engaged and disengaged positions. Thus, in essence, the nozzle 201 may be employed to operably engage and disengage the articulation drive system with the firing drive system in the various manners described in further detail in U.S. patent application Ser. No. 13/803, 086, now U.S. Patent Application Publication No. 2014/0263541.

As also illustrated in FIGS. 3 and 4, the elongate shaft assembly 200 can comprise a slip ring assembly 600 which can be configured to conduct electrical power to and/or from the end effector 300 and/or communicate signals to and/or from the surgical end effector 300, for example. The slip ring assembly 600 can comprise a proximal connector flange 604 mounted to a chassis flange 242 extending from the chassis 240 and a distal connector flange 601 positioned within a slot defined in the shaft housings 202, 203. The proximal connector flange 604 can comprise a first face and the distal connector flange 601 can comprise a second face which is positioned adjacent to and movable relative to the first face. The distal connector flange 601 can rotate relative to the proximal connector flange 604 about the shaft axis SA-SA. The proximal connector flange 604 can comprise a plurality of concentric, or at least substantially concentric, conductors 602 defined in the first face thereof. A connector 607 can be mounted on the proximal side of the distal connector flange 601 and may have a plurality of contacts (not shown) wherein each contact corresponds to and is in electrical contact with one of the conductors 602. Such arrangement permits relative rotation between the proximal connector flange 604 and the distal connector flange 601 while maintaining electrical contact therebetween. The proximal connector flange 604 can include an electrical connector 606 which can place the conductors 602 in signal communication with a shaft circuit board 610 mounted to the shaft chassis 240, for example. In at least one instance, a wiring harness comprising a plurality of conductors can extend between the electrical connector 606 and the shaft circuit board 610. The electrical connector 606 may extend proximally through a connector opening 243 defined in the chassis mounting flange 242. See FIG. 7. U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, is incorporated by reference herein in its entirety. U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481, is incorporated by reference herein in its entirety. Further details regarding slip ring assembly 600 may be found in U.S. patent application Ser. No. 13/803, 086, now U.S. Patent Application Publication No. 2014/0263541.

As discussed above, the elongate shaft assembly 200 can include a proximal portion which is fixably mounted to the handle 14 and a distal portion which is rotatable about a longitudinal shaft axis SA-SA. The rotatable distal shaft portion can be rotated relative to the proximal portion about the slip ring assembly 600, as discussed above. The distal connector flange 601 of the slip ring assembly 600 can be positioned within the rotatable distal shaft portion. Moreover, further to the above, the switch drum 500 can also be positioned within the rotatable distal shaft portion. When the rotatable distal shaft portion is rotated, the distal connector flange 601 and the switch drum 500 can be rotated synchronously with one another. In addition, the switch drum 500 can be rotated between a first position and a second position relative to the distal connector flange 601. When the switch drum 500 is in its first position, the articulation drive system (i.e., the proximal articulation driver 230) may be operably disengaged from the firing drive system and, thus, the operation of the firing drive system may not articulate the end effector 300 of the shaft assembly 200. When the switch drum 500 is in its second position, the articulation drive system (i.e., the proximal articulation driver 230) may be operably engaged with the firing drive system and, thus, the operation of the firing drive system may articulate the end effector 300 of the shaft assembly 200. When the switch drum 500 is moved between its first position and its second position, the switch drum 500 is moved relative to distal connector flange 601. In various instances, the shaft assembly 200 can comprise at least one sensor that is configured to detect the position of the switch drum 500.

Referring again to FIG. 4, the closure tube assembly 260 includes a double pivot closure sleeve assembly 271. According to various forms, the double pivot closure sleeve assembly 271 includes an end effector closure sleeve 272 that includes upper and lower distally projecting tangs 273, 274. An upper double pivot link 277 includes upwardly projecting distal and proximal pivot pins that engage respectively an upper distal pin hole in the upper proximally projecting tang 273 and an upper proximal pin hole in an upper distally projecting tang 264 on the closure tube 260. A lower double pivot link 278 includes upwardly projecting distal and proximal pivot pins that engage respectively a lower distal pin hole in the lower proximally projecting tang 274 and a lower proximal pin hole in the lower distally projecting tang 265. See also FIG. 6.

Figure 5:
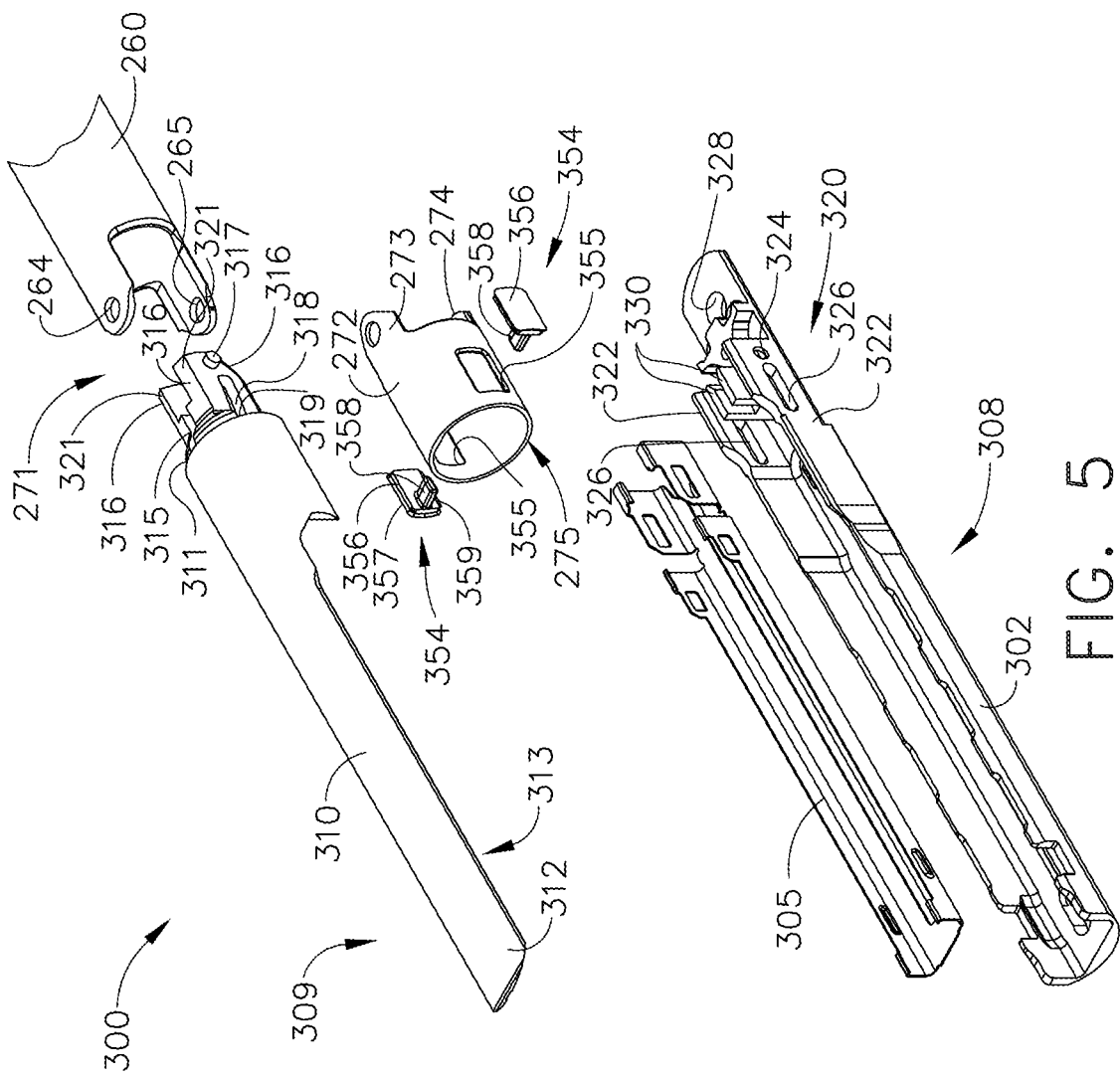
FIG. 5 is an exploded assembly view of a portion of a surgical end effector embodiment and closure sleeve embodiment.
Figure 6:
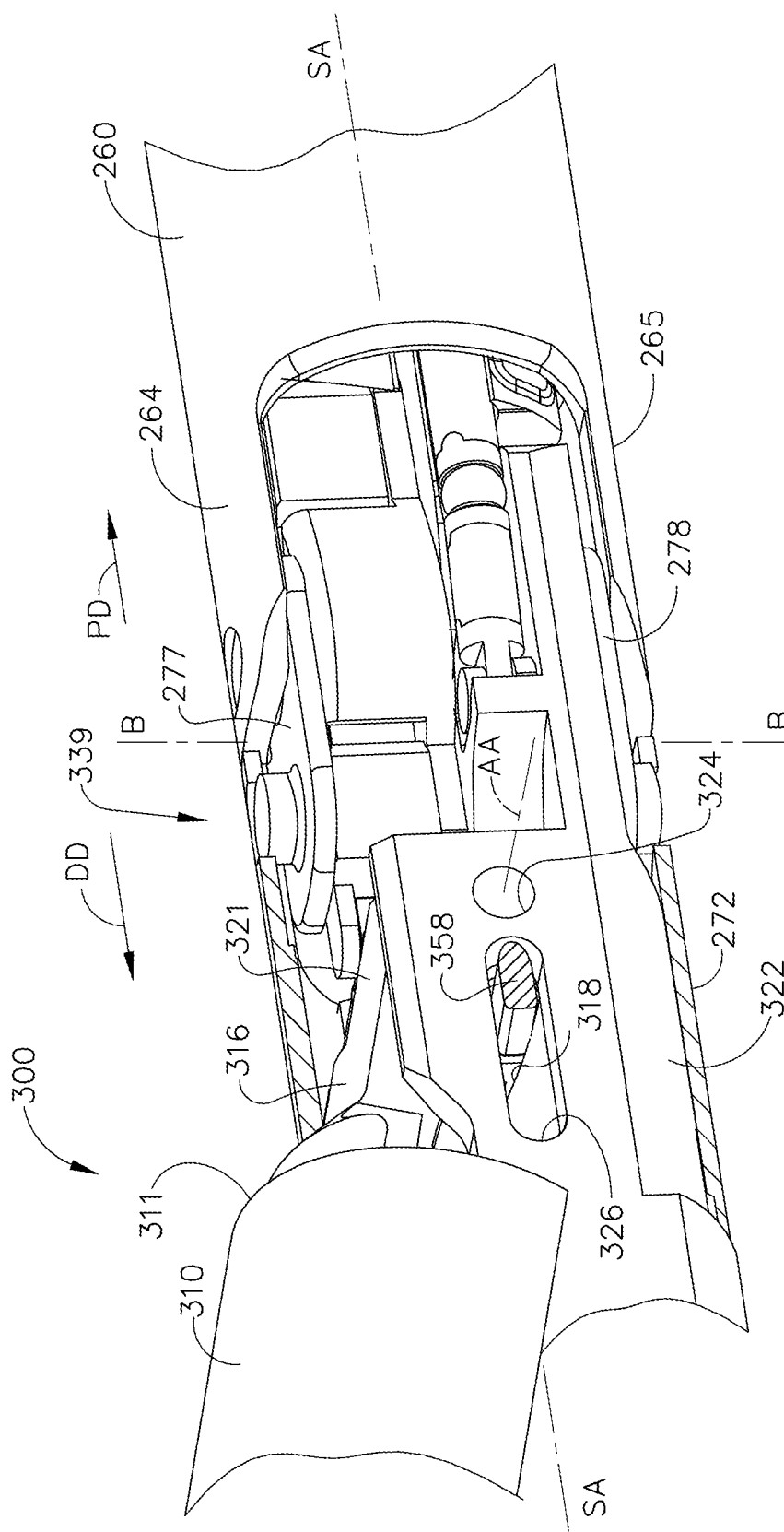
FIG. 6 is a partial cross-sectional view of a portion of the surgical end effector and closure sleeve arrangement of FIG. 5.

FIGS. 5-8 illustrate one form of surgical end effector 300 that is configured to be operably attached to an elongate shaft assembly of a surgical instrument of the type described above or other surgical instrument arrangements that include a closure system that is configured to generate control motions for axially moving a closure member that is configured to apply closing and opening motions to portions of the surgical end effector. In the illustrated example, as will be discussed in further detail below, the surgical end effector is configured to be articulated relative to a proximal portion of the elongate shaft assembly about an articulation joint, generally designated as 339. Other arrangements, however, may not be capable of articulation. As can be seen in FIG. 6, the articulation joint 339 defines an articulation axis B-B about which the surgical end effector 300 may be selectively articulated. In the illustrated example, the articulation axis B-B is substantially transverse to the shaft axis SA-SA of the elongate shaft assembly.

Figure 7:
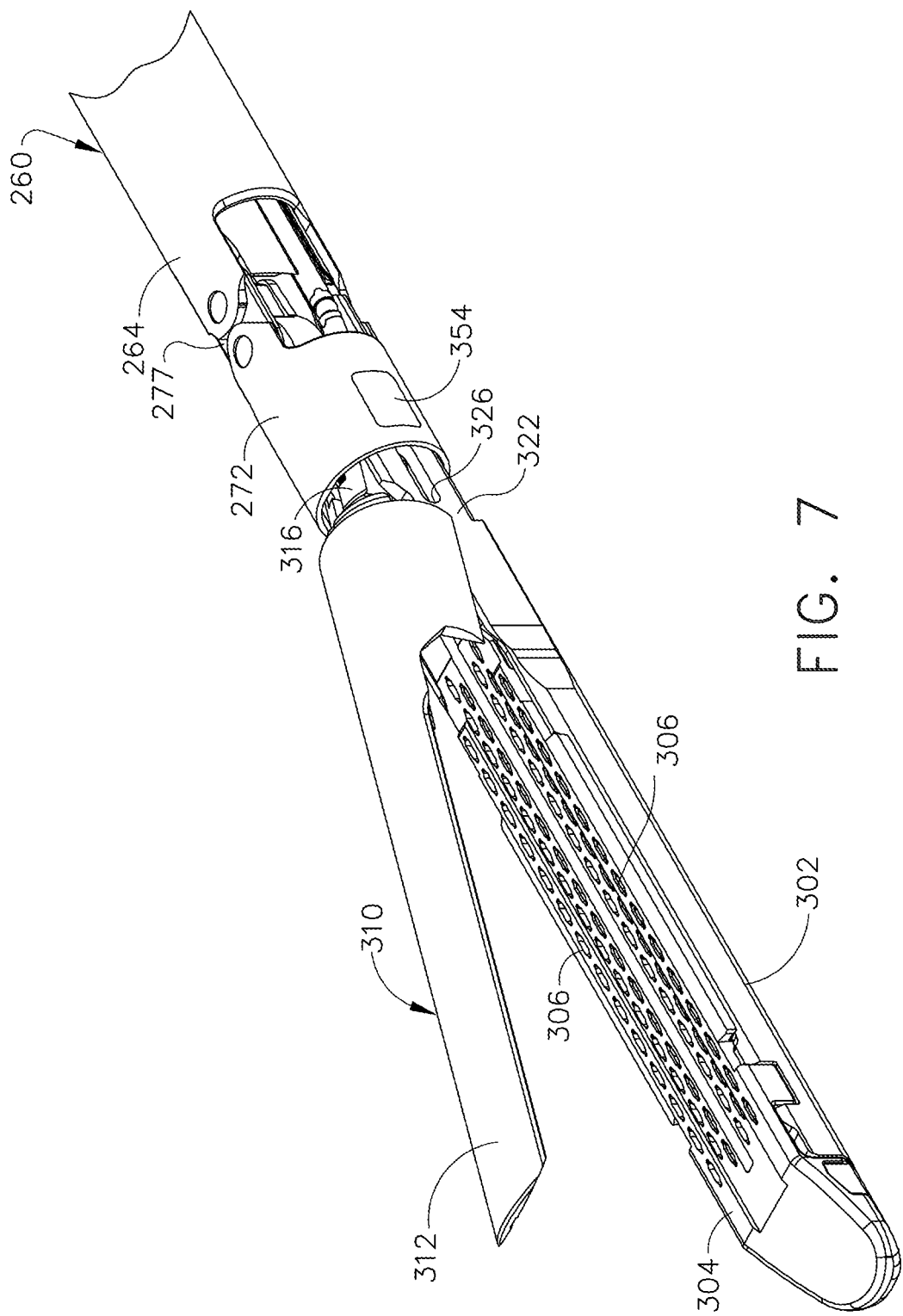
FIG. 7 is a perspective view of the surgical end effector and closure sleeve arrangement of FIGS. 5 and 6 with the anvil thereof in an open position or configuration.
Figure 8:
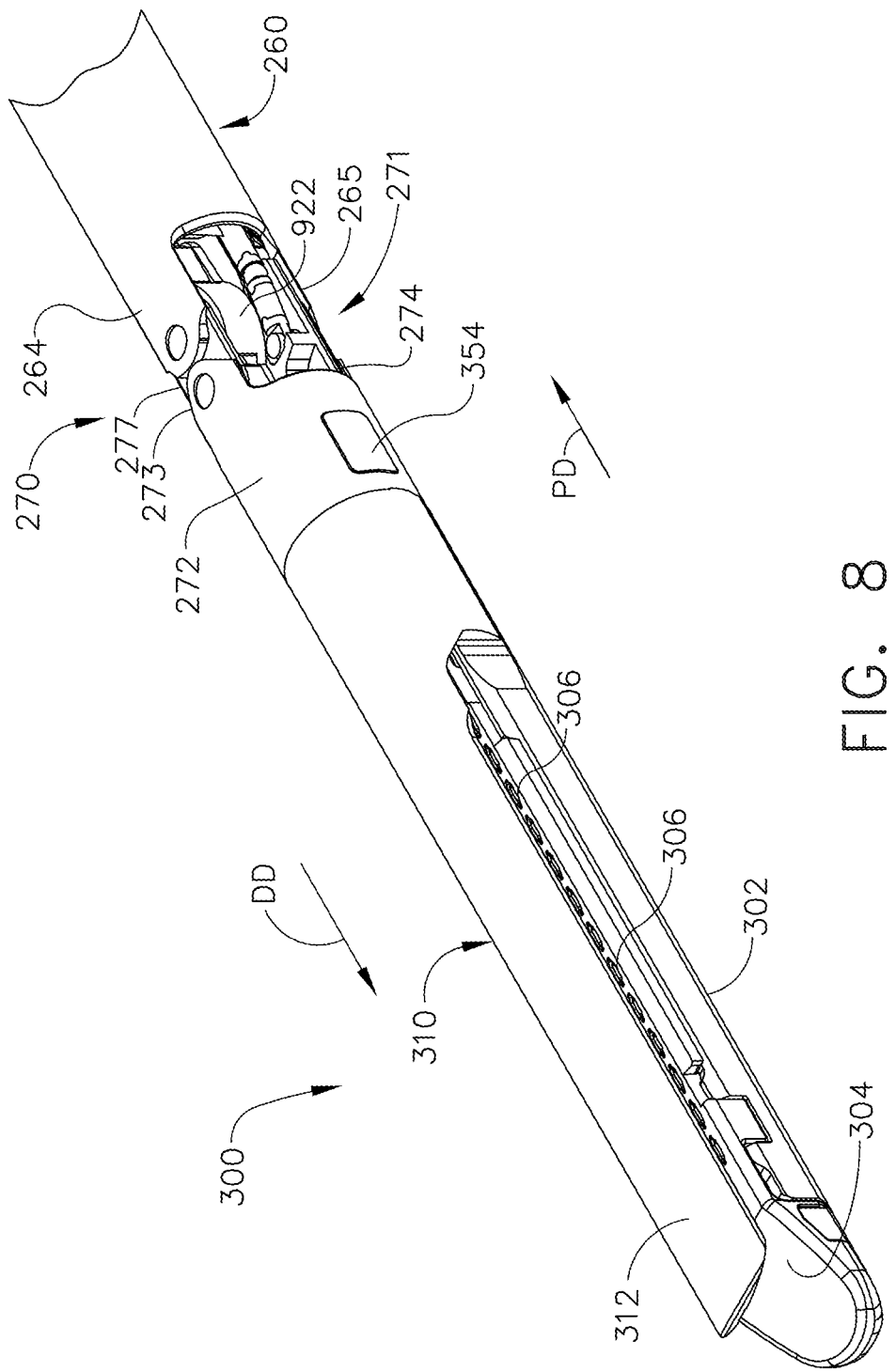
FIG. 8 is another perspective view of the surgical end effector and closure sleeve arrangement of FIGS. 5-7 with the anvil thereof in a closed position or configuration.

The illustrated surgical end effector 300 includes a first jaw 308 and a second jaw 309 that is selectively movable relative to the first jaw 308 between an open position (FIG. 7) and various closed positions (FIG. 8). In the illustrated embodiment, the first jaw 308 comprises an elongate channel 302 that is configured to operably support a surgical staple cartridge 304 therein and the second jaw 309 comprises an anvil 310. However, other surgical jaw arrangements may be employed without departing from the spirit and scope of the present invention. As can be seen in FIG. 5, a support pan 305 may be attached to the surgical staple cartridge 304 to provide added support thereto as well as to prevent the staple drivers (not shown) that are supported in the staple pockets 306 that are formed in the surgical staple cartridge 304 from falling out of the surgical staple cartridge prior to use. As can be seen in FIG. 5, the elongate channel 302 has a proximal end portion 320 that includes two upstanding lateral walls 322. The anvil 310 includes an anvil body 312 that has a staple-forming undersurface 313 formed thereon. A proximal end 314 of the anvil body is bifurcated by a firing member slot 315 that defines a pair of anvil attachment arms 316. Each anvil attachment arm 316 includes a sloping upper surface 321 and includes a laterally protruding anvil trunnion 317 and a cam slot 318 that defines a cam surface or "slotted cam surface" 319. See FIG. 5. One of the cam slots 318 may be referred to herein as a "first cam slot" with the cam surface thereof being referred to as the "first cam surface". Similarly, the other cam slot 318 may be referred to as a "second cam slot" with the cam surface thereof being referred to herein as the "second cam surface". A trunnion hole 324 is provided in each lateral wall 322 of the elongate channel 302 for receiving a corresponding one of the anvil trunnions 317 therein. Such arrangement serves to movably affix the anvil 310 to the elongate channel 302 for selective pivotable travel about an anvil axis A-A that is defined by trunnion holes 324 and which is transverse to the shaft axis SA-SA. See FIG. 6.

In the illustrated arrangement, the anvil 310 is pivotally moved relative to the elongate channel 302 and the surgical staple cartridge 304 supported therein to an open position by a pair of opening cams 354 that may be removably supported in or removably attached to or permanently attached to or integrally formed in an anvil actuator member. In the illustrated embodiment, the anvil actuator member comprises the end effector closure sleeve 272. See FIG. 5. Each opening cam 354 includes an outer body portion 356 that has a cam tab 358 protruding inwardly therefrom. The outer body portion 356 is, in at least one arrangement, configured to be snapped into removable engagement within a corresponding cam hole 355 formed in the end effector closure sleeve 272. For example, the outer body portion 356 may include a chamfered stop portion 357 that is configured to snappingly engage a corresponding portion of the end effector closure sleeve wall that defines the cam hole 355. Another portion of the outer body portion 356 may have a dog leg feature 359 formed thereon that is configured to be received inside a portion of the end effector closure sleeve 272 adjacent the cam hole 355. Other snap tab arrangements may also be employed to removably affix the outer body portion 356 to the end effector closure sleeve 272. In other arrangements, for example, the outer body portion may not be configured for snapping engagement with the end effector closure sleeve 272. In such arrangements, the outer body portions may be retained in position by an annular crimp ring that extends around the outer circumference of the end effector closure sleeve over the outer body portions of the opening cams and be crimped in place. The crimp ring serves to trap the outer body portions against the outer surface of the end effector closure sleeve. To provide the end effector closure sleeve with a relatively smooth or uninterrupted outer surface which may advantageously avoid damage to adjacent tissue and/or collection of tissue/fluid etc. between those components, the crimp ring may actually be crimped into an annular recess that is formed in the end effector closure sleeve.

When the opening cams 350 are installed in the end effector closure sleeve 272, each cam tab 358 extends through an elongate slot 326 in the corresponding lateral wall 322 of the elongate channel 302 to be received in a corresponding cam slot 318 in the anvil 310. See FIG. 6. In such arrangement, the opening cams 350 are diametrically opposite of each other in the end effector closure sleeve. In use, the closure tube 260 is translated distally (direction "DD") to close the anvil 310, for example, in response to the actuation of the closure trigger 32. The anvil 310 is closed as the closure tube 260 is translated in the distal direction "DD" so as to bring the distal end 275 of the of end effector closure sleeve 272 into contact with a closure lip 311 on the anvil body 312. In particular, the distal end 275 of the end effector closure sleeve 272 rides on the upper surfaces 321 of the anvil attachment arms 316 as the closure tube 260 is moved distally to begin to pivot the anvil 310 to a closed position. In one arrangement for example, closure of the anvil 310 is solely caused by contact of the end effector closure sleeve 272 with the anvil 310 and is not caused by the interaction of the opening cams with the anvil. In other arrangements, however, the opening cams could be arranged to also apply closing motions to the anvil as the closure tube 260 is moved distally. The anvil 310 is opened by proximally translating the closure tube 260 in the proximal direction "PD" which causes the cam tabs 358 to move in the proximal direction "PD" within the cam slots 318 on the cam surfaces 319 to pivot the anvil 310 into the open position as shown in FIGS. 6 and 7.

The surgical end effector embodiment 300 employs two opening cams to effect positive opening of the end effector jaws, even when under a load. Other arrangements could conceivably employ only one opening cam or more than two opening cams without departing from the spirit and scope of the present invention. In the illustrated example, the opening cams are removably affixed to the end effector closure sleeve which facilitates easy assembly or attachment of the surgical end effector components to the elongate shaft assembly as well as disassembly thereof. Such configurations also enable the use of more compact or shorter articulation joint arrangements which further facilitate better manipulation of the surgical end effector within the confined spaces inside of a patient. To facilitate easy detachment of those opening cams that are snapped in place, additional strategically placed holes may be provided in the end effector closure sleeve to enable a pry member to be inserted therethrough to pry the opening cams out of the end effector closure sleeve. In still other arrangements, the opening cam(s) may be integrally formed in the anvil actuator member or end effector closure sleeve. For example, the opening cam(s) may each comprise a tab that is cut into or otherwise formed into the wall of the anvil actuator member or end effector closure sleeve and then bent, crimped or permanently deformed inward so as to engage the corresponding cam surface on the second jaw. For example, the tab may be bent inward at ninety degrees relative to the outer wall of the end effector closure sleeve. Such arrangements avoid the need for separate opening cam components. Other variations may employ a pin or pins that are attached to the second jaw and configured to ride on corresponding cam surfaces on the first jaw. The pin or pins may be pressed into the first jaw, knurled and then pressed in and/or welded to the first jaw, for example. While the opening cam arrangements discussed above have been described in the context of a surgical end effector that is configured to support a surgical staple cartridge and includes an anvil that is configured to move relative to the surgical staple cartridge, the reader will appreciate that the opening cam arrangements may also be employed with other end effector arrangements that have jaw(s) that are movable relative to each other.

Figure 9:
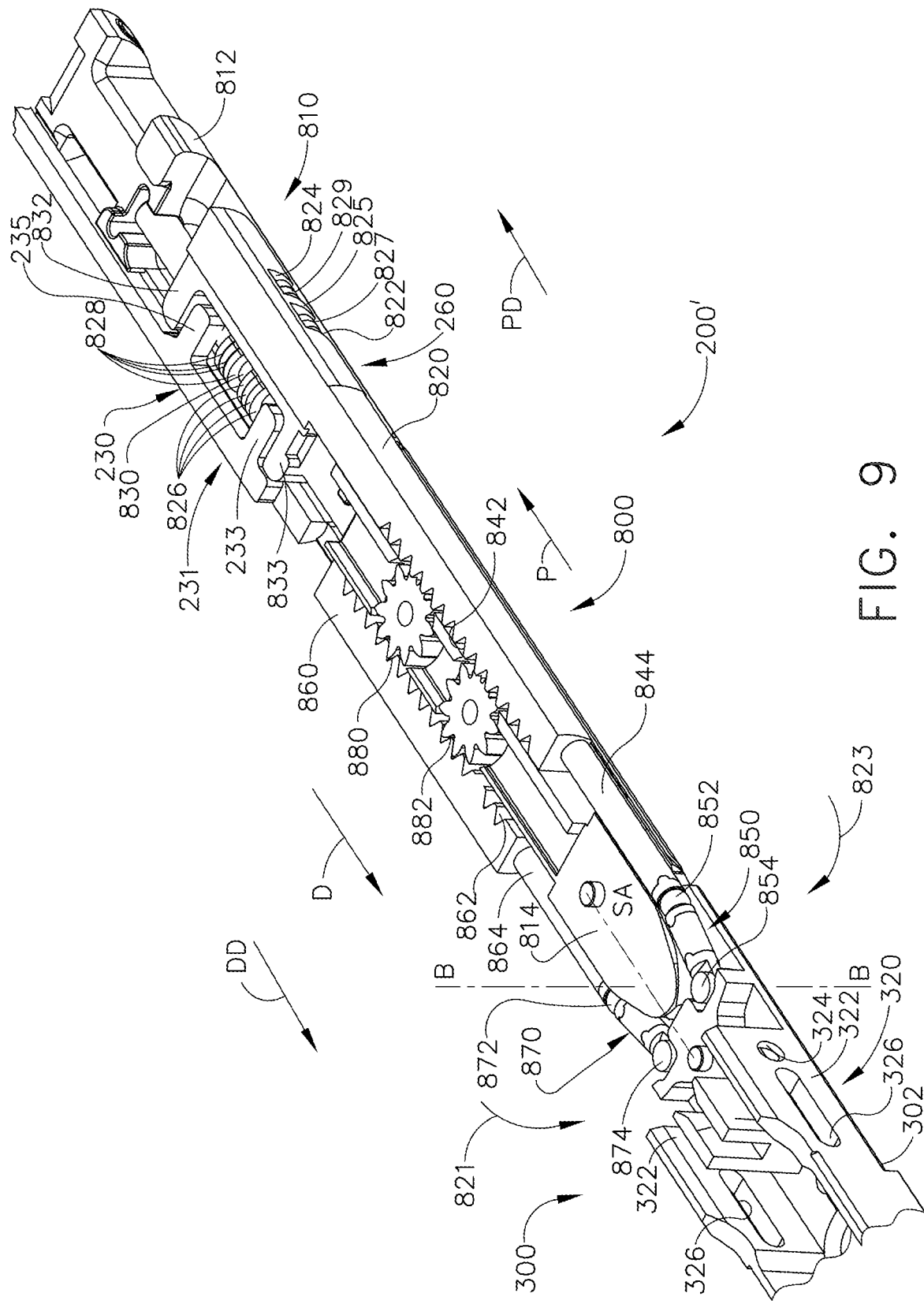
FIG. 9 is a perspective view of a surgical end effector and elongate shaft assembly embodiment with portions thereof omitted for clarity.
Figure 10:
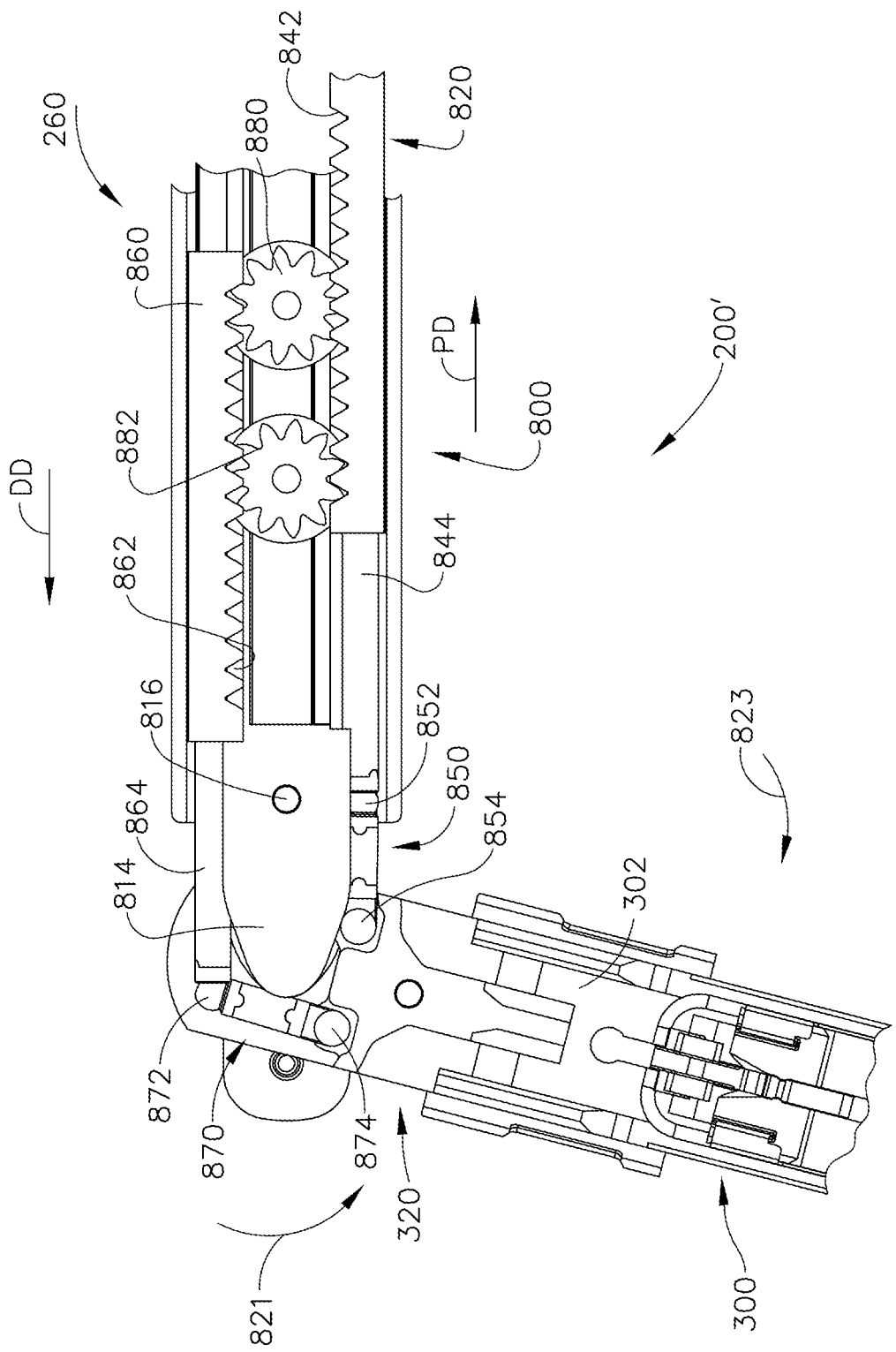
FIG. 10 is a top view of portions of the surgical end effector and elongate shaft assembly embodiment of FIG. 9 with the surgical end effector in an articulated position or configuration.

FIGS. 9 and 10 illustrate an elongate shaft assembly designated as 200' that employs many of the features of elongate shaft assembly 200 described above. In the illustrated example, the elongate shaft assembly 200' includes a dual articulation link arrangement designated as 800 that employs an articulation lock 810 that is similar to articulation lock 350 described above. Those components of articulation lock 810 that differ from the components of articulation lock 350 and which may be necessary to understand the operation of articulation lock 350 will be discussed in further detail below. Further details regarding articulation lock 350 may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. The articulation lock 810 can be configured and operated to selectively lock the surgical end effector 300 in various articulated positions. Such arrangement enables the surgical end effector 300 to be rotated, or articulated, relative to the shaft closure tube 260 when the articulation lock 810 is in its unlocked state.

As was discussed above, when the proximal articulation driver 230 is operatively engaged with the firing member 220 via the clutch system 400, the firing member 220 can move the proximal articulation driver 230 proximally and/or distally. For instance, proximal movement of the firing member 220 can move the proximal articulation driver 230 proximally and, similarly, distal movement of the firing member 220 can move the proximal articulation driver 230 distally. Movement of the proximal articulation driver 230, whether it be proximal or distal, can unlock the articulation lock 810, as described in greater detail further below. As can be seen in FIG. 9 for example, the elongate shaft assembly 200' includes a shaft frame 812 which is somewhat co-extensive with a first distal articulation driver 820. A first distal articulation driver 820 is supported within the elongate shaft assembly 200' for selective longitudinal travel in a distal direction "DD" and a proximal direction "PD" in response to corresponding articulation control motions applied thereto. The shaft frame 812 includes a distal end portion 814 that has a downwardly protruding pivot pin (not shown) thereon that is adapted to be pivotally received within a pivot hole 328 formed in the proximal end portion 320 of the elongate channel 302. See, for example, the similar arrangement depicted in FIG. 5. Such arrangement facilitates pivotal travel of the elongate channel 302 of the surgical end effector 300 relative to the shaft frame 812 about an articulation axis B-B that is defined by the pivot hole 328. As indicated above, the articulation axis B-B is transverse to the shaft axis SA-SA that is defined by elongate shaft assembly 200'.

Referring again to FIG. 9, the first distal articulation driver 820 includes a first, or distal, lock cavity 822 and a second, or proximal, lock cavity 824, wherein the first lock cavity 822 and the second lock cavity 824 can be separated by an intermediate frame member 825. The articulation lock 810 can further include at least one first lock element 826 at least partially positioned within the first lock cavity 822 which can be configured to inhibit or prevent the proximal movement of the first distal articulation driver 820. In the embodiment illustrated in FIG. 9, for example, there are three first lock elements 826 positioned within the first lock cavity 822 which can all act in a similar, parallel manner and can co-operatively act as a single lock element. Other embodiments are envisioned which can utilize more than three or less than three first lock elements 826. Similarly, the articulation lock 810 can further include at least one second lock element 828 at least partially positioned within the second lock cavity 824 which can be configured to inhibit or prevent the distal movement of the first distal articulation driver 820. With regard to the particular embodiment illustrated in FIG. 9, there are three second lock elements 828 positioned within the second lock cavity 824 which can all act in a similar, parallel manner and can co-operatively act as a single lock element. Other embodiments are envisioned which can utilize more than three or less than three second lock elements 828.

Further to the above, referring primarily to FIG. 9, each first lock element 826 is slidably supported on a frame rail 830 and includes a lock tang 827. Each of the first lock elements 826 have a lock aperture therein (not shown) for receiving the frame rail 830 therethrough. The lock tang 827 can be disposed within the first lock cavity 822 and the lock aperture can be slidably engaged with a frame rail 830 mounted to the shaft frame 812. The first lock elements 826 are not oriented in a perpendicular arrangement with the frame rail 830; rather, the first lock elements 826 are arranged and aligned at a non-perpendicular angle with respect to the frame rail 830 such that the edges or sidewalls of the lock apertures are engaged with the frame rail 830. Moreover, the interaction between the sidewalls of the lock apertures and the frame rail 830 can create a resistive or friction force therebetween which can inhibit relative movement between the first lock elements 826 and the frame rail 830 and, as a result, resist a proximal pushing force P applied to the first distal articulation driver 820. Stated another way, the first lock elements 826 can prevent or at least inhibit the surgical end effector 300 from rotating in a direction indicated by arrow 821. If a torque is applied to the end effector 300 in the direction of arrow 821, a proximal pushing force P will be transmitted to the distal articulation driver 820. The proximal pushing force P will only serve to bolster the locking engagement between the first lock elements 826 and the frame rail 830. More particularly, the proximal pushing force P can be transmitted to the tangs 827 of the first lock elements 826 which can cause the first lock elements 826 to rotate and decrease the angle defined between first lock elements 826 and the frame rail 830 and, as a result, increase the bite between the sidewalls of the lock apertures and the frame rail 830. Ultimately, then, the first lock elements 826 can lock the movement of the first distal articulation driver 820 in one direction.

To release the first lock elements 826 and permit the surgical end effector 300 to be rotated in the direction indicated by arrow 821, the proximal articulation driver 230 can be pulled proximally to straighten, or at least substantially straighten, the first lock elements 826 into a perpendicular, or at least substantially perpendicular, position. In such a position, the bite, or resistive force, between the sidewalls of the lock apertures and the frame rail 830 can be sufficiently reduced, or eliminated, such that the first distal articulation driver 820 can be moved proximally. To straighten the first lock elements 826, the proximal articulation driver 230 can be pulled proximally such that a distal arm 233 of the proximal articulation driver 230 contacts the first lock elements 826 to pull and rotate the first lock elements 826 into their straightened position. In various circumstances, the proximal articulation driver 230 can continue to be pulled proximally until a proximal arm 235 extending therefrom contacts, or abuts, a proximal drive wall 832 of the first distal articulation driver 820 and pulls the distal articulation driver 820 proximally to articulate the surgical end effector 300. In essence, a proximal pulling force can be applied from the proximal articulation driver 230 to the distal articulation driver 820 through the interaction between the proximal arm 235 and the proximal drive wall 832 wherein such a pulling force can be transmitted through the first distal drive member 820 to the end effector 300 as will be further discussed below to articulate the end effector 300 in the direction indicated by arrow 821. After the surgical end effector 300 has been suitably articulated in the direction of arrow 821, the first distal articulation driver 820 can be released, in various circumstances, to permit the articulation lock 810 to re-lock the first distal articulation driver 820, and the surgical end effector 300, in position.

Concurrent to the above, referring again to FIG. 9, the second lock elements 828 can remain in an angled position while the first lock elements 826 are locked and unlocked as described above. The reader will appreciate that, although the second lock elements 828 are arranged and aligned in an angled position with respect to the shaft rail 830, the second lock elements 828 are not configured to impede, or at least substantially impede, the proximal motion of the first distal articulation driver 820. When the first distal articulation driver 820 and articulation lock 810 are slid proximally, as described above, the second lock elements 828 can slide distally along the frame rail 830 without, in various circumstances, changing, or at least substantially changing, their angled alignment with respect to the frame rail 830. While the second lock elements 828 are permissive of the proximal movement of the first distal articulation driver 820 and the articulation lock 810, the second lock elements 828 can be configured to selectively prevent, or at least inhibit, the distal movement of the first distal articulation driver 820, as discussed in greater detail further below.

Each second lock element 828 can comprise a lock aperture (not shown) and a lock tang 829. The lock tang 829 can be disposed within the second lock cavity 824 and the lock aperture can be slidably engaged with the frame rail 830 mounted to the shaft frame 812. The frame rail 830 extends through the apertures in the second lock elements 828. The second lock elements 828 are not oriented in a perpendicular arrangement with the frame rail 830; rather, the second lock elements 828 are arranged and aligned at a non-perpendicular angle with respect to the frame rail 830 such that the edges or sidewalls of the lock apertures are engaged with the frame rail 830. Moreover, the interaction between the sidewalls of the lock apertures and the frame rail 830 can create a resistive or friction force therebetween which can inhibit relative movement between the second lock elements 828 and the frame rail 830 and, as a result, resist a distal force D applied to the first distal articulation driver 820. Stated another way, the second lock elements 828 can prevent or at least inhibit the surgical end effector 300 from rotating in a direction indicated by arrow 823. If a torque is applied to the end effector 300 in the direction of arrow 823, a distal pulling force D will be transmitted to the first distal articulation driver 820. The distal pulling force D will only serve to bolster the locking engagement between the second lock elements 828 and the frame rail 830. More particularly, the distal pulling force D can be transmitted to the tangs 829 of the second lock elements 828 which can cause the second lock elements 828 to rotate and decrease the angle defined between second lock elements 828 and the frame rail 830 and, as a result, increase the bite between the sidewalls of the lock apertures and the frame rail 830. Ultimately, then, the second lock elements 828 can lock the movement of the first distal articulation driver 820 in one direction.

To release the second lock elements 828 and permit the surgical end effector 300 to be articulated in the direction indicated by arrow 823, the proximal articulation driver 230 can be pushed distally to straighten, or at least substantially straighten, the second lock elements 828 into a perpendicular, or at least substantially perpendicular, position. In such a position, the bite, or resistive force, between the sidewalls of the lock apertures and the frame rail 830 can be sufficiently reduced, or eliminated, such that the first distal articulation driver 820 can be moved distally. To straighten the second lock elements 828, the proximal articulation driver 230 can be pushed distally such that the proximal arm 235 of the proximal articulation driver 230 contacts the second lock elements 828 to push and rotate the second lock elements 828 into their straightened position. In various circumstances, the proximal articulation driver 230 can continue to be pushed distally until the distal arm 233 extending therefrom contacts, or abuts, a distal drive wall 833 of the first distal articulation driver 820 and pushes the first distal articulation driver 820 distally to articulate the surgical end effector 300. In essence, a distal pushing force can be applied from the proximal articulation driver 230 to the first distal articulation driver 820 through the interaction between the distal arm 233 and the distal drive wall 833 wherein such a pushing force can be transmitted through the first distal articulation driver 820 to articulate the end effector 300 in the direction indicated by arrow 823. After the surgical end effector 300 has been suitably articulated in the direction of arrow 823, the first distal articulation driver 820 can be released, in various circumstances, to permit the articulation lock 810 to re-lock the first distal articulation driver 820, and the surgical end effector 300, in position.

Concurrent to the above, the first lock elements 826 can remain in an angled position while the second lock elements 828 are locked and unlocked as described above. The reader will appreciate that, although the first lock elements 826 are arranged and aligned in an angled position with respect to the shaft rail 830, the first lock elements 826 are not configured to impede, or at least substantially impede, the distal motion of the first distal articulation driver 820. When the first distal articulation driver 820 and articulation lock 810 are slid distally, as described above, the first lock elements 826 can slide distally along the frame rail 830 without, in various circumstances, changing, or at least substantially changing, their angled alignment with respect to the frame rail 830. While the first lock elements 826 are permissive of the distal movement of the first distal articulation driver 820 and the articulation lock 810, the first lock elements 826 are configured to selectively prevent, or at least inhibit, the proximal movement of the first distal articulation driver 820, as discussed above.

In view of the above, the articulation lock 810, in a locked condition, can be configured to resist the proximal and distal movements of the first distal articulation driver 820. In terms of resistance, the articulation lock 810 can be configured to prevent, or at least substantially prevent, the proximal and distal movements of the first distal articulation driver 820. Collectively, the proximal motion of the first distal articulation driver 820 is resisted by the first lock elements 826 when the first lock elements 826 are in their locked orientation and the distal motion of the first distal articulation driver 820 is resisted by the second lock elements 828 when the second lock elements 828 are in their locked orientation, as described above. Stated another way, the first lock elements 826 comprise a first one-way lock and the second lock elements 828 comprise a second one-way lock which locks in an opposite direction.

Discussed in connection with the exemplary embodiment illustrated in FIGS. 9 and 10, an initial proximal movement of the proximal articulation driver 230 can unlock the proximal movement of the first distal articulation driver 820 and the articulation lock 810 while a further proximal movement of the proximal articulation driver 230 can drive the first distal articulation driver 820 and the articulation lock 810 proximally. Similarly, an initial distal movement of the proximal articulation driver 230 can unlock the distal movement of the first distal articulation driver 820 and the articulation lock 810 while a further distal movement of the proximal articulation driver 230 can drive the first distal articulation driver 820 and the articulation lock 810 distally. Such a general concept is discussed in connection with several additional exemplary embodiments disclosed below. To the extent that such discussion is duplicative, or generally cumulative, with the discussion provided above, such discussion is not reproduced for the sake of brevity.

Still referring to FIGS. 9 and 10, the dual articulation link arrangement 800 is configured to establish a "push/pull" arrangement when an articulation force is applied thereto through the first distal articulation driver 820. As can be seen in those Figures, the first distal articulation driver 820 has a first drive rack 842 formed therein. A first articulation rod 844 protrudes distally out of the first distal articulation driver 820 and is attached to a first movable coupler 850 that is attached to the first distal articulation driver 820 by a first ball joint 852. The first coupler 850 is also pivotally pinned to the proximal end portion 320 of the elongate channel 302 by a first pin 854 as can be seen in FIG. 9. The dual articulation link arrangement 800 further comprises a second distal articulation driver 860 that has a second drive rack 862 formed therein. The second distal articulation driver 860 is movably supported within the elongate shaft assembly 200' for longitudinal travel in the distal direction "DD" and the proximal direction "PD". A second articulation rod 864 protrudes distally out of the second distal articulation driver 860 and is attached to a second movable coupler 870 that is attached to the second distal articulation driver 860 by a second ball joint 872. The second coupler 870 is also pivotally pinned to the proximal end portion 320 of the elongate channel 302 by a second pin 874 as can be seen in FIG. 9. As can be seen in FIG. 9, the first coupler 850 is attached to the elongate channel 302 on one lateral side of the shaft axis SA and the second coupler 870 is attached to the elongate channel 302 on an opposite lateral side of the shaft axis. Thus, by simultaneously pulling on one of the couplers 850, 870 and pushing on the other coupler 850, 870, the surgical end effector 300 will be articulated about the articulation axis B-B relative to the elongate shaft assembly 200'. In the illustrated arrangements, although the couplers 850, 870 that facilitate relative movement between the first and second distal articulation drivers 820, 860, respectively and the elongate channel 302 are fabricated from relatively rigid components, other arrangements may employ relatively "flexible" coupler arrangements. For example cable(s), etc. may extend through one or both of the distal articulation drivers 820, 860, couplers 850, 870 and the ball joints 852, 872, to be coupled to the elongate channel to facilitate the transfer of articulation motions thereto.

As can also be seen in FIGS. 9 and 10, a proximal pinion gear 880 and a distal pinion gear 882 are centrally disposed between the first drive rack 842 and the second drive rack 862 and are in meshing engagement therewith. In alternative embodiments, only one pinion gear or more than two pinion gears may be employed. Thus, at least one pinion gear is employed. The proximal pinion gear 880 and the distal pinion gear 882 are rotatably supported in the shaft frame 812 for free rotation relative thereto such that as the first distal articulation driver 820 is moved in the distal direction "DD", the pinion gears 870, 872 serve to drive the second distal articulation driver 860 in the proximal direction "PD". Likewise, when the first distal articulation driver 820 is pulled in the proximal direction "PD", the pinion gears 880, 882 drive the second distal articulation driver 860 in the distal direction "DD". Thus, to articulate the end effector 300 about the articulation axis B-B in the direction of arrow 821, the articulation driver 230 is operatively engaged with the firing member 220 via the clutch system 400 such that the firing member 220 moves or pulls the proximal articulation driver 230 in the proximal direction "PD". Movement of the proximal articulation driver 230 in the proximal direction moves the first distal articulation driver 820 in the proximal direction as well. As the first distal articulation driver 820 moves the in the proximal direction, the pinion gears 880, 882 serve to drive the second distal articulation driver 860 in the distal direction "DD". Such movement of the first and second distal articulation drivers 820, 860 causes the surgical end effector 300 and more specifically, the elongate channel 302 of the surgical end effector 300 to pivot about the articulation axis B-B in the articulation direction of arrow 821. Conversely, to articulate the end effector 300 in the direction of arrow 823, the firing member 220 is actuated to push the first distal articulation driver 820 in the distal direction "DD". As the first distal articulation driver 820 moves the in the distal direction, the pinion gears 880, 882 serve to drive the second distal articulation driver 860 in the proximal direction "PD". Such movement of the first and second distal articulation drivers 820, 860 causes the surgical end effector 300 and more specifically, the elongate channel 302 of the surgical end effector 300 to pivot about the articulation axis B-B in the articulation direction of arrow 823.

The dual solid link articulation arrangement 800 and its variations may afford the surgical end effector with a greater range of articulation when compared to other articulatable surgical end effector configurations. In particular, the solid link articulation arrangements disclosed herein may facilitate ranges of articulation that exceed ranges of 45-50 degrees that are commonly achieved by other articulatable end effector arrangements. Use of at least one pinion gear to interface between the distal articulation drivers enable the end effector to be "pushed" and "pulled" into position also may reduce the amount of end effector "slop" or undesirable or unintended movement during use. The dual solid link articulation arrangements disclosed herein also comprise an articulation system that has improved strength characteristics when compared to other articulation system arrangements.

Figure 11:
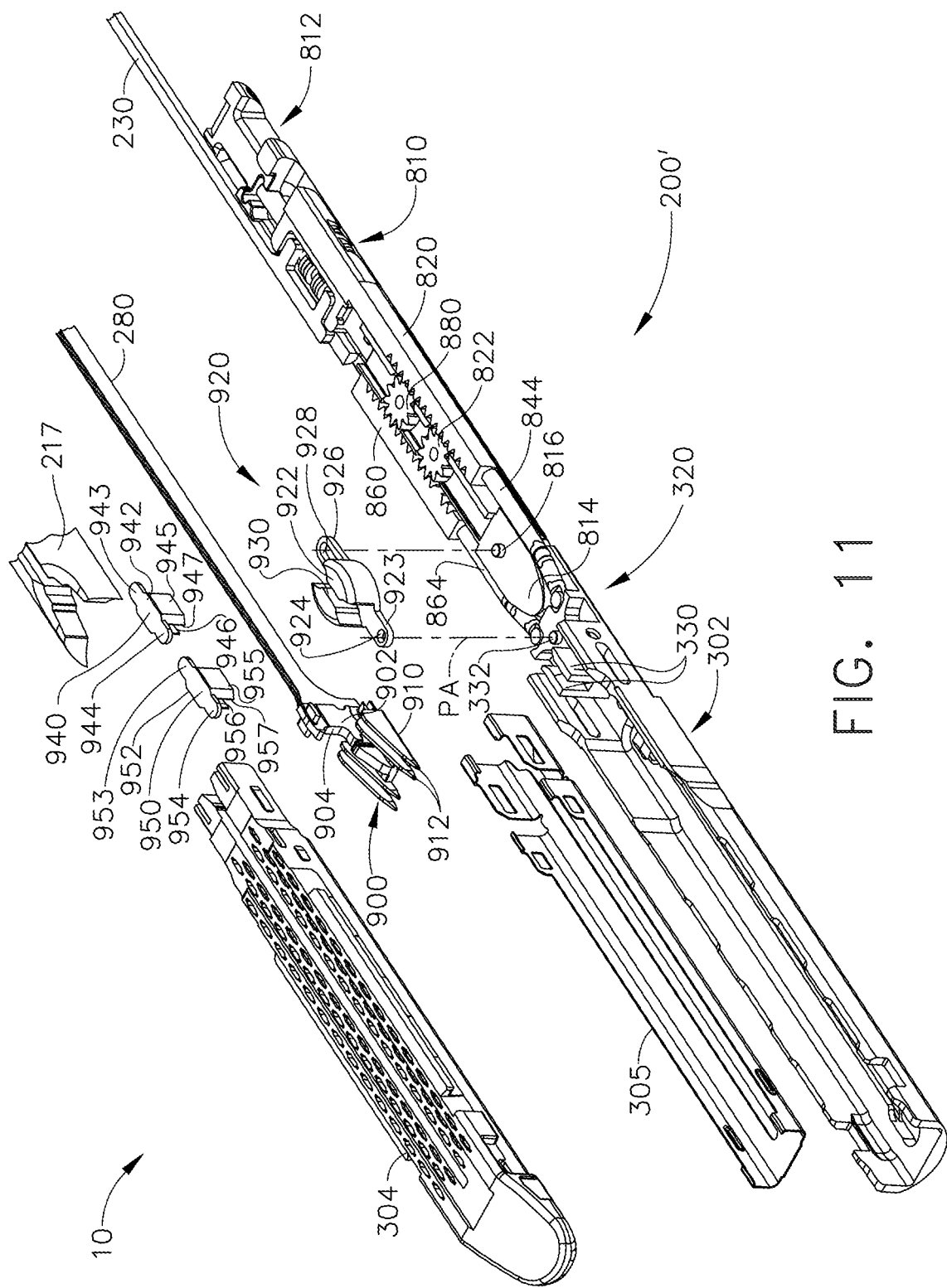
FIG. 11 is a partial exploded assembly view of portions of the surgical end effector and elongate shaft assembly embodiment of FIGS. 9 and 10.

As was briefly discussed above, the intermediate firing shaft portion 222 is configured to operably interface with a distal cutting or firing beam 280. The distal firing beam 280 may comprise a laminated structure. Such arrangement enables the distal firing beam 280 to sufficiently flex when the surgical end effector 300 is articulated about the articulation axis B-B. The distal firing beam 280 is supported for axial movement within the shaft assembly 200' and is slidably supported by two upstanding lateral support walls 330 formed on the proximal end of the elongate channel 302. Referring to FIG. 11, the distal firing beam 280 is attached to a firing member 900 that includes a vertically-extending firing member body 902 that has a tissue cutting surface or blade 904 thereon. In addition, a wedge sled 910 may be mounted within the surgical staple cartridge 304 for driving contact with the firing member 900. As the firing member 900 is driven distally through the cartridge body 304, the wedge surfaces 912 on the wedge sled 910 contact the staple drivers to actuate the drivers and the surgical staples supported thereon upwardly in the surgical staple cartridge 304.

End effectors that employ firing beams or firing members and which are capable of articulating over a range of, for example, forty five degrees may have numerous challenges to overcome. To facilitate operable articulation of such end effectors, the firing member or firing beam must be sufficiently flexible to accommodate such range of articulation. However, the firing beam or firing member must also avoid buckling while encountering the compressive firing loads. To provide additional support to the firing beam or firing member various "support" or "blowout" plate arrangements have been developed. Several of such arrangements are disclosed in U.S. Pat. No. 6,964,363, entitled SURGICAL STAPLING INSTRUMENT HAVING ARTICULATION JOINT SUPPORT PLATES FOR SUPPORTING A FIRING BAR and U.S. Pat. No. 7,213,736, entitled SURGICAL STAPLING INSTRUMENT INCORPORATING AN ELECTROACTIVE POLYMER ACTUATED FIRING BAR TRACK THROUGH AN ARTICULATION JOINT, the entire disclosures of each being hereby incorporated by reference herein. Blowout plates that provide substantial buckle resistance also are difficult to bend in general which adds to the forces the articulation joint system must accommodate. Other firing beam support arrangements are disclosed in U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309, the entire disclosure of which is hereby incorporated by reference herein.

Figure 12:
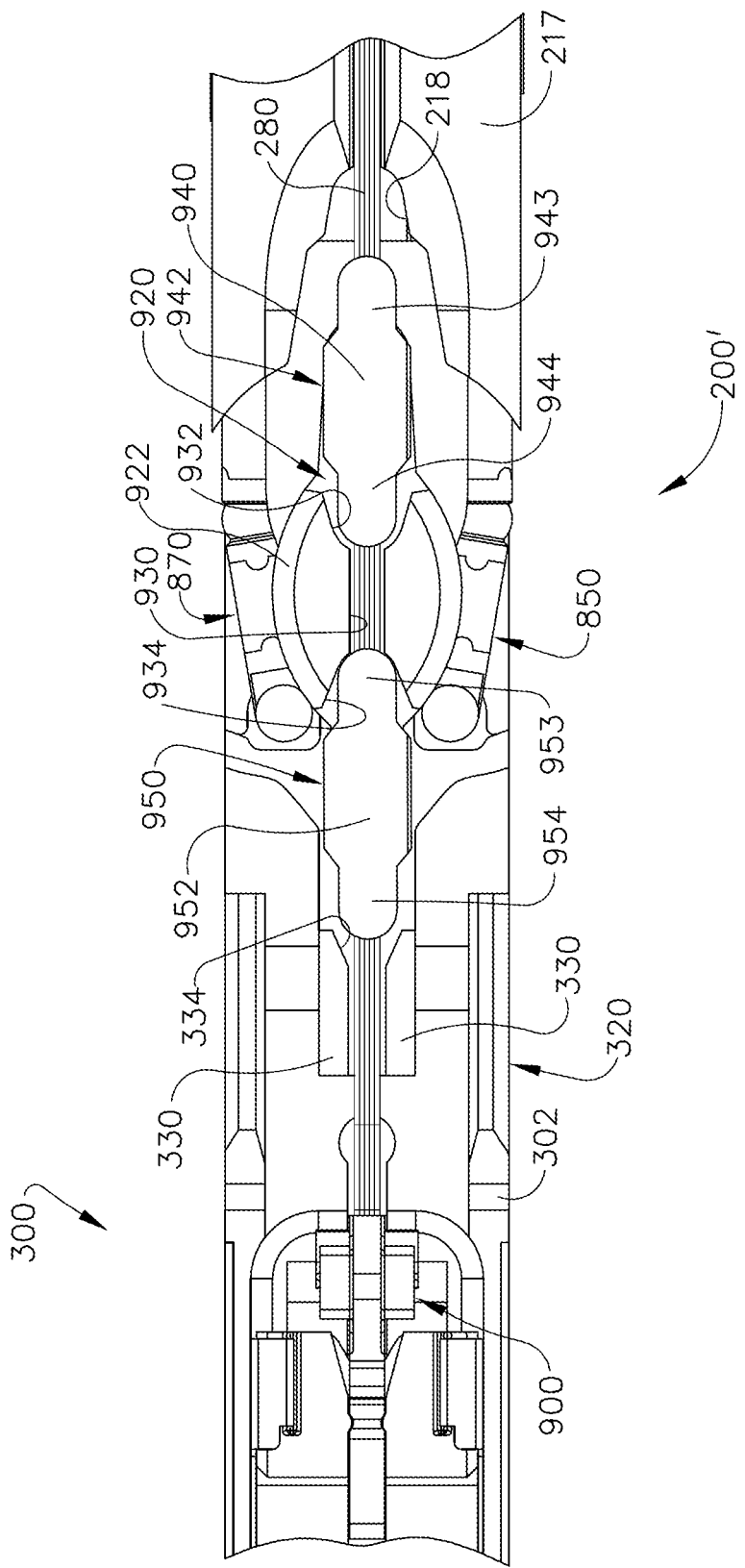
FIG. 12 is a top view of portions of the surgical end effector and elongate shaft assembly of FIGS. 9-11.
Figure 13:
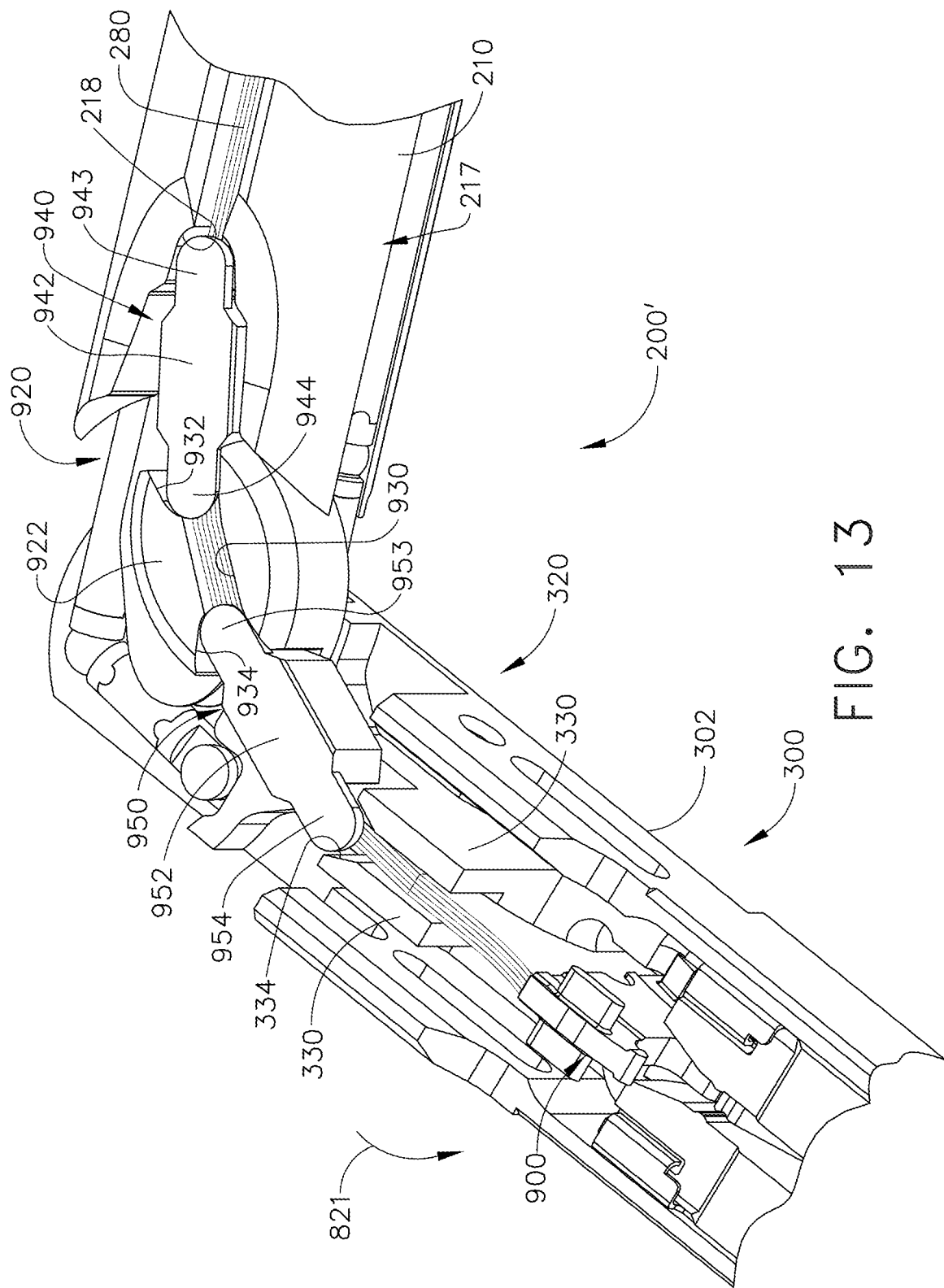
FIG. 13 is a perspective view of portions of the surgical end effector and elongate shaft assembly embodiment of FIGS. 9-12 with the surgical end effector in an articulated position or configuration.

Referring to FIGS. 11-15, the elongate shaft assembly 200' further comprises a multiple support link assembly 920 for providing lateral support to the distal firing beam 280 as the surgical end effector 300 is articulated about the articulation axis B-B. As can be seen in FIG. 11, the multiple support link assembly 920 comprises a middle support member 922 that is movably coupled to the surgical end effector 300 as well as the elongate shaft assembly 200'. For example, the middle support member 922 is pivotally pinned to the proximal end 320 of the elongate channel 302 such that it is pivotable relative thereto about a pivot axis PA. As can be seen in FIG. 11, the middle support member 922 includes a distally protruding tab 923 that has a distal pivot hole 924 therein for receiving an upstanding support pin 332 that is formed on the proximal end portion 320 of the elongate channel 302. As can be further seen in FIG. 11, the middle support member 922 further includes a proximally protruding tab 926 that has an elongate proximal slot 928 therein. The proximal slot 928 is configured to slidably receive a middle support pin 816 that is formed on the frame portion 812. Such arrangement enables the middle support member 922 to pivot and move axially relative to said elongate shaft assembly 200', for example. As can be seen in FIGS. 11-13, the middle support member 922 further includes centrally disposed slot 930 for movably receiving the distal firing beam 280 therethrough.

Figure 14:
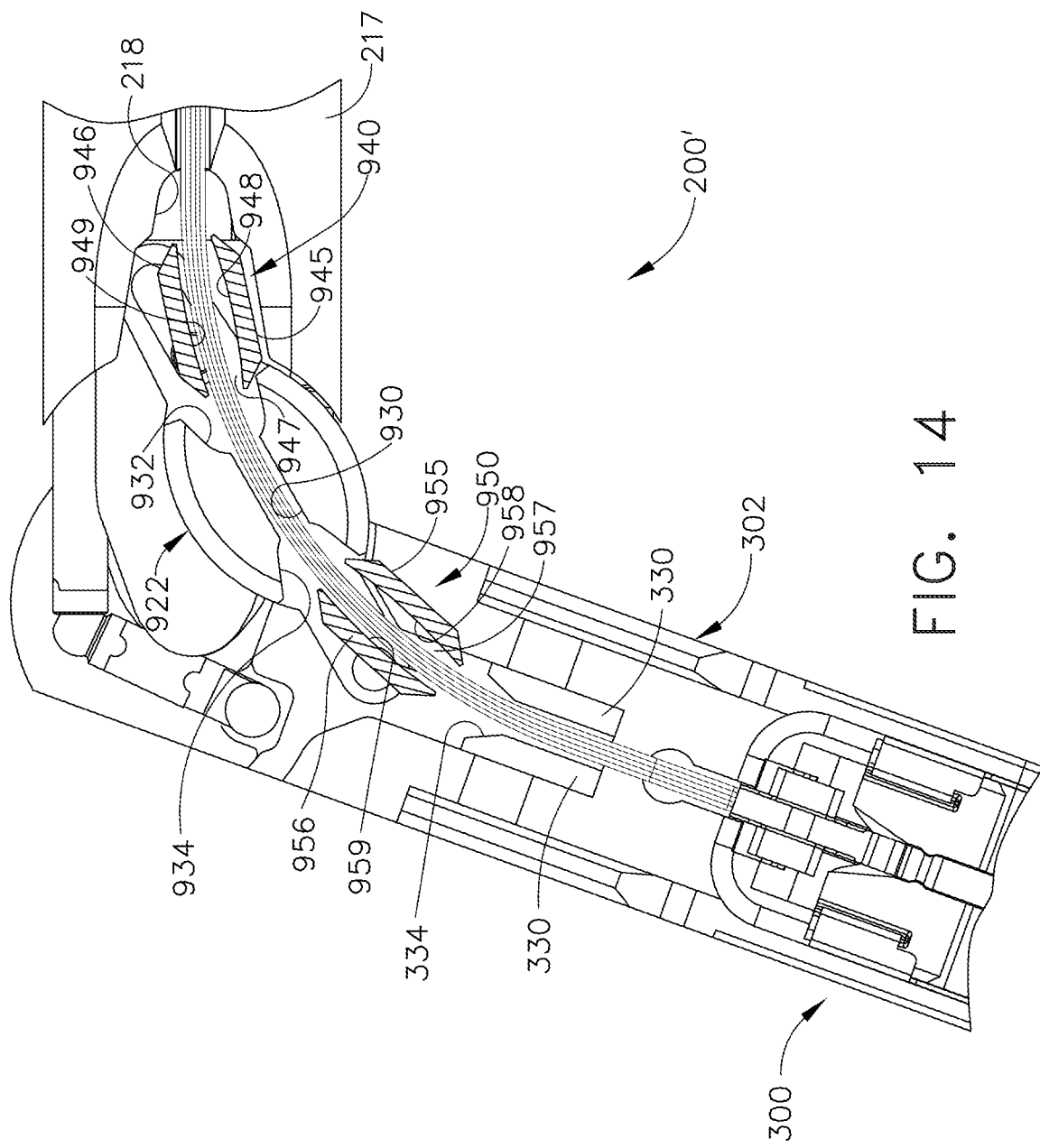
FIG. 14 is a top view of portions of the surgical end effector and elongate shaft assembly embodiment of FIGS. 9-13 with the surgical end effector in an articulated configuration and with some of the components thereof shown in cross-section for clarity.
Figure 15:
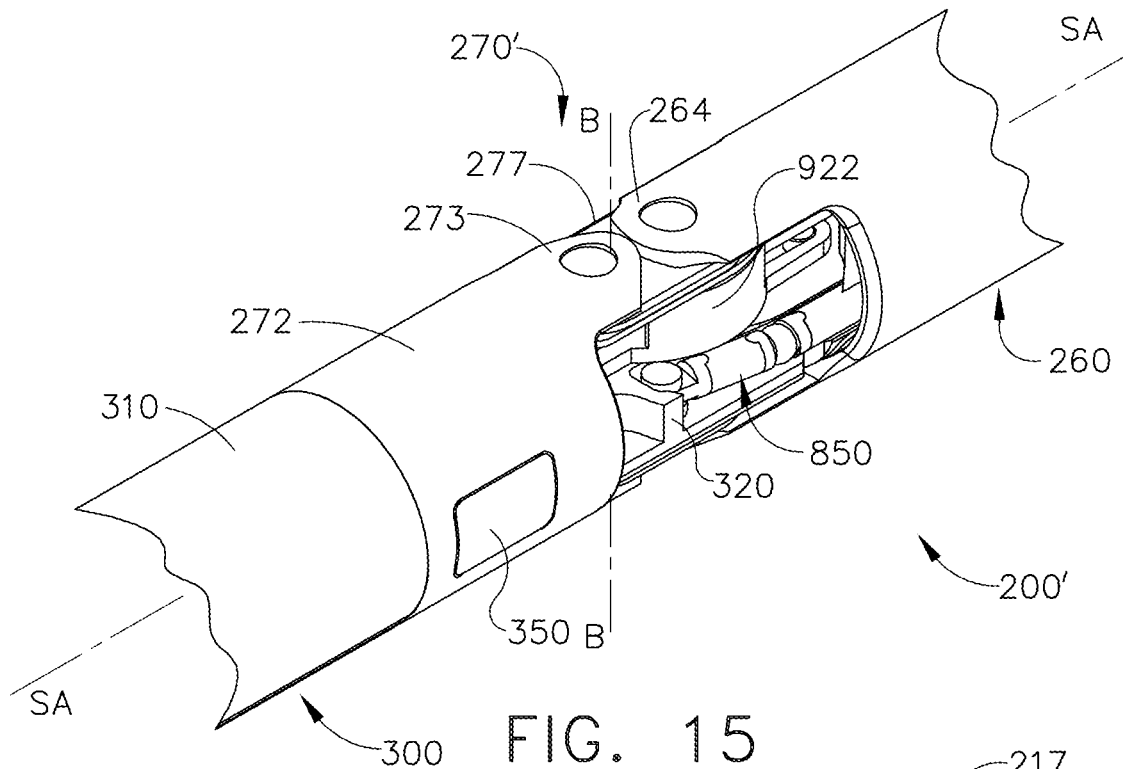
FIG. 15 is a perspective view of a portion of another elongate shaft assembly embodiment.

Still referring to FIGS. 11-15, the multiple support link assembly 920 further comprises a proximal support link 940 and a distal support link 950. The proximal support link 940 includes an elongate proximal body 942 that has a rounded proximal nose portion 943 and a rounded distal nose portion 944. The proximal support link 940 further includes a pair of downwardly protruding, opposed proximal support walls 945, 946 that define a proximal slot 947 therebetween. Similarly, the distal support link 950 includes an elongate distal body 952 that has a rounded proximal nose portion 953 and a rounded distal nose portion 954. The distal support link 950 further includes a pair of downwardly protruding opposed distal support walls 955, 956 that define a distal slot 957 therebetween. As can be seen in FIG. 14, the flexible distal firing beam 280 is configured to extend between the proximal support walls 945, 946 of the proximal support link 940 and the distal support walls 955, 956 of the distal support link 950. The proximal support wall 945 includes an inwardly facing proximal arcuate surface 948 and the proximal support wall 946 includes an inwardly facing proximal arcuate support surface 949 that opposes said inwardly facing proximal arcuate surface 948. The proximal arcuate support surfaces 948, 949 serve to provide lateral support to the lateral side portions of a proximal portion of the flexible distal firing beam 280 as it flexes during articulation of the end effector and traverses the articulation joint. The radiused surfaces may match the outer radius of the distal firing beam 280 depending upon the direction of articulation. Similarly, the distal support wall 955 includes an inwardly facing distal arcuate surface 958 and the distal support wall 956 includes an inwardly facing distal arcuate support surface 959 that opposes said distal arcuate surface 958. The distal arcuate support surfaces 958, 959 serve to provide lateral support to the lateral side portions of a distal portion of the distal firing beam 280 as it flexes during articulation of the surgical end effector 300 and traverses the articulation joint. The distal arcuate surfaces 958, 959 may match the outer radius of the distal firing beam 280 depending upon the direction of articulation. As can be seen in FIGS. 12 and 13, the distal end 217 of the shaft spine 210 includes a distally-facing arcuate spine pocket 218 into which the rounded proximal nose portion 943 of the proximal support link 940 extends. The rounded distal nose portion 944 of the proximal support link 940 is pivotally received in an arcuate proximal pocket 932 in the middle support member 922. In addition, the rounded proximal nose portion 953 of the distal support link is received in an arcuate distal support member pocket 934 in the distal end of the middle support member 922. The rounded distal nose portion 954 of the distal support link 950 is movably received within a V-shaped channel cavity 334 formed in the upstanding lateral support walls 330 formed on the proximal end 320 of the elongate channel 302.

The multiple support linkage assembly may provide higher lateral support to the flexible firing beam laminates as the beam flexes across higher articulation angles. Such arrangements also prevent the firing beam from buckling under high firing loads and across relatively high articulation angles. The elongate support links, in connection with the middle support member, serve to provide improved lateral support to the firing beam across the articulation zone than many prior support arrangements. In alternative arrangements, the support links may be configured to actually interlock with the middle support member at various articulation angles. The U-shaped support links facilitate easy installation and serve to provide support to the flexible support beams on each lateral side as well as the top of the beam to prevent the firing beam from bowing upwards during firing while being articulated.

In those embodiments wherein the firing member includes a tissue cutting surface, it may be desirable for the elongate shaft assembly to be configured in such a way so as to prevent the inadvertent advancement of the firing member unless an unspent staple cartridge is properly supported in the elongate channel 302 of the surgical end effector 300. If, for example, no staple cartridge is present at all and the firing member is distally advanced through the end effector, the tissue would be severed, but not stapled. Similarly, if a spent staple cartridge (i.e., a staple cartridge wherein at least some of the staples have already been fired therefrom) is present in the end effector and the firing member is advanced, the tissue would be severed, but may not be completely stapled, if at all. It will be appreciated that such occurrences could lead to undesirable catastrophic results during the surgical procedure. U.S. Pat. No. 6,988,649 entitled SURGICAL STAPLING INSTRUMENT HAVING A SPENT CARTRIDGE LOCKOUT, U.S. Pat. No. 7,044,352 entitled SURGICAL STAPLING INSTRUMENT HAVING A SINGLE LOCKOUT MECHANISM FOR PREVENTION OF FIRING, and U.S. Pat. No. 7,380,695 entitled SURGICAL STAPLING INSTRUMENT HAVING A SINGLE LOCKOUT MECHANISM FOR PREVENTION OF FIRING each disclose various firing member lockout arrangements. Each of those U.S. patents is hereby incorporated by reference in its entirety herein.

Such lockout arrangements may be effectively employed with a variety of surgical stapling instruments. Those arrangements, however, may not be particularly well-suited for use in connection with various surgical stapling instruments disclosed herein that employ relatively compact and short articulation joint configurations. For example, FIGS. 15-19 illustrate a surgical end effector 300 that is operably attached to an elongate shaft assembly 200' by an articulation joint 270'. The elongate shaft assembly 200' defines a shaft axis SA-SA and the articulation joint 270' facilitates selective articulation of the surgical end effector 300 relative to the elongate shaft assembly 200' about an articulation axis B-B that is transverse to the shaft axis SA-SA. In the illustrated embodiment, a dual solid link articulation arrangement 800 (as was described above) may be employed to selectively apply articulation motions to the surgical end effector 300. The elongate shaft assembly 200' comprises a distal firing beam 280 of the type described above that is selectively axially movable within the surgical end effector 300 from a starting position to an ending position upon application of firing motions thereto. The distal firing beam 280 extends through the articulation joint 270' and is configured to flex about the articulation axis B-B to accommodate articulation of the surgical end effector 300 in the various manners described herein. In the illustrated embodiment, the articulation joint 270' includes a middle support member 922 that is movably attached to the distal end 814 of the shaft frame 812 and the proximal end 320 of the elongate channel 302. As was discussed above, the middle support member 922 includes a distally protruding tab 923 that has a distal pivot hole 924 therein for receiving an upstanding support pin 332 formed on the proximal end portion 320 of the elongate channel 302. The middle support member 922 further includes a proximally protruding tab 926 that has an elongate proximal slot 928 therein. The proximal slot 928 is configured to slidably receive a middle support pin 816 formed on the frame portion 812. The middle support 922 further includes a centrally disposed slot 930 for axially receiving the distal firing beam 280 therethrough. The middle support member 922 provides lateral support to the distal firing beam 280 during articulation of the surgical end effector 300 about the articulation axis B-B while facilitating its axial passage of the distal firing beam 280 therethrough during firing.

Figure 16:
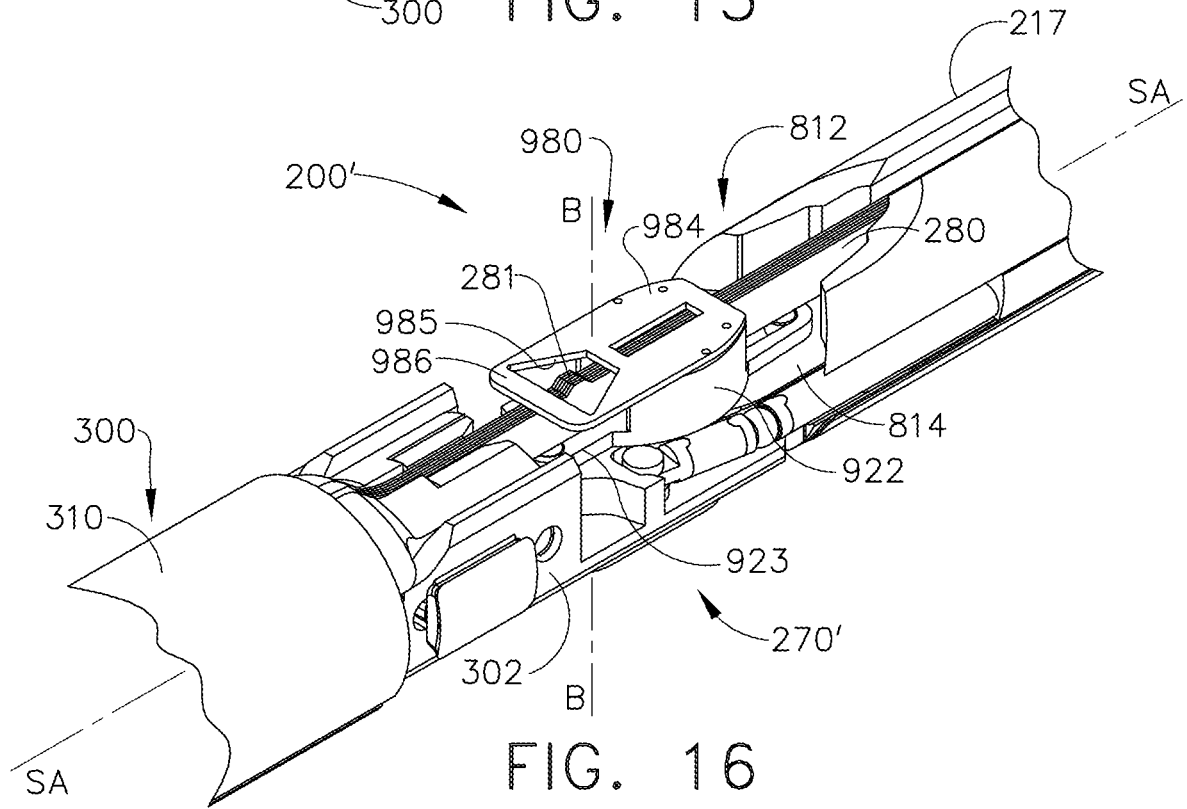
FIG. 16 is another perspective view of the elongate shaft assembly embodiment of FIG. 15 with the closure tube and closure sleeve components omitted for clarity.

In the illustrated embodiment, a firing beam locking assembly 980 is employed to prevent the distal firing beam 280 from being inadvertently advanced from the starting position to the ending position unless an unfired surgical staple cartridge 304 has been operably seated in the cartridge support member or elongate channel 302. As can be seen in FIGS. 15-19, the firing beam locking assembly 980 in one form includes a locking cam or detent 281 that is formed in the distal firing beam 280 such that it protrudes upwardly from the upper surface thereof. A biasing member 984 is supported on and attached to the middle support member 922. As can be seen in FIG. 16, for example, the biasing member 984 is substantially planar and includes a window 985 that is configured to accommodate the locking cam 281 therein during articulation of the surgical end effector 300. Thus, as the surgical end effector 300 is articulated about the articulation axis B-B, the biasing member 984 does not apply any biasing force or load to the distal firing beam 280. This feature may avoid adding to the amount of articulation forces that must be generated to articulate the surgical end effector 300 about the articulation axis B-B. The biasing member 984 may be tack welded to the middle support member 922 or be attached thereto by other fastener methods such as by screws, pins, adhesive, etc. The window 985 may also define a locking band or portion 986 that serves to contact the locking cam 281 when the distal firing beam 280 is in the starting position. The locking cam 281 may be formed with a distal-facing sloping surface 283 and a proximally-facing sloping surface 285 to reduce the amount of firing force and retraction force required to axially move the distal firing beam 280. See FIG. 19.

As was described above, the distal firing beam 280 is operably attached to a firing member 900 that includes a tissue cutting surface 904 on the firing member body 902. In alternative arrangements, the tissue cutting surface may be attached to or otherwise formed on or directly supported by a portion of the distal firing beam 280. In the illustrated arrangement, a laterally extending foot 905 is formed on the bottom of the firing member body 902. The firing member body 902 further includes a wedge sled engagement member 906 that is configured to engage a wedge sled in the surgical staple cartridge 304 as will be discussed in further detail below.

Figure 19:
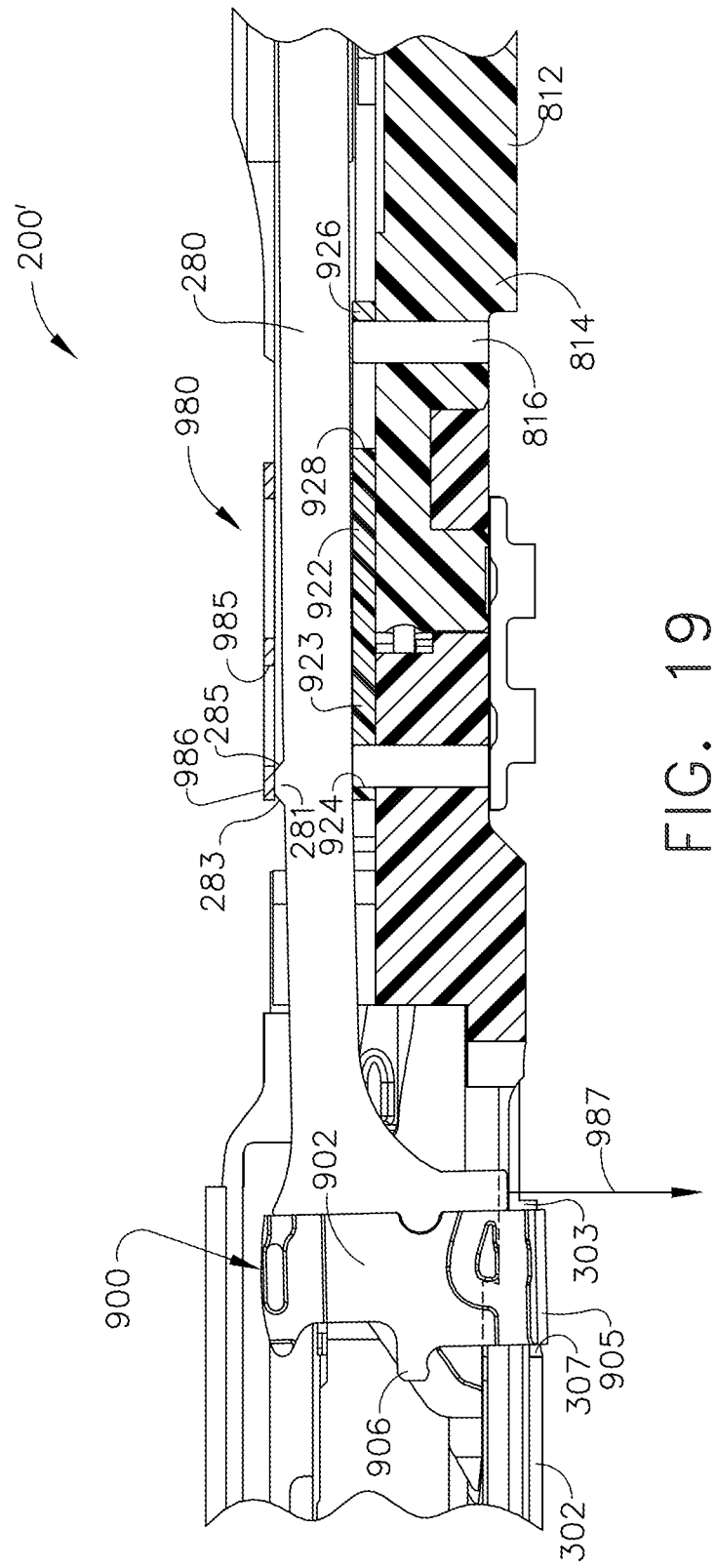
FIG. 19 is another cross-sectional side elevational view of the elongate shaft assembly of FIGS. 15-18 with a surgical staple cartridge mounted in the surgical end effector portion.

FIG. 18 illustrates an "unspent" or "unfired" surgical staple cartridge 304 that has been properly installed in the elongate channel 302. As can be seen in that Figure, the wedge sled 910 is located in an "unfired" (proximal-most) position in the surgical staple cartridge 304. The wedge sled 910 includes a proximally-facing sloping surface 914 that is configured to engage the wedge sled engagement member 906 on the firing member 900 to thereby bias the firing member 900 in an upward direction represented by arrow 988 such that the bottom portion and foot 905 of the firing member 900 are free to clear a lock wall 307 formed by a lock opening 303 in the bottom of the elongate channel 302. When in that position, the distal firing beam 280 and the firing member 900 may be distally advanced within the elongate channel 302 and, more precisely, the surgical staple cartridge 304 mounted therein from the starting position illustrated in FIG. 18 to the ending position with the surgical staple cartridge 304 wherein the wedge sled 910 has ejected all of the surgical staples that were operably supported in the surgical staple cartridge 304. In such arrangements, after the firing member 900 has been completely fired (i.e., completely advanced from its starting position to is ending position within the surgical staple cartridge 304), the firing member 900 is retracted back to the starting position shown in FIG. 19. Because the wedge sled 910 has been distally advanced to the ending position in the staple cartridge 304 by the firing member 900 and the firing member 900 is not attached to the wedge sled 910, when the firing member 900 is retracted back to the starting position, the wedge sled 910 remains in the ending position within the surgical staple cartridge 304 and does not return with the firing member 900 back to the starting position. Thus, the surgical staple cartridge 304 is said to be in a "used", "spent" or "fired" condition. As can be seen in FIG. 19, when no wedge sled is present in an unfired state, the bottom of the body portion 902 as well as the foot 905 of the firing member 900 extends into the lock opening 303 in the bottom of the elongate channel 302 due to the biasing motion applied by the locking band 986 of the biasing member 984 to locking cam 281 on the distal firing beam 280. When in that position, if the clinician were to unwittingly attempt to refire the spent surgical staple cartridge, the body portion 902 and/or the foot 905 would contact the wall 307 in the elongate channel 302 and would be prevented from moving from the starting position to the ending position. Thus, the firing beam locking assembly 980 prevents the advancement of the distal firing beam 280 as well as the firing member 900 from the starting position to the ending position unless an unfired or unspent surgical staple cartridge has been properly/operably installed in the elongate channel of the surgical end effector. It will also be appreciated that the firing beam locking assembly 980 also prevents advancement of the distal firing beam 280 when no staple cartridge at all has been installed in the elongate channel 302. In addition to accommodating articulation of the surgical end effector 300 about the articulation axis B-B without applying additional load to the distal firing beam which could result in the need for increased articulation forces to articulate the surgical end effector, the firing beam locking assembly 980 applies no additional load on the firing member and/or the distal firing beam once it has been distally advanced past the lockout wall whether or not the end effector jaws are open or closed.

Figure 20:
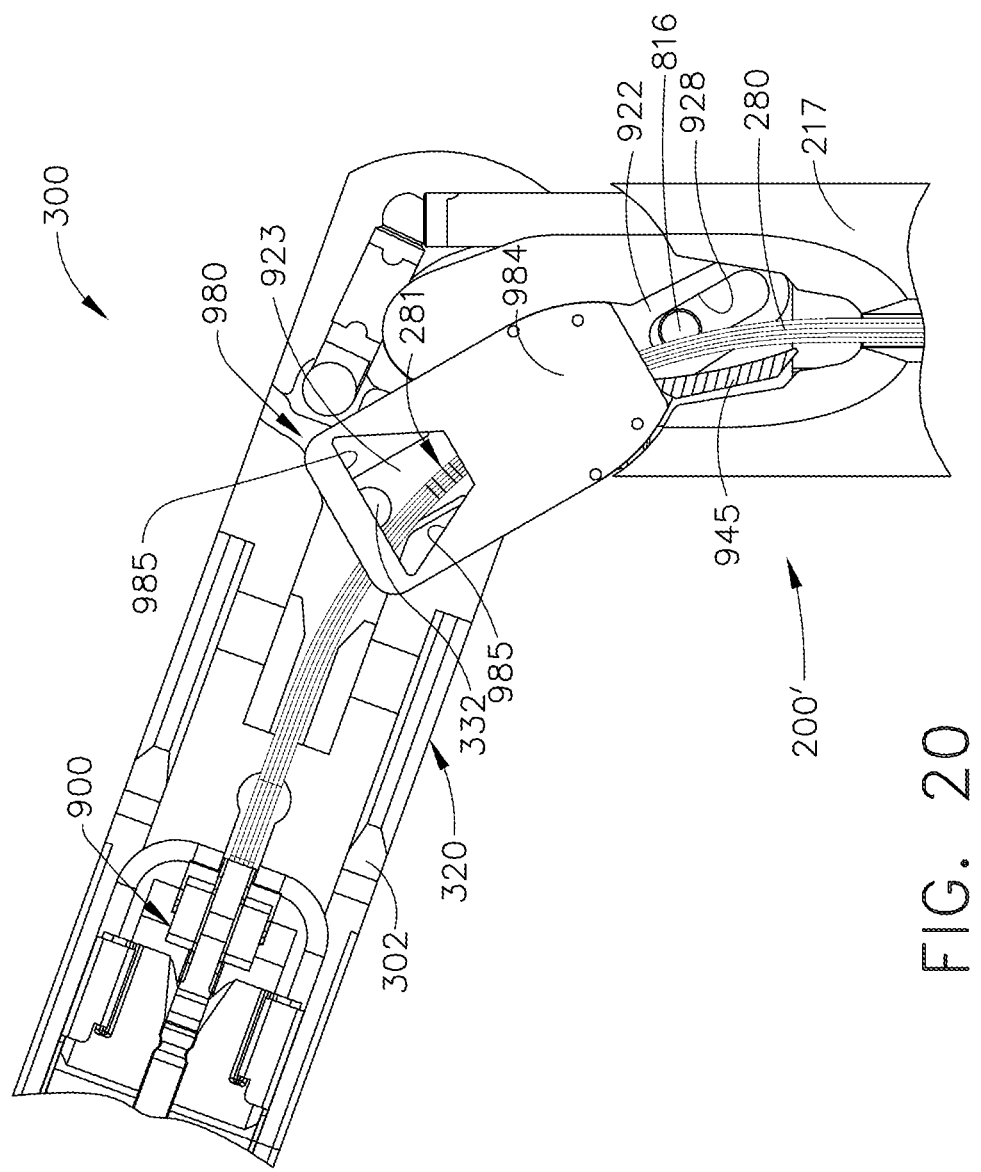
FIG. 20 is a top view of portions of the surgical end effector and elongate shaft assembly of FIGS. 15-19 with the surgical end effector in an articulated position or configuration.
Figure 20A:
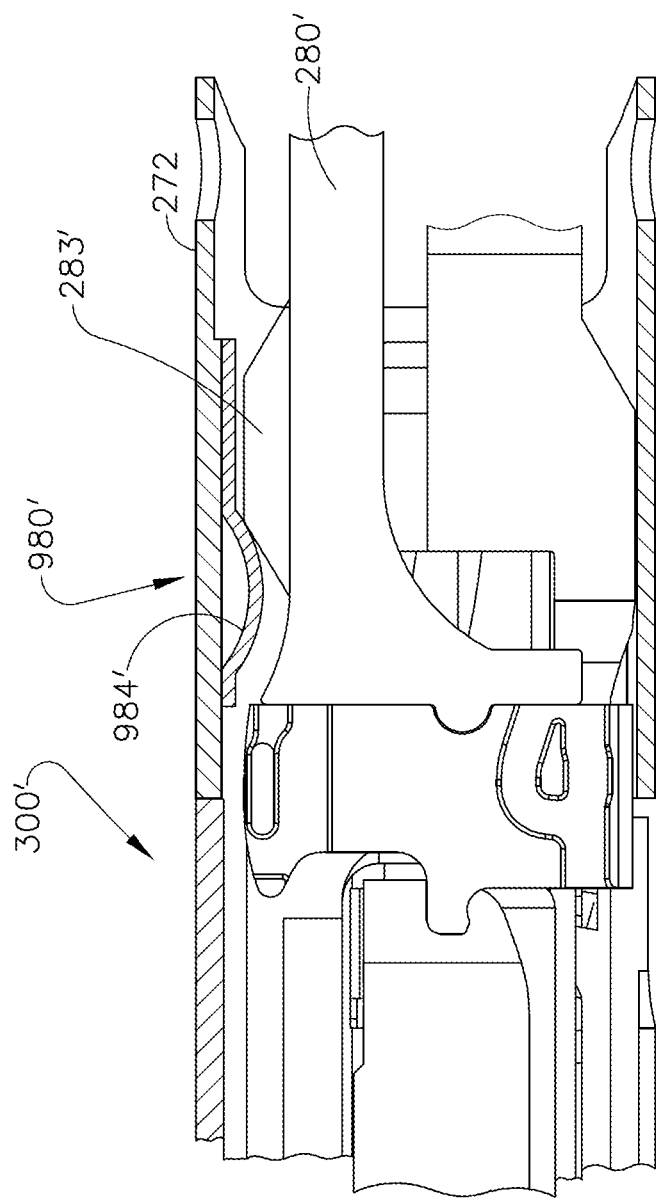
FIG. 20A is a side elevational view of a portion of another surgical end effector and closure sleeve embodiment.

FIG. 20A illustrates another articulatable surgical end effector embodiment 300' that employs a firing beam locking assembly 980' that comprises a biasing member 984' that is mounted within the end effector closure sleeve 272. As can be seen in that Figure, for example, the biasing member 984' applies a biasing force to a sloped or tapered portion 283' of the distal firing beam 280'. The firing beam locking assembly 980' otherwise operates in the same manner as described above with respect to the firing beam locking assembly 980. More specifically, the biasing member 984' applies a biasing force to the distal firing beam 280' that forces the distal firing beam 280' and the firing member attached thereto downward within the elongate channel. Unless an unspent surgical staple cartridge with a wedge sled or other staple ejector member in an unfired position has been properly installed within the elongate channel or cartridge support member so as to operably engage with the firing member or firing beam to move the firing member/firing beam out of engagement with the lock wall, the firing member/firing beam would be prevented from being axially advanced from the starting to ending position.

Figure 21:
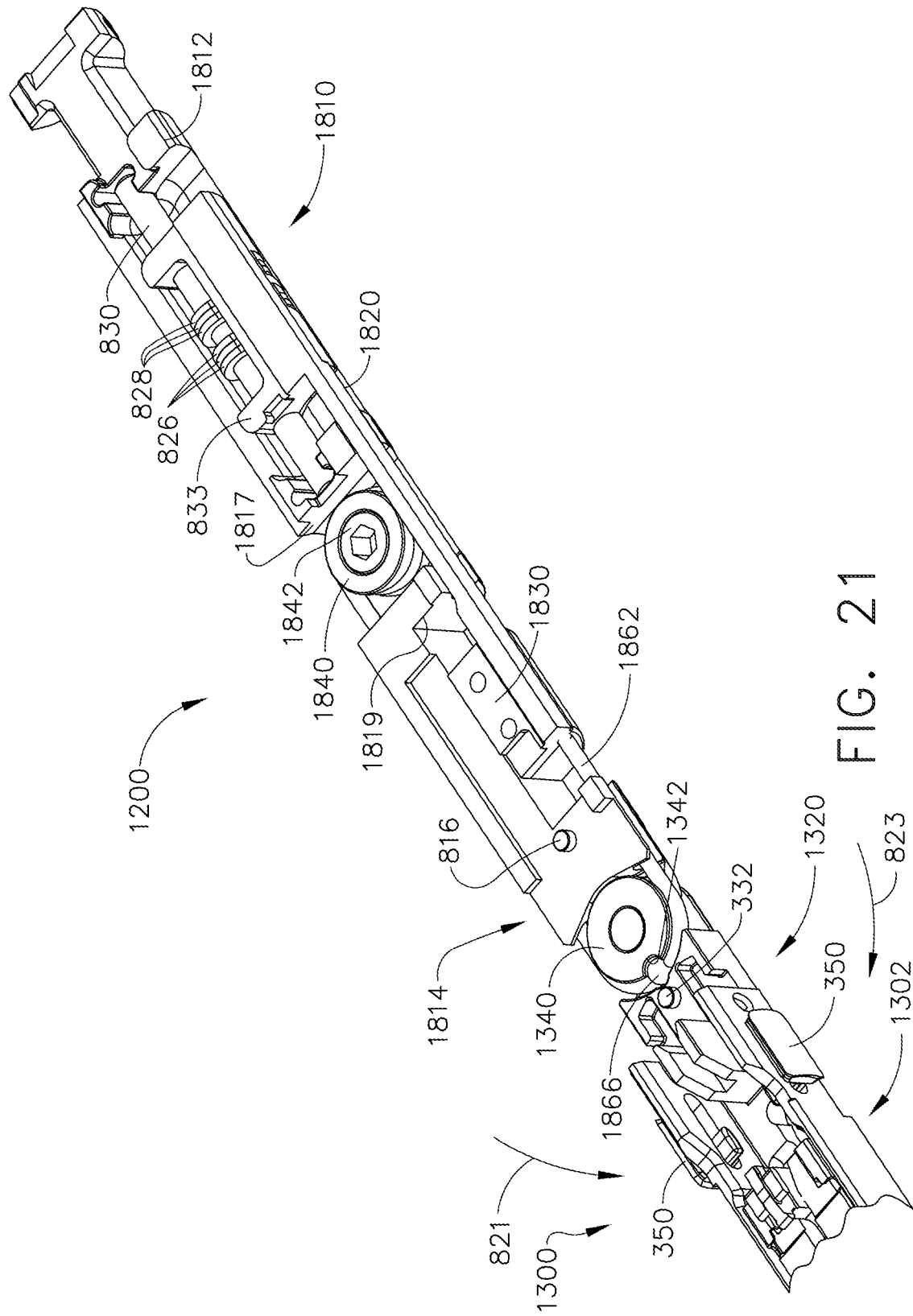
FIG. 21 is a perspective view of another surgical end effector and elongate shaft assembly embodiment with portions thereof omitted for clarity.
Figure 22:
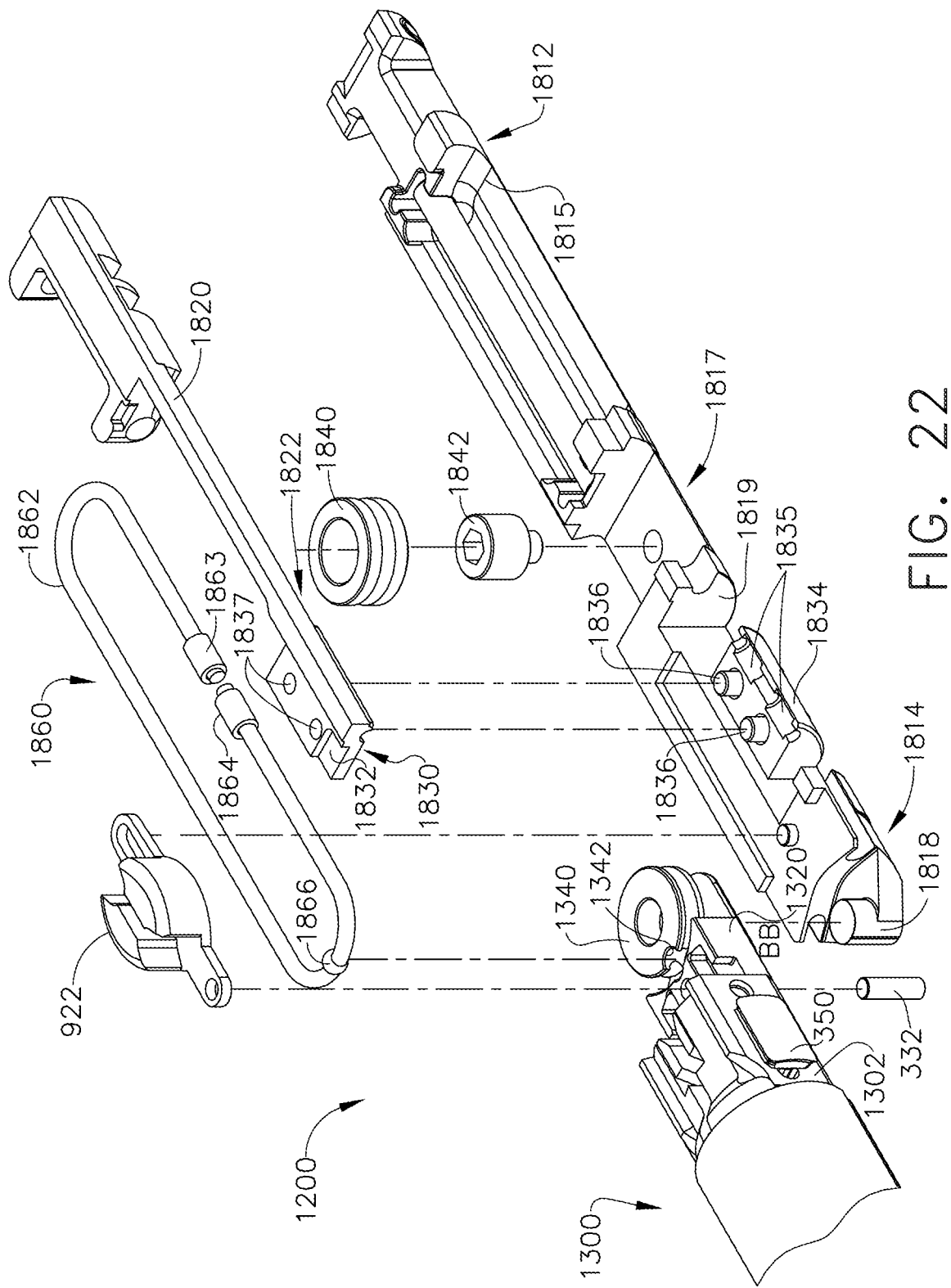
FIG. 22 is an exploded assembly view of portions of the surgical end effector and elongate shaft assembly embodiment of FIG. 21.
Figure 25:
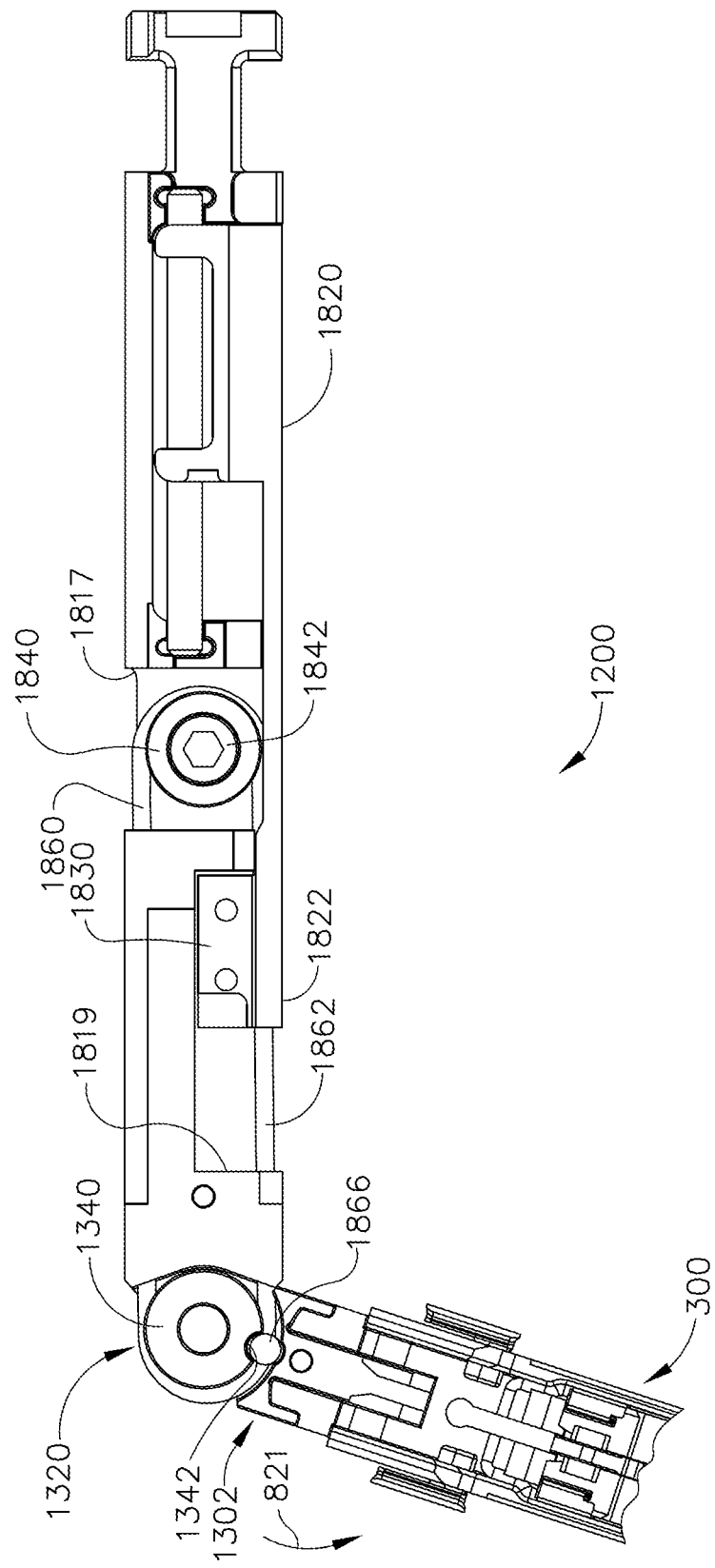
FIG. 25 is another top view of the portions of the surgical end effector and elongate shaft assembly embodiment of FIGS. 21-24 with the surgical end effector in an articulated position or configuration.

FIGS. 21-25 illustrate a portion of another elongate shaft assembly 1200 that is similar to the elongate shaft assembly 200 described above, except for various differences discussed in further detail below. Those components of the elongate shaft assembly 1200 that have been discussed in detail above are referenced with like element numbers and, for the sake of brevity, will not be further discussed in great detail beyond that which may be necessary to understand the operation of shaft assembly 1200 when, for example, employed with portions of the surgical instrument 10 as described above. As can be seen in FIG. 21, the elongate shaft assembly 1200 includes an articulation lock 1810 that is substantially similar to articulation lock 810 and operates in essentially the same manner. As can be seen in FIG. 22, the elongate shaft assembly 1200 includes a shaft frame 1812 that has a proximal cavity 1815 that is configured to movably support a proximal portion 1821 of a first distal articulation driver 1820 therein. The first distal articulation driver 1820 is movably supported within the elongate shaft assembly 1200 for selective longitudinal travel in a distal direction "DD" and a proximal direction "PD" in response to articulation control motions applied thereto. The shaft frame 1812 further includes a distal end portion 1814 that has a pivot pin 1818 formed thereon. The pivot pin 1818 is adapted to be pivotally received within a pivot hole (not shown) in a proximal end portion 1320 of an elongate channel 1302 of a surgical end effector 1300. Such arrangement facilitates pivotal travel (i.e., articulation) of the elongate channel 1302 of the relative to the shaft frame 1812 about an articulation axis B-B defined by the pivot hole and the pin 1818. The shaft frame 1812 further includes a centrally disposed cavity 1817 and a distal notch 1819 that is located between the distal end 1814 and the centrally disposed cavity 1817.

The shaft assembly 1200 further includes a second distal articulation driver 1860 that comprises an endless member 1862 that is rotatably journaled on a proximal pulley 1840 and a distal pulley 1340. Still referring to FIG. 22, the proximal pulley 1840 is rotatably journaled on a pulley spindle 1842 that is mounted within the centrally disposed cavity 1817 within the shaft frame 1812. The distal pulley 1340 is non-rotatably supported or formed on the proximal end 1320 of the elongate channel 1302 of the surgical end effector 1300. In one form, the endless member 1862 comprises a cable that is fabricated from stainless steel, tungsten, aluminum, titanium, etc., for example. The cable may be of braided or multi-stranded construction with various numbers of strands to attain desired levels of tensile strength and flexibility. In various arrangements, for example, the cable 2382 may have a diameter in the range of 0.03 inches to 0.08 inches and more preferably in the range of 0.05-0.08 inches. A preferred cable may, for example, be fabricated from 300 series stainless steel—half hard to full hard. In various arrangements, the cable may also be coated with, for example, Teflon®, copper, etc. for improved lubricity and/or to reduce stretching, for example. A first lug 1863 is attached to one end of the cable and a second lug 1864 is attached to the other end of the cable by, for example, crimping. The cable is stretched in tension while the ends and/or the lugs 1863, 1864 are welded, glued, mechanically fastened, etc. together to form the endless member 1862. The spindle 1842 may comprise a cam mount that engages the proximal pulley 1840 so as to move the pulley 1840 proximally. Other forms of tensioning arrangements such as belt tensioners, turn-buckle arrangements, etc. may also be employed to tension the endless member 1862.

Still referring to FIG. 22, the endless member 1862 is coupled to a distal end 1821 of the first distal articulation driver 1820 by a coupler assembly 1830. The coupler assembly 1830 comprises an upper coupler portion 1832 formed on the distal end 1822 of the first distal articulation driver 1820 and a lower coupler portion 1834. The lower coupler portion 1834 is formed with two cradles 1835 that are configured to receive the lugs 1862, 1864 therein. A pair of attachment pins 1836 is configured to be pressed into holes 1837 in the upper coupler portion 1832 to affix the two coupler portions 1832 and 1834 together. Other fastener arrangements, screws, rivets, adhesive, etc. may be employed. When the endless member 1862 is journaled on the pulleys 1840 and 1340, the coupler assembly 1830 is free to move axially within the distal notch 1819 in the shaft frame 1812 in response to the axial movement of the first distal articulation driver 1820. The articulation motions generated by the axial movement of the first distal articulation driver 1820 are transferred to the second distal articulation driver 1860 or the endless member 1862. An attachment ball or lug 1866 is attached to the endless member 1862 and is received in a groove or pocket 1342 formed in the distal pulley 1340. Thus, movement of the endless member 1862 is transferred to the surgical end effector 1300 and more specifically to the elongate channel 1302 of the surgical end effector 1300 to articulate the end effector about articulation axis B-B. Thus, when the first distal articulation driver 1820 is moved in the distal direction "DD", the endless member 1862 causes the surgical end effector 1300 to articulate about the articulation axis B-B in the articulation direction represented by arrow 823. See FIG. 21. Likewise, when the first distal articulation driver 1820 is moved in the proximal direction "PD", the endless member 1862 causes the surgical end effector 1300 to articulate about the articulation axis B-B in the articulation direction represented by arrow 821. See FIGS. 21 and 25. As shown in FIG. 21, articulation direction 823 is opposite to articulation direction 821.

Figure 26:
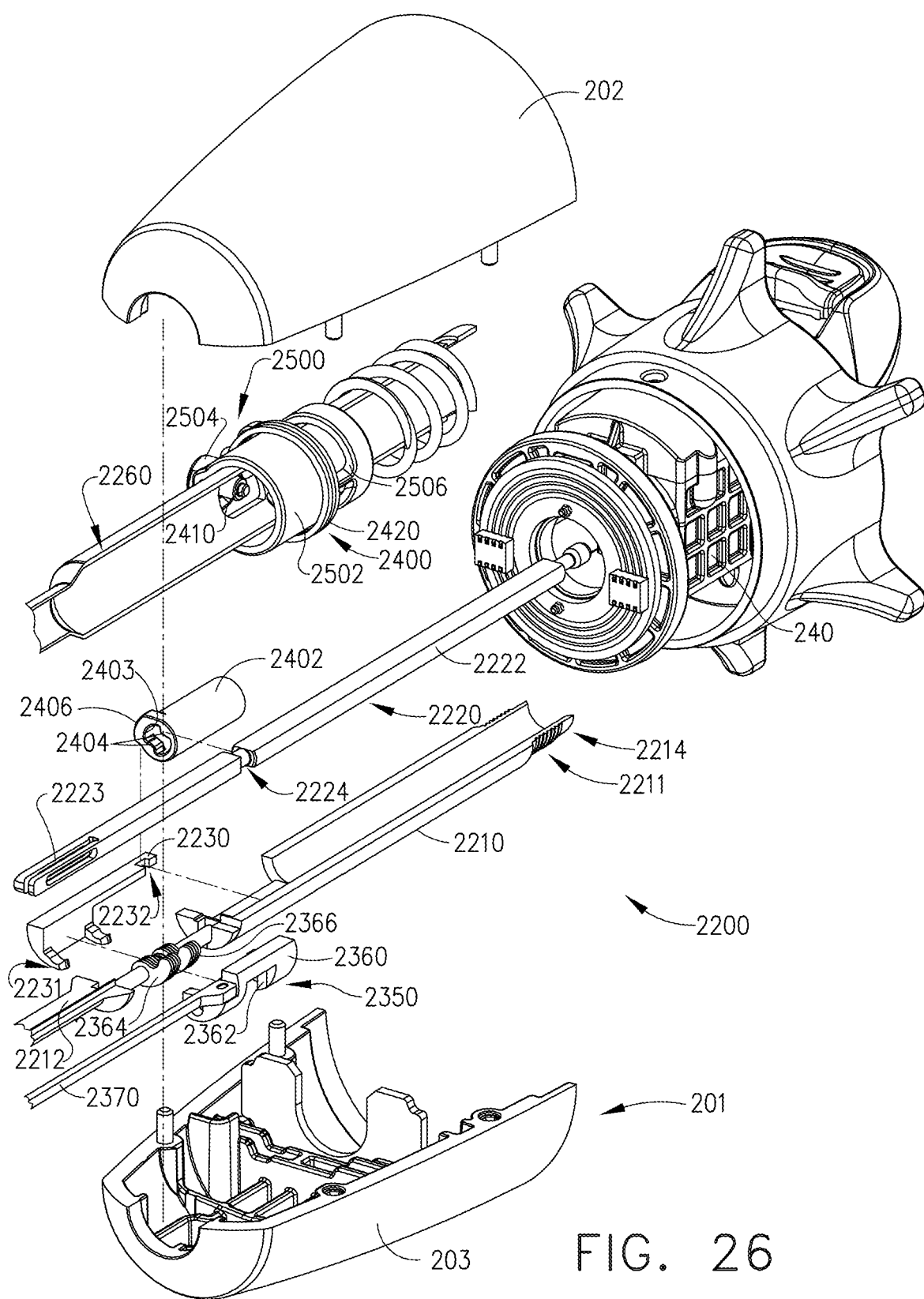
FIG. 26 is an exploded perspective view of a portion of another elongate shaft assembly embodiment.

FIGS. 26-31 illustrate portions of another elongate shaft assembly 2200 that is similar to the elongate shaft assembly 200 described above, except for various differences discussed in further detail below. Those components of the elongate shaft assembly 2200 that have been discussed in detail above are referenced with like element numbers and, for the sake of brevity, will not be further discussed in great detail beyond that which may be necessary to understand the operation of the elongate shaft assembly 2200 when, for example, employed with portions of the surgical instrument 10 as described above. As can be seen in FIG. 26, the elongate shaft assembly 2200 includes a proximal housing or nozzle 201 comprised of nozzle portions 202 and 203. The elongate shaft assembly 2200 further includes an anvil actuator member in the form of a closure tube 2260 which can be utilized to close and/or open the anvil 2310 of the surgical end effector 2300 that is operably attached thereto. As can be seen in FIG. 26, the elongate shaft assembly 2200 includes a proximal spine 2210 which is configured to operably interface with an articulation lock 2350. The proximal spine 2210 is configured to, one, slidably support a firing member 2220 therein and, two, slidably support the closure tube 2260 which extends around the proximal spine 2210. The proximal spine 2210 also slidably supports a proximal articulation driver 2230. The proximal articulation driver 2230 has a distal end 2231 that is configured to operably engage the articulation lock 2350.

In the illustrated arrangement, the proximal spine 2210 comprises a proximal end 2211 which is rotatably supported in a chassis 240. In one arrangement, for example, the proximal end 2211 of the proximal spine 2210 has a thread 2214 formed thereon for threaded attachment to a spine bearing configured to be supported within the chassis 240. Such an arrangement facilitates rotatable attachment of the proximal spine 2210 to the chassis 240 such that the proximal spine 2210 may be selectively rotated about a shaft axis SA-SA relative to the chassis 240. The proximal end of the closure tube 2260 is attached to a closure shuttle supported in the chassis as was described in detail above. When the elongate shaft assembly 2200 is operably coupled to the handle or housing of the surgical instrument 10, operation of the closure trigger distally advances the closure tube 2260.

As was also indicated above, the elongate shaft assembly 2200 further includes a firing member 2220 that is supported for axial travel within the proximal spine 2210. The firing member 2220 includes an intermediate firing shaft portion 2222 that is configured for attachment to a distal cutting or firing beam assembly 2280. See FIG. 27. The intermediate firing shaft portion 2222 may include a longitudinal slot 2223 in the distal end thereof which can be configured to receive a tab on the proximal end of the distal firing beam assembly 2280. The longitudinal slot 2223 and the proximal end of the distal firing beam assembly 2280 can be sized and configured to permit relative movement therebetween and can comprise a slip joint. The slip joint can permit the intermediate firing shaft portion 2222 of the firing drive 2220 to be moved to articulate the end effector 300 without moving, or at least substantially moving, the distal firing beam assembly 2280. Once the surgical end effector 2300 has been suitably oriented, the intermediate firing shaft portion 2222 can be advanced distally until a proximal sidewall of the longitudinal slot 2223 comes into contact with the tab in order to advance the distal firing beam assembly 2280 and fire a staple cartridge that may be supported in the end effector 300. The proximal spine 2210 is also coupled to a distal spine 2212.

Similar to the elongate shaft assembly 200, the illustrated elongate shaft assembly 2200 includes a clutch assembly 2400 which can be configured to selectively and releasably couple the proximal articulation driver 2230 to the firing member 2220. In one form, the clutch assembly 2400 includes a lock collar, or sleeve 2402, positioned around the firing member 2220 wherein the lock sleeve 2402 can be rotated between an engaged position in which the lock sleeve 2402 couples the proximal articulation driver 2230 to the firing member 2220 and a disengaged position in which the proximal articulation driver 2230 is not operably coupled to the firing member 2220. When the lock sleeve 2402 is in its engaged position, distal movement of the firing member 2220 can move the proximal articulation driver 2230 distally and, correspondingly, proximal movement of the firing member 2220 can move the proximal articulation driver 2230 proximally. When lock sleeve 2402 is in its disengaged position, movement of the firing member 2220 is not transmitted to the proximal articulation driver 2230 and, as a result, the firing member 2220 can move independently of the proximal articulation driver 2230. In various circumstances, the proximal articulation driver 2230 can be held in position by the articulation lock 2350 when the proximal articulation driver 2230 is not being moved in the proximal or distal directions by the firing member 2220.

As discussed above, the lock sleeve 2402 can comprise a cylindrical, or at least a substantially cylindrical body including a longitudinal aperture 2403 defined therein configured to receive the firing member 2220. The lock sleeve 2402 can comprise diametrically-opposed, inwardly-facing lock protrusions 2404 and an outwardly-facing lock member 2406. The lock protrusions 2404 can be configured to be selectively engaged with the firing member 2220. More particularly, when the lock sleeve 2402 is in its engaged position, the lock protrusions 2404 are positioned within a drive notch 2224 defined in the firing member 2220 such that a distal pushing force and/or a proximal pulling force can be transmitted from the firing member 2220 to the lock sleeve 2402. When the lock sleeve 2402 is in its engaged position, the second lock member 2406 is received within a drive notch 2232 defined in the articulation driver 2230 such that the distal pushing force and/or the proximal pulling force applied to the lock sleeve 2402 can be transmitted to the proximal articulation driver 2230. In effect, the firing member 2220, the lock sleeve 2402, and the proximal articulation driver 2230 will move together when the lock sleeve 2402 is in its engaged position. On the other hand, when the lock sleeve 2402 is in its disengaged position, the lock protrusions 2404 may not be positioned within the drive notch 2224 of the firing member 2220 and, as a result, a distal pushing force and/or a proximal pulling force may not be transmitted from the firing member 2220 to the lock sleeve 2402. Correspondingly, the distal pushing force and/or the proximal pulling force may not be transmitted to the proximal articulation driver 2230. In such circumstances, the firing member 2220 can be slid proximally and/or distally relative to the lock sleeve 2402 and the proximal articulation driver 2230.

As was also discussed above, the elongate shaft assembly 2200 further includes a switch drum 2500 that is rotatably received on the closure tube 2260. The switch drum 2500 comprises a hollow shaft segment 2502 that has a shaft boss 2504 formed thereon for receive an outwardly protruding actuation pin 2410 therein. In various circumstances, the actuation pin 2410 extends through a slot into a longitudinal slot provided in the lock sleeve 2402 to facilitate axial movement of the lock sleeve 2402 when it is engaged with the articulation driver 2230. A rotary torsion spring 2420 is configured to engage the boss 2504 on the switch drum 2500 and a portion of the nozzle housing 203 to apply a biasing force to the switch drum 2500. The switch drum 2500 can further comprise at least partially circumferential openings 2506 defined therein which can be configured to receive circumferential mounts extending from the nozzle halves 202, 203 and permit relative rotation, but not translation, between the switch drum 2500 and the proximal nozzle 201. As described above, rotation of the switch drum 2500 will ultimately result in the rotation of an actuation pin 2410 and the lock sleeve 2402 between its engaged and disengaged positions. Thus, in essence, the nozzle 201 may be employed to operably engage and disengage the articulation drive system with the firing drive system in the various manners described above as well as in U.S. patent application Ser. No. 13/803,086, now U.S. Patent Application Publication No. 2014/0263541.

Figure 27:
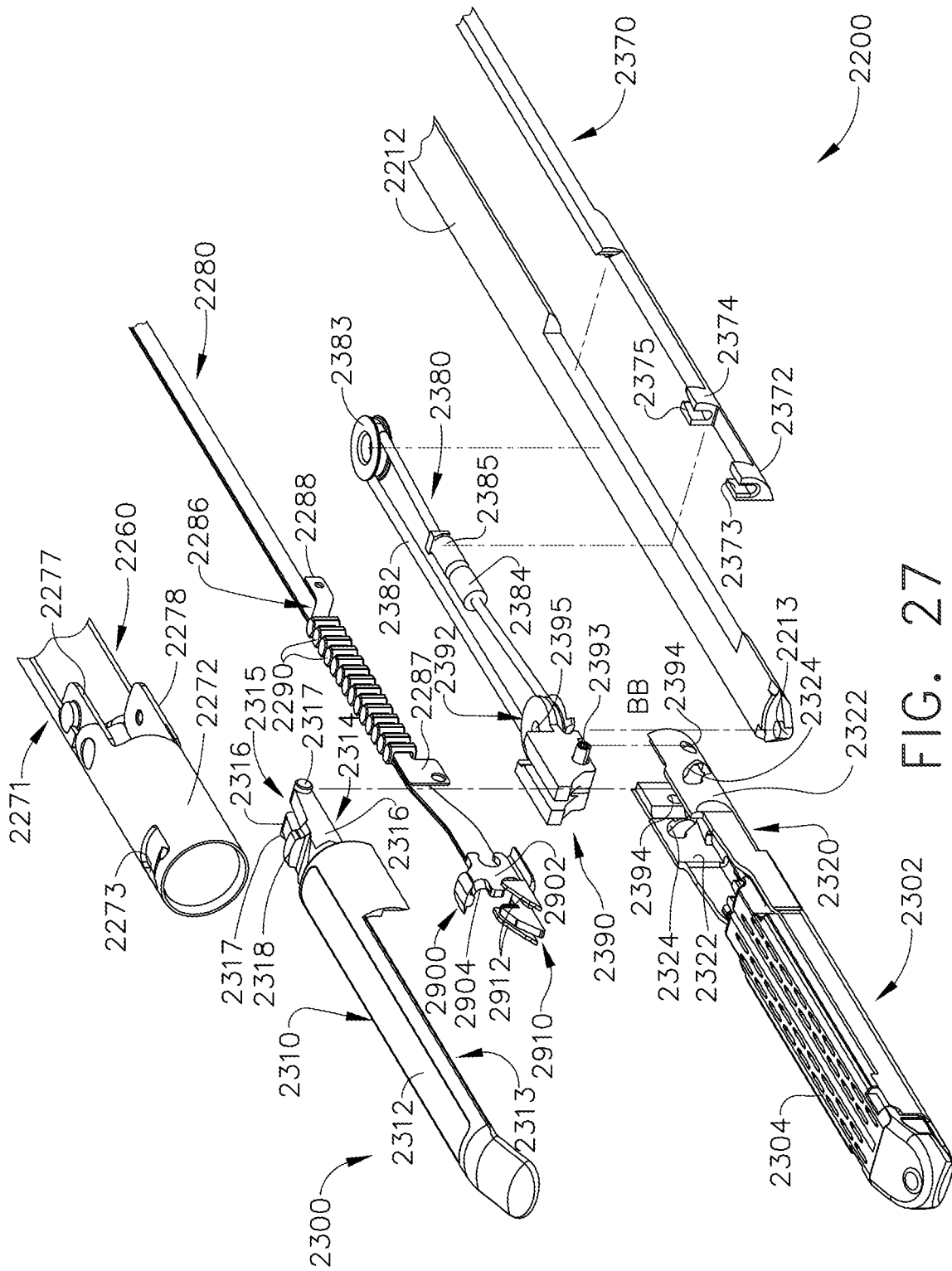
FIG. 27 is an exploded assembly view of portions of another surgical end effector and elongate shaft assembly embodiment.

Referring to FIG. 27, the closure tube assembly 2260 includes a double pivot closure sleeve assembly 2271. According to various forms, the double pivot closure sleeve assembly 2271 includes an end effector closure sleeve 2272 having upper and lower distally projecting tangs. An upper double pivot link 2277 includes upwardly projecting distal and proximal pivot pins that engage respectively an upper distal pin hole in the upper proximally projecting tang and an upper proximal pin hole in an upper distally projecting tang on the closure tube 2260. A lower double pivot link 2278 includes upwardly projecting distal and proximal pivot pins that engage respectively a lower distal pin hole in the lower proximally projecting tang and a lower proximal pin hole in the lower distally projecting tang.

The elongate shaft assembly 2200 also includes a surgical end effector 2300 that is similar to the surgical end effector 300 that was described above. As can be seen in FIG. 27, the surgical end effector 2300 includes an elongate channel 2302 that is configured to operably support a surgical staple cartridge 2304 therein. The elongate channel 2302 has a proximal end portion 2320 that includes two upstanding lateral walls 2322. The surgical end effector 2300 further includes an anvil 2310 that has an anvil body 2312 that has a staple-forming undersurface 2313 formed thereon. The proximal end 2314 of the anvil body 2312 is bifurcated by a firing member slot 2315 to form two anvil attachment arms 2316. Each anvil attachment arm 2316 includes a laterally protruding anvil trunnion 2317. A trunnion slot 2324 is provided in each lateral wall 2322 of the elongate channel 2302 for receiving a corresponding one of the anvil trunnions 2317 therein. Such arrangement serves to movably affix the anvil 2310 to the elongate channel 2302 for selective pivotable travel between open and closed or clamped positions. The anvil 2310 is moved to a closed position by distally advancing the closure tube 2260 and more particularly, the end effector closure sleeve 2272 up the tapered attachment arms 2316 which causes the anvil 2310 to move distally while pivoting to the closed position. A horseshoe-shaped opening 2273 is provided in the end effector closure sleeve 2272 that is configured to engage an upstanding tab 2318 on the anvil 2310 of the end effector 2300. To open the anvil 2310, the closure tube 2260 and, more particularly, the end effector closure sleeve 2272 is moved in the proximal direction. In doing so, a central tab portion defined by the horseshoe shaped opening 2273 cooperates with the tab 2318 on the anvil 2310 to pivot the anvil 2310 back to an open position.

Figure 28:
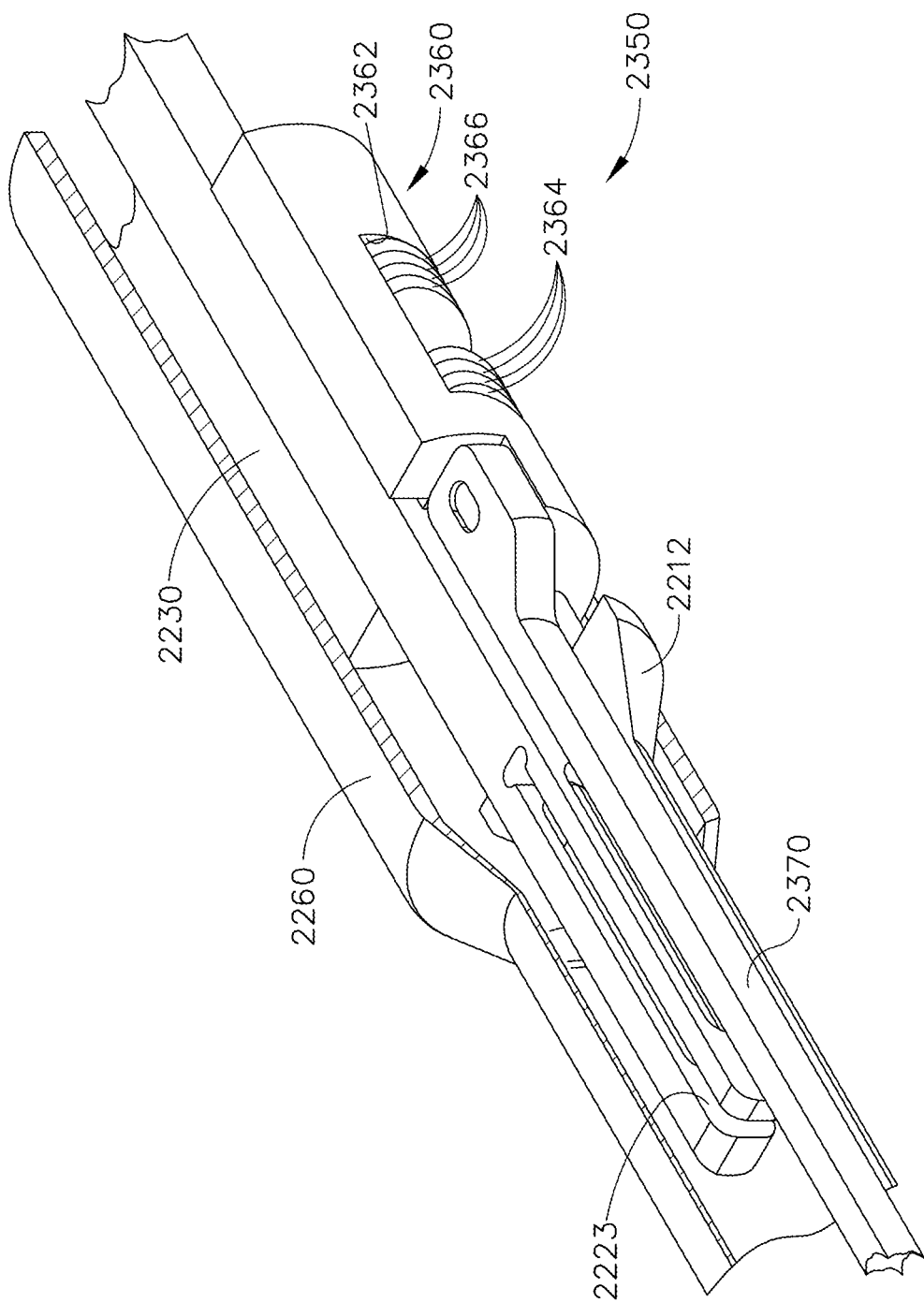
FIG. 28 is a partial perspective view of a portion of the elongate shaft assembly embodiment of FIG. 27 with portions thereof omitted for clarity.
Figure 29:
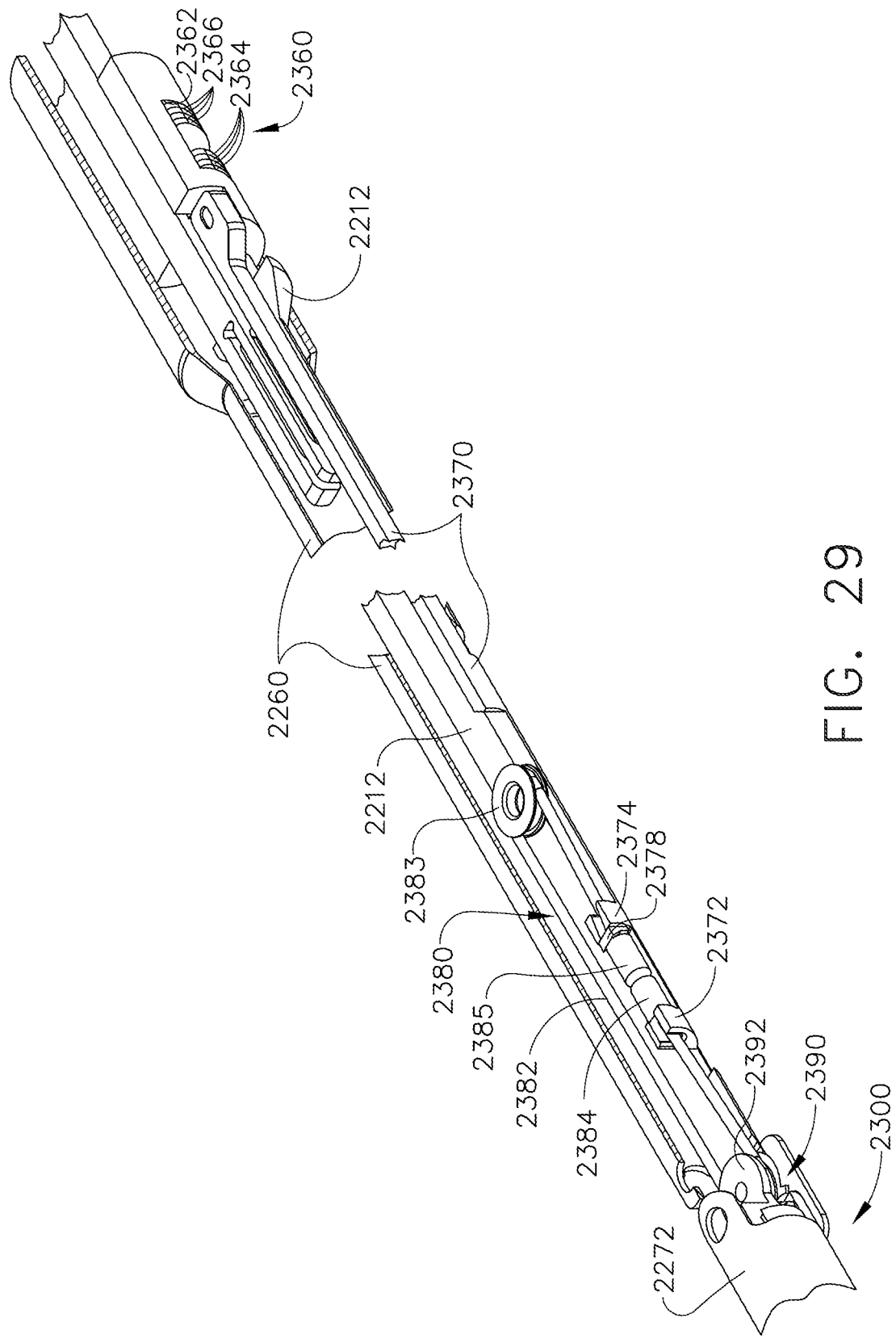
FIG. 29 is another partial perspective view of portions of the elongate shaft assembly embodiment of FIGS. 27 and 28 with portions thereof omitted for clarity.
Figure 30:
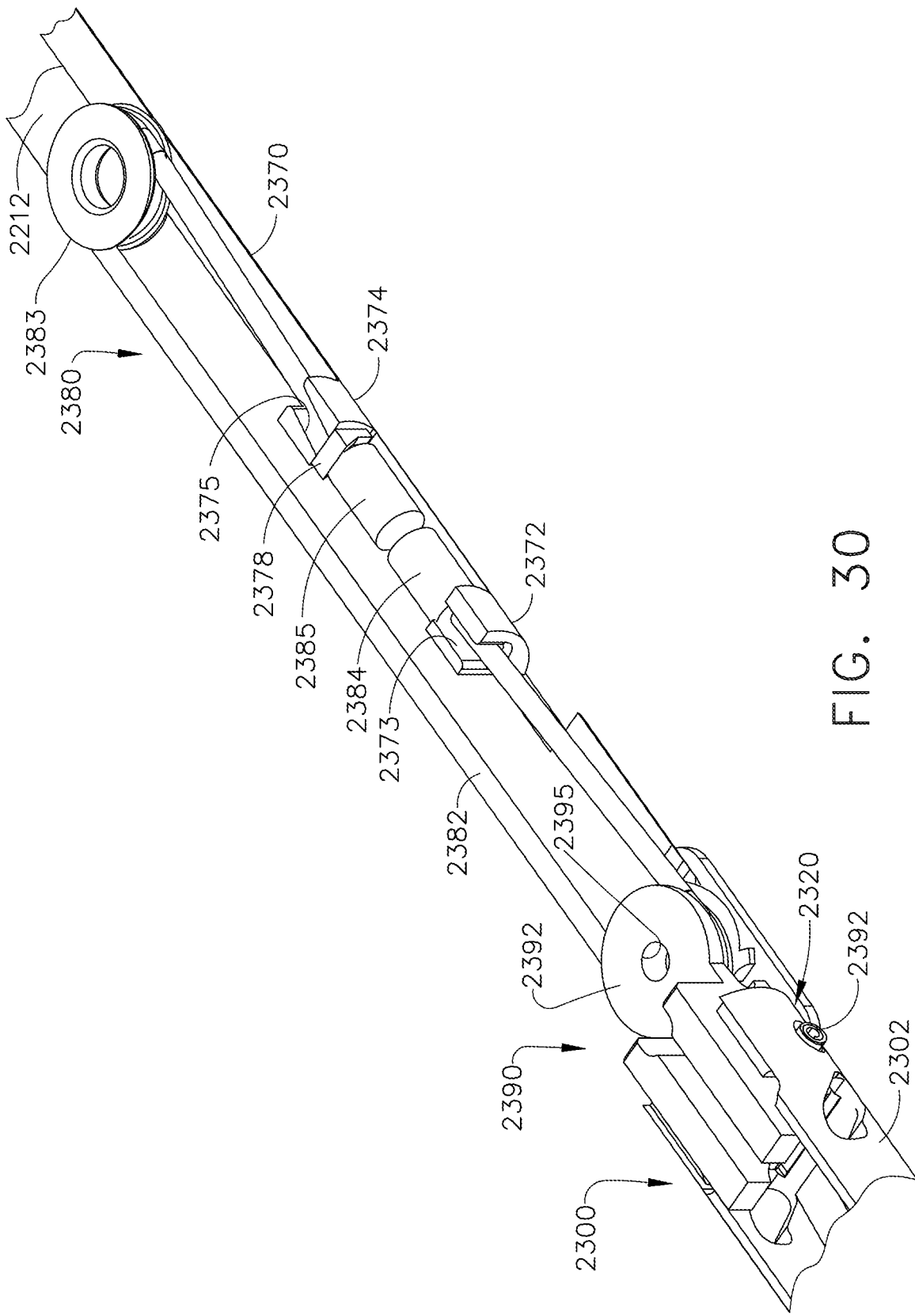
FIG. 30 is another partial perspective view of portions of the elongate shaft assembly embodiment of FIGS. 27-29 with portions thereof omitted for clarity.

Turning to FIGS. 26, 28 and 29, as mentioned above, the elongate shaft assembly 2200 includes an articulation lock 2350 that is substantially similar to articulation locks 350 and 810 that were described above. Those components of articulation lock 2350 that differ from the components of articulation lock 350 and are necessary to understand the operation of articulation lock 350 will be discussed in further detail below. As discussed above, the articulation lock 2350 can be configured and operated to selectively lock the end effector 2300 in position. Such arrangement enables the surgical end effector 2300 to be rotated, or articulated, relative to the shaft closure tube 2260 when the articulation lock 2350 is in its unlocked state. When the proximal articulation driver 2230 is operatively engaged with the firing member 2220 via the clutch system 2400, further to the above, the firing member 2220 can move the proximal articulation driver 2230 proximally and/or distally. Movement of the proximal articulation driver 2230, whether it is proximal or distal, can unlock the articulation lock 2350 as was described above. This embodiment includes a proximal lock adapter member 2360 that is movably supported between the proximal spine 2210 and the distal spine 2212. The proximal lock adapter 2360 includes a lock cavity 2362 for receiving therein first lock elements 2364 and second lock elements 2366 that are journaled on a frame rail 2368 that extends between the proximal frame 2210 and the distal frame 2212. The articulation lock 2350 operates in the various manners described above and, for the sake of brevity, will not be further discussed herein.

As can be seen in FIGS. 26, 28 and 29, a first distal articulation driver 2370 is attached to the proximal lock adapter 2360. The first distal articulation driver 2370 is operably attached to a second distal articulation driver 2380 that operably interfaces with the elongate channel 2302 of the end effector 2300. The second distal articulation driver 2380 comprises a cable 2382 that is rotatably journaled on a proximal pulley 2383 and a distal pulley 2392. The distal pulley 2392 is non-rotatably supported or integrally formed on an end effector mounting assembly 2390 and includes a detent or pocket 2396. In the illustrated example, the end effector mounting assembly 2390 is non-movably attached to the proximal end 2320 of the elongate channel 2302 by a spring pin 2393 that extends through a hole in the end effector mounting assembly 2390 and holes 2394 in the proximal end 2320 of the elongate channel 2302. The proximal pulley 2383 is rotatably supported on the distal spine 2212. The distal end of the distal spine 2212 has a pivot pin 2213 formed thereon that is configured to be rotatably received within a pivot hole 2395 formed in the end effector mounting member 2390. Such arrangement facilitates pivotal travel (i.e., articulation) of the elongate channel 2302 relative to the distal spine 2212 about an articulation axis B-B defined by the pivot hole 2395 and the pin 2213.

Figure 35:
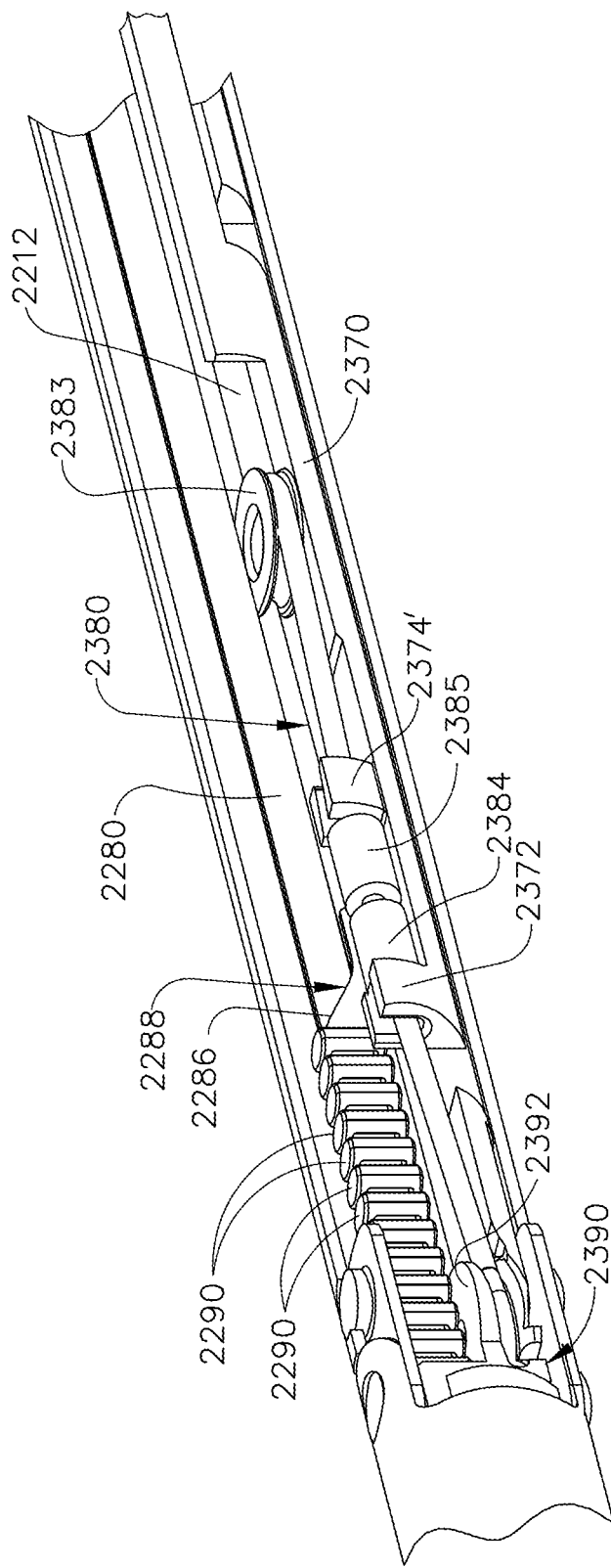
FIG. 35 is another partial perspective view of portions of the surgical end effector and elongate shaft assembly embodiment of FIGS. 27-34 with portions thereof omitted for clarity.

In one form, the cable 2382 may be fabricated from stainless steel, tungsten, aluminum, titanium, etc., for example. The cable may be of braided or multi-stranded construction with various numbers of strands to attain desired levels of tensile strength and flexibility. In various arrangements, for example, the cable 2382 may have a diameter in the range of 0.03 inches to 0.08 inches and more preferably in the range of 0.05-0.08 inches. A preferred cable may, for example, be fabricated from 300 series stainless steel—half hard to full hard. In various arrangements, the cable may also be coated with, for example, Teflon®, copper, etc. for improved lubricity and/or to reduce stretching, for example. In the illustrated example, the cable 2382 has a lug 2384 attached to one end thereof and a lug 2385 attached to the other end thereof by, for example, crimping. The first distal articulation driver 2370 includes a pair of spaced cleats 2372, 2374 that are spaced from each other sufficiently so as to accommodate the lugs 2384, 2385 therebetween. For example, the proximal cleat 2372 includes a proximal slot 2373 for receiving a portion of the cable 2382 adjacent the lug 2384 and the distal cleat 2374 includes a distal slot 2375 for receiving a corresponding portion of the cable 2382 adjacent the lug 2385. The slots 2373 and 2375 are sized relative to the lugs 2384, 2385, respectively so as to prevent the lugs 2384, 2385 from pulling therethrough. The proximal slot 2375 is oriented at an angle as compared to the distal slot 2375 so as to cinchingly grip the corresponding portion of the cable 2382 therein. See FIG. 30. An attachment ball or lug 2398 is attached to the endless member 2382 and is received in the detent or pocket 2396 formed in the distal pulley 2392. See FIG. 31. Thus, when the first distal articulation driver 2370 is axially retracted in the proximal direction "PD", in the manners described above, the endless member 2382 will articulate the end effector 2300 in the direction represented by arrow 2376 in FIG. 31. Conversely, when the first distal articulation driver 2370 is axially advanced in the distal direction "DD", the surgical end effector 2300 is articulated in the direction represented by arrow 2399 in FIG. 31. In addition, the proximal and distal cleats 2372, 2374 are spaced sufficiently so as to accommodate the lugs 2384, 2385 therebetween. A tensioning wedge 2378 is used as shown in FIGS. 29-32 to apply sufficient tension to the cable 2382 such that when the cable is actuated, it will apply an articulation motion to the end effector 2300. In the alternative arrangement depicted in FIG. 35, the proximal cleat 2374' is initially not attached to the first articulation driver 2370. The proximal cleat 2374' is positioned on the first distal articulation driver 2370 so as to capture the lugs 2384 and 2385 between the distal cleat 2372 and the proximal cleat 2374'. The proximal cleat 2374' is moved toward the distal cleat 2372 until a sufficient amount of tension is generated in the cable 2382 and then the proximal cleat 2374' is attached to the first distal articulation driver 2370. For example, the proximal cleat 2374' may be attached to the first distal articulation driver 2370 by laser welding or other suitable form of attachment means or fastener arrangement.

Figure 36:
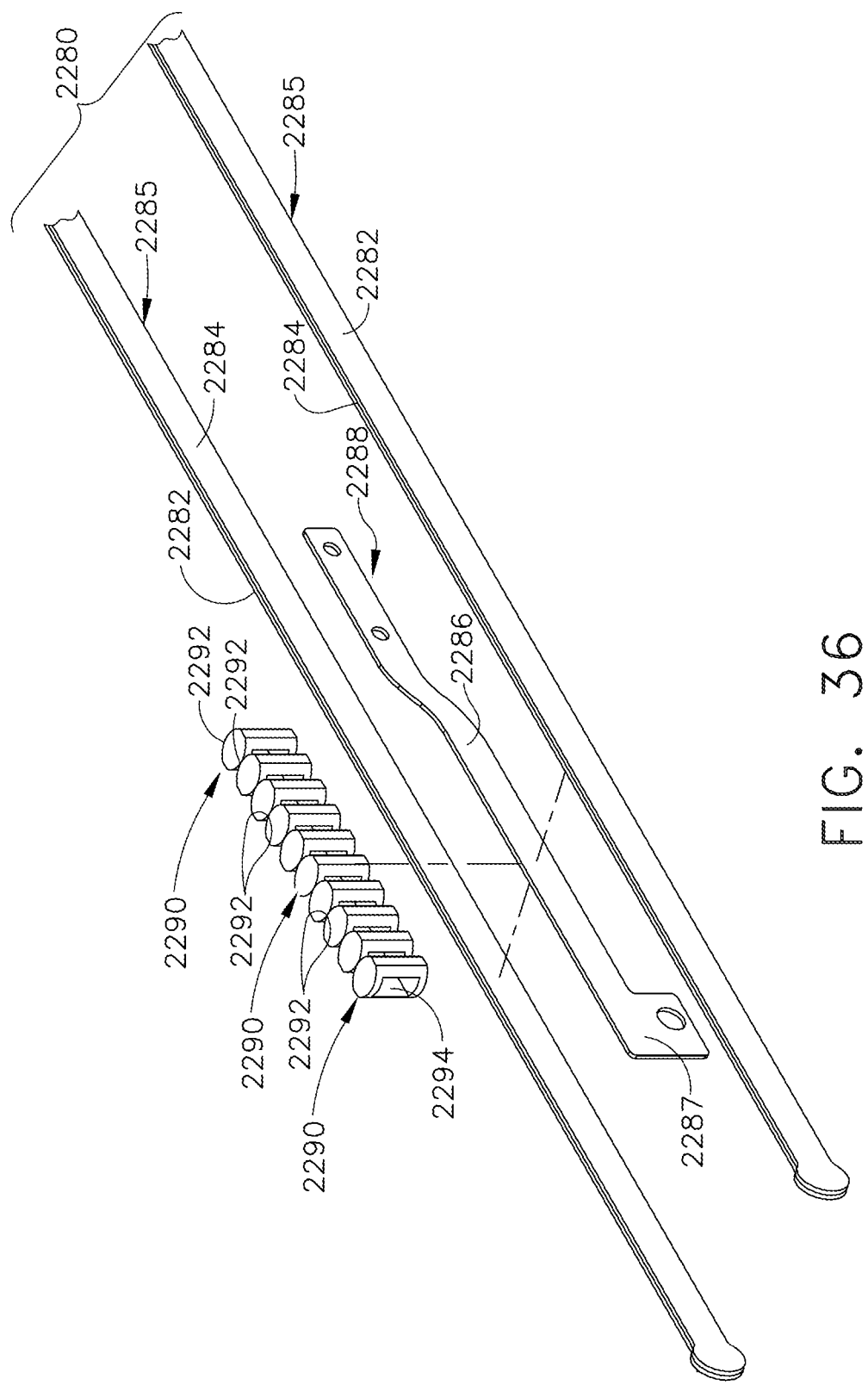
FIG. 36 is an exploded assembly view of portions of a distal firing beam assembly embodiment and lateral load carrying member embodiments.
Figure 40:
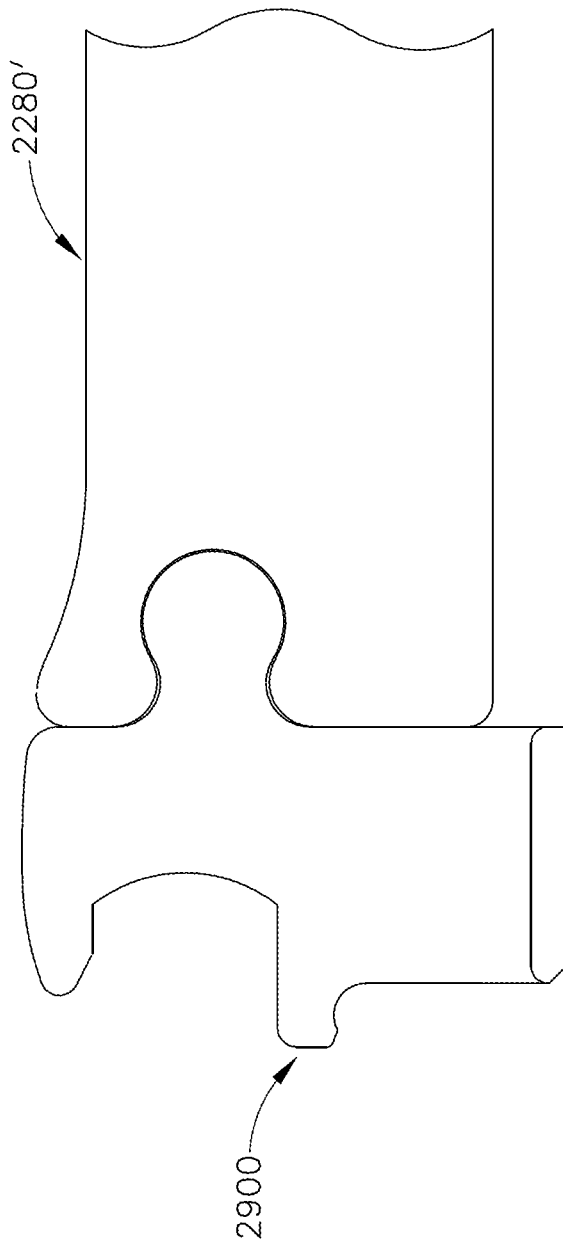
FIG. 40 is a side elevational view of a portion of a distal firing beam assembly embodiment attached to a firing member embodiment.
Figure 41:
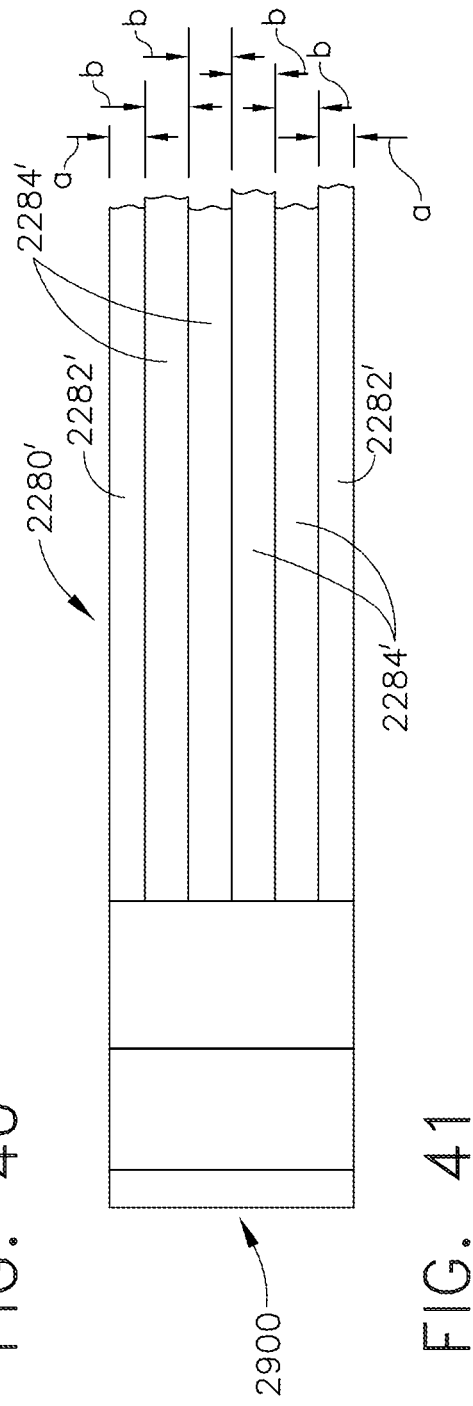
FIG. 41 is a top view of a portion of the distal firing beam assembly embodiment and firing member embodiment of FIG. 40.

Referring FIGS. 36-39, the surgical instrument includes for example, a central firing beam support member 2286 that is configured to extend across an articulation joint to provide support to a flexible firing beam assembly 2280. In one form, the central firing beam support member 2286 comprises a flexible plate member or band and includes a downwardly protruding distal attachment tab 2287 that is attached to the surgical end effector and an upwardly extending proximal end portion 2288 that is attached to the elongate shaft assembly. In at least one arrangement, the distal attachment tab 2287 is attached to the end effector mounting assembly 2390 by the spring pin 2393 and the proximal end portion 2288 is pinned to the distal spine 2212 by pins (not shown). The central firing beam support member 2286 is located along the centerline or shaft axis of the device and serves to provide support to the firing beam during articulation. This is different from those arrangements that employ "blow-out" plates or lateral support plates that are located on the lateral sides of the firing beam and which are thereby offset from the shaft axis increasing the tension and compression forces that they experience during articulation. In the illustrated example, the longitudinally movable flexible firing beam assembly 2280 comprises a laminated beam structure that includes at least two beam layers wherein at least one beam layer is configured to pass adjacent one lateral side of the central firing beam support member and at least one other beam member is configured to pass adjacent another lateral side of the central firing beam support member. In the illustrated example, two laminated layers 2282 and 2284 are configured to pass adjacent each side of the flexible tension carrying member. See, for example, FIGS. 35 and 36. In various embodiments, the laminated layers 2282 and 2284 may comprise, for example, stainless steel bands that are interconnected by, for example, welding or pinning together at their proximal ends, while their respective distal ends are not connected together to allow the laminates or bands to splay relative to each other when the end effector is articulated. Each pair of laminated layers or bands 2282, 2284 is represented as a lateral firing band assembly 2285 of the firing beam assembly 2280. Thus, as shown in FIG. 36, one lateral firing band assembly 2285 is supported on each lateral side of the central articulation bar 2286 for axial travel relative thereto by a series of lateral load carrying members 2290. Each lateral load carrying member 2290 may be fabricated from, for example, stainless steel, aluminum, titanium, liquid crystal polymer material, plastic material, Nylon, Acrylonitrile butadiene styrene (ABS), polyethylene, etc. and be formed with opposed arcuate ends 2292.

Each lateral load carrying member 2290 also has an axial passage 2294 extending therethrough to receive the assembly of the lateral firing band assemblies 2285 and the central articulation bar 2286. As can be most particularly seen in FIG. 38, each axial passage is defined by two opposed arcuate surfaces 2295 that facilitate movement of lateral load carrying members 290 on the longitudinally movable flexible firing beam assembly 2280. The lateral load carrying members 2290 are serially arranged on the lateral firing band assemblies 2285 and the central articulation bar 2286 such that the opposed arcuate ends 2292 abut corresponding arcuate ends 2292 of adjacent lateral load carrying members 2290. See, for example, FIGS. 36 and 37.

Referring again to FIG. 37, it can be seen that the proximal end portion 2288 central articulation bar 2286 extends downwardly for attachment to the distal spine 2212. The distal end 2287 of the firing beam assembly 2280 is attached to a firing member 2900 of the type and construction describe above, for example. As can be seen in that Figure, the firing member 2900 includes a vertically-extending firing member body 2902 that has a tissue cutting surface or blade 2904 thereon. In addition, a wedge sled 2910 may be mounted within the surgical staple cartridge 2304 for driving contact with the firing member 2900. As the firing member 2900 is driven distally through the cartridge body 2304, the wedge surfaces 2912 of the wedge sled 2910 contact the staple drivers to actuate the drivers and the surgical staples supported thereon upwardly in the cartridge 2304. The firing beam assembly 2280 is operated in the various manners described above. As the firing beam assembly 2280 is distally advanced about the articulation joint, the lateral load carrying members 2290 may help to resist buckling loads on the firing beam assembly 2280. The lateral load carrying members 2290 may also reduce the amount of force required to articulate the end effector and also accommodate greater articulation angles when compared to other articulation joint arrangements. The fixed central firing beam support member 2286 serves to carry the tension loads that are generated during articulation and firing.

As described above, the firing beam assembly comprises a laminated beam structure that includes at least two beam layers. As the firing beam assembly is advanced distally (during firing), the firing beam assembly is essentially bifurcated by the central firing beam support member so that portions of the firing beam assembly (i.e., laminate layers) pass on both sides of the of the central firing beam support member.

FIGS. 40-43 illustrate a portion of another firing beam assembly 2280' that is attached to a firing member 2900. As can be seen in those Figures, the firing beam assembly 2280 comprises a laminated structure that includes two outer lateral beams or layers 2282' that each have a thickness that is designated as "a" and four central layers 2284' that each have a thickness designated as "b". In at least one arrangement, for example, "a" may be approximately 0.005-0.008 inches and more preferably 0.008 inches and "b" may be approximately 0.008-0.012 inches and more preferably 0.010 inches. However, other thicknesses may be employed. In the illustrated example, "a" is less than "b". In other arrangements, "a" is greater than "b". In alternative arrangements, for example, the laminates may be made up of three different thicknesses "a", "b", "c", wherein "a"=0.006 inches, "b"=0.008 inches, and "c"=0.010 inches (with the thickest laminate or band being in the center of the assembly). In various arrangements, there may be an odd number of laminates or bands where "c" is the single thickest laminate in the center.

The laminate composition is relevant because of the amount of strain that is applied to a beam assembly based on its thickness and its distance from the centerline of bending. Thicker laminates or bands that are closer to the centerline may experience the same levels of strain as the thinner ones that are farther away from the centerline because they have to be bent more in view of the fact that they are stacked together. The radius of curvature is more aggressive on the inside of the curve the father away from the centerline. Thicker laminates or bands tend to experience more internal stress than thinner laminates given the same radius of curvature. Thus, thinner side laminates or bands that have the smallest radius of curvature may have the same likelihood of plastically deforming as the thicker ones that are closure to the centerline. Stated another way, when the end effector articulates in one direction, the laminates or bands located away from the direction of articulation have the largest bend radius and the laminates or bands closest to the direction of articulation have the tightest bend radius. However, when the end effector is articulated in the opposite direction, the inverse is true. The laminates on the inside of the laminate stack experience the same deviation, but their bend radius will always fall within the range of the outer ones. Thus, to maintain flexibility, locating thinner laminates on the outside of the stack may be desired. However, to maximize stiffness and buckling resistance, thicker materials on the inside add additional benefit. Alternately, if the end effector needs only to articulate in a single direction, the laminates or bands located away from the direction of articulation will experience the greatest bend radius and the laminates or bands located in the direction of articulation have the tightest bend radius. However, because the end effector does not articulate in an opposite direction, the inverse is no longer true and therefor, the laminate stack does not need to be symmetric. Thus, in such arrangement, it would be desirable to have the thinnest laminate or band be the one that will experience the tightest bend radius (the laminate or band on the side of the direction of articulation).

In still other arrangements, the laminates or bands may be fabricated from different metals with different strengths and modulus. For example, the outer laminates or bands could have the same thickness as the inner laminates or bands with the inner laminates or bands being fabricated from 300 series stainless steel and the outer laminates or bands being fabricated from titanium or nitinol.

Figure 42:
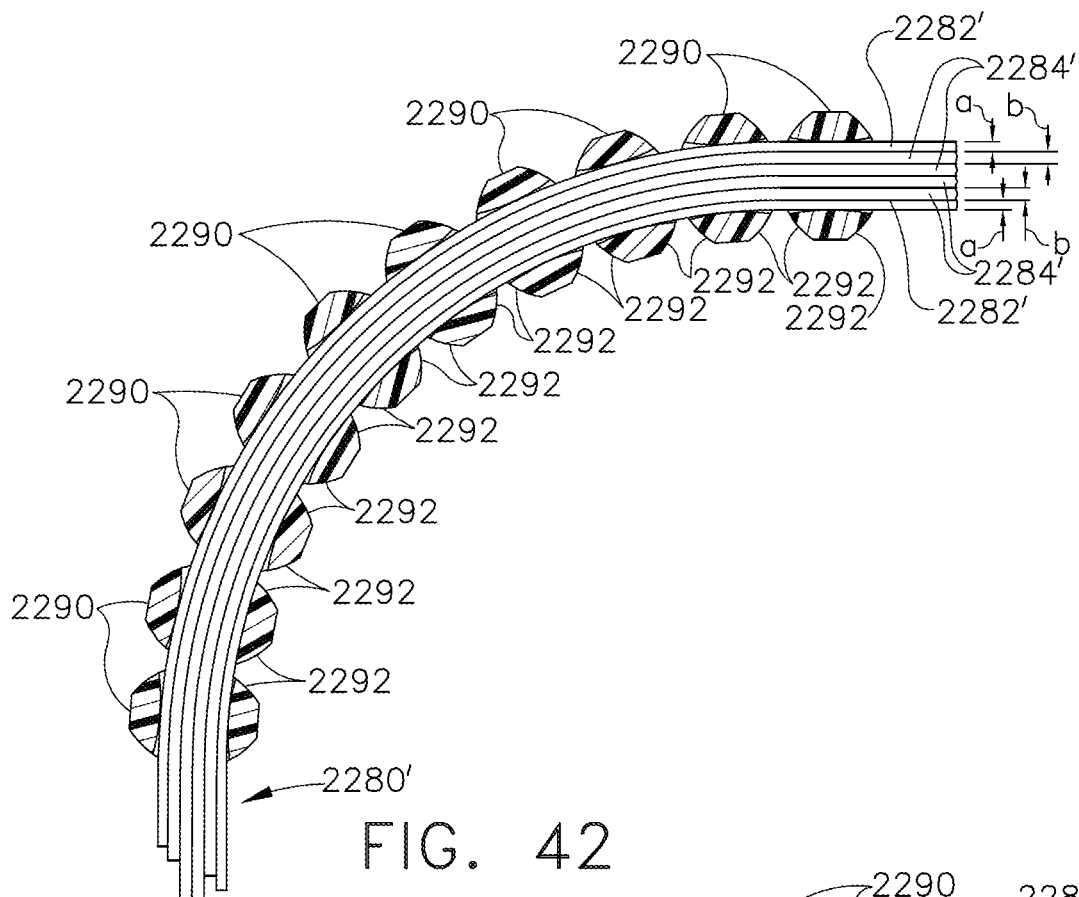
FIG. 42 is a cross-sectional view of a portion of the distal firing beam assembly embodiment of FIGS. 40 and 41 with lateral load carrying members journaled thereon and with the distal firing beam assembly embodiment in a flexed position or configuration.
Figure 43:
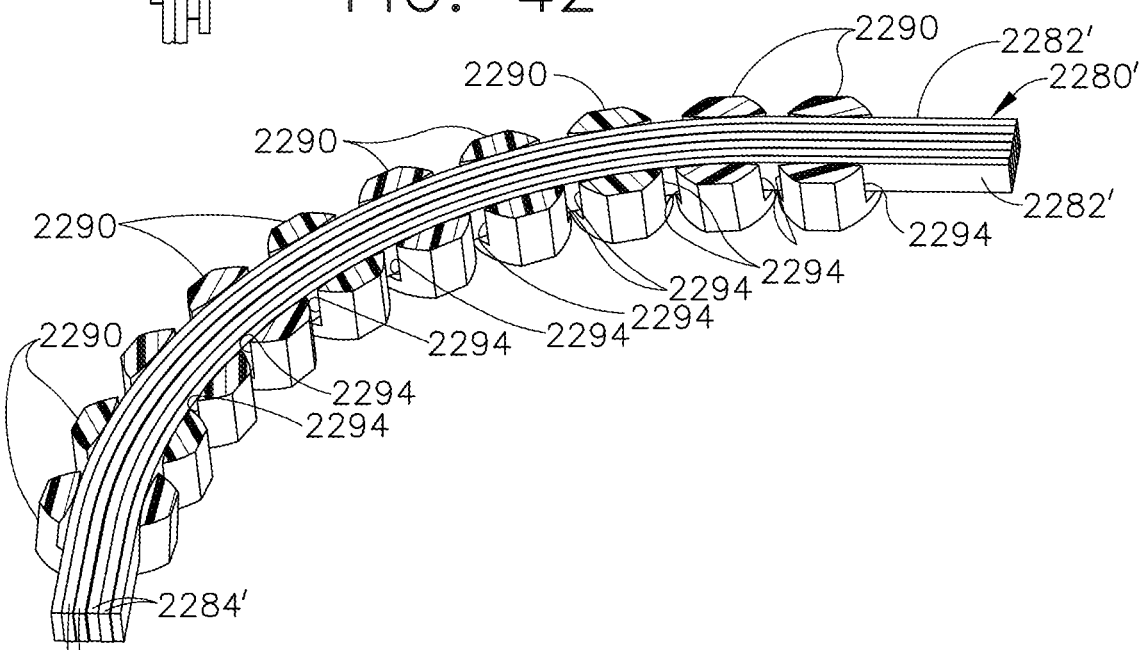
FIG. 43 is a perspective view of the distal firing beam assembly embodiment and lateral load carrying embodiments of FIG. 42.

As can also be seen in FIGS. 42 and 43, the distal firing beam assembly 2280' may be effectively employed with the series of lateral load carrying members 2290 described above. It will be appreciated that the distal firing beam assembly 2280 may also be used in connection with a central articulation bar 2286 in the manner described above so that some of the layers or lateral beams (or bands or laminates) thereof axially advance along the sides of the central articulation bar. In some embodiments, the layers advancing on each side of the central articulation bar 2286 may have the same thickness, composition, shape and configuration. In other arrangements the layer or layers passing along one side of the central articulation bar may have a different thickness and/or composition and/or shape than the thickness and/or composition and/or shape of the layer or layers passing along the opposite side of the central articulation bar, so as to achieve a desired range of travel and flexibility while maintaining a desired amount of stiffness so as to avoid buckling during firing.

Figure 44:
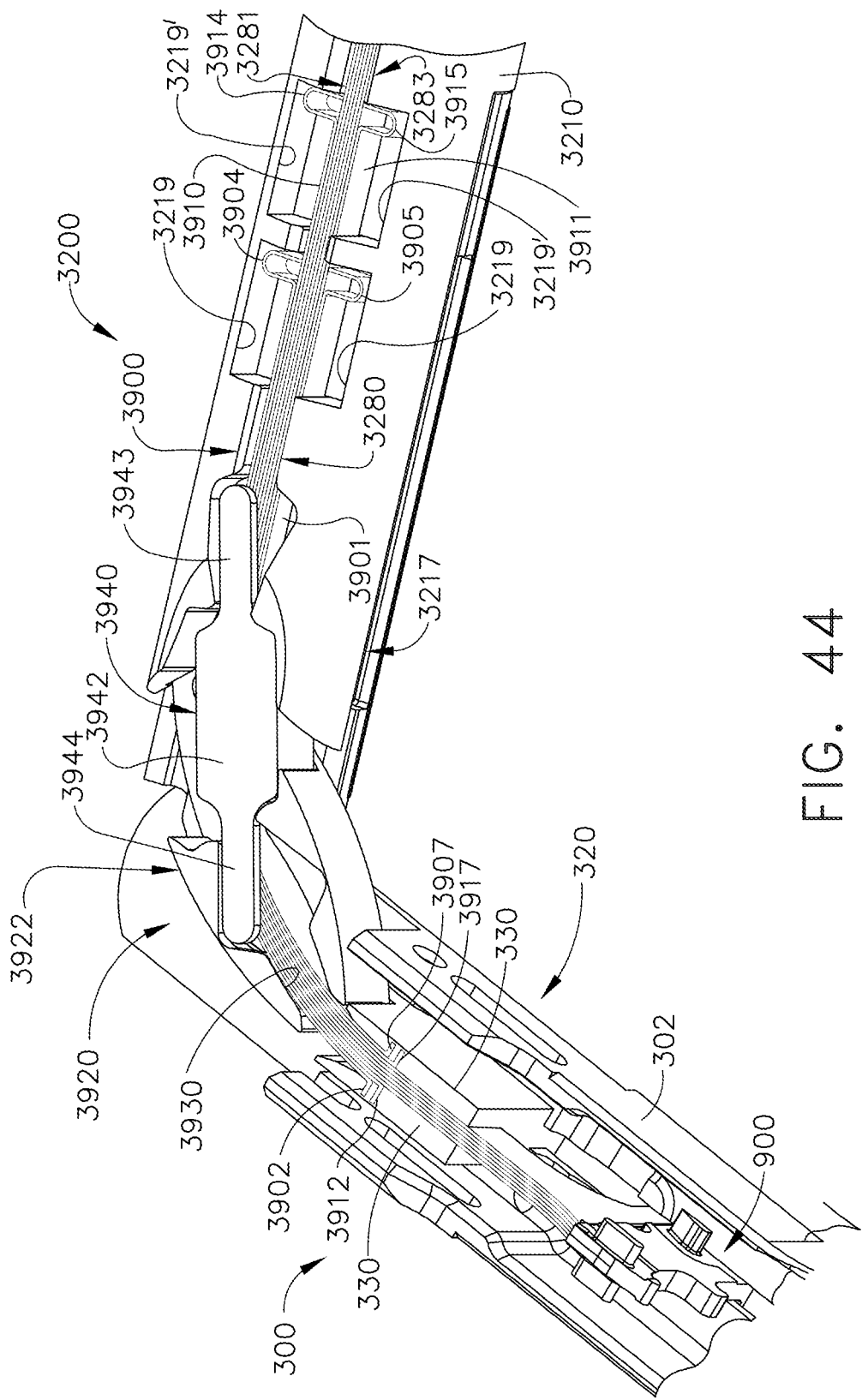
FIG. 44 is a perspective view of portions of another surgical end effector embodiment and elongate shaft assembly embodiment with portions thereof omitted for clarity and with the surgical end effector in an articulated position or configuration.
Figure 45:
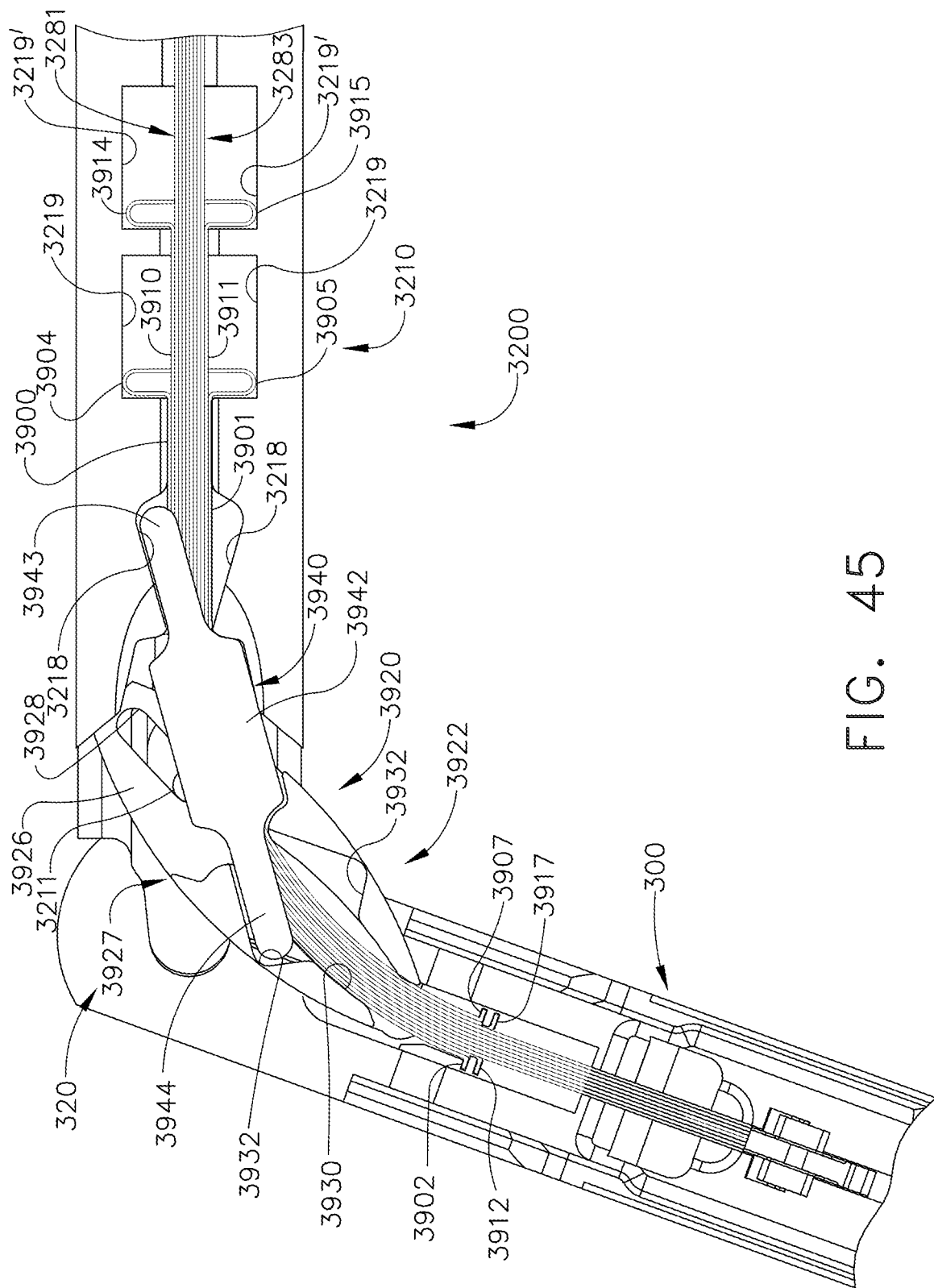
FIG. 45 is a top view of the surgical end effector embodiment and elongate shaft assembly embodiment of FIG. 44.
Figure 46:
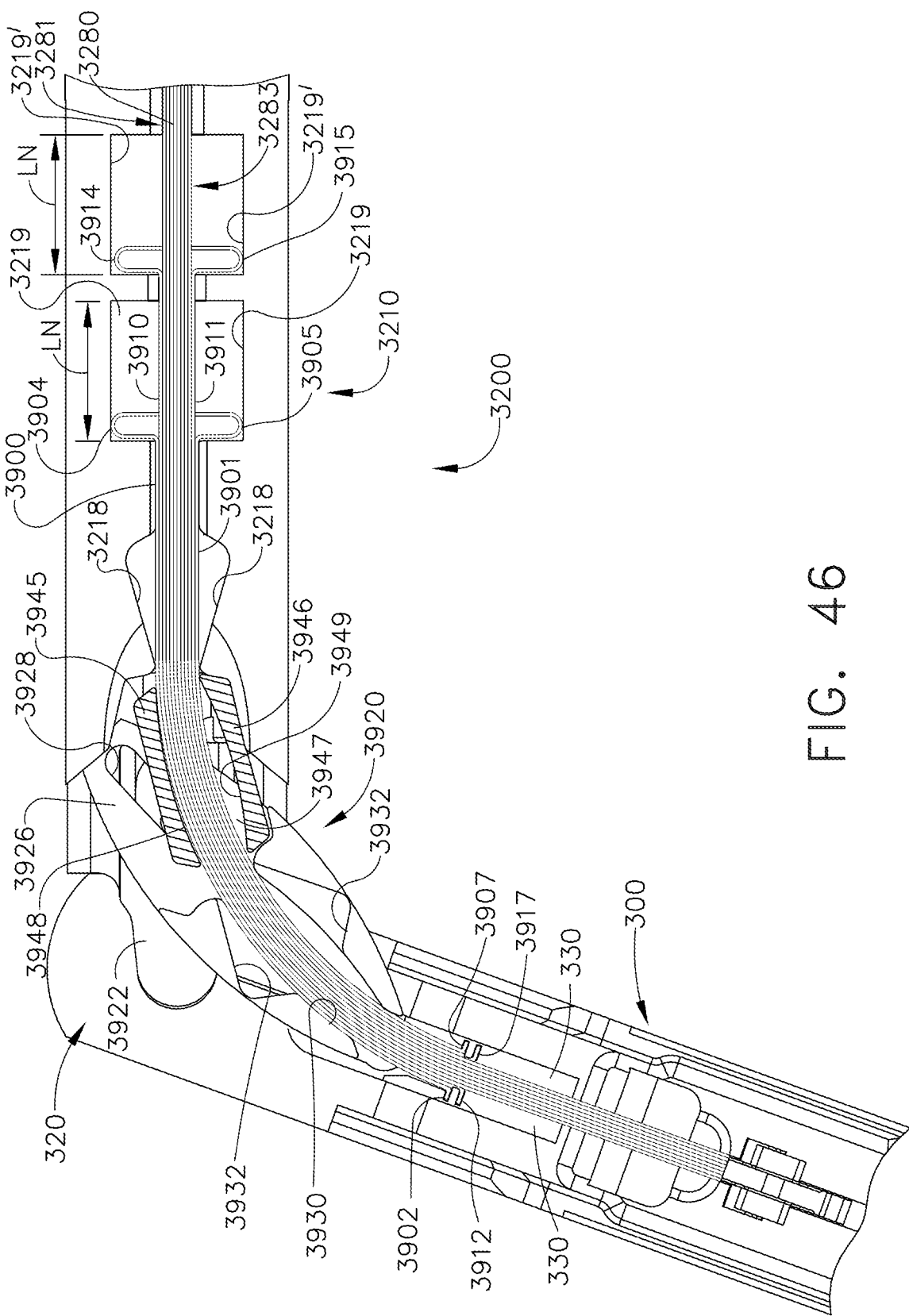
FIG. 46 is another top view of the surgical end effector embodiment and elongate shaft assembly embodiment of FIG. 45 with portions of the pivot link thereof shown in cross-section.

FIGS. 44-46 illustrate a portion of another elongate shaft assembly 3200 that includes a surgical end effector 300 of the type and construction described above. Other forms of surgical end effectors may also be employed. The elongate shaft assembly 3200 also includes a longitudinally movable flexible firing beam assembly 3280 that is attached to a firing member 900. In alternative arrangements, the distal end of the firing beam assembly 3280 may be configured to perform various actions within the surgical end effector without the need for a firing member attached thereto. The flexible firing beam assembly 3280 may comprise a laminated beam arrangement of the various types described herein. In one arrangement, at least two compression bands are employed to provide lateral support to the flexible firing beam assembly 3280 as it traverses the articulation joint. The illustrated embodiment employs a total of four compression bands for providing lateral support to the flexible firing beam as it traverses the articulation joint. For example, the elongate shaft assembly 3200 further includes a spine 3210 that includes a distal end 3217 that has two distal cavities, or notches 3219, and two proximal cavities, or notches 3219', formed therein. One distal cavity 3219 accommodates a first proximal end 3904 of a first compression band 3900 located on one lateral side 3281 of said flexible firing beam assembly 3280 and the other distal cavity 3219 accommodates a second proximal end 3905 of a second compression band 3901 located on another lateral side 3283 of the flexible firing beam assembly 3280. The first compression band 3900 includes a first distal end 3902 that is mounted within a corresponding upstanding lateral support wall 330 formed on the proximal end 320 of the elongate channel 302 of the surgical end effector 300. Similarly, the second compression band 3901 includes a second distal end 3907 that is also mounted within a corresponding upstanding lateral support wall 330 formed on the proximal end 320 of the elongate channel 302 of the surgical end effector 300. The first and second distal compression bands 3900, 3901 may be fabricated from spring steel or the like and the proximal ends 3904, 3905 may be folded in a U-shaped fashion to form a biasing portion configured to be movably received within the distal notches 3219 as shown. Such arrangement permits the first and second distal compression bands 3900, 3901 to flex in response to the articulation of the surgical end effector 300 while retaining the proximal ends 3904, 3905 within their corresponding distal notches 3219.

As can also be seen in FIGS. 44-46, the elongate shaft assembly 3200 further includes a third compression band 3910 and a fourth compression band 3911. Like the first and second compression bands 3900, 3901, the third and fourth compression bands 3910, 3911 may be fabricated from spring steel. As can be seen in FIGS. 44-46, the third compression band 3910 may be situated between the first compression band 3900 and the lateral side 3281 of the flexible firing beam assembly 3280 and the fourth compression band 3911 may be situated between the second compression band 3901 and the another lateral side 3283 of the flexible firing band assembly 3280. The third proximal end 3914 of the third compression band 3910 as well as the fourth proximal end 3915 of the fourth compression band 3911 may each be folded in a U-shaped fashion to form a biasing portion that is movably received within a corresponding proximal cavity 3219' in the spine 3210. The third distal end 3912 of the third compression band 3910 and the fourth distal end 3917 of the fourth compression band 3911 are mounted in a corresponding lateral support wall 330 in the surgical end effector 300.

The elongate shaft assembly 3200 further comprises a movable support link assembly 3920 for providing further lateral support to the flexible firing beam assembly 3280 as the end effector 300 is articulated about the articulation axis.

As can be seen in FIGS. 44-46, the movable support link assembly 3920 comprises a middle support member 3922 that is movably coupled to the surgical end effector 300 as well as the elongate shaft assembly 3200. In one embodiment, the middle support member 3922 is pivotally pinned to the proximal end 320 of the elongate channel 302. The middle support member 3922 further includes a proximally protruding tab 3926 that has an elongate proximal slot 3928 therein. The proximal slot 3928 is configured to slidably receive a middle support pin 3211 formed on the spine 3210. Such arrangement permits the relative pivotal and axial movement between the middle support member 3922 and the spine 3210 of the elongate shaft assembly 3200 so as to accommodate a larger range of articulation while being able to dynamically move so as to maintain adequate lateral support on the firing beam assembly 3280. As can be seen in FIGS. 44-46, the middle support member 3922 further includes centrally disposed slot 3930 for axially receiving the firing beam assembly 3280 therethrough.

As can be further seen in FIGS. 44-46, the movable support link assembly 3920 further comprises an elongate movable pivot link 3940. The pivot link 3940 includes a central body portion 3942 that has proximally protruding proximal nose portion 3943 and a distally-protruding distal nose portion 3944. The pivot link 3940 further includes a first downwardly-protruding lateral support wall 3945 and a second downwardly protruding lateral support wall 3946 that define a beam slot 3947 therebetween. As can be seen in FIG. 46, the firing beam assembly 3280 is configured to extend between the first and second lateral support walls 3945, 3946 during actuation of the firing beam assembly 3280 and articulation of the surgical end effector 300. Further, in the illustrated arrangement, for example, the first compression band 3900 extends between the first lateral support wall 3945 and the third compression band 3910 and the second compression band 3901 extends between the second lateral support wall 3946 and the fourth compression band 3911. The first lateral support wall 3945 includes an inwardly facing first arcuate surface 3948 and the second lateral support wall 3946 includes an inwardly facing second arcuate surface 3949. The first and second arcuate surfaces 3948, 3949 serve to provide lateral support to the firing beam assembly 3280 as it flexes during articulation of the end effector 300. The radiused surfaces may match the outer radius of the firing beam assembly 3280 and compression bands 3900, 3901, 3910, 3911 depending upon the direction and degree of articulation. As can also be seen in FIGS. 44 and 45, the distal end 3217 of the spine 3210 includes a pair of right and left opposing shaft notches 3218 into which the rounded proximally-protruding proximal nose portion 3943 of the pivot link 3940 extends depending upon the direction in which the surgical end effector is articulated about the articulation axis. Similarly, right and left opposed support notches 3932 are provided in the middle support 3922 to accommodate the distally-protruding distal nose portion 3944 of the pivot link 3940 depending upon the direction in which the end effector is articulated. Such notch arrangements serve to properly align the pivot link 3940 in an orientation suited to accommodate the direction of articulation while affording lateral support to the pivot link 3940.

Figure 47:
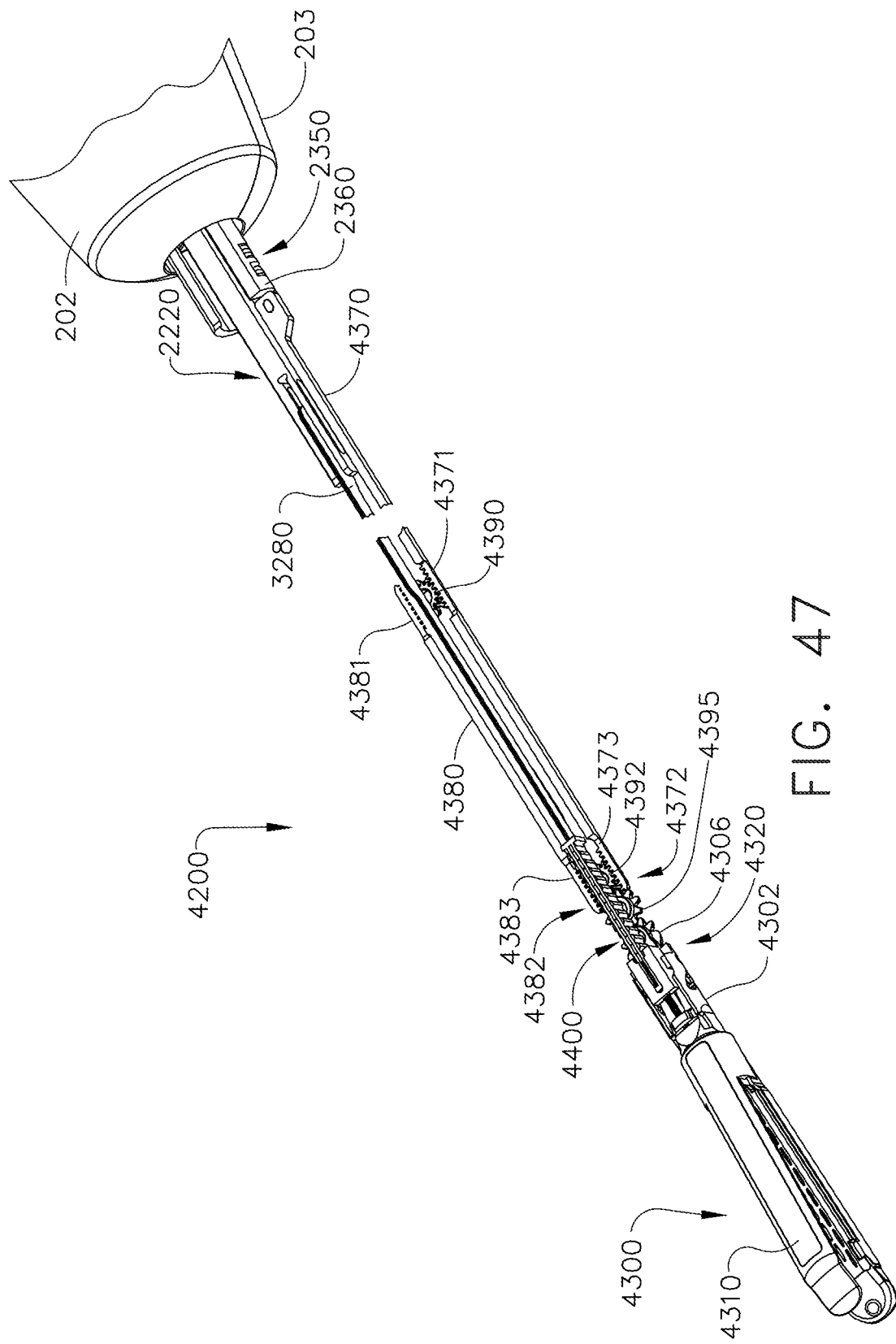
FIG. 47 is a partial perspective view of portions of another surgical end effector embodiment and elongate shaft assembly embodiment with portions thereof omitted for clarity.
Figure 50:
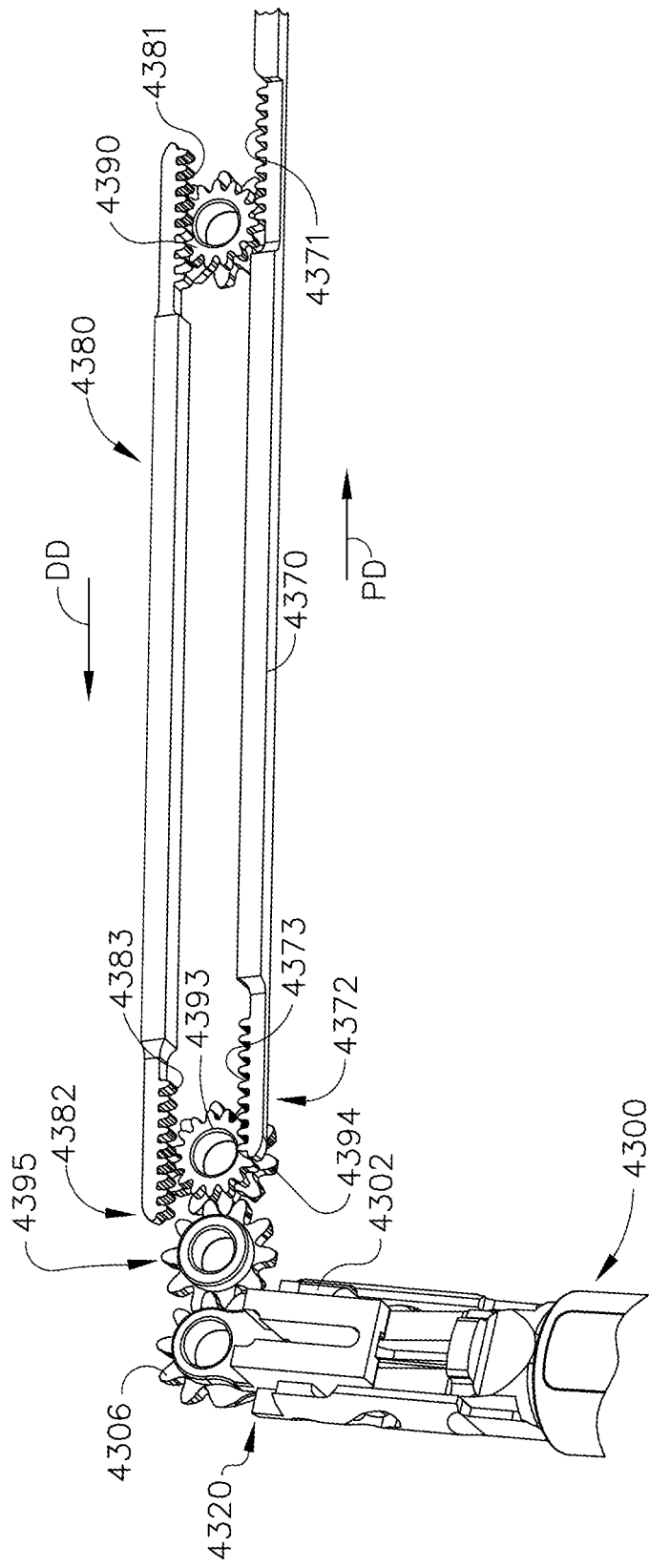
FIG. 50 is a top perspective view of portions of the surgical end effector embodiment and elongate shaft assembly embodiment of FIGS. 47-49 with portions thereof omitted for clarity and the surgical end effector in an articulated position or configuration.

FIGS. 47-51 illustrate another elongate shaft assembly 4200 that is, in some aspects, similar to the elongate shaft assembly 2200 described above, except for various differences discussed in further detail below. Those components of the elongate shaft assembly 2200 that have been discussed in detail above will contain like element numbers and, for the sake of brevity, will not be further discussed in great detail beyond that which may be necessary to understand the operation of elongate shaft assembly 4200 when, for example, employed with portions of the surgical instrument 10 as described above. As can be seen in FIG. 47, in at least one example, the elongate shaft assembly 4200 includes an articulation lock 2350. As was discussed in detail above, the articulation lock assembly 2350 includes a proximal lock adapter 2360 that is coupled (e.g., pinned) to a first distal articulation driver 4370. As can be seen in FIGS. 47 and 50, the first distal articulation driver 4370 includes a first proximal gear rack segment 4371 and a first distal gear rack segment 4373 formed on a distal end 4372 thereof. The elongate shaft assembly 4200 also includes a second distal articulation driver 4380 that includes a second proximal gear rack segment 4381 and a second distal gear rack segment 4383 that is formed on a distal end 4382 thereof.

Figure 51:
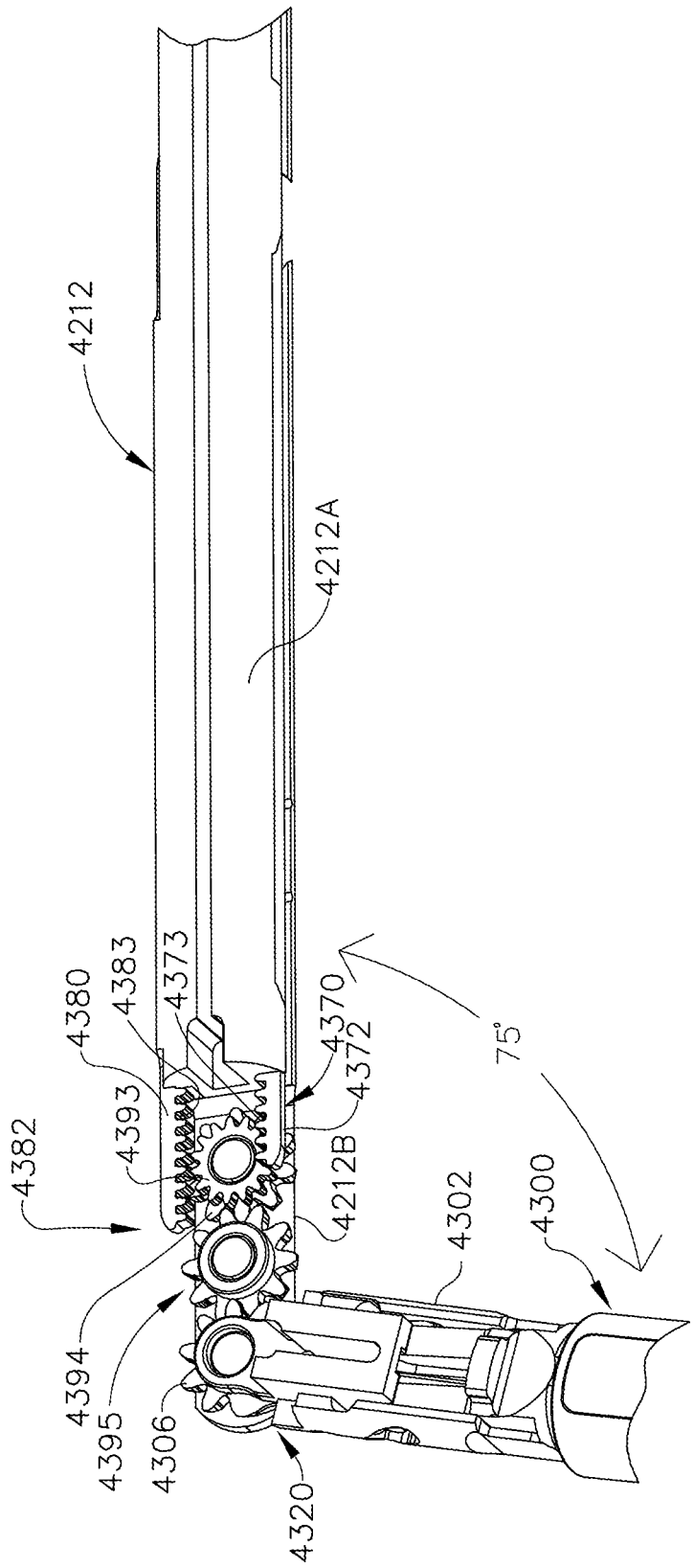
FIG. 51 is another top perspective view of portions of the surgical end effector embodiment and elongate shaft assembly embodiment of FIG. 50.

The first distal articulation driver 4370 and the second distal articulation driver 4380 are configured to move axially relative to the distal spine assembly 4212 in the proximal direction "PD" and the distal direction "DD". As can be seen in FIG. 50, the first proximal gear rack segment 4371 and the second proximal gear rack segment 4381 are in meshing engagement with a proximal power transfer gear 4390 that is rotatably supported by the distal spine assembly 4212. Likewise, the first distal gear rack segment 4373 and the second distal gear rack segment 4383 are in meshing engagement with a distal power transfer gear assembly 4392. In particular, in at least one arrangement, the distal power transfer gear assembly 4392 includes a pinion gear 4393 that is in meshing engagement with the first distal gear rack segment 4373 and the second distal gear rack segment 4383. The distal power transfer gear assembly 4392 further includes a drive gear 4394 that is arranged in meshing engagement with an idler gear 4395. The idler gear 4395 is, in turn, supported in meshing engagement with a driven gear 4306 that is formed on the proximal end portion 4320 of the elongate channel 4302 of a surgical end effector 4300. The surgical end effector 4300 may otherwise be similar to the surgical end effector 2300 and include an anvil 4310 that may be opened and closed in the various manners described above. Referring to FIGS. 48, 49 and 51, the distal spine assembly 4212 may comprise an upper spine portion 4212A and a lower spine portion 4212B. The distal power transfer gear assembly 4392, the idler gear 4395 and the driven gear portion 4306 of the elongate channel 4302 are each pivotally attached to or supported on the bottom portion 4212B of the distal spine assembly 4212.

Figure 52:
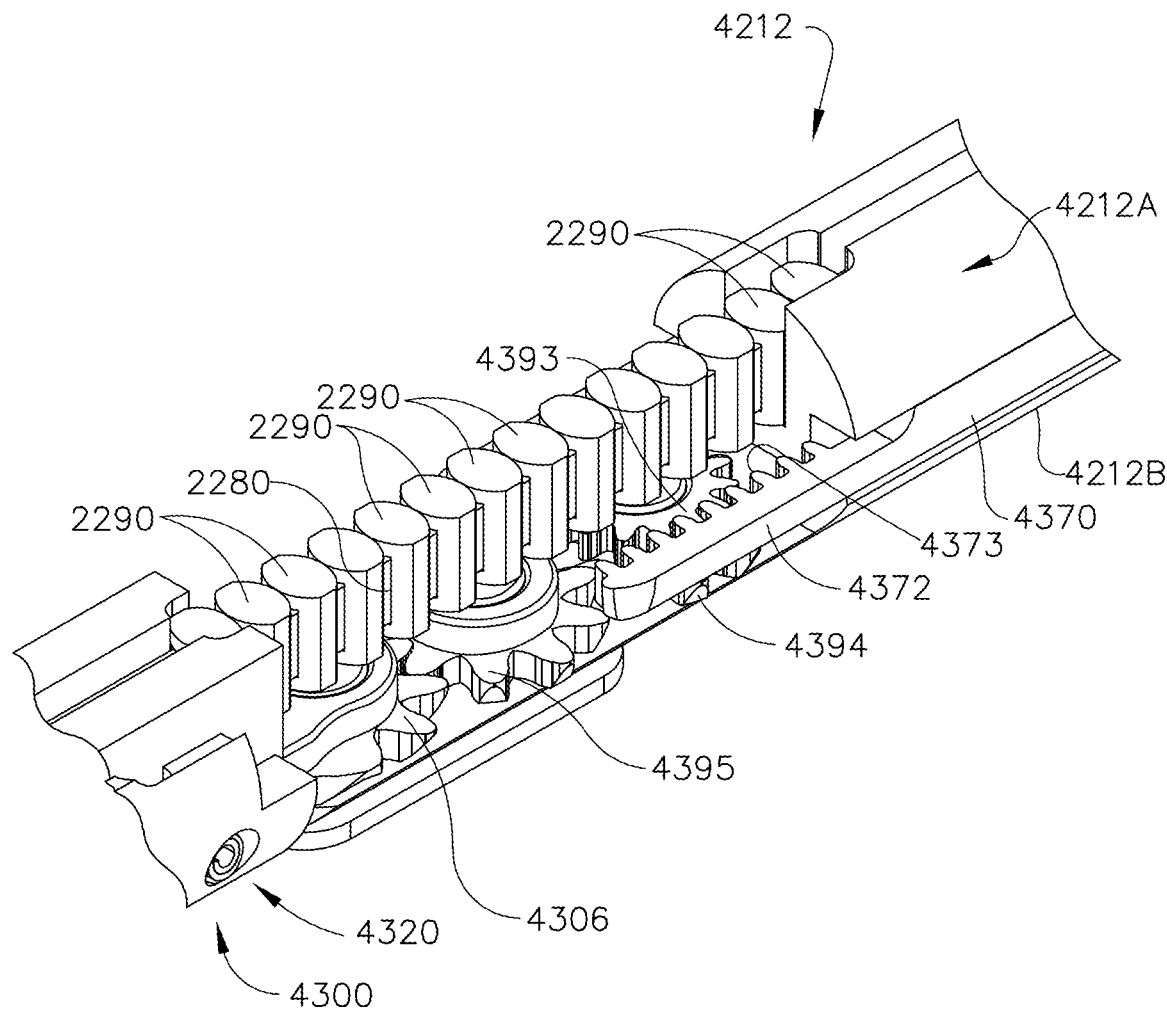
FIG. 52 is an enlarged perspective view of portions of the surgical end effector embodiment and elongate shaft assembly embodiment of FIG. 51.

The elongate shaft assembly 4200 depicted in FIG. 47 includes a firing beam assembly 3280 that is attached to a firing member (not shown). The firing beam assembly 3280 may comprise a laminated beam arrangement of the types described herein. Operation of the firing member was described in detail above and will not be repeated for the sake of brevity. As can also be seen in FIG. 47, a firing beam support member 4400 of the type disclosed in U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309, the entire disclosure of which is hereby incorporated by reference herein, is employed to provide support to the firing beam assembly 3280 during articulation of the surgical end effector 4300. FIG. 52 illustrates use of a distal firing beam assembly 2280 in an elongate shaft assembly 4200. As can be seen in that Figure, a plurality of lateral load carrying members 2290 are employed in the manner described above to provide support to the distal firing beam assembly 2280 as the surgical end effector 4300 is articulated.

FIGS. 53-58 illustrate another elongate shaft assembly 5200 that is, in some aspects, similar to the elongate shaft assembly 2200 described above, except for various differences discussed in further detail below. Those components of the elongate shaft assembly 5200 that have been discussed in detail above with respect to the elongate shaft assembly 2200 will be identified with like element numbers and, for the sake of brevity, will not be further discussed in great detail beyond that which may be necessary to understand the operation of the elongate shaft assembly 5200 when, for example, employed with portions of the surgical instrument 10 as described above.

Figure 53:
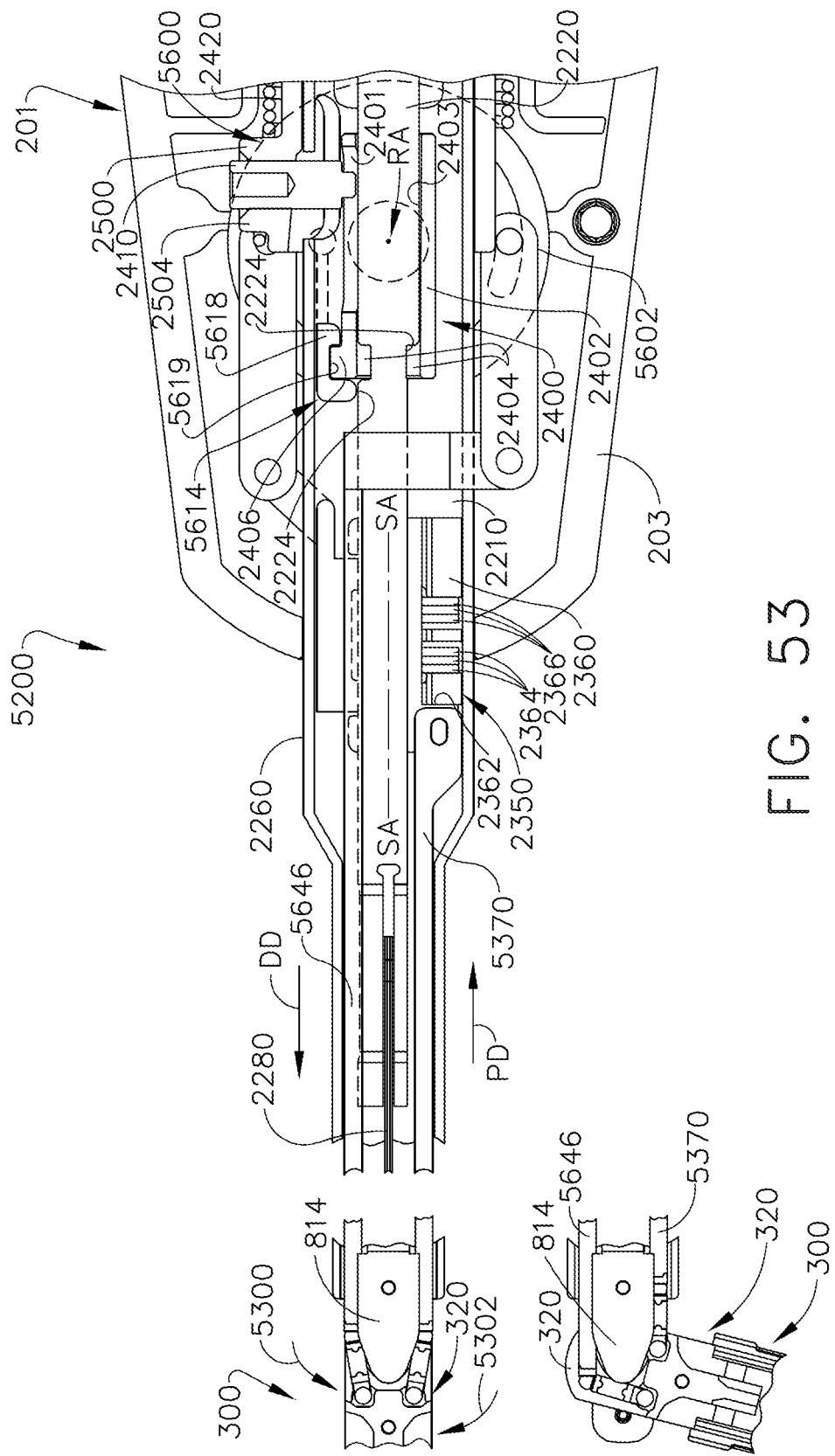
FIG. 53 is a top view of portions of another surgical end effector embodiment and elongate shaft assembly embodiment with portions thereof omitted for clarity and illustrating the surgical end effector in an unarticulated position or configuration and an articulated position or configuration.
Figure 54:
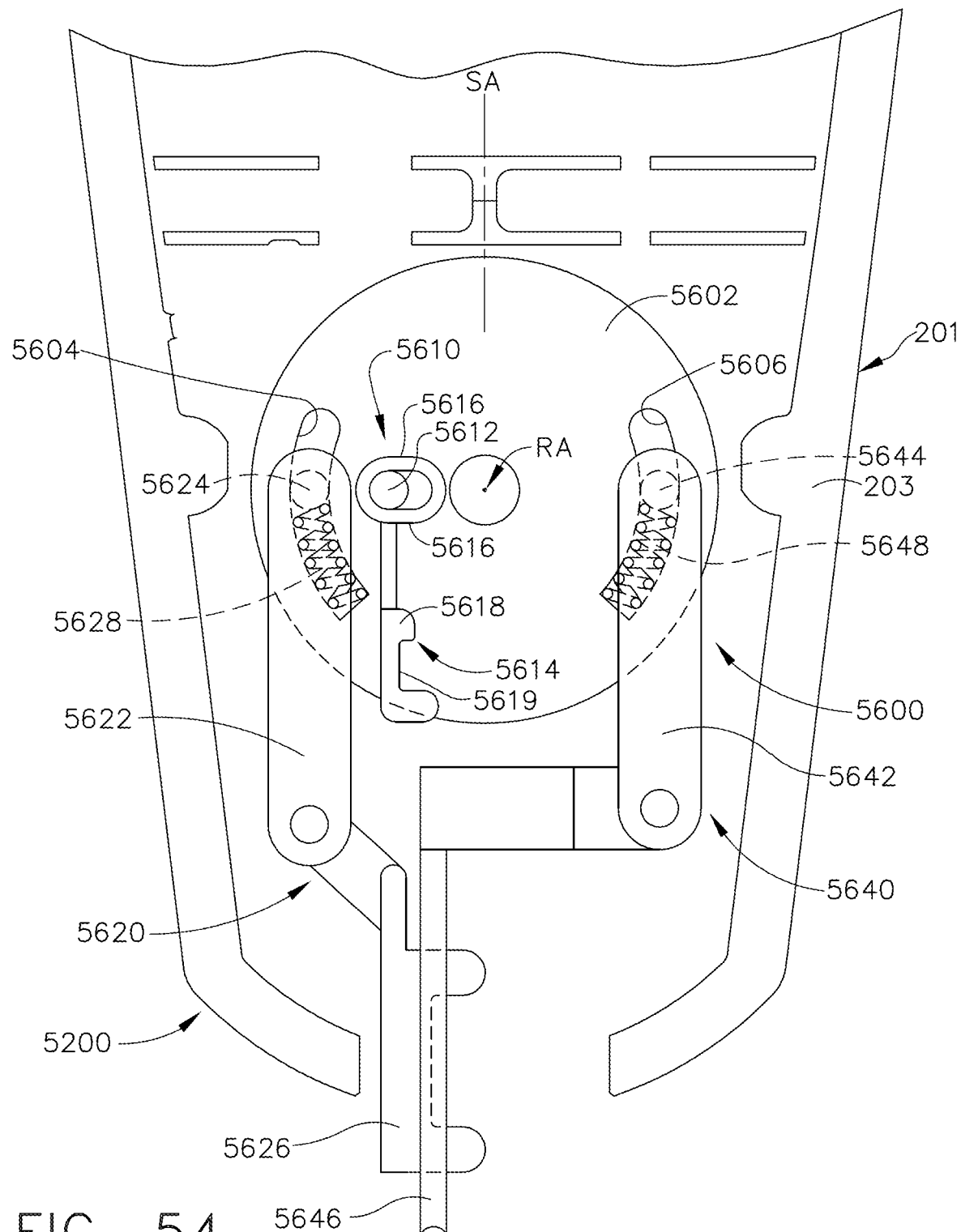
FIG. 54 is a top view of a portion of the elongate shaft assembly embodiment of FIG. 53 with the articulation system in a neutral or unarticulated position or configuration and with portions of the elongate shaft assembly omitted for clarity.
Figure 55:
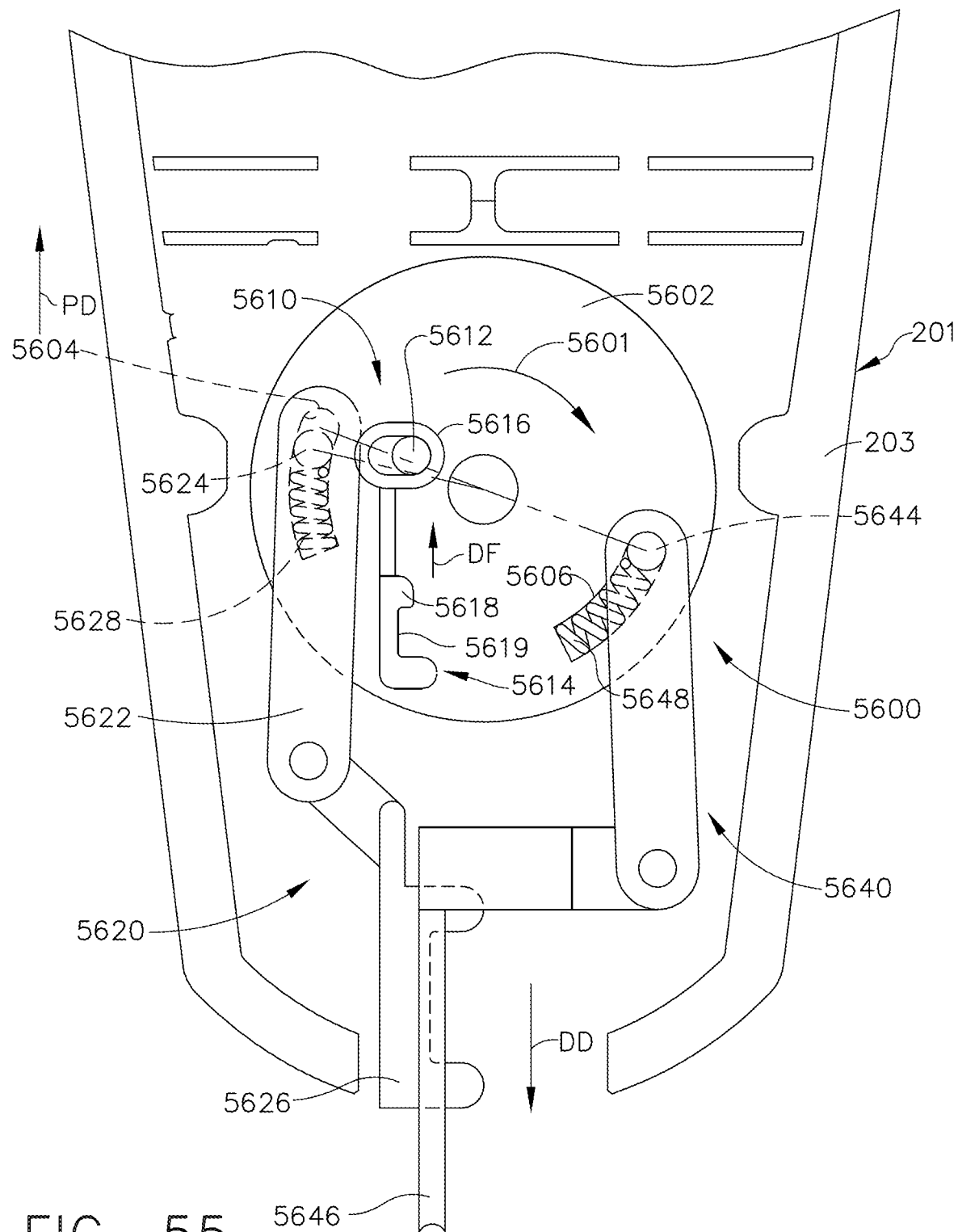
FIG. 55 is another top view of a portion of the elongate shaft assembly embodiment of FIG. 54 with the articulation system in a first articulated position or configuration.
Figure 56:
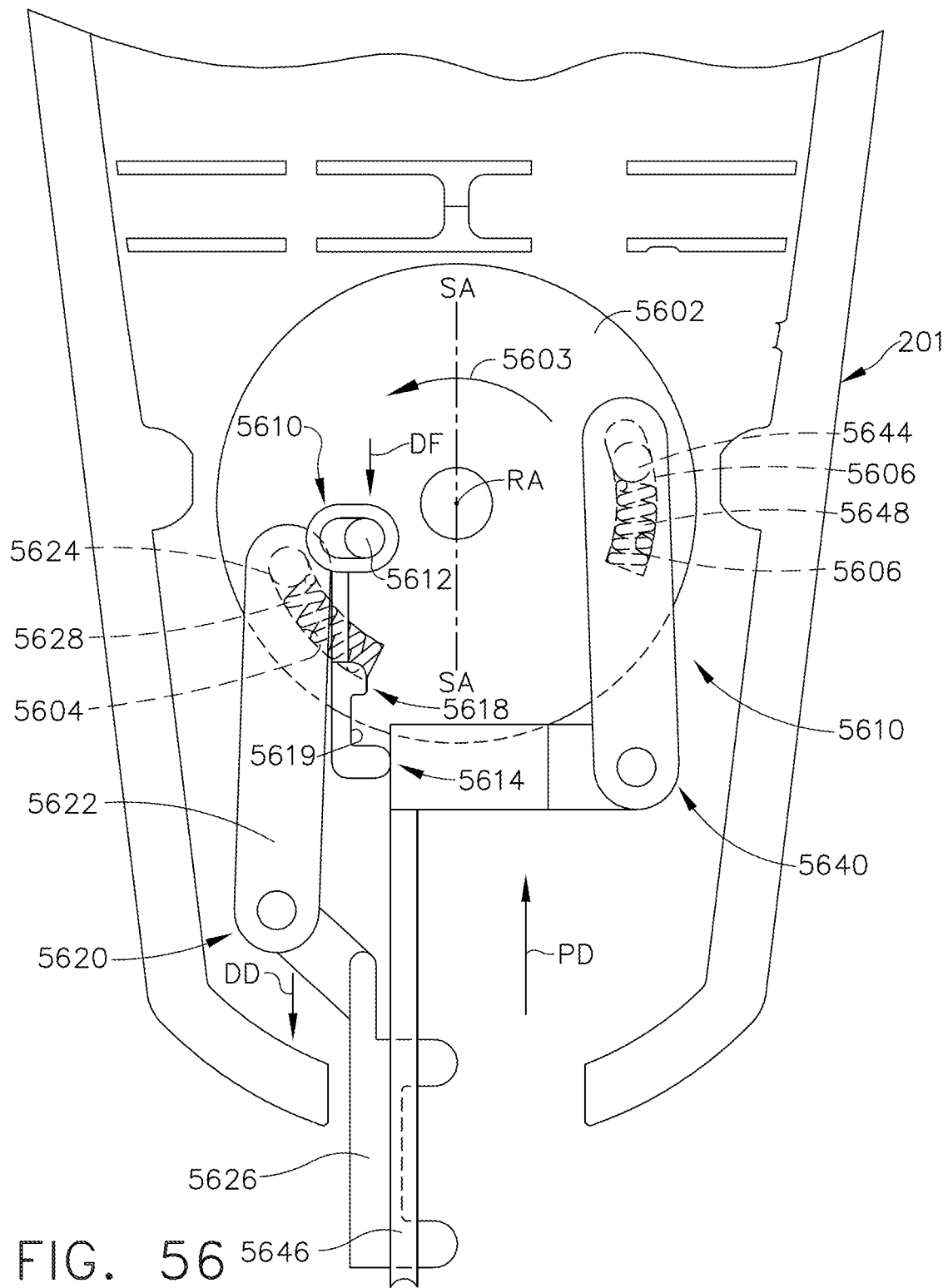
FIG. 56 is another top view of a portion of the elongate shaft assembly embodiment of FIGS. 54 and 55 with the articulation system in a second articulated position or configuration.

Similar to the elongate shaft assembly 2200, the illustrated elongate shaft assembly 5200 includes a clutch assembly 2400 which is configured to operably engage an articulation system 5600 that is configured to apply push and pulling articulation motions to the surgical end effector 300 that is operably coupled thereto. In this embodiment, the clutch assembly 2400 includes a lock collar, or lock sleeve 2402, that is positioned around the firing member 2220 wherein the lock sleeve 2402 can be rotated between an engaged position in which the lock sleeve 2402 operably engages the articulation system 5600 to the firing member 2220 and a disengaged position in which the articulation system 5600 is not operably coupled to the firing member 2220. Referring specifically to FIGS. 54-56, in the illustrated example, the articulation system 5600 comprises an articulation disc or rotary member 5602 that is supported for rotational movement within the nozzle 201. The articulation disc 5602 is rotatably driven by a drive connection assembly 5610. In the illustrated example, the drive connection assembly 5610 includes a drive pin 5612 that is attached to the articulation disc 5602. An articulation drive link 5614 is operably attached to the drive pin 5612 by a connector 5616 that facilitates some movement of the articulation drive link 5614 relative to the drive pin 5612. See FIGS. 54-56. The articulation drive link 5614 includes a drive coupler 5618 that is configured to drivingly engage the outwardly facing lock member 2406 on the lock sleeve 2402. See FIG. 53.

As discussed above, the lock sleeve 2402 can comprise a cylindrical, or at least a substantially cylindrical body including a longitudinal aperture 2403 defined therein configured to receive the firing member 2220. See FIG. 53. The lock sleeve 2402 can comprise diametrically-opposed, inwardly-facing lock protrusions 2404 and an outwardly-facing lock member 2406. The lock protrusions 2404 can be configured to be selectively engaged with the firing member 2220. More particularly, when the lock sleeve 2402 is in its engaged position, the lock protrusions 2404 are positioned within a drive notch 2224 defined in the firing member 2220 such that a distal pushing force and/or a proximal pulling force can be transmitted from the firing member 2220 to the lock sleeve 2402. When the lock sleeve 2402 is in its engaged position, the outwardly facing lock member 2406 is received within a drive notch 5619 in the drive coupler 5618 as shown in FIG. 53 such that the distal pushing force and/or the proximal pulling force applied to the lock sleeve 2402 can be transmitted to the articulation drive link 5614. In effect, the firing member 2220, the lock sleeve 2402, and the articulation drive link 5614 will move together when the lock sleeve 2402 is in its engaged position. On the other hand, when the lock sleeve 2402 is in its disengaged position, the lock protrusions 2404 may not be positioned within the drive notch 2224 of the firing member 2220 and, as a result, a distal pushing force and/or a proximal pulling force may not be transmitted from the firing member 2220 to the lock sleeve 2402. Correspondingly, a drive force "DF" may not be applied to the articulation disc 5602. In such circumstances, the firing member 2220 can be slid proximally and/or distally relative to the lock sleeve 2402 and the proximal articulation driver 2230.

As was also discussed above, the elongate shaft assembly 5200 further includes a switch drum 2500 that is rotatably received on the closure tube 2260. See FIG. 53. The switch drum 2500 comprises a hollow shaft segment 2502 that has a shaft boss 2504 formed thereon for receive an outwardly protruding actuation pin 2410 therein. In various circumstances, the actuation pin 2410 extends into a longitudinal slot 2401 provided in the lock sleeve 2402 to facilitate axial movement of the lock sleeve 2402 when it is engaged with the articulation drive link 5614. A rotary torsion spring 2420 is configured to engage the boss 2504 on the switch drum 2500 and a portion of the nozzle housing 201 to apply a biasing force to the switch drum 2500. As also discussed above, the switch drum 2500 can further comprise at least partially circumferential openings defined therein which can be configured to receive circumferential mounts extending from the nozzle halves and permit relative rotation, but not translation, between the switch drum 2500 and the nozzle housing 201. As described above, rotation of the switch drum 2500 will ultimately result in the rotation of an actuation pin 2410 and the lock sleeve 2402 between its engaged and disengaged positions. Thus, in essence, the nozzle housing 201 may be employed to operably engage and disengage the articulation system 5600 with the firing drive system in the various manners described above as well as in U.S. patent application Ser. No. 13/803,086, now U.S. Patent Application Publication No. 2014/0263541.

Referring again to FIGS. 53-56, the articulation system 5600 of the illustrated example, further includes a "first" or right articulation linkage 5620 and a "second" or left articulation linkage 5640. The first articulation linkage 5620 includes a first articulation link 5622 that includes a first articulation pin 5624 that is movably received within a first articulation slot 5604 in the articulation disc 5602. The first articulation link 5622 is movably pinned to a first articulation connector 5626 that is configured to engage an articulation lock 2350. As discussed above, the articulation lock 2350 can be configured and operated to selectively lock the surgical end effector 300 in position. Such arrangement enables the surgical end effector 300 to be rotated, or articulated, relative to the shaft closure tube 2260 when the articulation lock 2350 is in its unlocked state. When the articulation drive link 5614 is operably engaged with the firing member 2220 via the clutch system 2400, further to the above, the firing member 2220 can rotate the articulation disc 6502 to move the first articulation linkage 5620 proximally and/or distally. Movement of the first articulation connector 5626 of the first articulation linkage 5620, whether it is proximal or distal, can unlock the articulation lock 2350 as was described above. The proximal lock adapter 2360 includes a lock cavity 2362 for receiving therein first lock elements 2364 and second lock elements 2366 that are journaled on a frame rail that extends between the proximal frame 2210 and the distal frame. Operation of the articulation lock 2350 operates in the various manners described above and, for the sake of brevity, will not be further discussed herein. As can be seen in FIG. 53, a first distal articulation driver 5370 is attached to the proximal lock adapter 2360. The first distal articulation driver 5370 is operably attached to the proximal end 320 of the elongate channel 302 of the surgical end effector 300.

As was also indicated above, the articulation system 5600 of the illustrated example, further includes a "second" or left articulation linkage 5640. As can be seen in FIGS. 54-56, the second articulation linkage 5640 includes a second articulation link 5642 that includes a second articulation pin 5644 that is movably received within a second articulation slot 5606 in the articulation disc 5602. The second articulation link 5642 is pinned to a second articulation bar 5646 that is attached to the proximal end 320 of the elongate channel 302 of the surgical end effector 300. Referring to FIG. 54, the articulation system 5600 further includes a first articulation biasing member 5628 that is received within the first articulation slot 5604 and a second articulation biasing member 5648 that is received within the second articulation slot 5606. FIG. 54 illustrates the articulation system 5600 in a neutral or unarticulated configuration. As can be seen in that Figure, the first articulation pin 5624 is in contact with the first articulation biasing member 5628 and the second articulation pin 5644 is in contact with the second articulation biasing member 5648. However, when in that neutral position, the first and second articulation biasing members 5628, 5648 may not be in a compressed state. FIG. 55 illustrates application of the drive force "DF" to the articulation disc 5602 in the proximal direction "PD" by the articulation drive link 5614 in the above-described manner. Application of the drive force DF in the proximal direction PD results in rotation of the articulation disc 5602 in the rotary direction represented by arrow 5601. As the articulation disc 5602 rotates in the rotary direction 5601, the end of the second articulation slot contacts the second articulation pin 5644 and applies a pushing force to the second articulation linkage 5640 and ultimately to the second articulation bar 5646. Conversely, the first articulation biasing member 5628 urges the first articulation pin 5624 in the direction of arrow 5601 within the first articulation slot 5604 such that a pulling force is applied to the first articulation linkage 5620 in the proximal direction "PD". This proximal pulling force is transmitted to the first distal articulation driver 5370 through the articulation lock 2350. Such "pushing and pulling motions" as applied to the surgical end effector causes the surgical end effector 300 to articulate about the articulation axis in the direction represented by arrow 5300. See FIG. 53. When the articulation disc 5602 is in the position illustrated in FIG. 55, the second articulation biasing member 5648 may be in a compressed state and the first articulation biasing member may not be compressed. Thus, when the application of drive force DF to the articulation drive link 5614 is discontinued, the second articulation biasing member 5648 may bias the articulation disc 5602 back to the neutral position shown in FIG. 54, for example.

Conversely, when the drive force "DF" is applied to the articulation drive link 5614 in the distal direction "DD" as shown in FIG. 56, the articulation disc 5602 rotates in the rotary direction represented by arrow 5603. As the articulation disc 5602 rotates in the rotary direction 5603, the end of the first articulation slot 5604 contacts the first articulation pin 5624 and applies a pushing force to the first articulation linkage 5620 and ultimately to the first distal articulation driver 5370 through the articulation lock 2350. In addition, the second articulation biasing member 5648 urges the second articulation pin 5644 in the direction of arrow 5603 within the second articulation slot 5606 such that a pulling force is applied to the second articulation linkage 5640 in the proximal direction "PD". This proximal pulling force is transmitted to the second articulation bar 5646. Such "pushing and pulling motions" as applied to the surgical end effector 300 causes the surgical end effector 300 to articulate about the articulation axis in the direction represented by arrow 5302. See FIG. 53. When the articulation disc 5602 is in the position illustrated in FIG. 56, the first articulation biasing member 5628 may be in a compressed state and the second articulation biasing member 5648 may not be compressed. Thus, when the application of drive force DF to the articulation drive link 5614 is discontinued, the first articulation biasing member 5628 may bias the articulation disc 5602 back to the neutral position shown in FIG. 54, for example.

Figure 57:
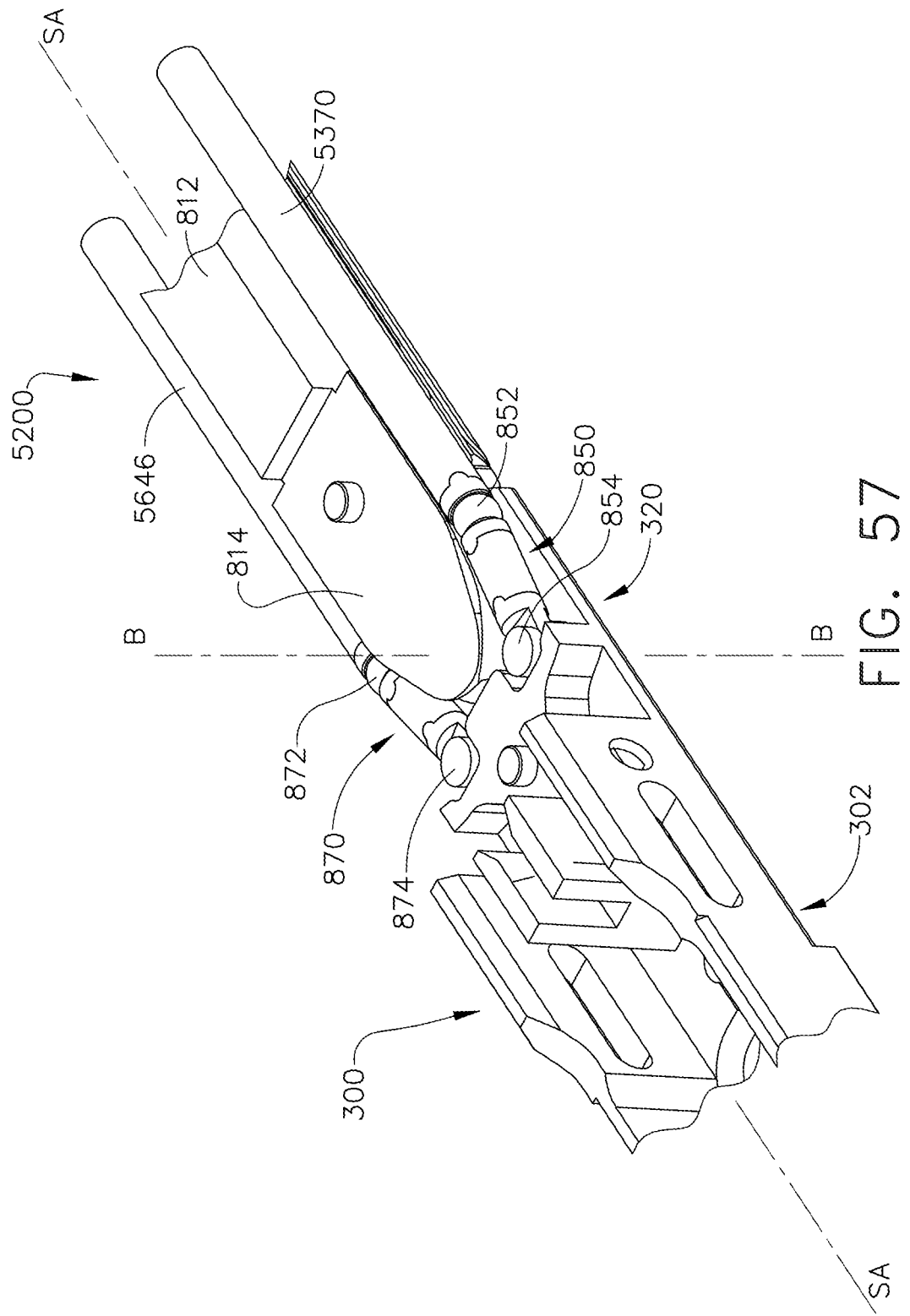
FIG. 57 is a partial perspective view of other portions of the elongated shaft assembly embodiment of FIGS. 53-56 and portions of the surgical end effector embodiment in an unarticulated position or configuration and with portions thereof omitted for clarity.

FIG. 57 illustrates the attachment of the distal end portion 814 of the shaft frame 812 to the surgical end effector 300 that is operably coupled to the elongate shaft assembly 5200. As described above, the distal end portion 814 has a downwardly protruding pivot pin (not shown) thereon that is adapted to be pivotally received within a pivot hole (not shown) that is formed in the proximal end portion 320 of the elongate channel 302. Such arrangement facilitates pivotal travel of the elongate channel 302 relative to the shaft frame 812 about an articulation axis B-B defined by the pivot hole. As can also be seen in FIG. 57, the first distal articulation driver 5370 is attached to a first coupler 850 by a first ball joint 852. The first coupler 850 is also pivotally pinned to the proximal end portion 320 of the elongate channel 302 by a first pin 854 as can be seen in FIG. 57. Similarly, the second articulation bar 5646 is attached to a second coupler 870 by a second ball joint 872. The second coupler 870 is also pivotally pinned to the proximal end portion 320 of the elongate channel 302 by a second pin 874 as can be seen in FIG. 57.

Figure 58:
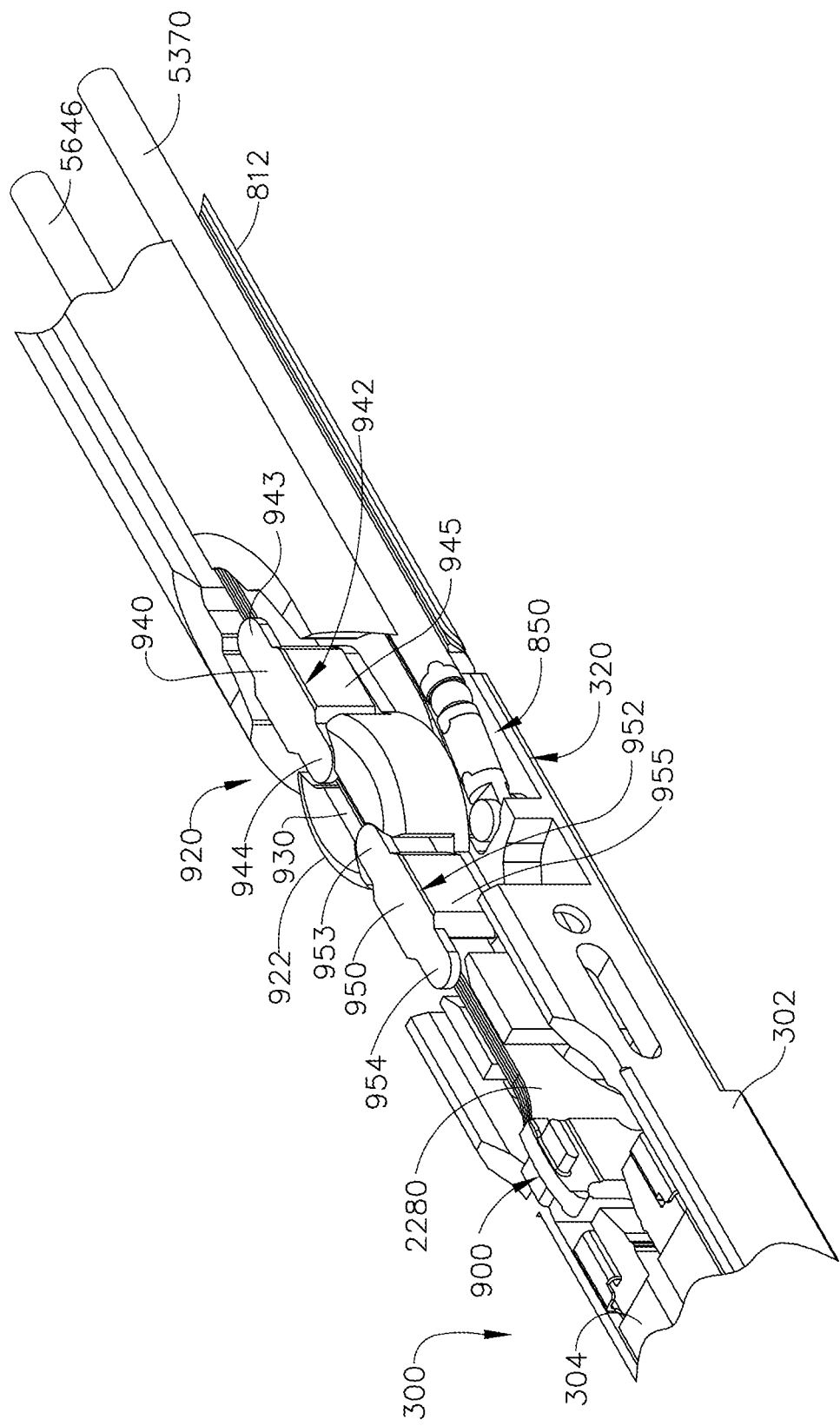
FIG. 58 is another partial perspective view of the surgical end effector embodiment and elongate shaft assembly embodiment of FIG. 57 with portions thereof omitted for clarity.

Referring to FIGS. 53 and 58, the elongate shaft assembly 5200 may also include a firing beam assembly 2280 that is attached to a firing member 900 of the type described above. The firing beam assembly 2280 is attached to the firing member 2220 and may be axially advanced and retracted in the various manners described above. The elongate shaft assembly 5200 may further comprise a multiple support link assembly 920 for providing lateral support to the distal firing beam 2280 as the surgical end effector 300 is articulated about the articulation axis B-B. As can be seen in FIG. 58, the multiple support link assembly 920 comprises a middle support member 922 that is pivotally pinned to the proximal end 320 of the elongate channel 302 in the manners described above. The middle support member 922 further includes centrally disposed slot 930 for axially receiving the distal firing beam 2280 therethrough. The multiple support link assembly 920 further comprises a proximal support link 940 and a distal support link 950. The proximal support link 940 includes a body portion 942 that has a rounded proximal end 943 and a rounded distal end 944. The proximal support link 940 further includes a pair of downwardly protruding lateral support walls 945 that define a proximal slot therebetween. Similarly, the distal support link 950 includes a body portion 952 that has a rounded proximal end 953 and a rounded distal end 954. The distal support link 950 further includes a pair of downwardly protruding lateral support walls 955 that define a distal slot therebetween. As can be seen in FIG. 58, the distal firing beam 2280 is configured to extend between the lateral support walls 945 of the proximal support link 940 and the lateral support walls 955 of the distal support link 950. Each support wall 945 and 955 includes an inwardly facing arcuate surface as was described above. The support surfaces serve to provide lateral support to the distal firing beam 2280 as it flexes during articulation of the surgical end effector 300. In addition, the closure tube assembly 2260 may include a double pivot closure sleeve assembly of the type described above that is configured to operably interact with the anvil on the surgical end effector 300. Operation of the closure tube assembly 2260 results in the opening and closing of the anvil of the surgical effector in the various manners described above.

Figure 59:
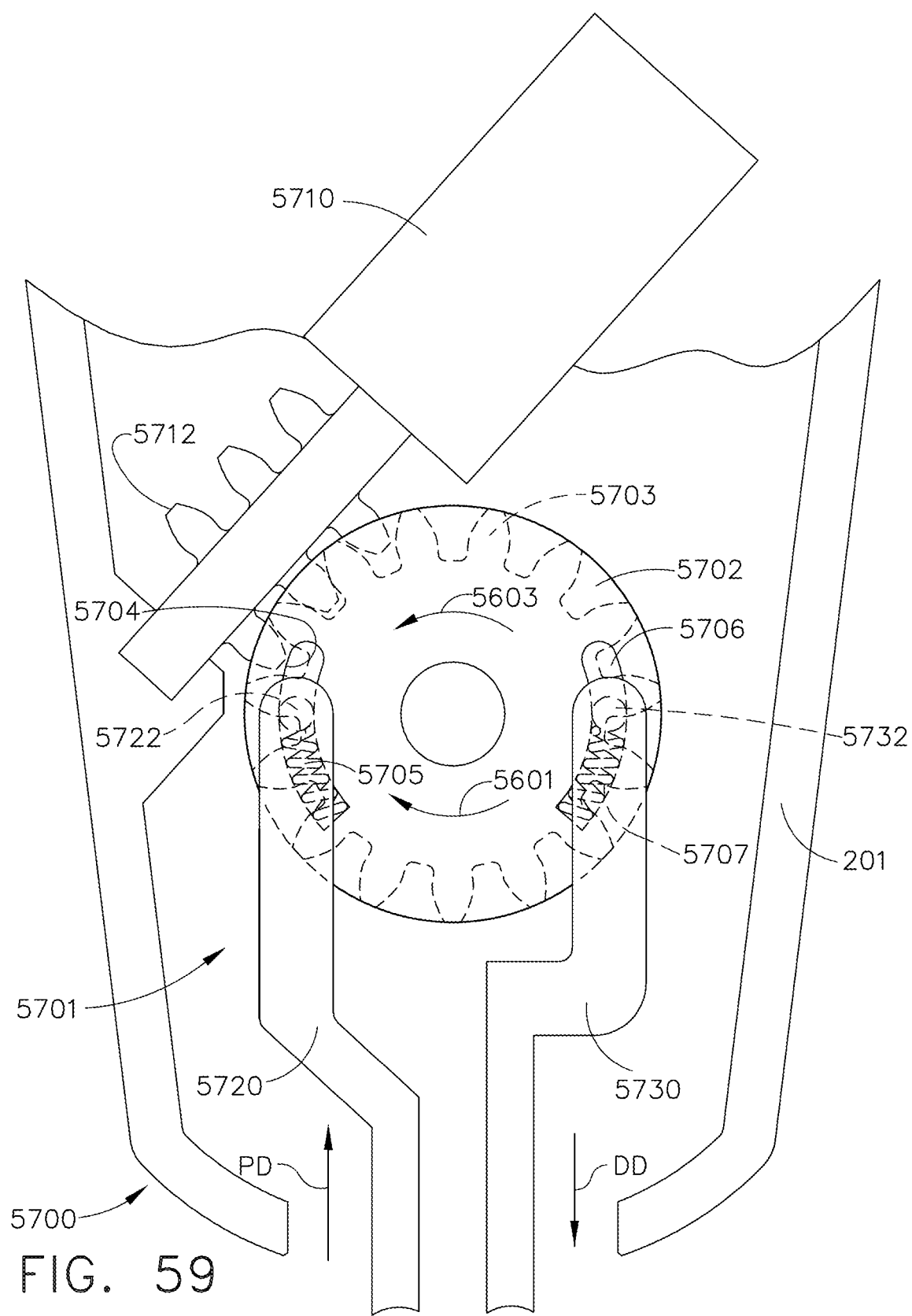
FIG. 59 is a top view of a portion of another elongate shaft assembly embodiment with portions thereof omitted for clarity.

FIG. 59 illustrates a portion of another elongate shaft assembly 5700 that may be substantially similar to the elongate shaft assembly 5200 except for the differences discussed below. In particular, the articulation disc 5702 of the articulation system 5701 is rotated by a worm gear motor 5710 that is operably supported in the nozzle housing 201. In one embodiment, for example, a driven gear 5703 is integrally formed or otherwise non-movably attached to the articulation disc 5702 such that it is in meshing engagement with the worm gear drive 5712 of the motor 5710. In the illustrated example, a first articulation rod or member 5720 may be directly attached to a portion of a surgical end effector in any of the various manners described herein. A first articulation pin 5722 is attached to the first articulation rod 5720 and is received within an arcuate first articulation slot 5704 formed in the articulation disc 5702. A first articulation biasing member 5705 is received within the first articulation slot 5704 for biasing contact with the first articulation pin 5722. Likewise, a second articulation rod or member 5730 may be directly or indirectly attached to a portion of a surgical end effector in any of the various manners described herein. A second articulation pin 5732 is attached to the second articulation rod 5730 and is received within an arcuate second articulation slot 5706 formed in the articulation disc 5702. A second articulation biasing member 5707 is received within the second articulation slot 5706 for biasing contact with the second articulation pin 5732.

FIG. 59 illustrates the articulation system 5701 in a neutral or unarticulated configuration. As can be seen in that Figure, the first articulation pin 5722 is in contact with the first articulation biasing member 5705 and the second articulation pin 5732 is in contact with the second articulation biasing member 5707. However, when in that neutral position, the first and second articulation biasing members 5705, 5707 may not be in a compressed state. Actuation of the motor 5710 to rotate the articulation disc 5702 in the rotary direction represented by arrow 5601 will apply a pulling motion to the first articulation rod 5720 to cause the first articulation rod 5720 to move in the proximal direction "PD" as well as to apply a pushing motion to the second articulation rod 5730 to cause the second articulation rod 5730 to move in the distal direction "DD". Conversely, actuation of the motor 5710 to rotate the articulation disc 5702 in the rotary direction represented by arrow 5603 will apply a pushing motion to the first articulation rod 5720 to cause the first articulation rod 5720 to move in the distal direction "DD" as well as to apply a pulling motion to the second articulation rod 5730 to cause the second articulation rod 5730 to move in the proximal direction "PD". Such "pushing and pulling motions" as applied to the surgical end effector, causes the surgical end effector to articulate about the articulation axis in the various manners described above.

FIGS. 60-65 illustrate another articulation system 5800 that may be employed with various elongate shaft assemblies and effector arrangements described herein. In this embodiment, however, the articulation system 5800 comprises a dual articulation disc assembly 5810 that comprises a driver articulation disc 5820 and a driven articulation disc 5830. Both of the articulation discs 5820, 5830 may, for example, be rotatably supported within the nozzle housing of the elongate shaft assembly such that both discs 5820, 5830 are independently rotatable about a common axis. In various embodiments, drive motions may be applied to the driver articulation disc 5820 by an articulation drive link 5614 and firing member arrangement 2220 as was described above. In other embodiments, rotary drive motions may be applied to the driver articulation disc 5820 by a worm gear motor 5710 in the manner described above.

Figure 62:
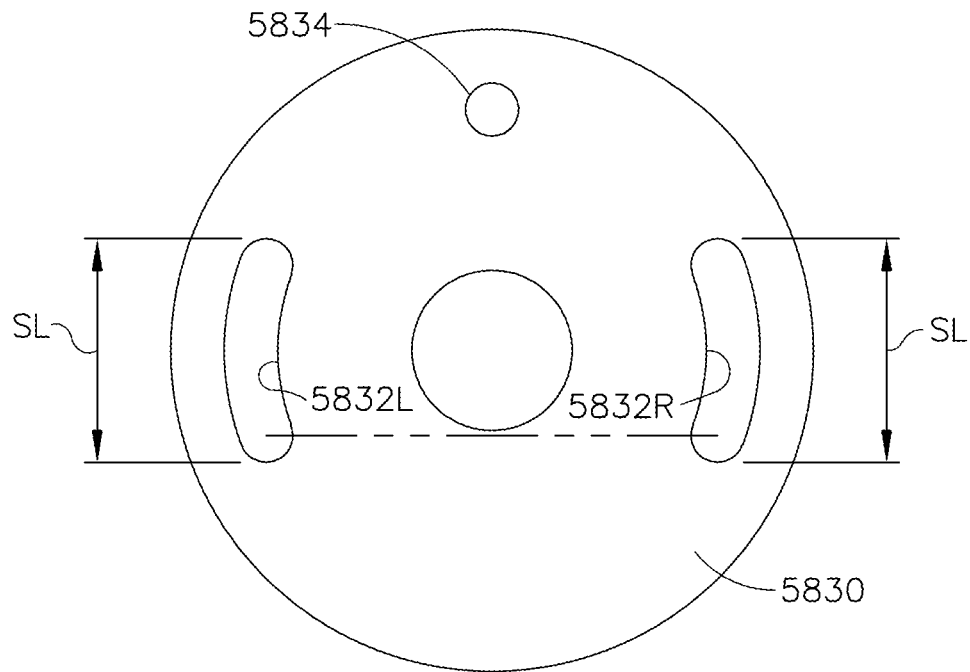
FIG. 62 is a top view of a driven articulation disc embodiment of the articulation system FIG. 60.
Figure 61:
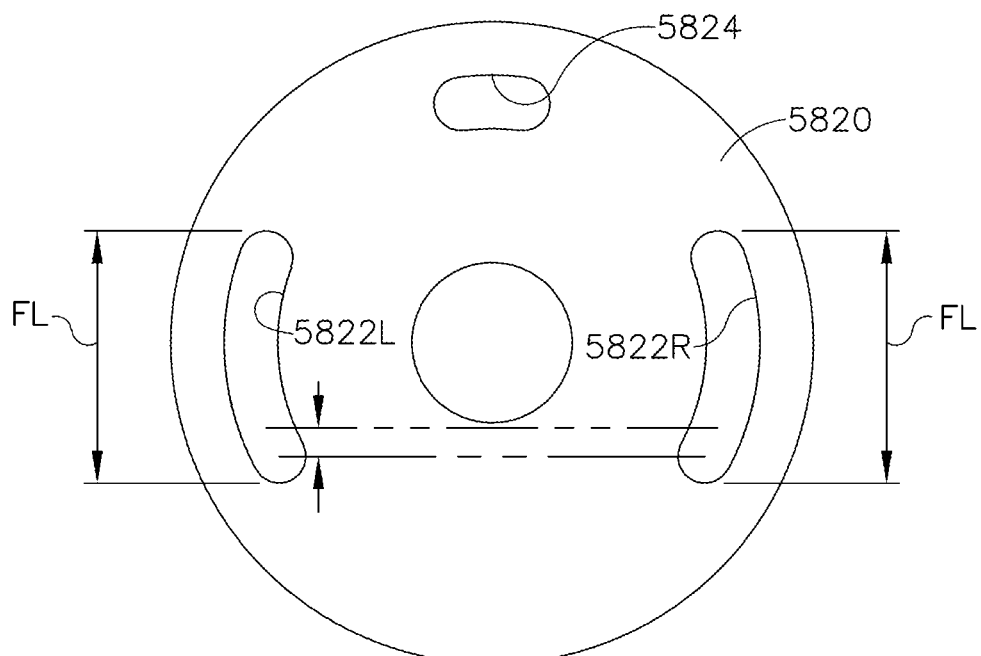
FIG. 61 is a top view of a driver articulation disc embodiment of the articulation system of FIG. 60.

FIG. 61 illustrates one form of a driver disc 5820. As can be seen in that Figure, the driver disc 5820 includes a first pair of first arcuate articulation slots 5822L, 5822R that each has a first arcuate length "FL". In addition, the driver articulation disc 5820 further includes a driver slot 5824 that is centrally disposed between the first articulation slots 5822 as can be seen in FIG. 61. Depending upon the method employed to drive the driver articulation disc 5820, the articulation drive link 5614 or the worm gear motor 5710 may interface with the driver articulation disc 5820 in the various manners described above to apply rotary motions to the driver articulation disc 5820. FIG. 62 illustrates one form of a driven articulation disc 5830. As can be seen in that Figure, the driven articulation disc 5830 includes a second pair of second arcuate articulation slots 5832L, 5832R that each have a second arcuate length "SL" that is less than the first arcuate length "FL". In addition, the driven articulation disc 5830 further includes a driver post 5834 that is configured to be movably received within the driver slot 5824.

Figure 60:
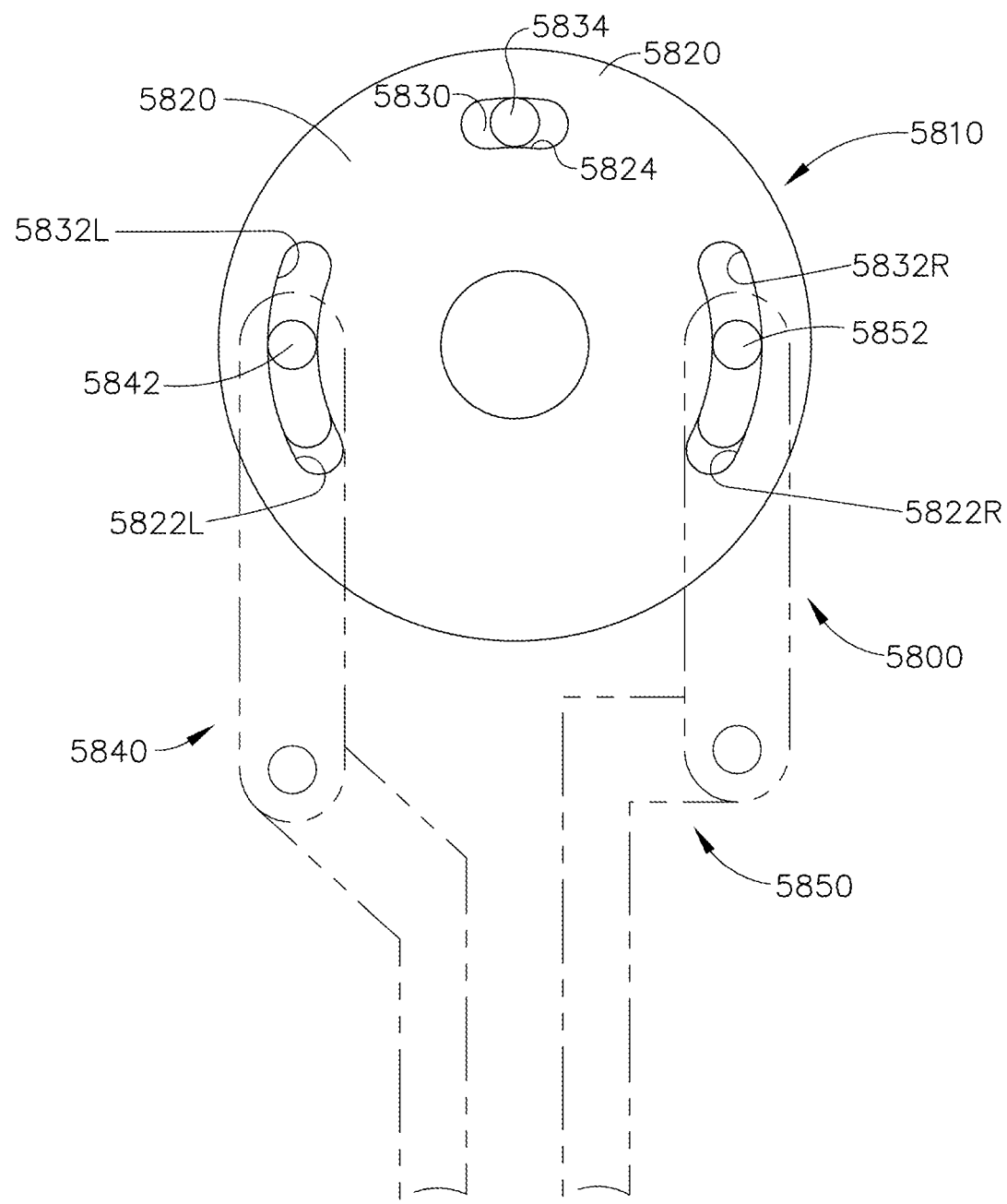
FIG. 60 is a top view of portions of another articulation system embodiment in a neutral or unarticulated position.
Figure 63:
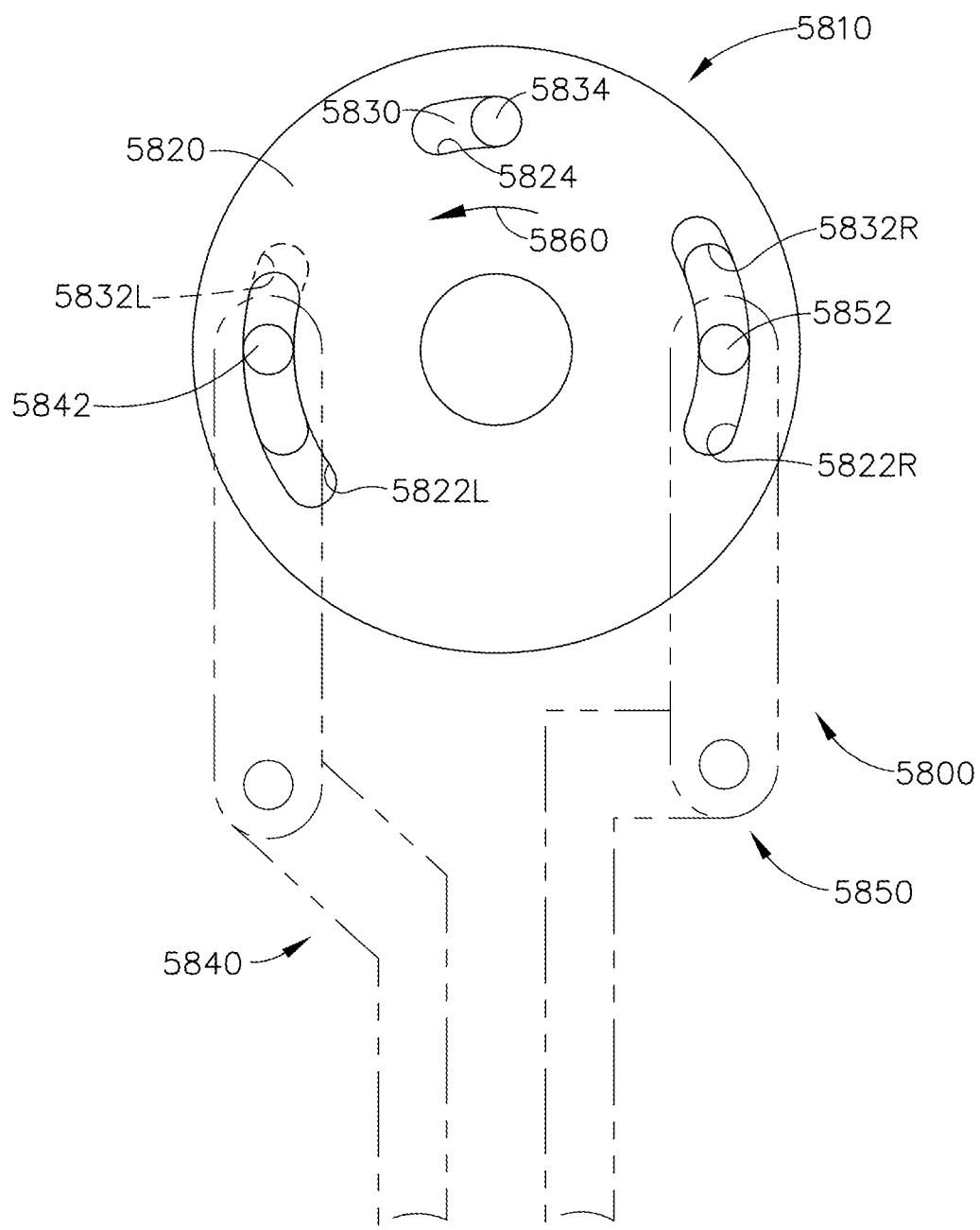
FIG. 63 is another top view of the articulation system embodiment of FIG. 60 in a position or configuration after an articulation control motion has been initially applied thereto.
Figure 64:
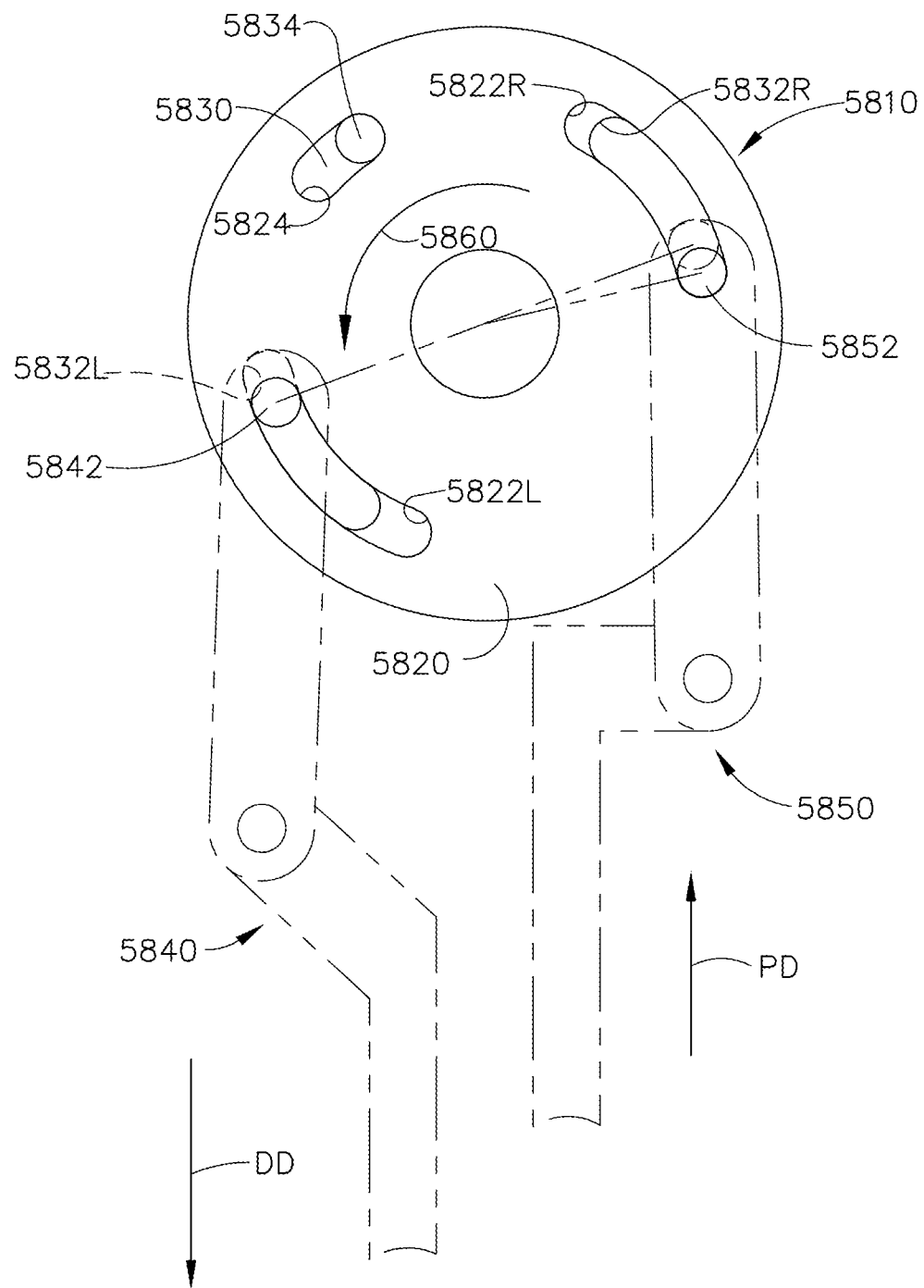
FIG. 64 is another top view of the articulation system embodiment of FIG. 63 in a first articulated position or configuration.
Figure 65:
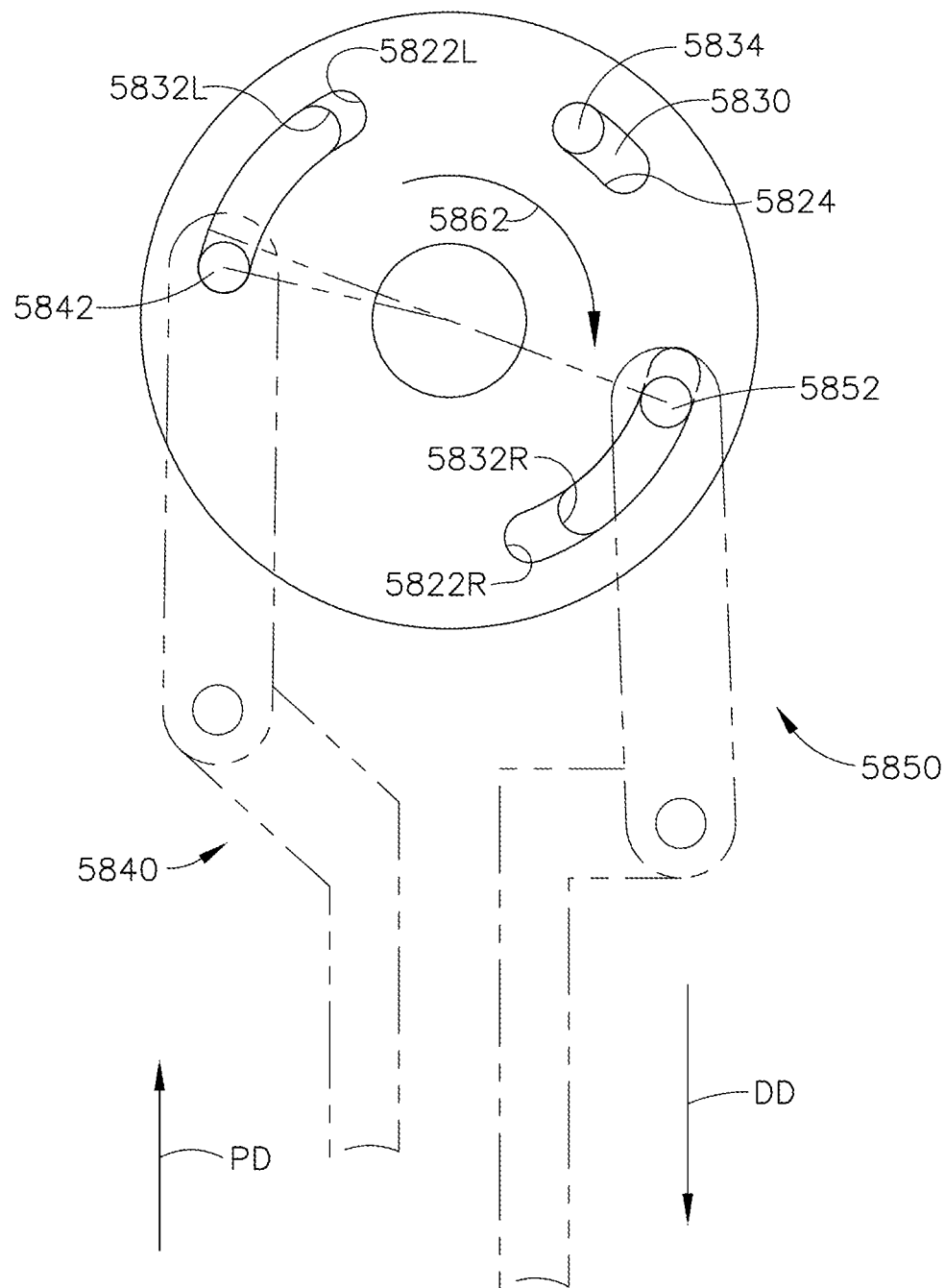
FIG. 65 is another top view of the articulation system embodiment of FIGS. 63 and 64 in a second articulated position or configuration.

Referring now to FIGS. 60 and 63-65, the articulation system 5800 further comprises a first articulation rod 5840 that may be directly or indirectly attached to a portion of a surgical end effector in any of the various manners described herein. A first articulation pin 5842 is attached to the first articulation rod 5720 and is received within corresponding first and second arcuate articulation slots 5822L, 5832L. Likewise, a second articulation rod or member 5850 may be directly attached to a portion of the same surgical end effector in any of the various manners described herein. A second articulation pin 5852 is attached to the second articulation rod 5850 and is received within corresponding first and second arcuate articulation slots 5822R, 5832R. FIG. 60 illustrates the articulation system 5800 in a null position wherein the surgical end effector may be freely moved. FIG. 63 illustrates the position of the articulation system 5800 upon an initial application of rotary motion to the driver articulation disc 5820 in the direction represented by arrow 5860. As can be seen in that Figure, upon initial rotation of the driver articulation disc 5820, the articulation slots 5822L, 5832L are offset from each other and the articulation slots 5822R, 5832R are offset from each other, but no motion has yet been transferred to articulation rods 5840, 5850. FIG. 64 illustrates the position of the articulation system 5800 upon continued application of the rotary motion to the driver articulation disc 5820 in the direction of arrow 5860 sufficient enough to result in, for example, a seventy-five degree of articulation of the surgical end effector relative to the shaft axis. As can be seen in that Figure, a pushing motion is applied to the first articulation rod 5840 to cause the first articulation rod 5840 to axially move in the distal direction "DD" and a pulling motion is applied to the second articulation rod 5850 to cause the second articulation rod 5850 to axially move in the proximal direction "PD". The movement of the first and second articulation rods 5840, 5850 in opposite directions results in the articulation of the surgical end effector operably interfacing therewith. FIG. 65 illustrates the position of the articulation system 5800 upon application of the rotary motion to the driver articulation disc 5820 in an opposite direction represented by arrow 5862 that is sufficient enough to result in, for example, a seventy-five degree of articulation of the surgical end effector relative to the shaft axis in an opposite articulation direction. As can be seen in that Figure, a pushing motion is applied to the second articulation rod 5850 to cause the second articulation rod 5850 to axially move in the distal direction "DD" and a pulling motion is applied to the first articulation rod 5840 to cause the first articulation rod 5840 to axially move in the proximal direction "PD". Such opposing movements of the first and second articulation rods 5840, 5850 result in the articulation of the surgical end effector that is operably attached thereto. In one configuration, the first articulation rod 5840 may only apply a pulling force to the surgical end effector when the articulation driver disc 5820 has been rotated a sufficient distance as to attain a seventy-five degree range of articulation.

FIGS. 66-70 illustrate a surgical end effector 6300 that comprises first and second jaws that are simultaneously movable between open and closed positions relative to the shaft axis SA-SA. The first and second jaws may comprise a variety of surgical jaw arrangements without departing from the spirit and scope of the present invention. Gaining access to target tissue with the jaws of a surgical end effector can, at times, be challenging. The maneuverability of a surgical end effector, particularly a surgical end effector that is configured to cut and staple tissue, may be enhanced if the distance between the point at which the jaws are supported relative to each other and the proximal-most staple locations is minimized. For example, those surgical end effectors that only employ one movable jaw (i.e., one of the jaws is fixed relative to the shaft axis) may require that the one movable jaw have a relatively large range of travel in order to accommodate the target tissue. Such larger range of travel can complicate the process of using the end effector to advantageously position the target tissue. The surgical end effector 6300 employs first and second jaws that move relative to each other and the shaft axis about a common pivot axis. Such arrangement enables the distance between the pivot axis and the proximal-most staple locations to be shortened when compared to the same distance on certain surgical end effectors that employ only one movable jaw, for example.

Figure 70:
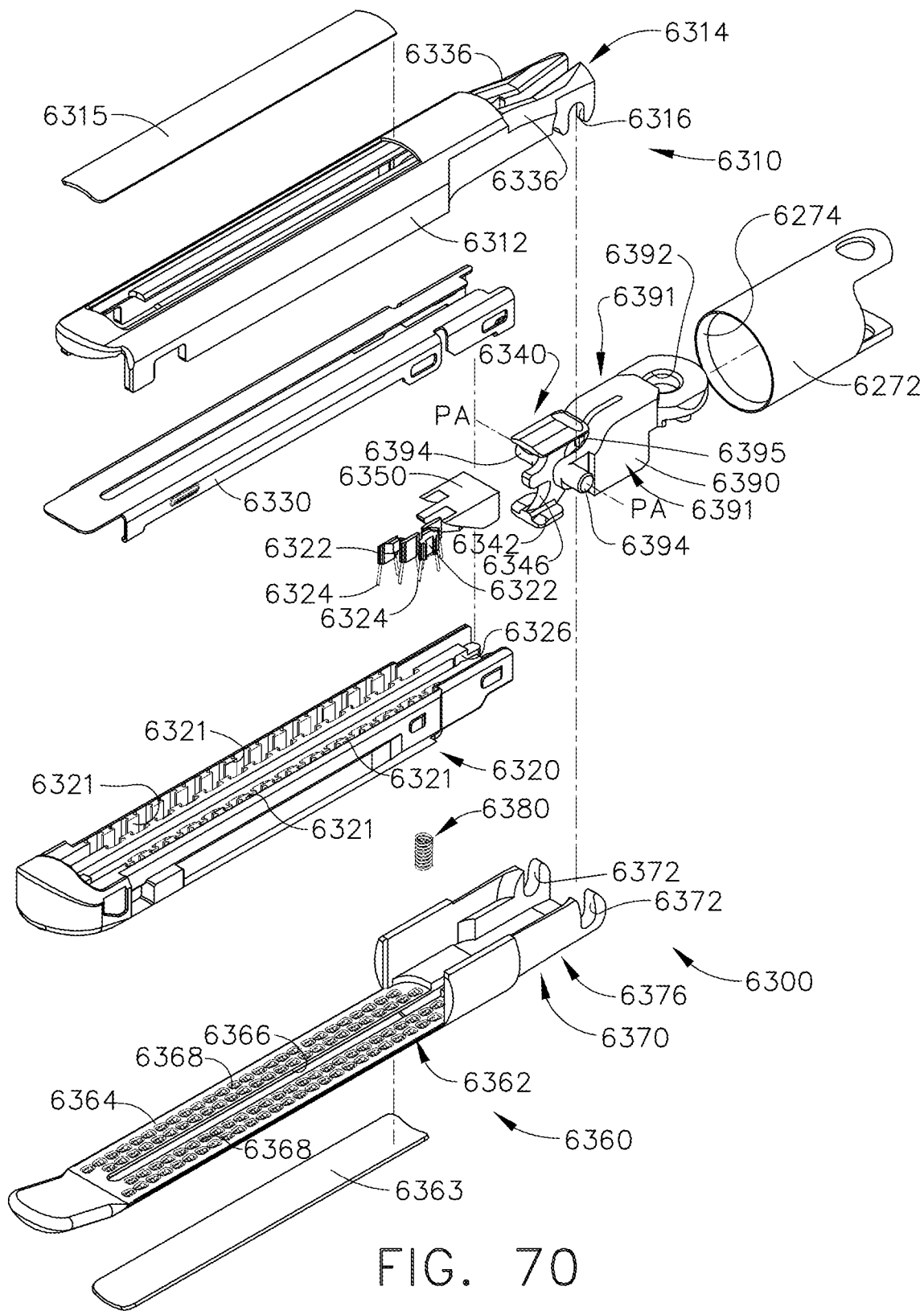
FIG. 70 is an exploded assembly view of the surgical end effector and closure sleeve embodiment of FIGS. 66-69.

In the illustrated example, a first jaw 6310 includes an elongate channel 6312 that is configured to support a surgical staple cartridge 6320 therein. As can be seen in FIG. 70, the surgical staple cartridge 6320 is configured to operably support a plurality of staple drivers 6322 therein that operably support surgical staples 6324 thereon. The staple drivers 6322 are movably supported within corresponding driver slots 6321 formed in the surgical staple cartridge 6320. The staple drivers 6322 are retained within their respective driver slot 6321 by a cartridge pan 6330 that clips to or is otherwise attached to the surgical staple cartridge 6320. The staple drivers 6322 are arranged in rows on each side of an elongate slot 6326 in the surgical staple cartridge 6320 to accommodate the axial passage of a firing member 6340 therethrough. A wedge sled 6350 is movably supported within the surgical staple cartridge 6320 and is configured to be drivingly engaged by the firing member 6340 as the firing member 6340 is driven from a starting position adjacent to the proximal end of the surgical staple cartridge 6320 and an ending position within a distal portion of the surgical staple cartridge 6320. As was discussed above, as the wedge sled 6350 is driven in the distal direction through the surgical staple cartridge 6320, the wedge sled 6350 drivingly contacts the staple drivers 6322 to drive them toward the cartridge deck surface 6323. The firing member 6340 includes a tissue cutting surface 6346 that serves to cut the tissue clamped between the jaws as the firing member 6340 is driven distally. A distal firing beam (not shown) of the various types described herein is operably attached to the firing member 6340 as well as to an intermediate firing shaft portion 2222 or other firing system arrangement. Operation of the intermediate firing shaft portion 2222 to drive and retract the distal firing beam was discussed in detail above and will not be repeated for the sake of brevity. Other firing beam and firing system arrangements (motor-powered as well as manually-powered) may also be employed to power the firing member without departing from the spirit and scope of the present invention.

The illustrated surgical end effector 6300 is also configured for selective articulation about an articulation axis B-B that is substantially transverse to the shaft axis SA-SA. As can be seen in FIGS. 66-70, the surgical end effector 6300 includes an end effector mounting assembly 6390 that is adapted to be pivotally mounted to, for example, a distal shaft frame (not shown) that includes a pivot pin that is configured to be rotatably received within the mounting hole 6392 in the end effector mounting assembly 6390. The surgical end effector 6300 may be articulated by an articulation lock and first and second articulation rod arrangements of the type described above. As can be seen in FIG. 70, the end effector mounting assembly 6390 further includes a pair of opposed, laterally extending trunnion pins 6394. The trunnion pins 6394 extend laterally from the opposed lateral sides 6391 of the end effector mounting assembly 6390 that also define a pocket area 6395 that is configured to receive the firing member 6340 therein. The trunnion pins 6394 serve to define a pivot axis PA-PA about which the first and second jaws 6310, 6360 may pivot. The proximal end 6314 of the first jaw 6310 or elongate channel 6312 includes a pair of opposed U-shaped or open ended slots 6316 that are adapted to receive a corresponding one of the trunnion pins 6394 therein. Such arrangement serves to movably or pivotally journal the first jaw 6310 to the end effector mounting assembly 6390.

Figure 67:
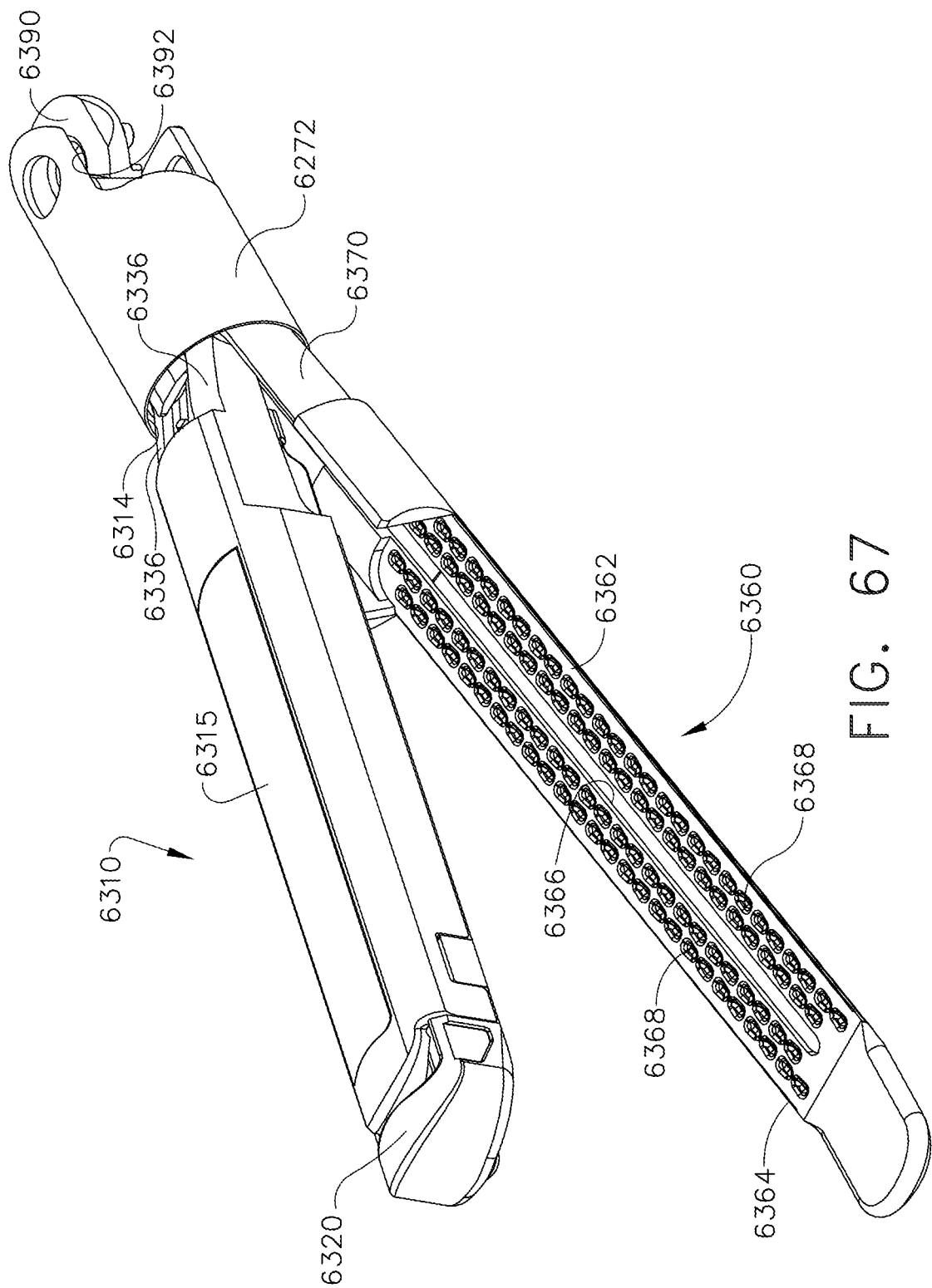
FIG. 67 is another perspective view of the surgical end effector and closure sleeve embodiment of FIG. 66 with the jaws thereof in an open position or configuration.
Figure 68:
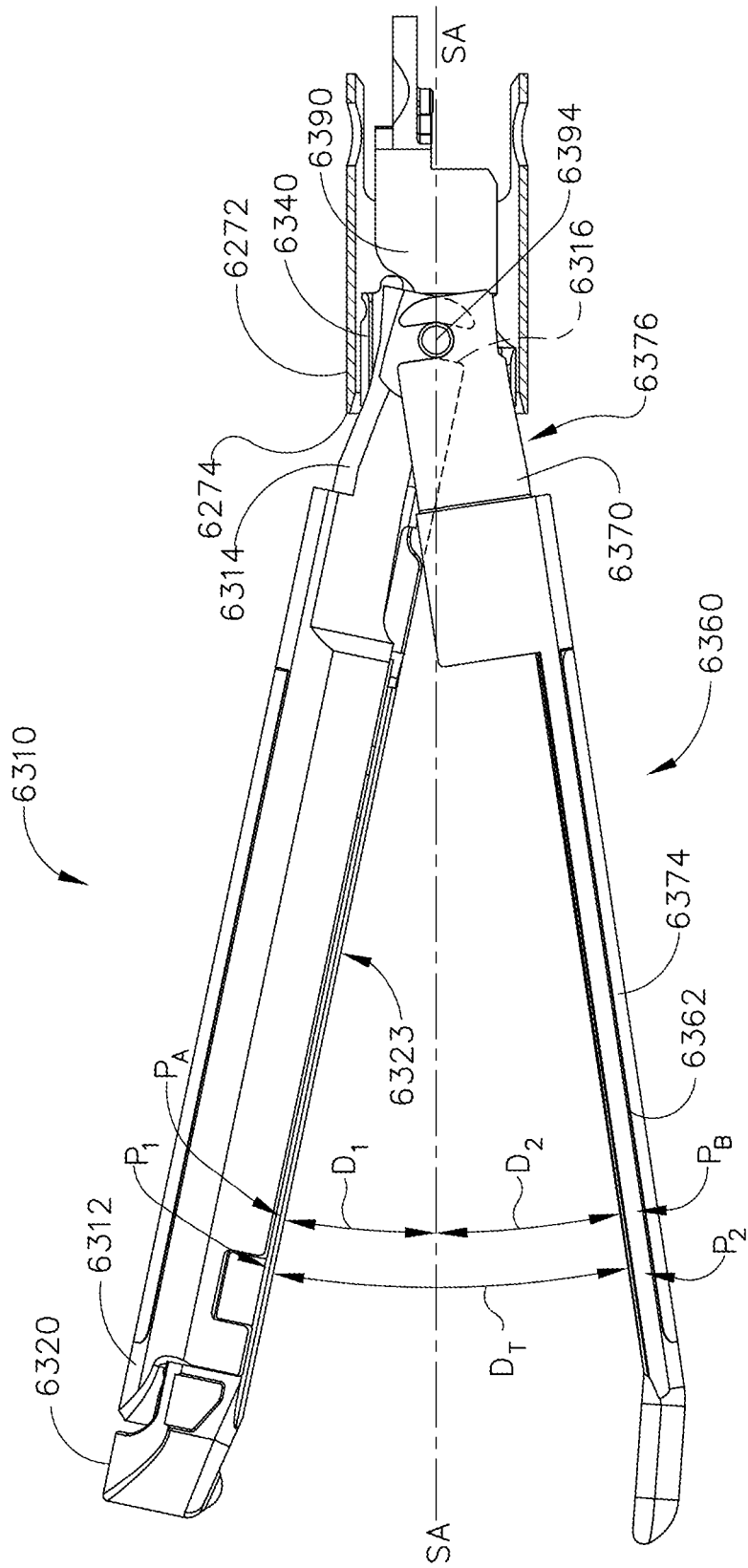
FIG. 68 is a side elevational view of the surgical end effector and closure sleeve embodiment of FIGS. 66 and 67 with the closure sleeve shown in cross-section and the jaws thereof in an open position or configuration.
Figure 69:
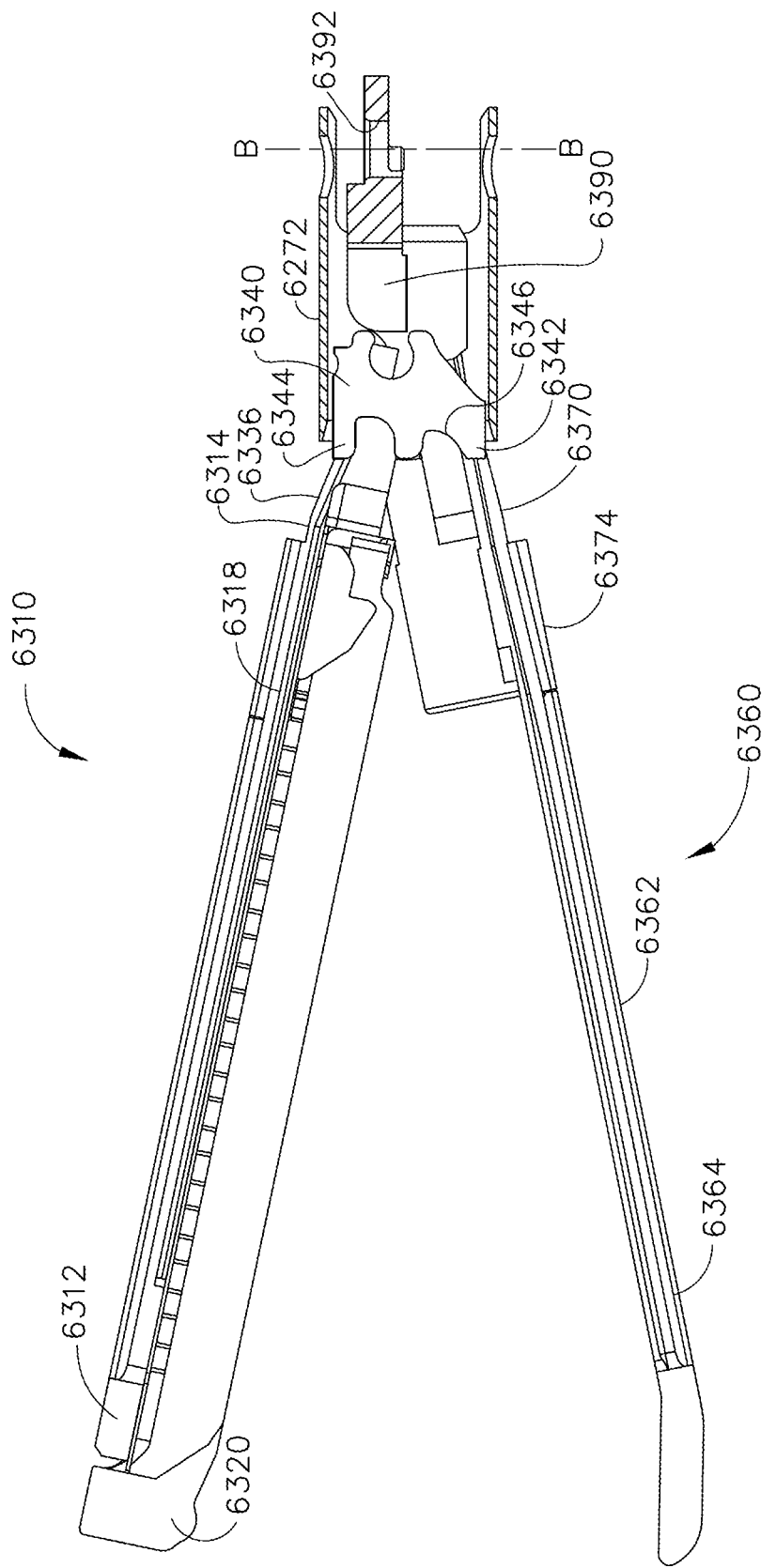
FIG. 69 is a side elevational view of the surgical end effector and closure sleeve embodiment of FIGS. 66-68 shown in cross-section and with the jaws thereof in an open position or configuration.

The illustrated surgical end effector 6300 further comprises a second jaw 6360 that may comprise an anvil 6362. The illustrated anvil 6362 includes an anvil body 6364 that includes an elongate slot 6366 and two staple forming surfaces 6368 formed on each side thereof. The anvil 6362 further has a proximal end portion 6370 that has a pair of U-shaped or open ended slots 6372 that are also adapted to receive a corresponding one of the trunnion pins 6394 therein. Such arrangement serves to movably or pivotally journal the second jaw 6360 to the end effector mounting assembly 6390 such that the first and second jaws may move relative to each other as well as to relative to the shaft axis SA-SA. The first and second jaws 6310 and 6360 may be movably actuated by a closure system of the various types disclosed herein. For example, a first closure drive system of the type described herein may be employed to actuate a closure tube in the above-described manner. The closure tube may also be attached to an end effector closure sleeve 6272 that may be pivotally attached to the closure tube by a double pivot closure sleeve assembly in the manner described above. As was described above, for example, axial movement of the closure tube may be controlled through actuation of a closure trigger 32. As can be seen in FIGS. 67-69, the end effector closure sleeve 6272 extends over the end effector mounting assembly 6390 and is configured to engage the proximal end 6370 of the second jaw 6360 as well as the proximal end 6314 of the first jaw 6310. At least one cam surface 6336 may be formed on the proximal end 6314 of the first jaw 6310 such that when the distal end 6274 of the end effector closure sleeve 6272 contacts the cam surface(s) 6336, the first jaw 6310 is cammed toward the second jaw and the shaft axis SA-SA. Likewise, one or more cam surfaces 6376 may be formed on the proximal end portion 6370 of the second jaw 6360 such that when contacted by the distal end 6274 of the end effector closure sleeve 6272, the second jaw 6360 is moved toward the first jaw 6310 and the shaft axis SA-SA. The cam surfaces 6336, 6376 may be configured and positioned relative to each other such that the first and second jaws close at different "closure rates" or closure times relative to each other. One such arrangement is depicted in FIG. 68. As can be seen in FIG. 68, the distance along an arcuate path between a point $P_1$ on the first jaw 6310 and a corresponding point $P_2$ on the second jaw 6360 when the first and second jaws are in their respective fully opened position is represented by $D_T$. The first and second points $P_1$ and $P_2$ are said to "correspond to" each other. For example, the first point $P_1$ and the second point $P_2$ may each lie on a common line or axis that extends therebetween and is perpendicular to the shaft axis SA-SA. The distance along an arcuate path between another point $P_A$ on the first jaw 6310 and the shaft axis SA-SA is represented by $D_1$ and the distance along another arcuate path between another corresponding point $P_B$ on the second jaw and the shaft axis SA-SA is represented by $D_2$. Point $P_A$ and point $P_B$ are also said to correspond to each other. For example, point $P_A$ and point $P_B$ may lie on a common line or axis that extends therebetween and which is perpendicular to the shaft axis SA-SA. In the illustrated arrangement, the distance $D_2$ that the second jaw 6360 or anvil 6362 moves from the fully open to the closed position wherein the staple-forming surface of the anvil 6362 lies along the shaft axis SA-SA is greater than the distance $D_1$ that the first jaw 6310 or surgical staple cartridge 6320 moves from the fully open position to the closed position wherein the cartridge deck surface lies along the shaft axis SA-SA. For example, in at least one arrangement, the second jaw or anvil will open or move ⅔ of the distance $D_T$ (or another distance along another travel path between the jaws) and the first jaw or staple cartridge will open or move ⅓ of the distance $D_T$ (or other distance along yet another travel path between the jaws), so that, in essence, one jaw attains its fully closed position quicker or faster than the other jaw attains its fully closed position even though a closure motion or motions were initially applied to both jaws at the same or similar times. For example, the cam surfaces on the first and second jaws may be arranged/configured to attain different jaw-movement ratios/rates without departing from the spirit and scope of this embodiment of the present invention. An opening spring 6380 (FIG. 70) may be positioned between the proximal end 6314 of the first jaw 6310 and the proximal end 6370 of the second jaw 6360 to bias the first and second jaws 6310, 6360 to the open position when the end effector closure sleeve 6272 is positioned in the starting or unactuated position. See FIGS. 67-69.

Figure 66:
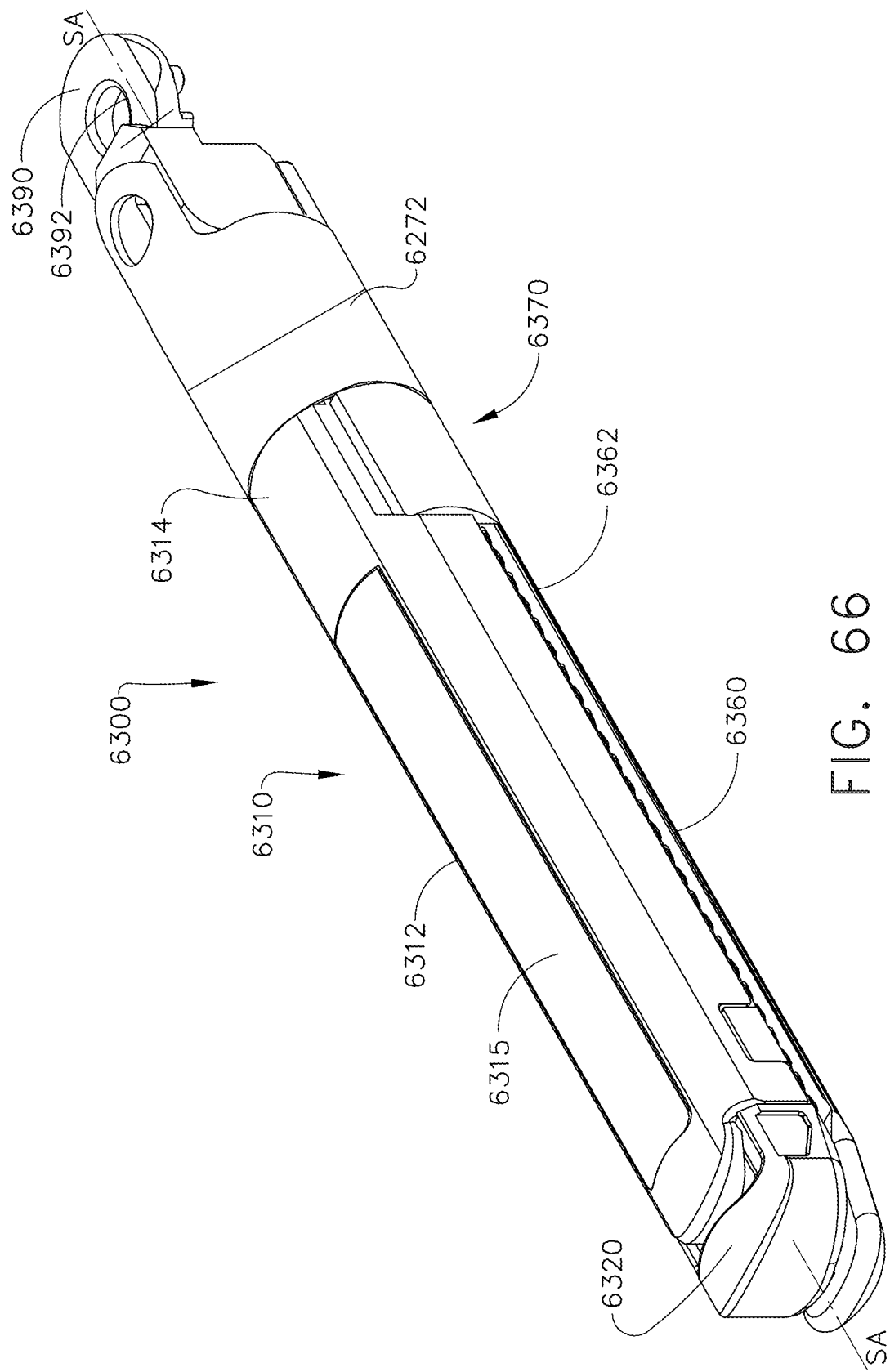
FIG. 66 is a perspective view of another surgical end effector and closure sleeve embodiment with the jaws thereof in a closed position or configuration.

To move the first and second jaws 6310, 6360 to a closed position (FIG. 66), the clinician actuates the closure system to move the end effector closure sleeve 6272 in the distal direction "DD" to simultaneously contact the cam surface(s) 6336 on the proximal end 6314 of the first jaw 6310 and the cam surface(s) 6376 on the proximal end 6370 of the second jaw 6360 to bias the first and second jaws 6310, 6360 towards each other (and shaft axis SA-SA) to the position shown in FIG. 66. While the end effector closure sleeve 6272 is retained in that position, the first and second jaws 6310 and 6360 are retained in that closed position. Thereafter, the firing system may be actuated to axially advance the firing member 6340 distally through the surgical end effector 6300. As can be seen in FIG. 70, the firing member

6340 may have a foot portion 6342 that is configured to slidably engage a slotted passage 6374 of the anvil 6362 and a top tab portion 6344 that is adapted to be slidably received within a slotted passage 6318 in the elongate channel 6312. See FIG. 69. Thus, such firing member arrangement serves to positively retain the first and second jaws 6310, 6360 at a desired spacing arrangement during firing of the firing member (i.e., during firing of the staples and cutting of the tissue that is clamped between the first and second jaws 6310, 6360). A first jaw cover 6315 is removably attached to the elongate channel 6312 and a second jaw cover 6363 is removably attached to the anvil 6362 for assembly purposes as well as to prevent the infiltration of tissue and/or body fluid into the first and second jaws which may hamper or interfere with operation of the firing member 6340.

Figure 71:
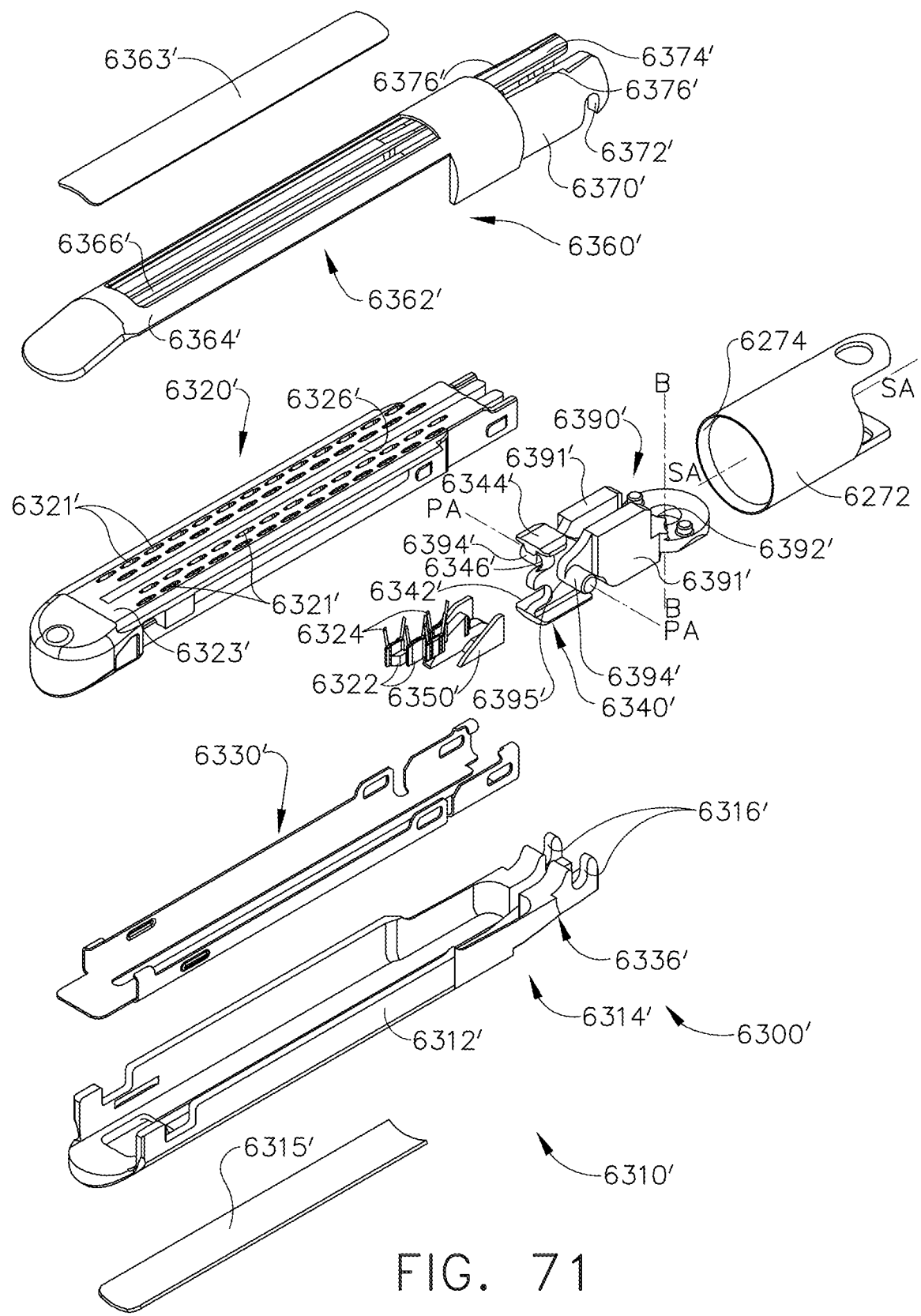
FIG. 71 is an exploded assembly view of another surgical end effector and closure sleeve embodiment.

FIG. 71 illustrates another surgical end effector 6300' that is similar to surgical end effector 6300. As can be seen in that Figure, the surgical end effector 6300' comprises two jaws that are simultaneously movable between open and closed positions relative to the shaft axis SA-SA. In the illustrated example, a first jaw 6310' includes an elongate channel 6312' that is configured to support a surgical staple cartridge 6320' therein. The surgical staple cartridge 6320' is configured to operably support a plurality of staple drivers 6322 therein that operably support surgical staples 6324 thereon. The staple drivers 6322 are movably supported within corresponding driver pockets 6321' formed in the surgical staple cartridge 6320'. The staple drivers 6322 are retained within their respective driver pocket 6321' by a cartridge pan 6330' that clips to or is otherwise attached to the surgical staple cartridge 6320'. The staple drivers 6322 are arranged in rows on each side of an elongate slot 6326' in the surgical staple cartridge 6320 to accommodate the axial passage of a firing member 6340' therethrough. A wedge sled 6350' is movably supported within the surgical staple cartridge 6320' and is configured to be driving engaged by the firing member 6340' as the firing member 6340' is driven from a starting position adjacent to the proximal end of the surgical staple cartridge 6320' and an ending position within a distal portion of the surgical staple cartridge 6320'. As was discussed above, as the wedge sled 6350' is driven in the distal direction through the surgical staple cartridge 6320', the wedge sled 6350' drivingly contacts the staple drivers 6322 to drive them toward the cartridge deck surface 6323'. The firing member 6340' includes a tissue cutting surface 6346' that serves to cut the tissue clamped between the jaws as the firing member 6340 is driven distally. A distal firing beam (not shown) of the various types described herein is operably attached to the firing member 6340' as well as to an intermediate firing shaft portion 2222 or other firing system arrangement. Operation of the intermediate firing shaft portion 2222 to drive and retract the distal firing beam was discussed in detail above and will not be repeated for the sake of brevity. Other firing beam and firing system arrangements (motor-powered as well as manually-powered) may also be employed to power the firing member without departing from the spirit and scope of the present invention.

The illustrated surgical end effector 6300' is also configured for selective articulation about an articulation axis B-B that is substantially transverse to the shaft axis SA-SA. The end effector 6300' includes an end effector mounting assembly 6390' that is adapted to be pivotally mounted to, for example, a distal shaft frame that includes a pivot pin configured to be rotatably received within a mounting hole 6392' in the end effector mounting assembly 6390'. The surgical end effector 6300' may be articulated by an articulation lock and first and second articulation rod arrangements of the type described above. As can be seen in FIG. 71, the end effector mounting assembly 6390' further includes a pair of opposed, laterally extending trunnion pins 6394'. The trunnion pins 6394' extend laterally from the opposed lateral sides 6391' of the end effector mounting assembly 6390' that also define a pocket area 6395' that is configured to receive the firing member 6340' therein. The trunnion pins 6394' serve to define a pivot axis PA-PA about which the first and second jaws 6310', 6360' may pivot. 'The proximal end 6314' of the first jaw 6310' or elongate channel 6312' includes a pair of opposed U-shaped or open ended slots 6316' that are adapted to receive a corresponding one of the trunnion pins 6394' therein. Such arrangement serves to movably or pivotally journal the first jaw 6310' to the end effector mounting assembly 6390'.

The illustrated surgical end effector 6300' further comprises a second jaw 6360' that may comprise an anvil 6362'. The illustrated anvil 6362' includes an anvil body 6364' that includes an elongate slot 6366' and two staple forming surfaces formed on each side thereof. The anvil 6362' further has a proximal end portion 6370' that has a pair of U-shaped or open ended slots 6372' that are also adapted to receive a corresponding one of the trunnion pins 6394' therein. Such arrangement serves to movably or pivotally journal the second jaw 6360' to the end effector mounting assembly 6390'. The first and second jaws 6310' and 6360' are movably actuated by a closure system of the various types disclosed herein. For example, a first closure drive system 30 may be employed to actuate a closure tube 260 in the manner described herein. The closure tube 260 may also be attached to an end effector closure sleeve 6272 that may be pivotally attached to the closure tube 260 by a double pivot closure sleeve assembly 271 in the manner described above. As was described above, for example, axial movement of the closure tube 260 may be controlled through actuation of a closure trigger 32. The end effector closure sleeve 6272 extends over the end effector mounting assembly 6390' and is configured to engage the proximal end 6370' of the second jaw 6360' as well as the proximal end 6314' of the first jaw 6310'. At least one cam surface 6336' may be formed on the proximal end 6314' of the first jaw 6310' such that when the distal end 6274 of the end effector closure sleeve 6272 contacts the cam surfaces 6336', the first jaw 6310' is cammed toward the second jaw 6360' and the shaft axis SA-SA. Likewise, one or more cam surfaces 6376' may be formed on the proximal end portion 6370' of the second jaw 6360' such that when contacted by the distal end 6274 of the end effector closure sleeve 6272, the second jaw 6360' is moved toward the first jaw 6310' and the shaft axis SA-SA. A spring (not shown) may b positioned between the proximal end 6314' of the first jaw 6310' and the proximal end 6370' of the second jaw 6360' to bias the first and second jaws 6310', 6360' to the open position when the end effector closure sleeve 6272 is positioned in the starting or unactuated position.

To move the first and second jaws 6310', 6360' to a closed position, the clinician actuates the closure system to move the end effector closure sleeve 6272 in the distal direction "DD" to simultaneously contact the cam surface(s) 6336' on the proximal end 6314' of the first jaw 6310' and the cam surface(s) 6376' on the proximal end 6370' of the second jaw 6360' to bias the first and second jaws 6310', 6360' towards each other (and shaft axis SA-SA). While the end effector closure sleeve 6272 is retained in that position, the first and second jaws 6310' and 6360' are retained in that closed position. Thereafter, the firing system may be actuated to axially advance the firing member 6340' distally through the surgical end effector 6300'. The firing member 6340' may have a top tab portion 6344' that is configured to slidably engage a slotted passage 6374' of the anvil 6362' and a foot portion 6342' that is adapted to be slidably received within a slotted passage in the elongate channel 6312'. Thus, such firing member arrangement serves to positively retain the first and second jaws 6310', 6360' at a desired spacing arrangement during firing of the firing member (i.e., during firing of the staples and cutting of the tissue that is clamped between the first and second jaws 6310', 6360'). A first jaw cover 6315' is removably attached to the elongate channel 6312' and a second jaw cover 6363' is removably attached to the anvil 6362' for assembly purposes as well as to prevent the infiltration of tissue and/or body fluid into the first and second jaws which may hamper or interfere with operation of the firing member 6340'.

The surgical end effector embodiments described herein that employ jaws that both move relative to each other and relative to the shaft axis may offer various advantages over other surgical end effector arrangements wherein one of the jaws is fixed and does not move, for example relative to the shaft axis. In such configurations, it is often desirable for the one movable jaw to have a relatively large range of movement relative to the fixed jaw to enable the target tissue to be manipulated, positioned and then clamped therebetween. In the embodiments wherein both jaws are movable, each jaw doesn't require as large of range of motion to accommodate manipulation, positioning and clamping of the target tissue between the jaws. Such reduced movement of the anvil, for example, may provide for improved tissue positioning. Such arrangements may also enable the distance between the pivot axis and the first staple positions to be minimized. In addition, the firing member may always remain engaged with the movable jaws (anvil and elongate channel) even during opening and closing actions.

FIGS. 72-79 illustrate another surgical end effector 6400 that is configured to be operably attached to an elongate shaft assembly of the types described herein which define a shaft axis SA-SA. The surgical end effector 6400 comprises two jaws that are simultaneously movable between open and closed positions relative to the shaft axis SA-SA. The first and second jaws may comprise a variety of different surgical related jaw arrangements. In the illustrated example, a first jaw 6410 includes an elongate channel 6412 that is configured to support a surgical staple cartridge 6420 therein. As in the various surgical staple cartridges discussed above, the surgical staple cartridge 6420 is configured to operably support a plurality of staple drivers (not shown) therein that operably support surgical staples (not shown) thereon. The staple drivers are movably supported within corresponding driver pockets formed in the surgical staple cartridge 6420. The staple drivers are arranged in rows on each side of an elongate slot (not shown) in the surgical staple cartridge 6420 to accommodate the axial passage of a firing member 6440 therethrough. A wedge sled (not shown) is movably supported within the surgical staple cartridge 6420 and is configured to be driving engaged by the firing member 6440 as the firing member 6440 is driven from a starting position adjacent to the proximal end of the surgical staple cartridge 6420 and an ending position within a distal portion of the surgical staple cartridge 6420. As was discussed above, as the wedge sled is driven in the distal direction through the surgical staple cartridge 6420, the wedge sled drivingly contacts the staple drivers to drive them toward the cartridge deck surface (not shown). The firing member 6440 includes a tissue cutting surface 6446 that serves to cut the tissue clamped between the jaws as the firing member 6440 is driven distally. A distal firing beam (not shown) of the various types described herein is operably attached to the firing member 6440 as well as to an intermediate firing shaft portion 2222 or other firing system arrangement. Operation of the intermediate firing shaft portion 2222 to drive and retract the distal firing beam was discussed in detail above and will not be repeated for the sake of brevity. Other firing beam and firing system arrangements (motor-powered as well as manually-powered) may also be employed to power the firing member without departing from the spirit and scope of the present invention.

Figure 74:
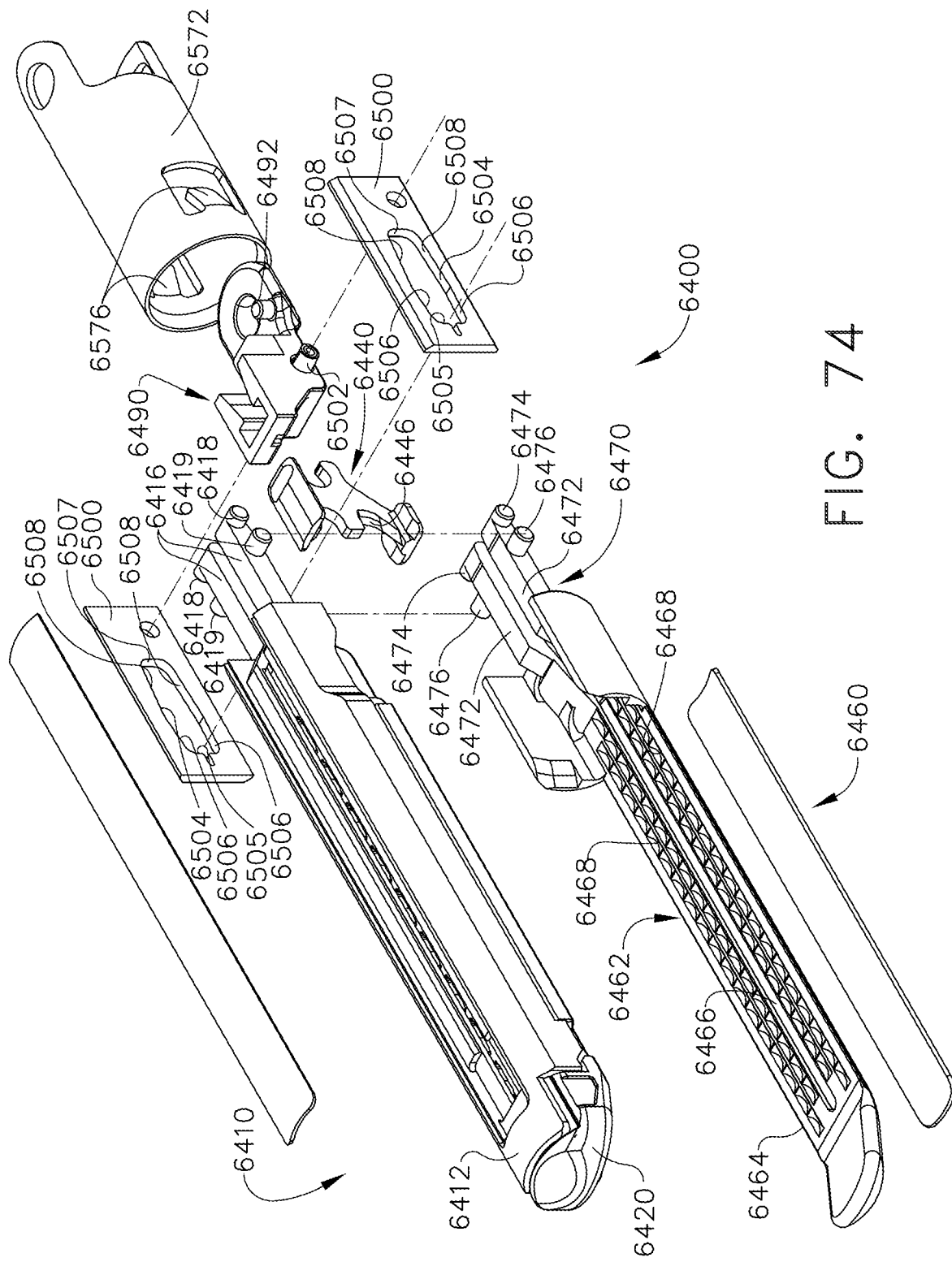
FIG. 74 is an exploded perspective assembly view of the surgical end effector and closure sleeve embodiment of FIGS. 72 and 73.

The illustrated surgical end effector 6400 is also configured for selective articulation about an articulation axis B-B that is substantially transverse to the shaft axis SA-SA. As can be seen in FIGS. 72-79, the surgical end effector 6400 includes an end effector mounting assembly 6490 that is adapted to be pivotally mounted to, for example, a distal shaft frame that includes a pivot pin that is configured to be rotatably received within the mounting hole 6492 in the end effector mounting assembly 6490. The surgical end effector 6400 may be articulated by an articulation lock and first and second articulation rod arrangements of the type described above. As can be seen in FIG. 74, a pair of cam plates 6500 is non-movably attached by a spring pin 6502, for example, to the end effector mounting assembly 6490. As can be further seen in FIG. 74, each cam plate 6500 has a cam slot 6504 that has a closure wedge portion 6505 and an opening wedge portion 6507. The closure wedge portion 6505 is formed from two opposed closure cam surfaces 6506 and the opening wedge portion 6507 is formed from two opposed opening cam surfaces 6508. The elongate channel 6412 includes two proximally extending actuator arms 6416 that each has an opening trunnion pinion 6418 and a closing trunnion pin 6419 protruding laterally therefrom. The opening and closing trunnion pins 6418 and 6419 are received with the cam slot 6504 of a corresponding cam plate 6500. Such arrangement serves to movably or pivotally journal the first jaw 6410 to the end effector mounting assembly 6490.

The illustrated surgical end effector 6400 further comprises a second jaw 6460 that may comprise an anvil 6462. The illustrated anvil 6462 includes an anvil body 6464 that includes an elongate slot 6466 and two staple forming surfaces 6468 formed on each side thereof. The anvil 6462 further has a proximal end portion 6470 that includes two proximally extending actuator arms 6472 protruding therefrom. Each actuator arm 6472 has an opening trunnion pinion 6474 and a closing trunnion pin 6476 protruding laterally therefrom that are also received in the cam slot 6504 of a corresponding cam plate 6500. Such arrangement serves to movably or pivotally journal the second jaw 6460 to the end effector mounting assembly 6490.

Figure 77:
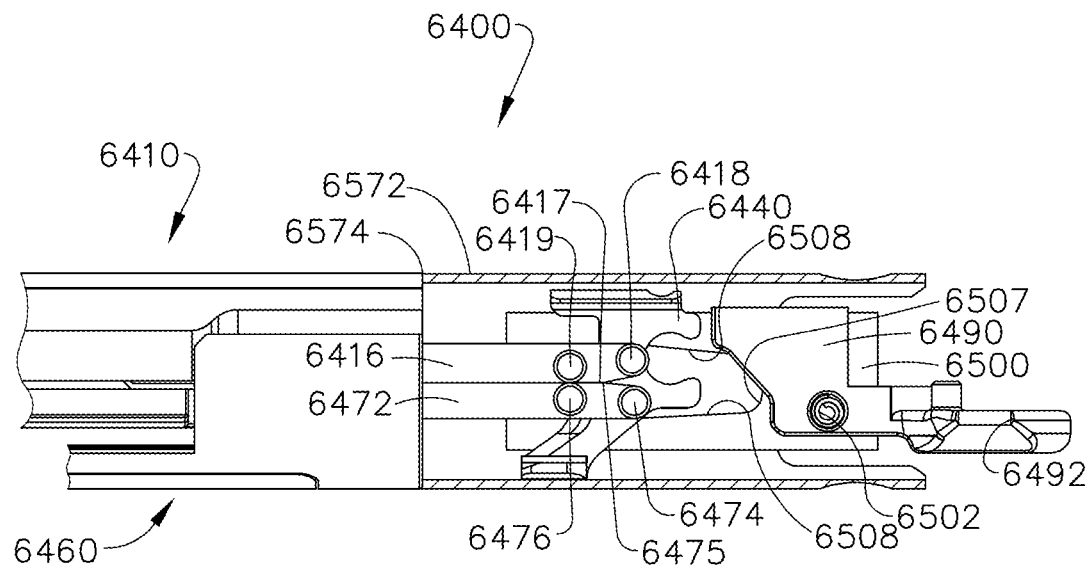
FIG. 77 is a side cross-sectional view of the surgical end effector and closure sleeve embodiment of FIGS. 72-76 with the jaws thereof in a closed position or configuration.
Figure 78:
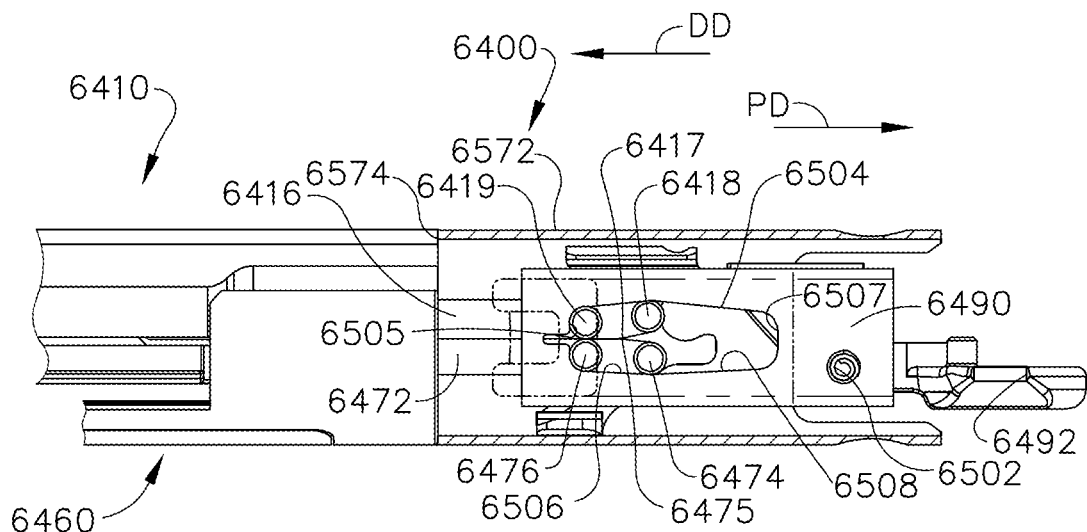
FIG. 78 is another side cross-sectional view including one of the cam plates of the surgical end effector and closure sleeve embodiment of FIGS. 72-77 with the jaws thereof in a closed position or configuration.

The first and second jaws 6410 and 6460 are movably actuated by a closure system of the various types disclosed herein. For example, a first closure drive system 30 may be employed to actuate a closure tube in the manner described herein. The closure tube 260 may also be attached to an end effector closure sleeve 6572 that may be pivotally attached to the closure tube by a double pivot closure sleeve assembly in the manner described above. As was described above, for example, axial movement of the closure tube may be controlled through actuation of a closure trigger. As can be seen in FIGS. 77 and 78, the end effector closure sleeve 6572 extends over the end effector mounting assembly 6490 as well as the actuator arms 6416 of the first jaw 6410 and the actuator arms 6472 of the second jaw 6460. As the closure sleeve 6572 is advanced distally, the distal end 6574 of the closure sleeve 6572 contacts a proximal end 6411 of the first jaw 6410 and a proximal end 6461 of the second jaw 6460 and moves the first and second jaws 6410, 6460 in the distal direction "DD". As the first and second jaws 6410, 6460 move distally, the closing trunnions 6419, 6476 enter the closure wedge portion 6505 of the cam slot 6504 and the closure cam surfaces 6506 cam the first and second jaws 6410, 6460 toward each other to a closed position (FIGS. 73, 75, 77 and 78).

Figure 72:
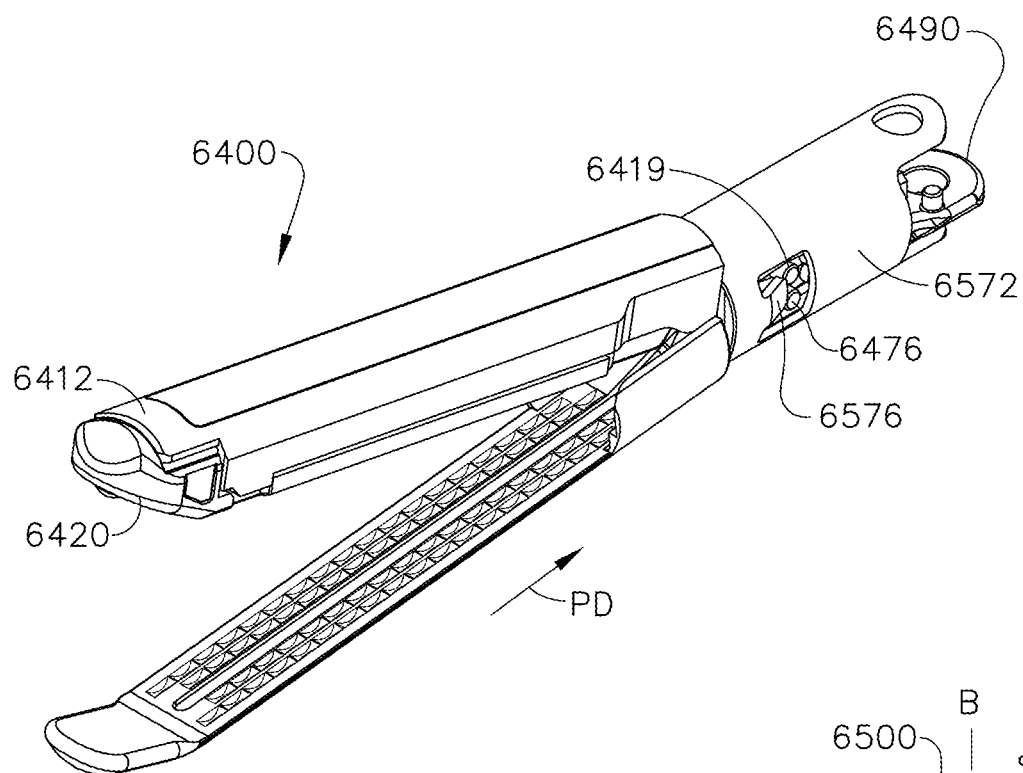
FIG. 72 is a perspective view of another surgical end effector and closure sleeve embodiment with the jaws thereof in an open position or configuration.
Figure 73:
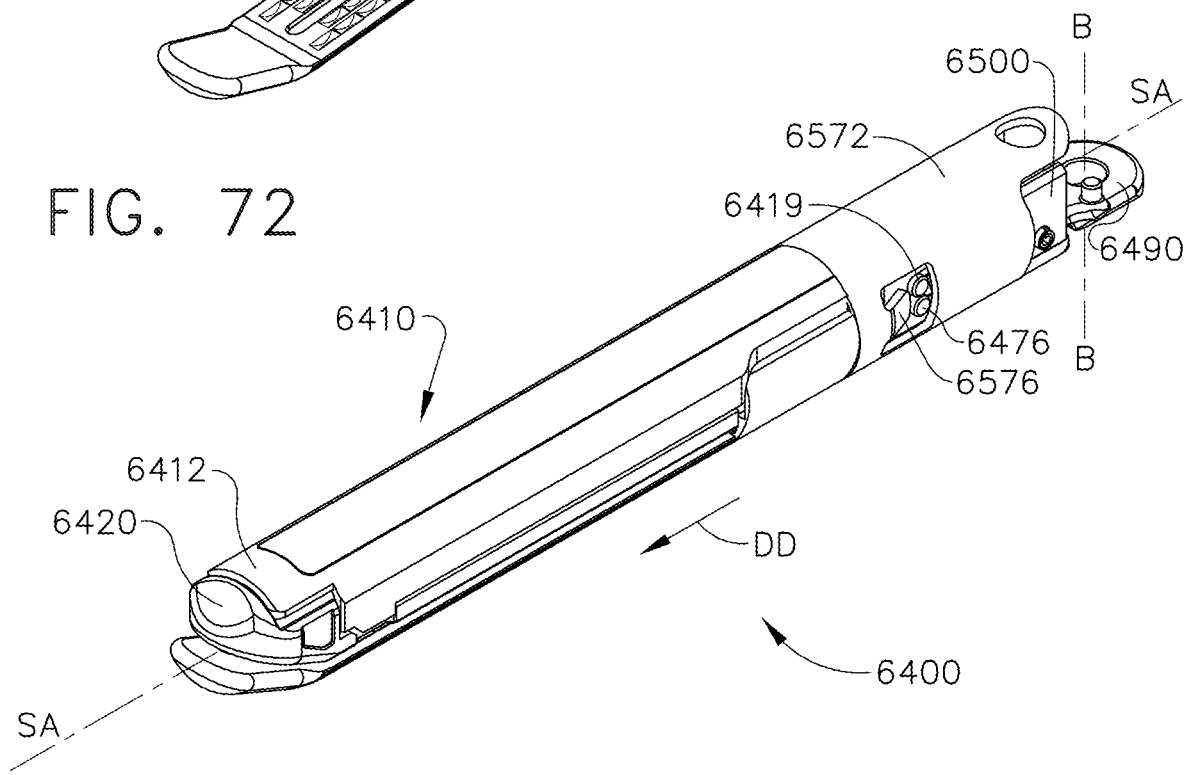
FIG. 73 is another perspective view of the surgical end effector and closure sleeve embodiment of FIG. 72 with the jaws thereof in a closed position or configuration.
Figure 79:
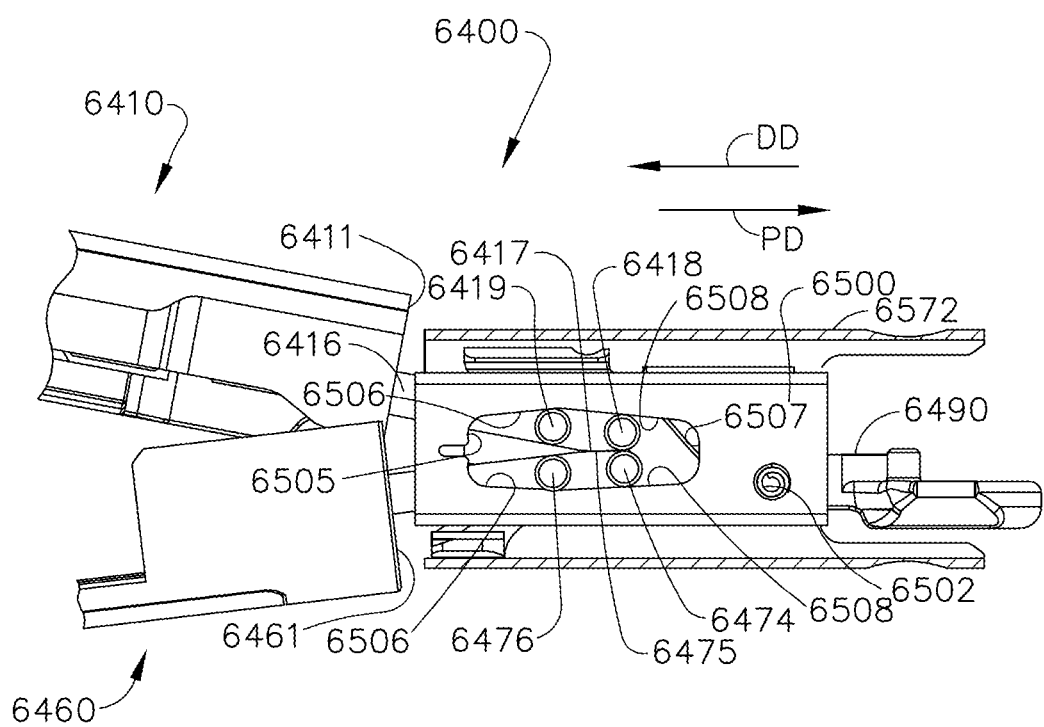
FIG. 79 is another side cross-sectional view including one of the cam plates of the surgical end effector and closure sleeve embodiment of FIGS. 72-78 with the jaws thereof in an open position or configuration.
Figure 80:
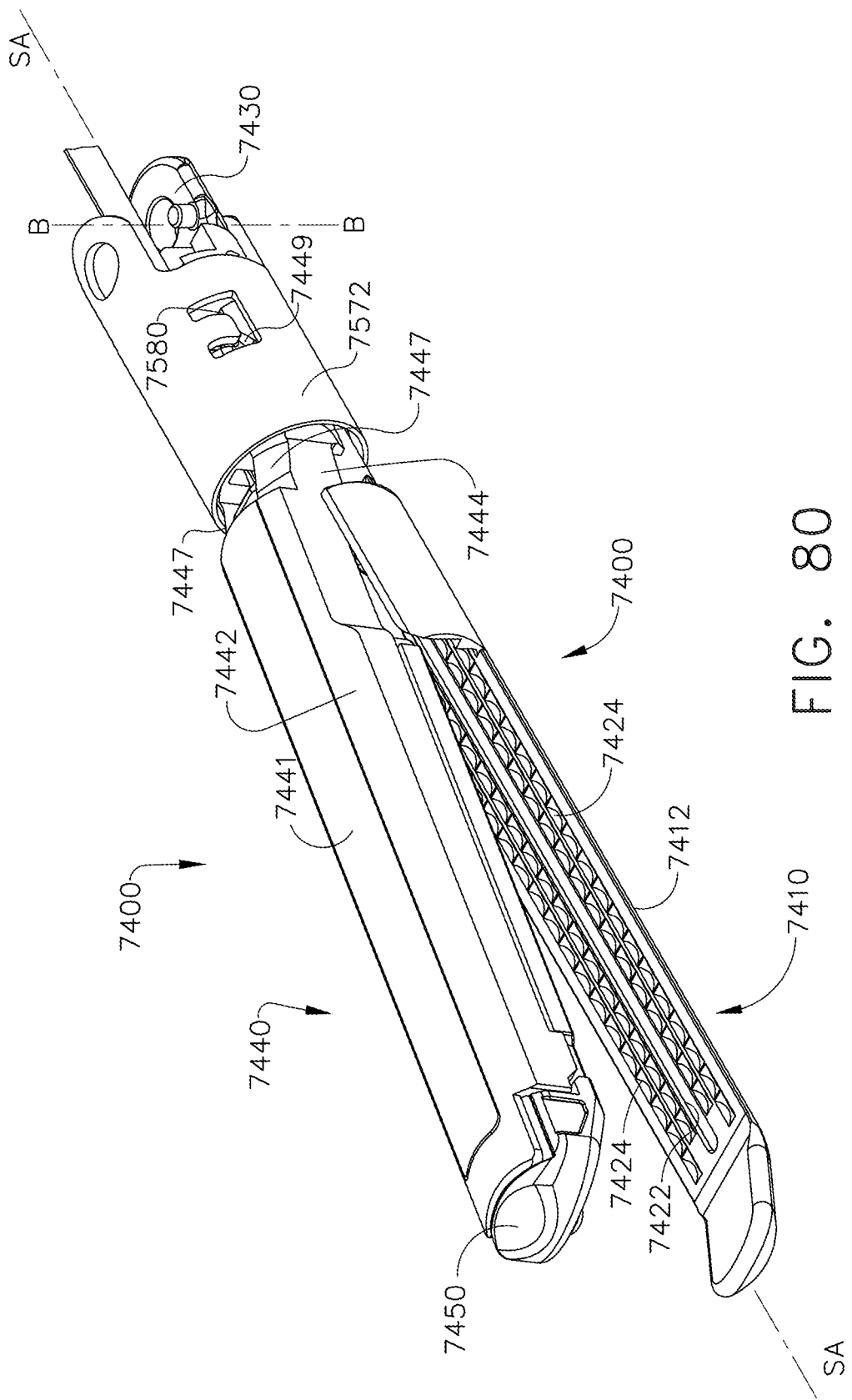
FIG. 80 is a partial perspective view of another surgical end effector and closure sleeve embodiment with the jaws thereof in an open position or configuration.
Figure 81:
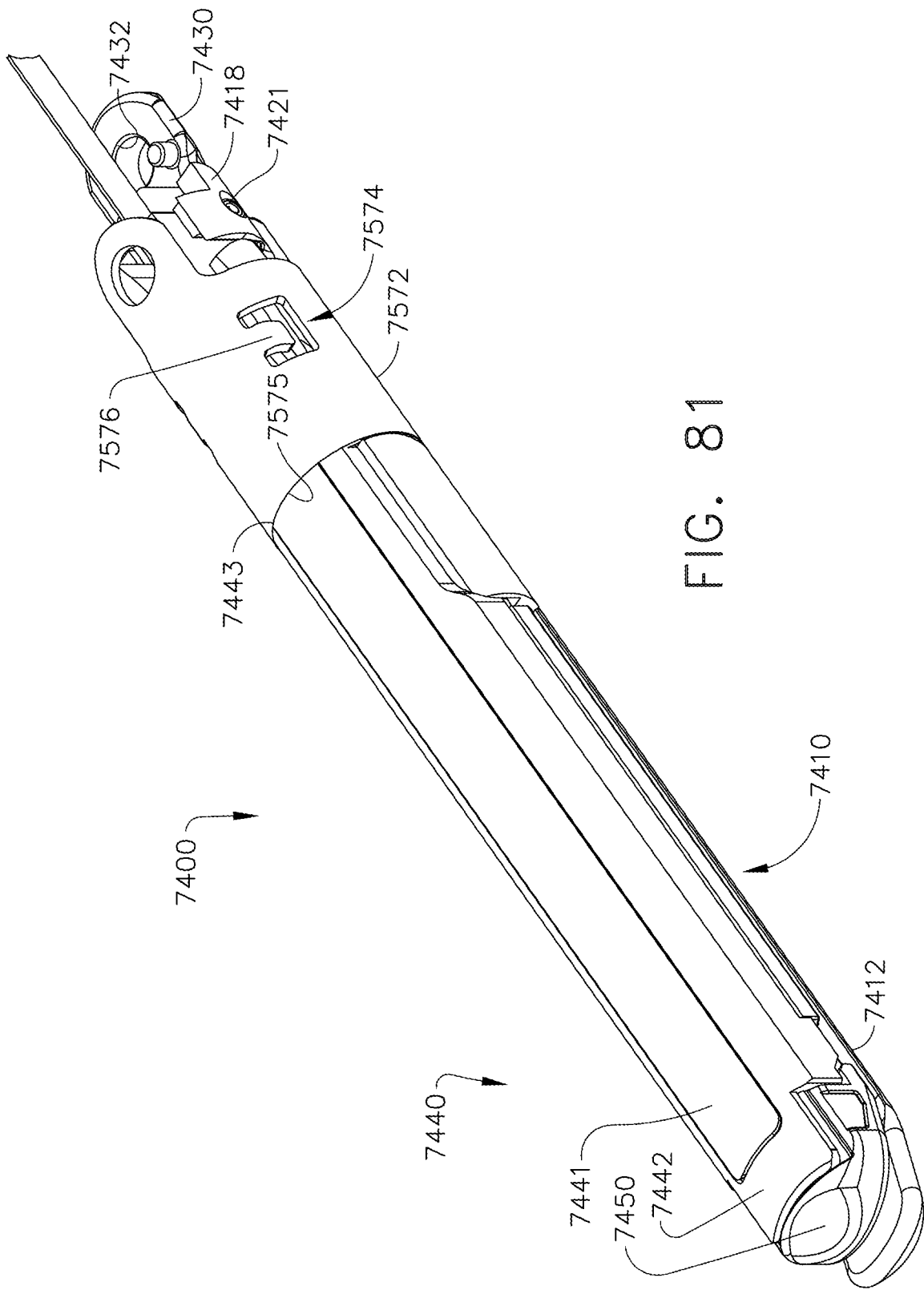
FIG. 81 is a partial perspective view of the surgical end effector and closure sleeve embodiment of FIG. 80 with the jaws thereof in a closed position or configuration.

To facilitate opening of the first and second jaws 6410, 6460 with the closure sleeve 6572, the closure sleeve 6572 is provided with two inwardly extending opening tabs 6576 that are configured to engage the closure trunnions 6419, 6476 when the closure sleeve 6572 is retracted in the proximal direction "PD" by the closure system. As can be seen in FIGS. 72 and 76, for example, as the closure sleeve 6572 moves in the proximal direction "PD", the opening tabs 6576 contact the closure trunnions 6419, 6476 and drives the closure trunnions 6419, 6476 in the proximal direction as well. The proximal movement of the closure trunnions 6419, 6476 causes the opening trunnions 6418 and 6474 to enter the opening wedge portion 6507 of the cam plate slots 6504. The opening cam surfaces 6508 interact with the opening trunnions 6418, 6474 and cause the actuator arms 6416 and 6472 to rock open on their respective rocker surfaces 6417 and 6475 as shown in FIGS. 76 and 79. As with the above-described arrangements wherein both the first and second jaws move relative to the shaft axis SA-SA, the closure wedge portion 6505 and the opening wedge portion 6507 may be configured so that the first and second jaws close at different closure rates or closure times relative to each other upon application of a closure motion thereto.

FIGS. 80-84 illustrate another surgical end effector 7400 that comprises two jaws wherein one jaw is movable relative to the other jaw between open and closed positions. In the illustrated example, the first jaw 7410 comprises an anvil 7412. The illustrated anvil 7412 has an anvil body 7414 that has a proximal end portion 7416 that is non-movably attached to an end effector mounting assembly 7430. For example, the proximal end portion 7416 comprises two upstanding lateral walls 7418 that each has a mounting hole 7419 therein. See FIG. 82. The end effector mounting assembly 7430 is received between the upstanding lateral walls 7418 and is non-movably attached thereto by a spring pin 7421 that extends therethrough into holes 7419. The end effector mounting assembly 7430 is adapted to be pivotally mounted to, for example, a distal shaft frame that includes a pivot pin that is configured to be rotatably received within the mounting hole 7432 in the end effector mounting assembly 7430. The surgical end effector 7400 may be articulated by an articulation lock and first and second articulation rod arrangements of the type described above or by any of the various articulation systems and articulation rod and/or rod/cable arrangements described herein without departing from the spirit and scope of the present invention. As can also be seen in FIGS. 80 and 82, the anvil body 7414 also includes an elongate slot 7422 with two staple forming surfaces 7424 formed on each side thereof.

The surgical end effector 7400 further includes a second jaw 7440 that comprises an elongate channel 7442 that is configured to support a surgical staple cartridge 7450 therein. As in certain surgical staple cartridges discussed above, the surgical staple cartridge 7450 is configured to operably support a plurality of staple drivers (not shown) therein that operably support surgical staples (not shown) thereon. The staple drivers are movably supported within corresponding driver pockets 7452 formed in the surgical staple cartridge 7450. The staple drivers are arranged in rows on each side of an elongate slot 7454 in the surgical staple cartridge 7450 to accommodate the axial passage of a firing member 7460 therethrough. A cartridge pan 7451 is attached to the staple cartridge 7450 to prevent the staple drivers from falling out of their respective driver pockets 7452 when the surgical end effector 7400 is manipulated into various orientations. A wedge sled 7462 is movably supported within the surgical staple cartridge 7450 and is configured to be driving engaged by the firing member 7460 as the firing member 7460 is driven from a starting position adjacent to the proximal end of the surgical staple cartridge 7450 and an ending position within a distal portion of the surgical staple cartridge 7450. As was discussed above, as the wedge sled 7462 is driven in the distal direction through the surgical staple cartridge 7450, the wedge sled 7462 drivingly contacts the staple drivers to drive them toward the cartridge deck surface (not shown). The firing member 7460 includes a tissue cutting surface 7464 that serves to cut the tissue clamped between the jaws 7410, 7440 as the firing member 7460 is driven distally. A distal firing beam 280 or of the other various types described herein is operably attached to the firing member 7460 as well as to an intermediate firing shaft portion 2222 or other firing system arrangement. Operation of the intermediate firing shaft portion 2222 to drive and retract the distal firing beam 280 was discussed in detail above and will not be repeated for the sake of brevity. Other firing beam and firing system arrangements (motor-powered as well as manually-powered) may also be employed to power the firing member without departing from the spirit and scope of the present invention. A first jaw cover 7415 is removably attached to the anvil 7412 a second jaw cover 7441 is removably attached to the second jaw 7440 for assembly purposes as well as to prevent the infiltration of tissue and/or body fluid into the first and second jaws which may hamper or interfere with operation of the firing member 6340.

Figure 82:
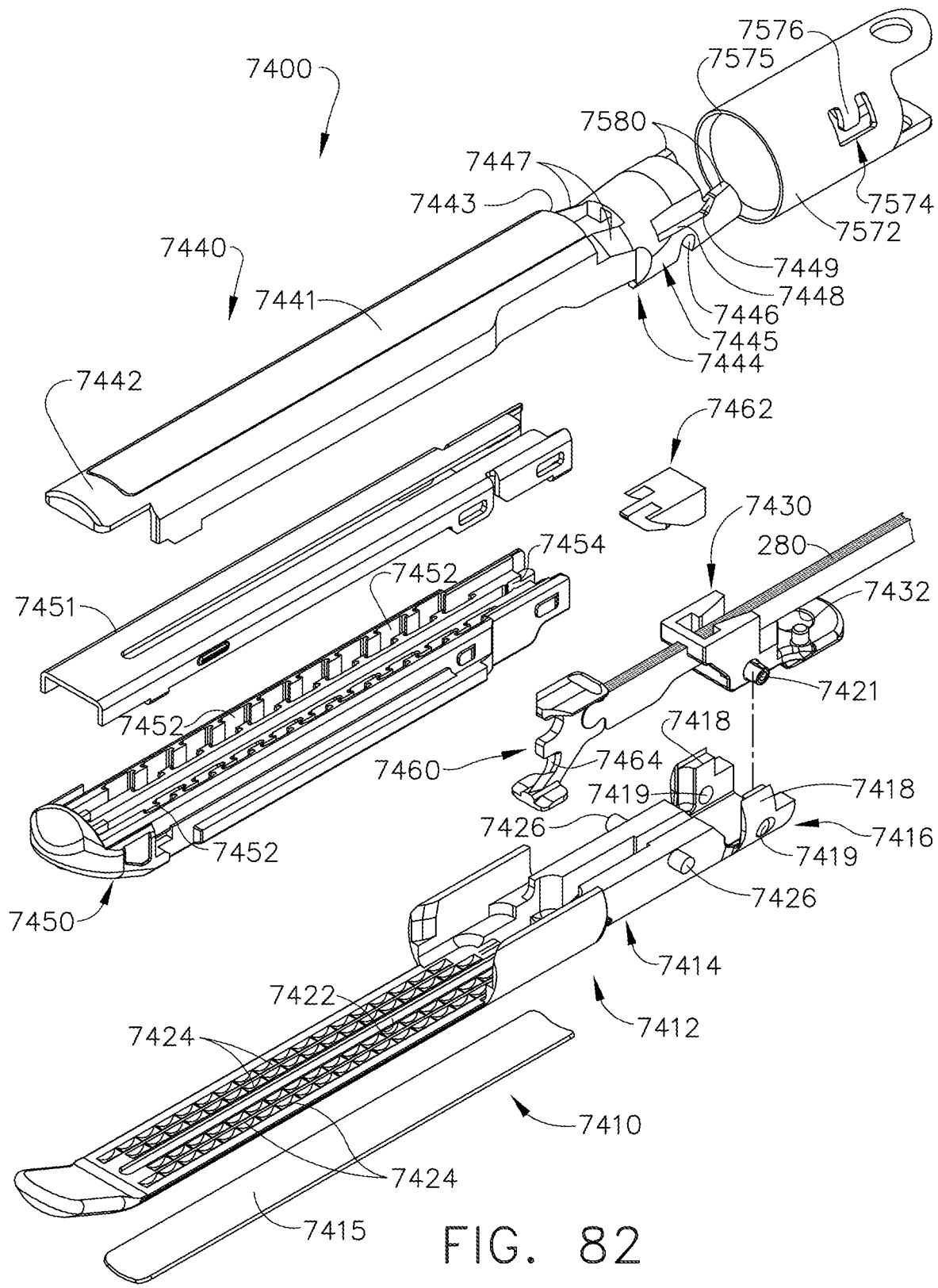
FIG. 82 is an exploded perspective assembly view of the surgical end effector and closure sleeve embodiment of FIGS. 80 and 81.
Figure 83:
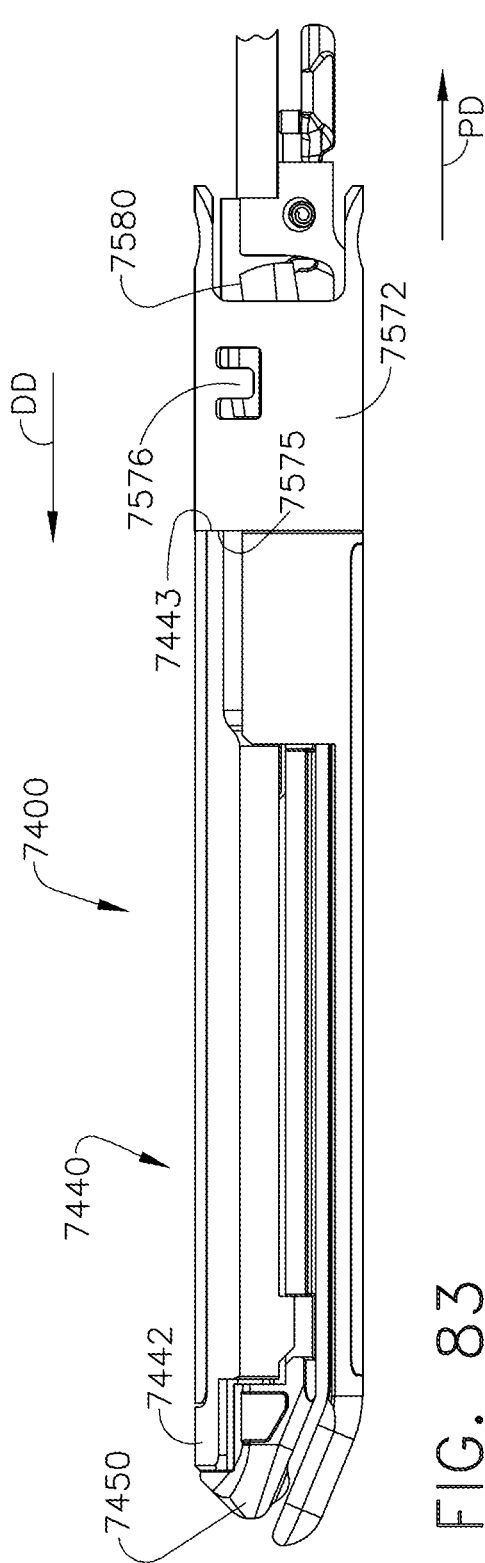
FIG. 83 is a side elevational view of the surgical end effector and closure sleeve embodiment of FIGS. 80-82 with the jaws thereof in a closed position or configuration.
Figure 84:
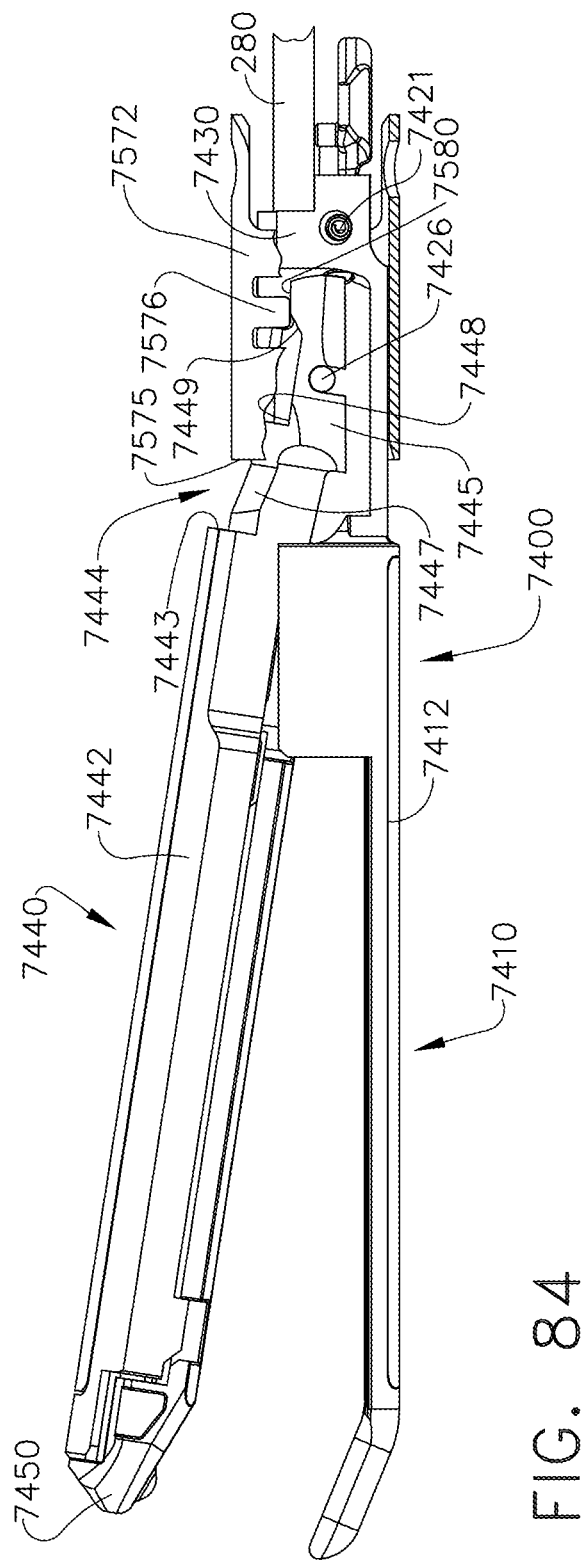
FIG. 84 is a side elevational view of the surgical end effector and closure sleeve embodiment of FIGS. 80-83 with a portion of the closure sleeve shown in cross-section and with the jaws thereof in an open position or configuration.

As can be seen in FIG. 82, the elongate channel 7442 includes a proximal end portion 7444 that has two lateral side portions 7445. Each lateral side portion 7445 has a corresponding U-shaped or open ended slot 7446 therein that is adapted to receive a corresponding pivot pin 7426 that laterally protrudes from the proximal end portion 7416 of the anvil body 7414. Such arrangement serves to movably or pivotally journal the second jaw 7440 or elongate channel 7442 to the first jaw 7410 or anvil 7412. As can be most particularly seen in FIGS. 80, 82 and 84, closure ramp segments 7447 are formed on the proximal end 7444 of the elongate channel 7442. In addition, each lateral side 7445 of the proximal end portion 7444 has a lateral recess area 7448 formed therein. Each lateral recessed area 7448 is located proximal to a corresponding closure ramp segment 7447. An opening ramp or cam 7449 is formed adjacent the proximal end of each lateral recessed area 7448. Each opening ramp or cam 7449 terminates in a top surface 7580. See FIGS. 82 and 84.

The second jaw 7440 or elongate channel 7442 may be movably actuated relative to the first jaw 7410 or anvil 7412 by a closure system of the various types disclosed herein. For example, a closure drive system of the types described herein may be employed to actuate a closure tube of the types described herein as was discussed in detail above. The closure tube may also be attached to an end effector closure sleeve 7572 that may be pivotally attached to the closure tube by a double pivot arrangement in the manner described above. As was described above, for example, axial movement of the closure tube may be controlled through actuation of a closure trigger. In other arrangements, the closure tube may be axially moved by means of a robotic control system, etc. As can be seen in FIGS. 80, 81, 83 and 84, the end effector closure sleeve 7572 extends over the end effector mounting assembly 7430 as well as the proximal end portion 7444 of the elongate channel 7442 of the second jaw 7440. The end effector closure sleeve 7572 includes two diametrically opposed opening members 7574 that are configured to operably engage the proximal end portion 7444 of the second jaw 7440 or elongate channel 7442. In the illustrated embodiment, the opening members 7574 comprise inwardly extending opening tabs 7576 that are formed in portions of the end effector closure sleeve 7572.

The second jaw 7440 is moved to a closed position (FIGS. 81 and 83) by advancing the end effector closure sleeve 7572 in the distal direction "DD". As the end effector closure sleeve 7572 moves distally, the distal end 7575 thereof contacts the closure ramp segments 7447 that are formed on the proximal end 7444 of the elongate channel 7442 and serves to cam the elongate channel 7442 towards the anvil 7412. Once the end effector closure sleeve 7552 has been moved to its distal-most position, the distal end 7575 contacts an abutment surface 7443 on the elongate channel 7442 to maintain the closure load or closing force on the elongate channel 7442. See FIGS. 81 and 83. When the end effector closure sleeve 7572 is in the fully-closed position, the ends of the opening tabs 7576 are received in the corresponding lateral recess areas 7448. To move the second jaw 7440 or elongate channel 7442 to an open position, the closure system is actuated to move the closure sleeve 7572 in the proximal direction "PD". As the end effector closure sleeve 7572 moves proximally, the opening tabs 7572 ride up the corresponding opening ramp or cam 7449 on the proximal end portion 7444 of the elongate channel 7442 to cam or pivot the elongate channel 7442 away from the anvil 7412. Each tab rides up the cam 7449 onto the top surface top surface 7580 and serves to positively retain the elongate channel 7442 in that fully open position. See FIG. 84.

Figure 85:
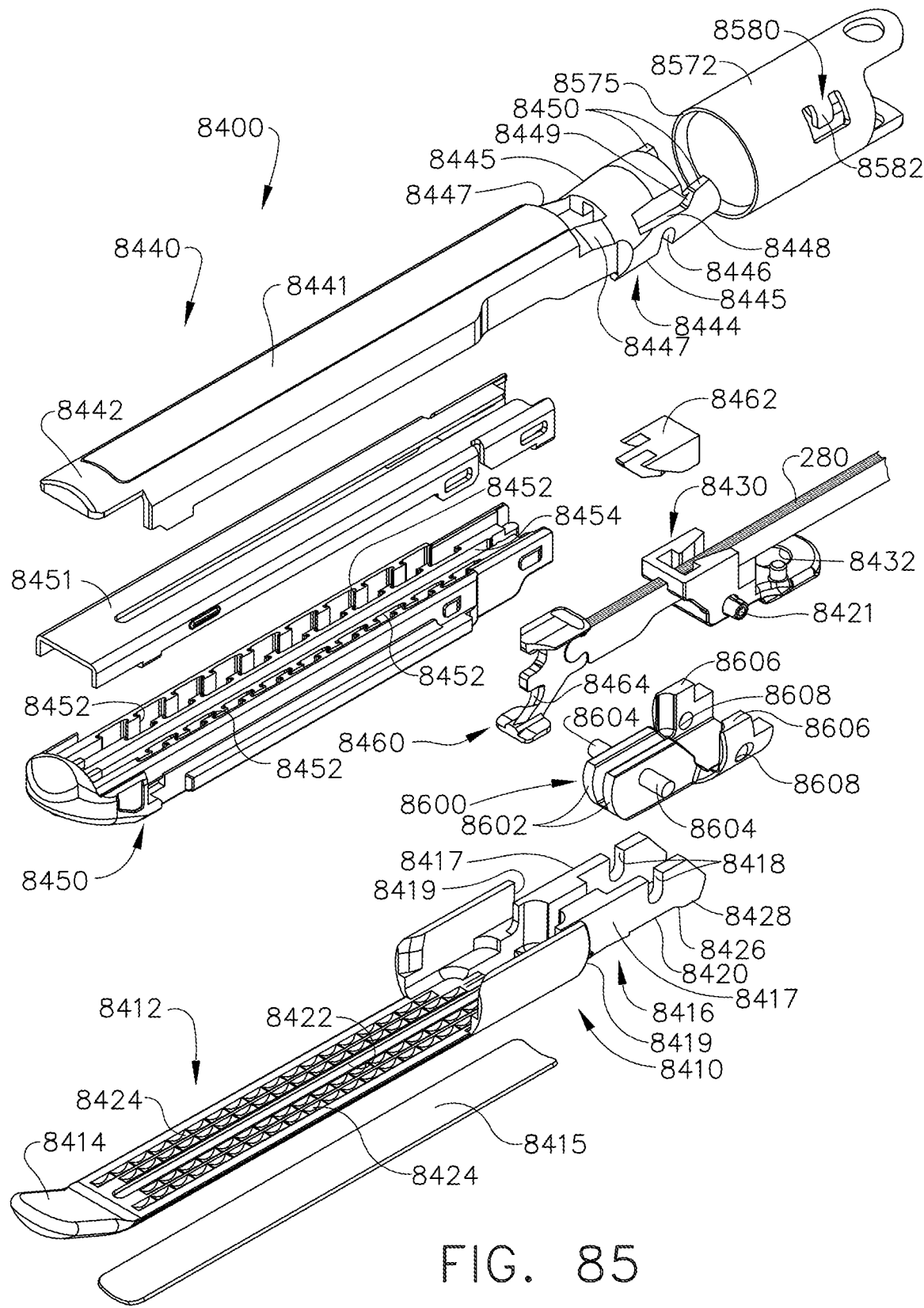
FIG. 85 is an exploded perspective assembly view of another surgical end effector and closure sleeve embodiment.
Figure 86:
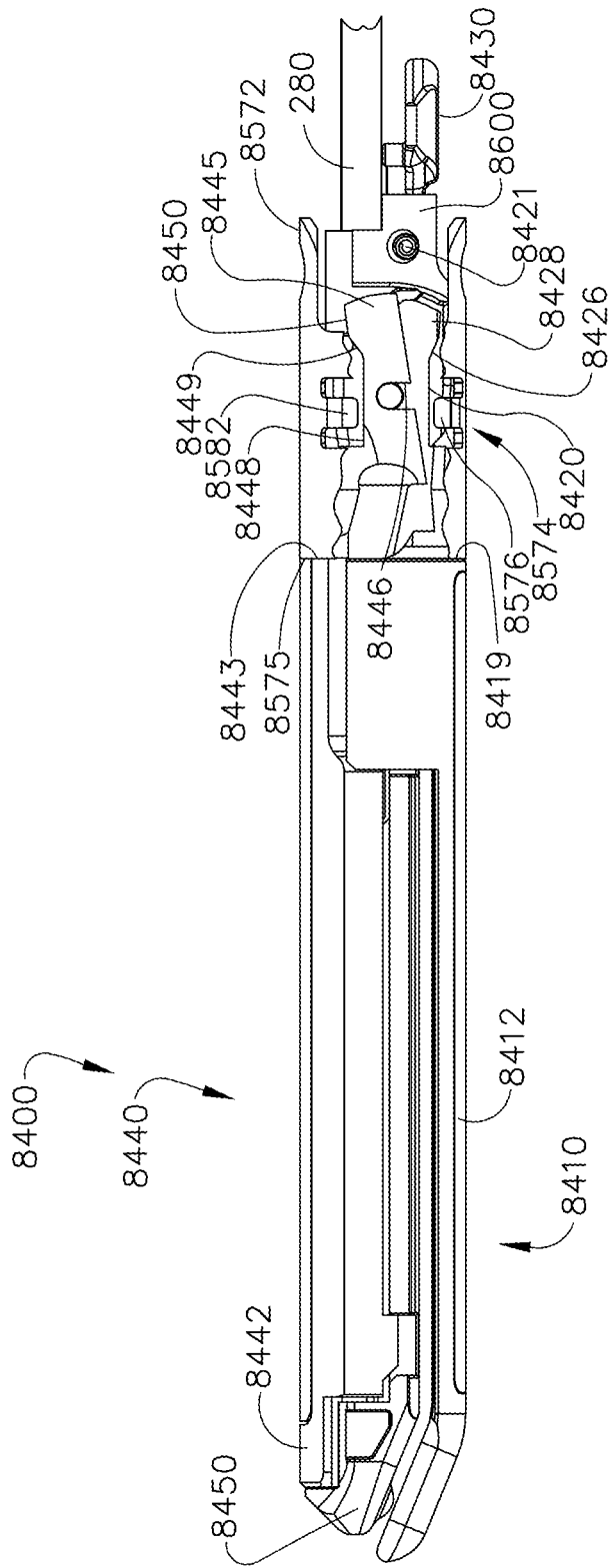
FIG. 86 is a side elevational view of the surgical end effector and closure sleeve embodiment of FIG. 85 with the jaws thereof in a closed position or configuration.
Figure 87:
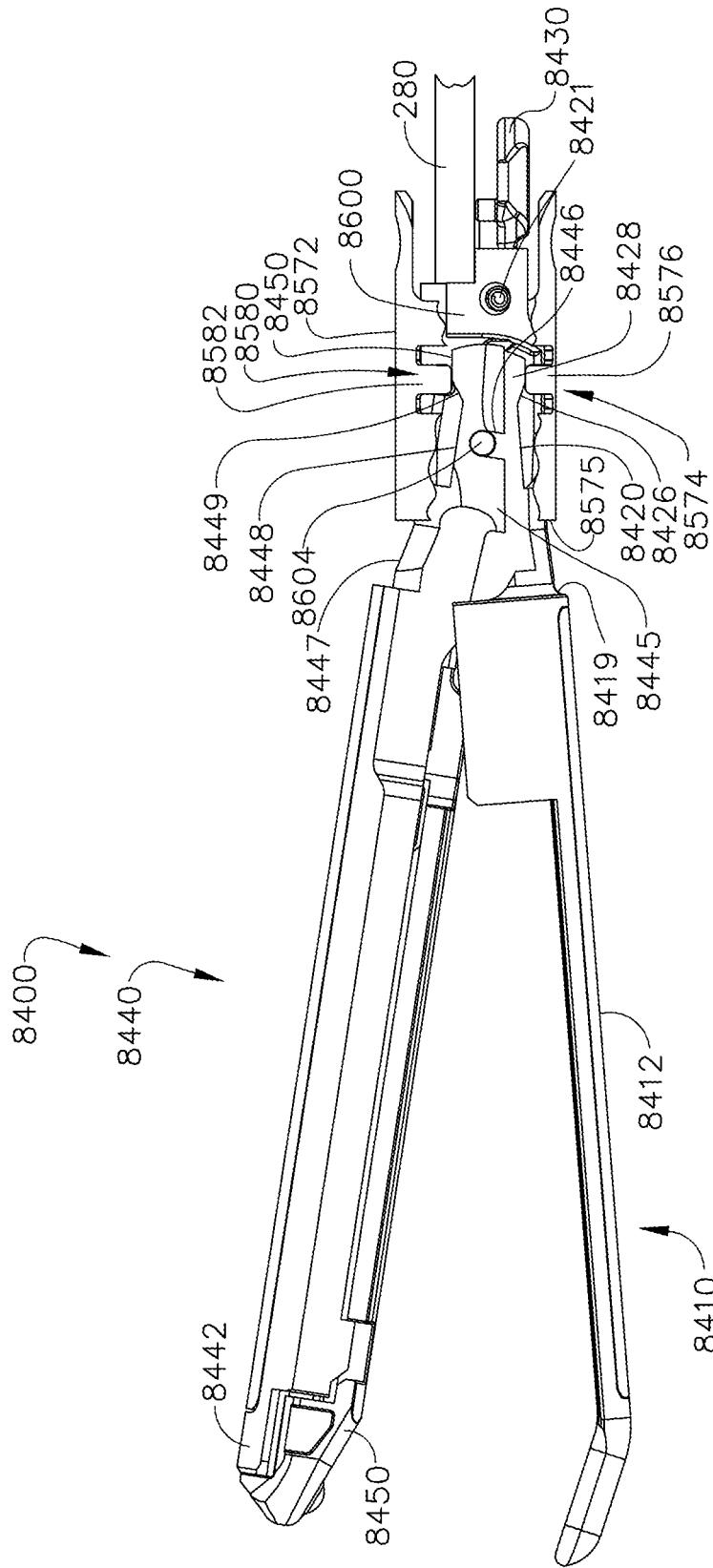
FIG. 87 is a side elevational view of the surgical end effector and closure sleeve embodiment of FIGS. 85 and 86 with the jaws thereof in an open position or configuration with a portion of the closure sleeve shown in cross-section.
Figure 88:
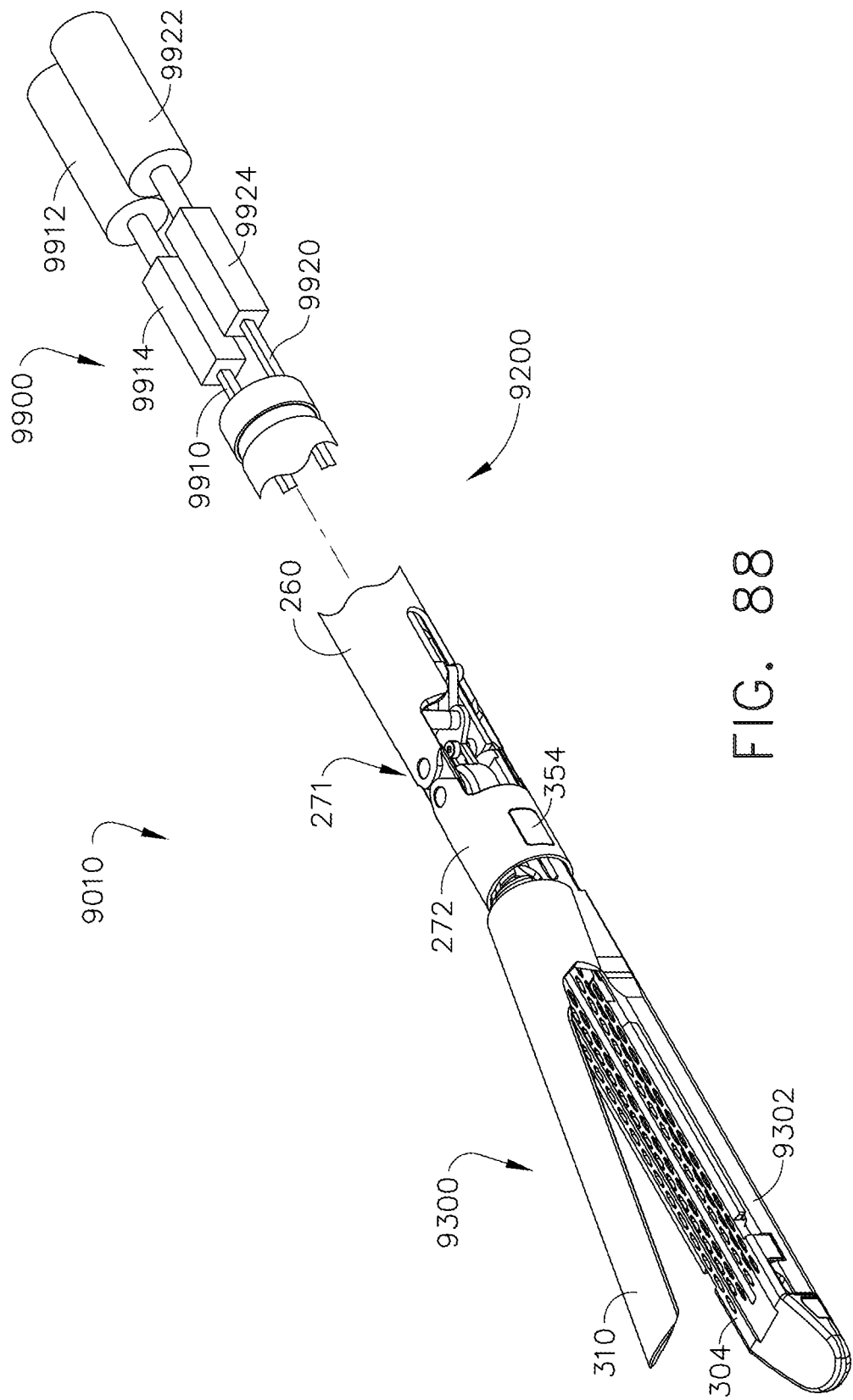
FIG. 88 is a perspective view of a portion of another elongate shaft assembly embodiment.
Figure 89:
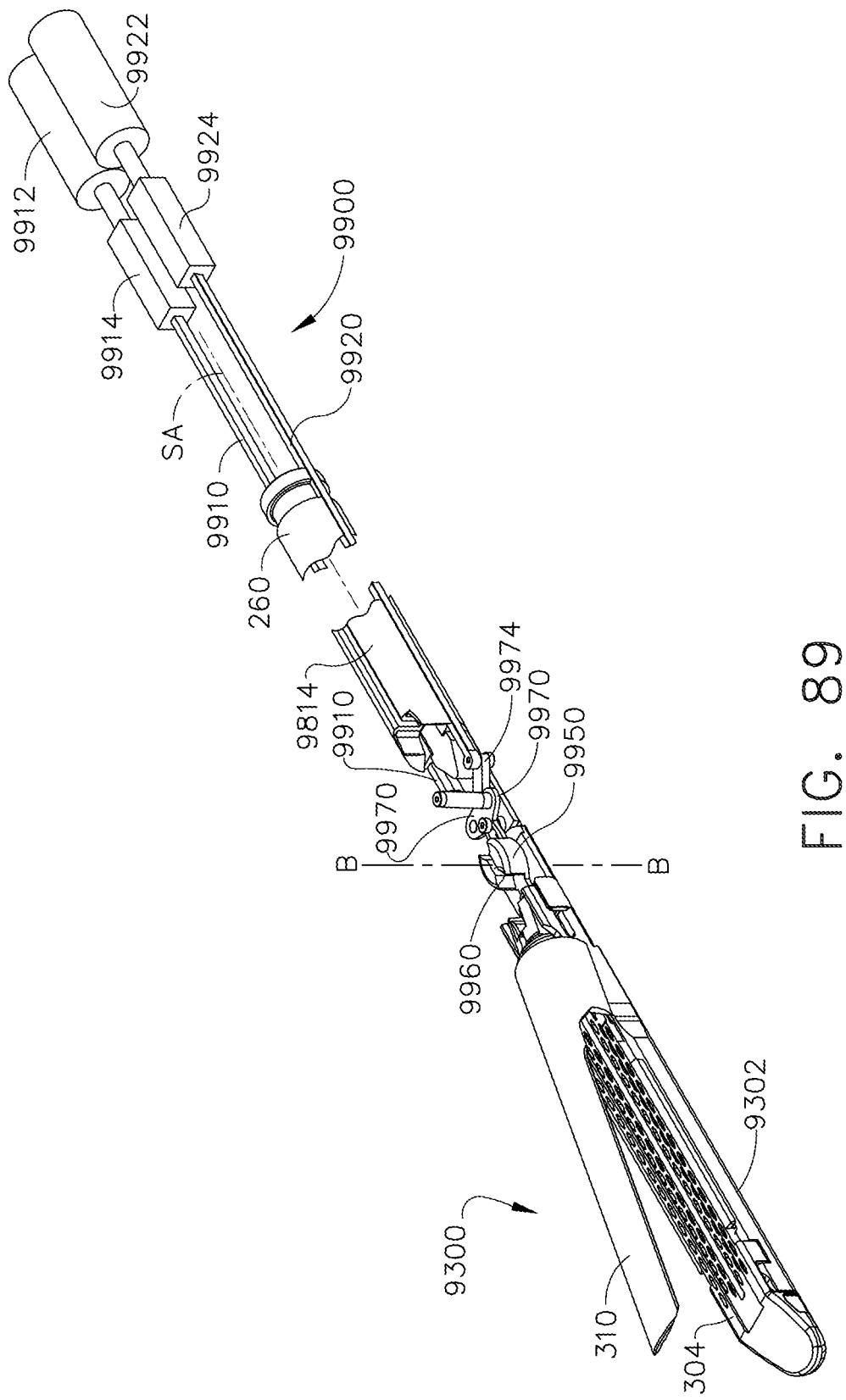
FIG. 89 is another perspective view of the elongate shaft assembly embodiment of FIG. 88 with some components thereof omitted for clarity.
Figure 90:
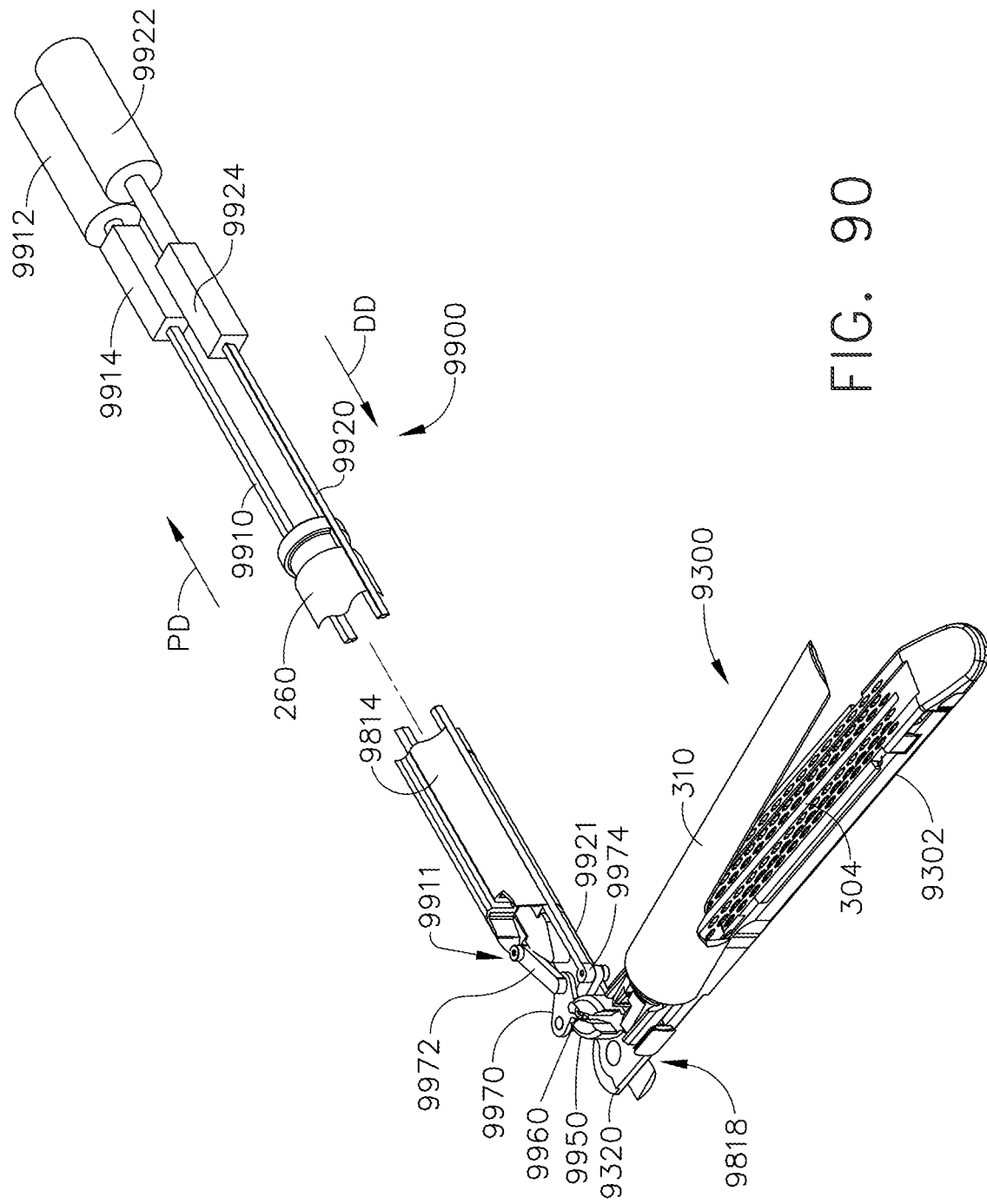
FIG. 90 is another perspective view of the elongate shaft assembly of FIGS. 88 and 89 with the surgical end effector in an articulated position or configuration.

FIGS. 85-87 illustrate another surgical end effector 8400 that comprises two jaws 8410, 8440 that are simultaneously movable between open and closed positions relative to the shaft axis SA-SA. In the illustrated example, the first jaw 8410 comprises an anvil 8412. The illustrated anvil 8412 has an anvil body 8414 that has a proximal end portion 8416 that movably interfaces with an end effector adapter 8600. As can be seen in FIG. 85, the end effector adapter 8600 includes two distally extending distal walls 8602 that each has a lateral pivot pin 8604 protruding laterally therefrom. Each lateral pivot pin 8604 is received in a corresponding open ended U-shaped slot 8418 formed in the lateral side walls 8417 of the proximal end portion 8416 of the anvil 8412. See FIG. 85. Such arrangement permits the elongate channel 8412 to move or pivot relative to the end effector adapter 8600. As can be further seen in FIG. 85, the end effector adapter 8600 is non-movably attached to and end effector mounting assembly 8430. For example, the end effector adapter 8600 further includes two upstanding lateral walls 8606 that each has a mounting hole 8608 therein. The end effector mounting assembly 8430 is received between the upstanding lateral walls 8606 and is non-movably attached thereto by a spring pin 8421 that extends therethrough into holes 8608. The effector mounting assembly 8430 is adapted to be pivotally mounted to, for example, a distal shaft frame that includes a pivot pin that is configured to be rotatably received within the mounting hole 8432 in the end effector mounting assembly 8430. The surgical end effector 8400 may be articulated by an articulation lock and first and second articulation rod arrangements of the type described above or by any of the various articulation systems and articulation rod and/or rod/cable arrangements described herein without departing from the spirit and scope of the present invention. As can also be seen in FIG. 85, the anvil body 8414 also includes an elongate slot 8422 with two staple forming surfaces 8424 formed on each side thereof.

The surgical end effector 8400 further includes a second jaw 8440 that comprises an elongate channel 8442 that is configured to support a surgical staple cartridge 8450 therein. As in the various surgical staple cartridges discussed above, the surgical staple cartridge 8450 is configured to operably support a plurality of staple drivers (not shown) therein that operably support surgical staples (not shown) thereon. The staple drivers are movably supported within corresponding driver pockets 8452 formed in the surgical staple cartridge 8450. The staple drivers are arranged in rows on each side of an elongate slot 8454 in the surgical staple cartridge 8450 to accommodate the axial passage of a firing member 8460 therethrough. A cartridge pan 8451 is attached to the staple cartridge 8450 to prevent the staple drivers from falling out of their respective driver pockets 8452 when the surgical end effector 8400 is manipulated into various orientations. A wedge sled 8462 is movably supported within the surgical staple cartridge 8450 and is configured to be drivingly engaged by the firing member 8460 as the firing member 8460 is driven from a starting position adjacent to the proximal end of the surgical staple cartridge 8450 and an ending position within a distal portion of the surgical staple cartridge 8450. As was discussed above, as the wedge sled 8462 is driven in the distal direction through the surgical staple cartridge 8450, the wedge sled 8462 drivingly contacts the staple drivers to drive them toward the cartridge deck surface (not shown). The firing member 8460 includes a tissue cutting surface 8464 that serves to cut the tissue clamped between the jaws 8410, 8440 as the firing member 8460 is driven distally. A distal firing beam 280 or of the other various types described herein is operably attached to the firing member 8460 as well as to an intermediate firing shaft portion 2222 or other firing system arrangement. Operation of the intermediate firing shaft portion 2222 to drive and retract the distal firing beam 280 was discussed in detail above and will not be repeated for the sake of brevity. Other firing beam and firing system arrangements (motor-powered as well as manually-powered) may also be employed to power the firing member without departing from the spirit and scope of the present invention. A first jaw cover 8415 is removably attached to the anvil 8412 and a second jaw cover 8441 is removably attached to the second jaw 8440 for assembly purposes as well as to prevent the infiltration of tissue and/or body fluid into the first and second jaws which may hamper or interfere with operation of the firing member 8460.

As can be seen in FIG. 85, the elongate channel 8442 includes a proximal end portion 8444 that has two lateral side portions 8445. Each lateral side portion 8445 has a corresponding U-shaped or open ended slot 8446 therein that is adapted to receive a corresponding t lateral pivot pin 8604 that protrudes laterally from the end effector adapter 8600. Such arrangement serves to movably or pivotally journal the second jaw 8440 or elongate channel 8442 to the first jaw 8410 or anvil 8412. As can also be seen in FIG. 85, closure ramp segments 8447 are formed on the proximal end 8444 of the elongate channel 8442. In addition, each lateral side 8445 of the proximal end portion 8444 has a second lateral recessed area 8448 formed therein. Each second lateral recessed area 8448 is located proximal to a corresponding second closure ramp segment 8447. A second opening ramp or cam 8449 is formed adjacent the proximal end of each second lateral recessed area 8448. Each second opening ramp or cam 8449 terminates in a second top surface 8450. Similarly, a first recessed area 8420 is formed on the bottom of each of the side walls 8417 of the proximal end portion 8416 of the anvil 8412. A first opening ramp or cam 8426 is formed adjacent the proximal end of each first lateral recessed area 8420. Each first opening ramp or cam 8426 terminates in a first top surface 8428.

The second jaw 8440 or elongate channel 8442 and the first jaw 8410 or anvil 8412 may be simultaneously moved between open and closed positions by a closure system of the various types disclosed herein. For example, a closure drive system 30 may be employed to actuate a closure tube 260 in the manner described herein. The closure tube 260 may also be attached to an end effector closure sleeve 8572 that may be pivotally attached to the closure tube 260 by a double pivot arrangement in the manner described above. As was described above, for example, axial movement of the closure tube 260 may be controlled through actuation of a closure trigger 32. In other arrangements, the closure tube may be axially moved by means of a robotic control system, etc. As can be seen in FIGS. 86 and 87, the end effector closure sleeve 8572 extends over the end effector mounting assembly 8430, the end effector adapter 8600 as well as the proximal end portion 8444 of the elongate channel 8442 of the second jaw 8440 and the proximal end portion 8416 of the first jaw 8410 or anvil 8412. The end effector closure sleeve 8572 includes two diametrically opposed, first opening members 8574 that are configured to operably engage the proximal end portion 8416 of the first jaw 8410. In the illustrated embodiment, the first opening members 8574 comprise inwardly extending first opening tabs 8576 that are formed in portions of the end effector closure sleeve 8572. Likewise, the end effector closure sleeve 8572 further includes two diametrically opposed, second opening members 8580 that are configured to operably engage the proximal end portion 8444 of the second jaw 8440. In the illustrated embodiment, the second opening members 8580 comprise inwardly extending second opening tabs 8582 that are formed in portions of the end effector closure sleeve 8572.

The first and second jaws, 8410, 8440 are simultaneously moved to a closed position (FIG. 86) by advancing the end effector closure sleeve 8572 in the distal direction "DD". As the end effector closure sleeve 8572 moves distally, the distal end 8575 thereof contacts the bottom of the proximal end portion 8416 of the first jaw 8410 or anvil 8412 as well as the closure ramp segments 8447 that are formed on the proximal end 8444 of the elongate channel 8442 and serves to cam the first and second jaws 8410, 8440 towards each other. Once the end effector closure sleeve 8572 has been moved to its distal-most position, the distal end 8575 of the end effector closure sleeve 8572 contacts first abutment surfaces 8419 on the first jaw 8410 or anvil 8412 as well as a second abutment surface 8443 on the second jaw 8440 or elongate channel 8442 to maintain the closure load or closing force on both of the jaws 8410, 8440. See FIG. 86. When the end effector closure sleeve 8572 is in the fully-closed position, the ends of the first opening tabs 8576 are received in the corresponding first lateral recesses areas 8420 and the ends of the second opening tabs 8582 are received in the corresponding second lateral recess areas 8448. To move the first and second jaws 8410, 8440 away from each other to open positions, the closure system is actuated to move the closure sleeve 8572 in the proximal direction "PD". As the end effector closure sleeve 8572 moves proximally, the first opening tabs 8576 ride up the corresponding first opening ramp or cam 8426 on the bottom of the proximal end portion 8416 of the first jaw 8410 to cam or pivot the first jaw 8410 or anvil 8412 in a direction away from the second jaw 8440 or elongate channel 8442 and the second opening tabs 8582 ride up the corresponding second ramps 8449 on the proximal end portion 8444 of the elongate channel 8442 to cam or pivot the elongate channel 8442 in a direction away from the first jaw or anvil 8412. Each of the first tabs 8576 rides up the corresponding cam or ramp 8426 onto the corresponding first locking surface 8428 and each of the second tabs 8582 rides up the corresponding second cam or ramp 8449 onto the corresponding second locking surface 8450 to thereby retain the first and second jaws 8410, 8400 in the open position. The reader will appreciate that the axial position of the first tabs 8576 relative to the second tabs 8582 may be positioned so as to simultaneously move the first and second jaws away from each other or they may be axially offset so that one of the jaws moves before the other jaw moves.

FIGS. 88-93 illustrate portions of another surgical instrument 9010 that includes a surgical end effector 9300 that operably interfaces with an elongate shaft assembly 9200. The surgical end effector 9300 is similar to surgical end effector 300 that was discussed in detail above and includes a first jaw in the form of an elongate channel 9302 that is configured to operably support a surgical staple cartridge 304 therein. The illustrated surgical end effector 9300 further includes a second jaw in the form of an anvil 310 that is supported on the elongate channel 9302 for movement relative thereto. The anvil 310 may be movably actuated by the closure system described above and shown in FIGS. 88 and 91. For example, a first closure drive system may be employed to actuate a closure tube 260 in the manner described herein. The closure tube 260 is attached to an end effector closure sleeve 272 that is pivotally attached to the closure tube 260 by a double pivot closure sleeve assembly 271 in the manner described above. As was described above, for example, axial movement of the closure tube 260 may be controlled through actuation of a closure trigger. As was also described above, the closure sleeve 272 incudes opening cams that serve to movably actuate the anvil 310 to an open position. In use, the closure tube 260 is translated distally (direction "DD") to close the anvil 310, for example, in response to the actuation of the closure trigger. The anvil 310 is closed by distally translating the closure tube 260 in the distal direction "DD" and as well as the end effector closure sleeve 272 that is pivotally coupled thereto. As the end effector closure sleeve 272 is driven distally, the cam tabs 358 of the opening cams 354 move distally within the cam slots 318 in the anvil 310 to operably interface or ride on the cam surfaces 319 to cam the body portion 312 of the anvil 310 away from the surgical staple cartridge 304 into an open position. The anvil 310 is closed by distally translating the closure tube 260 in the distal direction "DD" until the distal end 275 of the end effector closure sleeve 272 rides up the anvil attachment arms 316 to contact the which causes the cam tabs 358 to move in the proximal direction "PD" within the cam slots 318 on the cam surfaces 319 to pivot the anvil 310 into the open position.

Figure 91:
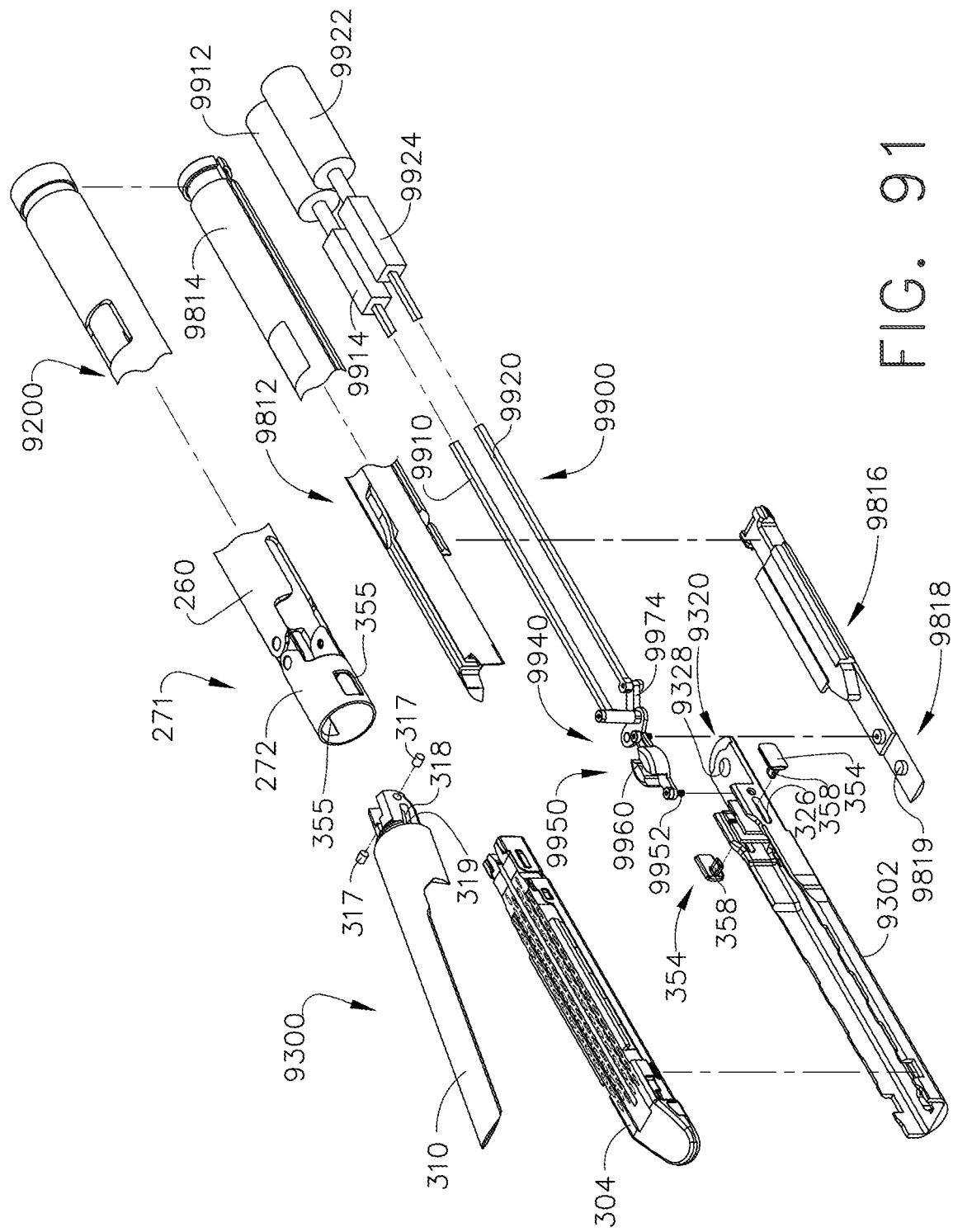
FIG. 91 is an exploded assembly view of the elongate shaft assembly of FIGS. 88-90.

As can be seen in FIG. 91 for example, the elongate shaft assembly 9200 includes a two piece shaft frame or spine assembly 9812 upon which the closure tube assembly 260 is received. The spine assembly 9812 includes a proximal spine portion 9814 and a distal spine portion 9816. The proximal spine portion 9816 may be rotatably journaled in the handle or housing (not shown) in the various manners described herein to facilitate rotation of the surgical end effector 9300 about the shaft axis SA. Although not shown, the surgical instrument 9010 may also include a firing beam arrangement and any of the various firing drive system arrangements disclosed herein for driving a firing member through the surgical staple cartridge in the various manners discussed above. As can be seen in FIG. 91, the distal spine portion 9816 includes a distal end portion 9818 that has an upwardly protruding pivot pin 9819 thereon that is adapted to be pivotally received within a pivot hole 9328 formed in the proximal end portion 9320 of the elongate channel 9302. Such arrangement facilitates pivotal travel of the elongate channel 9302 of the surgical end effector 9300 relative to the spine assembly 9812 about an articulation axis B-B that is defined by the pivot hole 9328. As indicated above, the articulation axis B-B is transverse to the shaft axis SA-SA that is defined by elongate shaft assembly 9200.

Still referring to FIG. 91, the elongate shaft assembly 9200 further includes an articulation system, generally designated as 9900 that includes a first articulation bar 9910 and a second articulation bar 9920. The first articulation bar 9910 operably interfaces with a first articulation motor 9912 that is operably supported in the surgical instrument handle or housing or portion of a robotically controlled system. As can be seen in FIGS. 92 and 93, the first articulation bar 9910 is attached to a first articulation nut 9914 that is threadably received on a first threaded drive shaft 9916 of the first articulation motor 9912. Rotation of the first threaded drive shaft 9916 in a first rotary direction will result in the distal advancement of the first articulation bar 9910 in the distal direction "DD" and rotation of the first threaded drive shaft 9916 in a second or opposite rotary direction will result in the proximal advancement of the first articulation drive bar 9910 in the proximal direction "PD".

The illustrated articulation system 9900 further includes a second articulation bar 9920 that operably interfaces with a second articulation motor 9922 that is operably supported in the surgical instrument handle or housing or portion of a robotically controlled system. As can be seen in FIGS. 92 and 93, the second articulation bar 9920 is attached to a second articulation nut 9924 that is threadably received on a second threaded drive shaft 9926 of the second articulation motor 9922. Rotation of the second threaded drive shaft 9926 in a first rotary direction will result in the proximal advancement of the second articulation bar 9920 in the proximal direction "PD" and rotation of the second threaded drive shaft 9926 in a second or opposite rotary direction will result in the distal advancement of the second articulation drive bar 9920 in the distal direction "DD".

The articulation system 9900 further includes a cross-linkage assembly 9940 that is operably attached to the first and second articulation bars 9910, 9920. As can be seen in FIG. 91, the cross-linkage assembly 9940 includes a middle support member 9950 that is pivotally pinned to the proximal end 9320 of the elongate channel 9302 with a first pin 9952. The middle support member 9950 further includes a proximal connector tab 9954 that includes a slot 9956 for receiving a second pin 9958 therein for pivotally attaching the proximal connector tab 9954 to the distal end portion 9818 of the distal spine portion 9816. The pin and slot arrangement facilitate pivotal and axial travel of the middle support member 9950 relative to the spine assembly 9812. The middle support member 9950 further includes a slot 9960 for receiving a firing beam therethrough. The middle support member 9950 serves to provide lateral support to the firing beam as it flexes to accommodate articulation of the surgical end effector 9300.

As can be most particularly seen in FIGS. 92 and 93, the middle support member 9950 has a proximal linkage tab portion 9970 that facilitates attachment of the first and second articulation bars 9910, 9920 thereto. In particular, a distal end 9911 of the first articulation bar 9910 is pivotally attached to a first articulation link 9972 that is pivotally pinned to the proximal linkage tab portion 9970. Likewise, a distal end 9921 of the second articulation bar 9920 is pivotally pinned to a second articulation link 9974 that is pivotally pinned to the proximal linkage tab portion 9970 of the middle support member 9950. FIG. 92 illustrates articulation of the surgical end effector 9300 in the direction represented by arrow 9980. As can be seen in that Figure, the first threaded drive shaft 9916 of the first articulation motor is rotated in a first rotary direction to drive the first articulation bar 9910 in the distal direction. In addition, the second threaded drive shaft 9926 of the second articulation motor 9922 is rotated in a second rotary direction to draw the second articulation bar 9920 in the proximal direction. The first and second articulation motors 9912, 9922 are operated by a computer controlled system and, as can be seen in FIG. 92, the distance that first articulation bar 9910 moves in the distal direction is not equal to the distance in which the second articulation bar 9920 moves in the proximal direction.

FIG. 93 illustrates articulation of the surgical end effector 9300 in the direction represented by arrow 9982. As can be seen in that Figure, the second threaded drive shaft 9926 of the second articulation motor 9922 is rotated in a first rotary direction to drive the second articulation bar 9920 in the distal direction. In addition, the first threaded drive shaft 9916 of the first articulation motor 9912 is rotated in a second rotary direction to draw the first articulation bar 9910 in the proximal direction. The first and second articulation motors 9912, 9922 are operated by a computer controlled system and, as can be seen in FIG. 92, the distance that second articulation bar 9920 moves in the distal direction is not equal to the distance in which the first articulation bar 9910 moves in the proximal direction. In alternative arrangements, only one articulation motor may be employed to articulate the end effector. In such arrangements, for example, the second link may be proximally coupled to the first link by means of a rack and pinion arrangement similar to those rack and pinion arrangements disclosed in detail herein.

Figure 94:
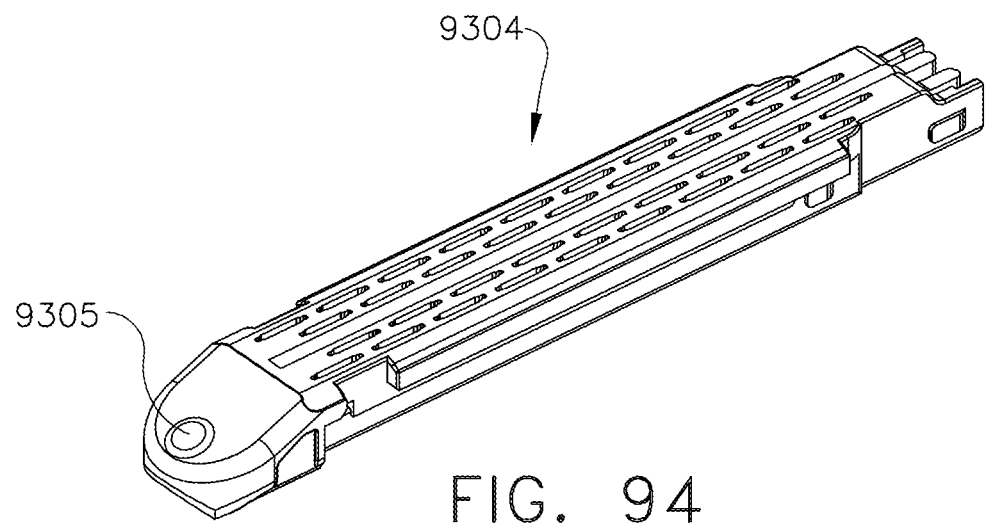
FIG. 94 is a perspective view of a surgical staple cartridge embodiment.
Figure 95:
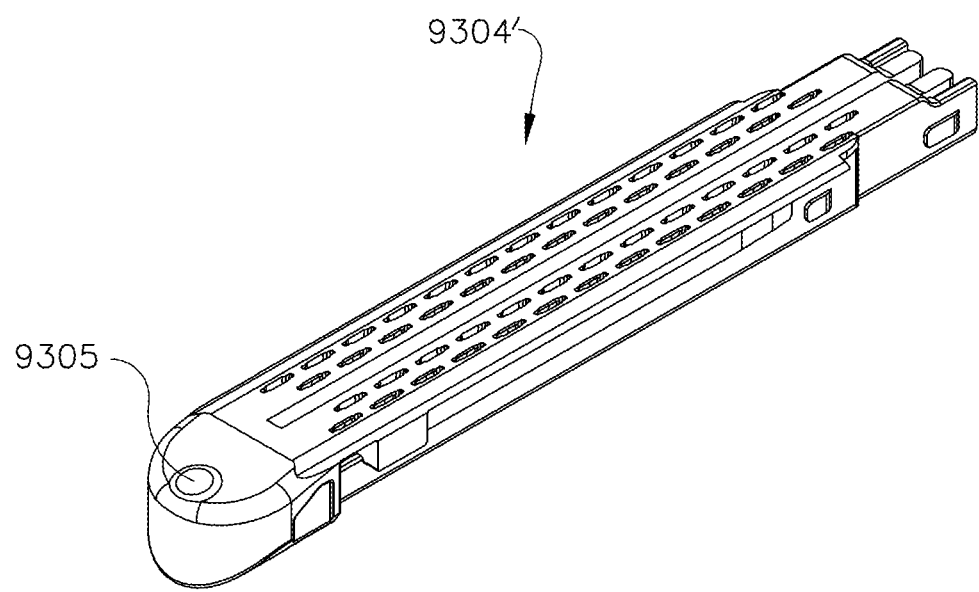
FIG. 95 is a perspective view of another surgical staple cartridge embodiment.

FIGS. 94 and 95 illustrate surgical staple cartridges 9304 and 9304' that each include a light member 9305 for illuminating the distal end of the surgical end effector in which it is supported. Each of the staple cartridges 9304, 9304' may have conductors (not shown) that are arranged on the bottom of the cartridge or on the cartridge sides that are configured to electrically contact corresponding conductors in the elongate channel that communicate with a source of electrical energy located in the instrument handle or housing. Thus, when the cartridge 9304, 9304' are properly seated in the elongate channel of the surgical end effector, the light 9305 therein may receive power from the source of electrical power in the handle or housing through the corresponding conductors.

The surgical instrument systems described herein are motivated by an electric motor; however, the surgical instrument systems described herein can be motivated in any suitable manner. In various instances, the surgical instrument systems described herein can be motivated by a manually-operated trigger, for example. The motor or motor(s) may comprise a portion or portions of a robotically controlled system.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The surgical instrument systems described herein are motivated by one or more electric motors; however, the surgical instrument systems described herein can be motivated in any suitable manner. In various instances, the surgical instrument systems described herein can be motivated by a manually-operated trigger, for example.

EXAMPLES

Example 1—A surgical instrument, comprising a surgical end effector. The surgical end effector comprises a first jaw and a second jaw that is movably supported relative to the first jaw between an open position and closed positions. The surgical instrument further comprises a closure member that is axially movable in response to applications of closing and opening motions. The closure member comprises at least one opening cam that protrudes therefrom to movably engage a corresponding slotted cam surface on the second jaw such that, upon application of the opening motion to the closure member, the at least one opening cam movably engages the corresponding slotted cam surface to move the second jaw to the open position and upon application of the closure motion to the closure member, the closure member engages the second jaw to move the second jaw to one of the closed positions.

Example 2—The surgical instrument of Example 1, wherein the at least one opening cam comprises a first opening cam that extends laterally inwardly from the closure member and engages a first one of the corresponding slotted cam surfaces. A second opening cam extends laterally inwardly from the closure member and engages a second one of the corresponding slotted cam surfaces.

Example 3—The surgical instrument of Example 2, wherein the second opening cam is diametrically opposite from the first opening cam on the closure member.

Example 4—The surgical instrument of Examples 1, 2 or 3, wherein the at least one opening cam is removably attached to the closure member.

Example 5—The surgical instrument of Examples 1, 2, 3 or 4, wherein the at least one opening cam is configured for snap engagement with the closure member.

Example 6—The surgical instrument of Examples 1, 2 or 3, wherein the at least one opening cam is integrally formed in the closure member.

Example 7—The surgical instrument of Examples 1, 2, 3 or 6, wherein the at least one opening cam is crimped into a wall of the closure member such that a crimped portion of the wall movably extends through a corresponding portion of the first jaw to movably engage the corresponding slotted cam surface on the second jaw.

Example 8—The surgical instrument of Examples 1, 2, 3, 4, 5, 6 or 7, wherein the at least one opening cam extends inwardly through a portion of the first jaw to engage the corresponding slotted cam surface.

Example 9—The surgical instrument of Examples 1, 2, 3, 4, 5, 6, 7 or 8, wherein the second jaw comprises a pair of laterally extending trunnions configured to be pivotally received in corresponding trunnion holes in the first jaw to facilitate pivotal travel of the second jaw relative to the first jaw.

Example 10—The surgical instrument of Examples 1, 2, 3, 4, 5, 6, 7, 8 or 9, wherein the first jaw is configured to operably support a surgical staple cartridge and wherein the second jaw comprises an anvil.

Example 11—A surgical instrument, comprising a surgical end effector. The surgical end effector comprises a first jaw and a second jaw that is pivotally supported on the first jaw for selective movement relative thereto between an open position and closed positions. The second jaw comprises first and second cam surfaces. The surgical instrument further comprises an end effector closure sleeve that comprises a first opening cam that extends laterally inwardly from the end effector closure sleeve through a portion of the first jaw to operably engage the first cam surface. A second opening cam extends laterally inwardly from the end effector closure sleeve through another portion of the first jaw to operably engage the second cam surface such that upon application of an opening motion to the end effector closure sleeve, the first opening cam movably engages the first cam surface and the second opening cam movably engages the second cam surface to move the second jaw to the open position and upon application of a closing motion to the end effector closure sleeve, the end effector closure sleeve movably engages the second jaw to move the second jaw to one of the closed positions.

Example 12—The surgical instrument of Example 11, wherein the first and second opening cams are removably attached to the end effector closure sleeve.

Example 13—The surgical instrument of Example 11, wherein the first and second opening cams comprise permanent deformations in the end effector closure sleeve.

Example 14—The surgical instrument of Examples 11 or 13, wherein the first and second opening cams are formed by crimping the end effector closure sleeve.

Example 15—The surgical instrument of Example 14, wherein the first and second opening cams are crimped at 90 degree angles relative to adjacent portions of an outer surface of the end effector closure sleeve.

Example 16—The surgical instrument of Examples 11, 12, 13, 14 or 15, wherein the first opening cam movably protrudes through a first slot in the first jaw to operably interface with the first cam surface in the second jaw and wherein the second opening cam movably protrudes through a second slot in the first jaw to operably interface with the second cam surface in the second jaw.

Example 17—The surgical instrument of Examples 11, 12, 13, 14, 15 or 16, wherein the second jaw comprises a pair of laterally extending trunnions configured to be pivotally received in corresponding trunnion holes in the first jaw to facilitate pivotal travel of the second jaw relative to the first jaw.

Example 18—The surgical instrument of Examples 11, 12, 13, 14, 15, 16 or 17, wherein the first jaw is configured to operably support a surgical staple cartridge and wherein the second jaw comprises an anvil.

Example 19—A surgical instrument, comprising a housing and a closure system that is operably supported by the housing and is configured to generate closing and opening motions. An elongate shaft assembly operably interfaces with the housing. The elongate shaft assembly comprises an end effector closure sleeve that is axially movable in response to applications of the closing and opening motions thereto. The surgical instrument further comprises a surgical end effector that comprises an elongate channel that operably interfaces with the elongate shaft assembly and is configured to operably support a surgical staple cartridge therein. An anvil is movably supported on the elongate channel for selective movement relative thereto between an open position and closed positions. The surgical instrument also comprises at least two opening cams that protrude from the end effector closure sleeve such that upon application of the opening motion to the end effector closure sleeve, the at least two opening cams operably interface with corresponding cam surfaces on the anvil in a first direction to move the anvil to the open position and upon application of the closing motion to the end effector closure sleeve, the end effector closure sleeve operably interfaces with the anvil in a second direction to cause the anvil to move to one of the closed positions.

Example 20—The surgical instrument of Example 19, wherein at least one opening cam is formed in the end effector closure sleeve.

Example 21—A surgical instrument, comprising an elongate shaft assembly that defines a shaft axis. An end effector mounting assembly is movably coupled to the elongate shaft assembly for selective articulation about an articulation axis that is transverse to the shaft axis. First and second jaws are movably coupled to the end effector mounting assembly such that the first and second jaws are each movable relative to each other and the shaft axis about a common pivot axis between an open position and closed positions. The first jaw comprises a first point and the second jaw comprises a second point wherein the first and second points lie along a common axis that is perpendicular to the shaft axis. The first point is a first distance from the shaft axis when the first jaw is in the open position and wherein the second point is a second distance from the shaft axis when the second jaw is in the open position and wherein said second distance is different from said first distance. The surgical instrument further comprises means for biasing the first and second jaws away from each other to the open position and means for applying closure motions to the first and second jaws to move the first and second jaws toward each other to the closed positions.

Example 22—The surgical instrument of Example 21, wherein the one of the first and second jaws comprises an elongate channel that is configured to operably support a surgical staple cartridge therein and wherein the other one of the first and second jaws comprises an anvil.

Example 23—The surgical instrument of Example 21, wherein the first jaw comprises a surgical staple cartridge and wherein the second jaw comprises an anvil and wherein the second distance is greater than the first distance.

Example 24—The surgical instrument of Examples 21, 22 or 23, further comprising a firing member that is supported for axial travel between the first and second jaws when the first and second jaws are in one of the closed positions.

Example 25—The surgical instrument of Examples 21, 22, 23 or 24, wherein the end effector mounting assembly comprises a pair of lateral sides. Each lateral side comprises a laterally protruding trunnion pin that defines the pivot axis. Each of the first and second jaws are pivotally supported on each of the laterally protruding trunnion pins.

Example 26—The surgical instrument of Examples 21, 22, 23, 24 or 25, wherein the means for biasing comprises a spring located between the first and second jaws.

Example 27—The surgical instrument of Examples 21, 22, 23, 24, 25 or 26, wherein the means for applying closure motions comprises an axially movable end effector closure sleeve that is configured to simultaneously engage portions of the first and second jaws when the end effector closure sleeve is axially moved in a first direction.

Example 28—The surgical instrument of Examples 21, 22, 23, 24, 25, 26 or 27, further comprising an axially movable firing member that is supported for axial travel between the first and second jaws when the first and second jaws are in one of the closed positions.

Example 29—The surgical instrument of Example 28, wherein the firing member comprises a tissue cutting surface.

Example 30—A surgical instrument, comprising an elongate shaft assembly that defines a shaft axis. An end effector mounting assembly is movably coupled to the elongate shaft assembly for selective articulation about an articulation axis that is transverse to the shaft axis. First and second jaws are movably coupled to the end effector mounting assembly such that the first and second jaws are each movable relative to each other and the shaft axis between an open position and closed positions such that upon application of a closing motion to the first and second jaws causes one of the first and second jaws to move to one of the closed positions at a closure rate that differs from another closure rate at which the other of the first and second jaws moves to the closed position. The surgical instrument further comprises means for selectively applying the closing motion to the first and second jaws and an opening motion to the first and second jaws to selectively move the first and second jaws from the closed positions to the open position.

Example 31—The surgical instrument of Example 30, further comprising an axially movable firing member that is supported for axial travel between the first and second jaws when the first and second jaws are in one of the closed positions.

Example 32—The surgical instrument of Examples 30 or 31, further comprising a first cam slot on the end effector mounting assembly. The first cam slot defines a first closure wedge portion and a first opening wedge portion. A second cam slot is also provided on the end effector mounting assembly. The second cam slot defines a second closure wedge portion and a second opening wedge portion. The first jaw comprises a pair of first opening members and a pair of first closing members wherein one of the first opening members and one of the first closing members are movably received within the first cam slot. Another one of the first opening members and another one of the first closing members are received within the second cam slot. The second jaw comprises a pair of second opening members and a pair of second closing members wherein one of the second opening members and one of the second closing members are movably received in the first cam slot. Another one of the second opening members and another one of the second closing members are movably received within the second cam slot. The means for selectively applying is configured to move the first and second jaws in a first direction so as to cause the one of the first closing members and the one of the second closing members to movably enter the first closure wedge portion and the another one of the first closing members and the another one of the second closing members to movably enter the second closure wedge portion to thereby cause the first and second jaws to move toward each other to one of the closed positions. The means for selectively applying is further configured to move the first and second jaws in a second direction so as to cause the one of the first opening members and the one of the second opening members to move into the first opening wedge portion and the another one of the first opening members and the another one of the second opening members to move into the second opening wedge portion to thereby cause the first and second jaws to move away from each other to the open position.

Example 33—The surgical instrument of Example 32, wherein the first cam slot is formed in a first cam plate that is coupled to the end effector mounting assembly. The second cam slot is formed in a second cam plate that is coupled to the end effector mounting assembly.

Example 34—The surgical instrument of Examples 32 or 33, wherein the means for selectively applying comprises an end effector closure sleeve that is axially movable in response to applications of the closing and opening motions thereto. The end effector closure sleeve comprises a first opening tab that corresponds to the one of the first opening members and the one of the second opening members for operable contact therewith when the end effector closure sleeve is moved in the second direction. A second opening tab corresponds to the another one of the first opening members and the another one of the second opening members for operable contact therewith when the end effector closure sleeve is moved in the second direction.

Example 35—The surgical instrument of Examples 30, 31, 32, 33 or 34, wherein one of the first and second jaws comprises an elongate channel that is configured to operably support a surgical staple cartridge therein and wherein the other one of the first and second jaws comprises an anvil.

Example 36—The surgical instrument of Examples 31, 32, 33, 34 or 35, further comprising a firing member that is supported for axial travel between the first and second jaws when the first and second jaws are in one of the closed positions.

Example 37—A surgical instrument, comprising a first jaw and a second jaw that are pivotally supported relative to each other for selective pivotal travel between an open position and closed positions. A closure member is axially movable in response to applications of closing and opening motions thereto. The closure member comprises at least two inwardly extending opening tabs that are configured to operably engage corresponding portions of at least one of the first and second jaws upon application of the opening motions to the closure member to move at least one of the first and second jaws to the open position.

Example 38—The surgical instrument of Example 37, wherein the at least one of the at least two inwardly extending opening tabs is integrally formed in the closure member.

Example 39—The surgical instrument of Example 37, wherein each of the at least two inwardly extending opening tabs are removably affixed to the closure member.

Example 40—The surgical instrument of Examples 37, 38 or 39, wherein one of the first and second jaws comprises an elongate channel that is configured to operably support a surgical staple cartridge therein and wherein the other one of the first and second jaws comprises an anvil.

Example 41—A surgical stapling instrument, comprising an elongate shaft assembly that defines a shaft axis. A surgical end effector is operably coupled to the elongate shaft assembly by an articulation joint such that the surgical end effector is selectively articulatable relative to the elongate shaft assembly about an articulation axis that is transverse to the shaft axis. The surgical end effector comprises a cartridge support member that is configured to operably support a surgical staple cartridge therein. A longitudinally movable firing beam extends through the articulation joint and is selectively axially movable from a starting position to an ending position within the surgical end effector. The surgical instrument further comprises a firing beam locking assembly that comprises a biasing member that is operably supported on the articulation joint and is configured to apply a biasing motion to the longitudinally movable firing beam to bias the longitudinally movable firing beam into a locked position wherein the longitudinally movable firing beam is prevented from moving from the starting to the ending position unless an unfired surgical staple cartridge is operably supported in the cartridge support member.

Example 42—The surgical stapling instrument of Example 41, wherein the biasing member is supported on a middle support member that interfaces with the cartridge support member and the elongate shaft assembly. The middle support member is configured to laterally support the longitudinally movable firing beam during articulation of the surgical end effector about the articulation axis.

Example 43—The surgical stapling instrument of Examples 41 or 42, wherein the biasing member is configured to avoid applying the biasing motion to the longitudinally movable firing beam when the surgical end effector is being articulated.

Example 44—The surgical stapling instrument of Examples 41, 42, or 43, wherein the longitudinally movable firing beam comprises a locking cam formed on a portion thereof for engagement with the biasing member.

Example 45—The surgical stapling instrument of Example 44, wherein the biasing member comprises a planar body comprising a window that located therein such that the locking cam protrudes into the window during articulation of the surgical end effector.

Example 46—The surgical stapling instrument of Examples 41, 42, 43, 44, or 45, wherein the biasing member biases the longitudinally movable firing beam into a locked position upon initial application of a firing motion to the longitudinally movable firing beam unless the unfired surgical staple cartridge is operably supported within the cartridge support member.

Example 47—The surgical stapling instrument of Examples 41, 42, 43, 44, 45, or 46, wherein the unfired surgical staple cartridge comprises a plurality of surgical staples operably supported within a cartridge body and a wedge sled that is axially movable through the cartridge body to eject the surgical staples therefrom when the wedge sled is moved from an unfired position to a fired position therein. The wedge sled is configured for operable engagement with the longitudinally movable firing beam when the longitudinally movable firing beam is in the starting position and the wedge sled is in the unfired position.

Example 48—The surgical stapling instrument of Examples 41, 42, 43, 44, 45, or 46, wherein the biasing member biases the firing beam into a locked position upon initial application of a firing motion to the firing beam unless a wedge sled in a surgical staple cartridge that is supported within the cartridge support member is in an unfired position within the surgical staple cartridge and in operable engagement with the longitudinally movable firing beam.

Example 49—The surgical stapling instrument of Example 48, wherein the wedge sled is configured to prevent the firing beam from entering a locked position when the wedge sled is in the unfired position and upon application of an initial firing motion to the longitudinally movable firing beam.

Example 50—A surgical stapling instrument, comprising a surgical end effector that comprises an elongate channel that is configured to operably support a surgical staple cartridge therein. An anvil is supported relative to the elongate channel such that one of the anvil and the elongate channel is selectively movable relative to the other one of the anvil and the elongate channel between open and closed positions. The surgical instrument further comprises an elongate shaft assembly that defines a shaft axis and comprises an articulation joint that is operably coupled to the surgical end effector to facilitate selective articulation of the surgical end effector relative to the elongate shaft assembly about an articulation axis that is transverse to the shaft axis. The elongate shaft assembly further comprises a closure assembly that is axially movable in response to closure motions that are applied thereto. The closure assembly comprises a distal closure member segment and a proximal closure member segment that movably interfaces with the distal closure member segment to accommodate articulation of the surgical end effector about the articulation axis. The proximal closure member segment is configured to move one of the anvil and the elongate channel between the open and closed positions upon application of the closure motions to the closure assembly. The surgical stapling instrument further comprises a longitudinally movable firing beam that extends through the articulation joint and is selectively axially movable from a starting position to an ending position within the surgical end effector. The longitudinally movable firing beam is configured to operably engage a corresponding portion of an unfired surgical staple cartridge that is operably supported in the elongate channel when the longitudinally movable firing beam is in the starting position. The surgical stapling instrument further comprises a firing beam locking assembly that comprises a biasing member that is operably supported on the distal closure member segment for biasing the longitudinally movable firing beam into a locked position wherein the longitudinally movable firing beam is prevented from moving from the starting position to the ending position unless an unfired surgical staple cartridge is operably supported in the elongate channel.

Example 51—The surgical stapling instrument of Example 50, wherein the longitudinally movable firing beam has a sloped portion that is configured for engagement with the biasing member when the longitudinally movable firing beam is in the starting position.

Example 52—The surgical stapling instrument of Examples 50 or 51, wherein the unfired surgical staple cartridge comprises a plurality of surgical staples operably supported within a cartridge body and a wedge sled that is axially movable through the cartridge body to eject the surgical staples therefrom when the wedge sled is moved from an unfired position to a fired position therein. The wedge sled is configured for operable engagement with the longitudinally movable firing beam when the longitudinally movable firing beam is in the starting position and the wedge sled is in the unfired position.

Example 53—The surgical stapling instrument of Examples 52 wherein the wedge sled is configured to prevent the firing beam from entering a locked position when the wedge sled is in the unfired position and upon application of an initial firing motion to the longitudinally movable firing beam.

Example 54—A surgical stapling instrument, comprising an elongate shaft assembly that defines a shaft axis. A surgical end effector is operably coupled to the elongate shaft assembly by an articulation joint such that the surgical end effector is selectively articulatable relative to the elongate shaft assembly about an articulation axis that is transverse to the shaft axis. The surgical end effector comprises a cartridge support member that is configured to operably support a surgical staple cartridge therein. The surgical stapling instrument further comprises a longitudinally movable firing beam that includes a portion that extends through the articulation joint and is selectively axially movable from a starting position to an ending position within the surgical end effector. The longitudinally movable firing beam is configured to operably engage a corresponding portion of an unfired surgical staple cartridge that is operably supported in the cartridge support member when the longitudinally movable firing beam is in the starting position. The surgical stapling instrument further includes means for providing lateral support to the portion of the longitudinally movable firing beam that extends through the articulation joint as the surgical end effector is articulated about the articulation axis. The means for providing further comprises means for preventing the longitudinally movable firing beam from moving from the starting position to the ending position unless an unfired surgical staple cartridge is operably supported in the cartridge support member.

Example 55—The surgical stapling instrument of Example 54, wherein the means for providing lateral support further comprises a middle support member that is movably attached to the cartridge support member and the elongate shaft assembly. The middle support member comprises a slot for movably receiving the portion of the longitudinally movable firing beam therethrough. The means for preventing comprises a biasing member that is supported on the middle support member and is configured to apply a biasing motion to the longitudinally movable firing beam to move the longitudinally movable firing beam into a locked position wherein the longitudinally movable firing beam is prevented from moving from the starting position to the ending position unless the unfired surgical staple cartridge is operably supported in the cartridge support member.

Example 56—The surgical stapling instrument of Example 55, wherein the longitudinally movable firing beam comprises a locking cam formed on the portion of the longitudinally movable firing beam for engagement with the biasing member.

Example 57—The surgical stapling instrument of Example 56, wherein the biasing member comprises a planar body that comprises a window located therein such that the locking cam protrudes therein during the articulation of the surgical end effector.

Example 58—The surgical stapling instrument of Examples 54, 55, 55 or 57, wherein the unfired surgical staple cartridge comprises a plurality of surgical staples that are operably supported within a cartridge body and a wedge sled that is axially movable through the cartridge body to eject the surgical staples therefrom when the wedge sled is moved from an unfired position to a fired position therein. The wedge sled is configured for operable engagement with the longitudinally movable firing beam when the longitudinally movable firing beam is in the starting position and the wedge sled is in the unfired position.

Example 59—The surgical stapling instrument of Example 58, wherein the wedge sled is configured to prevent the firing beam from entering a locked position when the wedge sled is in the unfired position and upon application of an initial firing motion to the longitudinally movable firing beam.

Example 60—A surgical instrument, comprising an elongate shaft assembly that defines a shaft axis. A surgical end effector is operably coupled to the elongate shaft assembly by an articulation joint such that the surgical end effector is selectively articulatable relative to the elongate shaft assembly about an articulation axis that is transverse to the shaft axis. A longitudinally movable flexible firing beam is configured to flexibly traverse the articulation joint and is selectively axially movable from a starting position to an ending position within the surgical end effector. A middle support member is movably coupled to the elongate shaft assembly and a portion of the surgical end effector. The middle support member comprises a middle body portion that includes a proximal end and a distal end. A firing beam slot extends between that proximal end and the distal end and is configured to movably support each lateral side of a portion of the flexible firing beam traversing the articulation joint. The surgical instrument further comprises a proximal support link that comprises an elongate proximal body that is located proximal to the middle support member and is configured to laterally support proximal lateral side portions of the flexible firing beam traversing the articulation joint. The proximal support link movably interfaces with the proximal end of the middle support member. The surgical instrument further comprises a distal support link that comprises an elongate distal body that is located distal to the middle support member and is configured to laterally support corresponding distal lateral side portions of the flexible firing beam traversing the articulation joint. The distal support link movably interfaces with the distal end of the middle support member.

Example 61—The surgical instrument of Example 60, wherein the elongate proximal body of the proximal support link comprises a proximal top member and two downwardly extending opposed proximal support walls. One of the proximal support walls is located adjacent one of the proximal lateral side portions of the flexible firing beam traversing the articulation joint. Another one of the opposed proximal support walls is adjacent another one of the proximal lateral side portions of the flexible firing beam traversing the articulation joint. The elongate distal body of the distal support link comprises a distal top member and two downwardly extending opposed distal support walls. One of the distal support walls is located adjacent one of the distal lateral side portions of the flexible firing beam traversing the articulation joint. Another one of the opposed distal support walls is adjacent another one of the distal lateral side portions of the flexible firing beam traversing the articulation joint.

Example 62—The surgical instrument of Example 61, wherein the one of the proximal support walls includes a proximal arcuate surface that faces one of the proximal lateral side portions of the flexible firing beam traversing the articulation joint and wherein the another one of the proximal support walls includes another proximal arcuate surface that faces another one of the proximal lateral side portions of the flexible firing beam traversing the articulation joint. One of the distal support walls includes a distal arcuate surface that faces one of the distal lateral side portions of the flexible firing beam traversing the articulation joint. Another one of the distal support walls includes another distal arcuate surface that faces another one of the distal lateral side portions of the flexible firing beam traversing the articulation joint.

Example 63—The surgical instrument of Examples 61 or 62, wherein the proximal end of the middle support member comprises an arcuate proximal pocket that is configured to movably receive a distal nose portion of the proximal top member of the proximal support link therein. The distal end of the middle support member comprises a distal arcuate pocket that is configured to movably receive a proximal nose portion of the distal top member of the distal support link therein.

Example 64—The surgical instrument of Examples 60, 61, 62 or 63, wherein the middle support member is pivotally coupled to the portion of the surgical end effector for pivotal travel relative thereto about a pivot axis. The middle support member is coupled to the elongate shaft assembly for pivotal and axial travel relative thereto.

Example 65—The surgical instrument of Example 64, wherein the middle support member is pinned to the elongate shaft assembly by a proximal pin that extends through an elongate slot in the middle support member.

Example 66—The surgical instrument of Examples 60, 61, 62, 63, 64 or 65, wherein the elongate shaft assembly comprises a distal spine comprising a distal spine pocket that is configured to movably receive therein a proximal nose portion of the proximal top member therein.

Example 67—The surgical instrument of Examples 60, 61, 62, 63, 64, 65 or 66, wherein the portion of the surgical end effector comprises a channel pocket that is configured to movably receive therein a distal nose portion of the distal top member therein.

Example 68—The surgical instrument of Examples 60, 61, 62, 63, 64, 65, 66 or 67, wherein the portion of the surgical end effector comprises an elongate channel that is configured to operably support a surgical staple cartridge therein.

Example 69—The surgical instrument of Example 68, further comprising an anvil supported relative to the elongate channel such that one of the anvil and the elongate channel is selectively movable relative to the other one of the anvil and the elongate channel between open and closed positions.

Example 70—A surgical instrument, comprising an elongate shaft assembly that defines a shaft axis and comprises right and left opposing shaft notches that are formed in a distal end thereof. A surgical end effector is operably coupled to the elongate shaft assembly by an articulation joint such that the surgical end effector is selectively articulatable relative to the elongate shaft assembly about an articulation axis that is transverse to the shaft axis. A longitudinally movable flexible firing beam is configured to flexibly traverse the articulation joint and is selectively axially movable from a starting position to an ending position within the surgical end effector. A middle support member is movably coupled to the elongate shaft assembly and a portion of the surgical end effector. The middle support member comprises a middle body portion that includes right and left opposing support notches that are formed in a distal end thereof and a firing beam slot that is configured to movably support lateral side portions of the longitudinally movable flexible firing beam traversing the articulation joint. A pivot link is configured to laterally support side portions of the longitudinally movable flexible firing beam traversing the articulation joint. The pivot link comprises a proximally protruding proximal nose portion that is configured to movably engage either one of the right and left opposing shaft notches as the longitudinally movable flexible firing beam flexes in response to articulation of the surgical end effector about the articulation axis. A distally protruding distal nose portion is configured to movably engage either one of the right and left opposing support notches in the movable support member as the longitudinally movable flexible firing beam flexes in response to articulation of the surgical end effector about the articulation axis.

Example 71—The surgical instrument of Example 70, wherein the pivot link further comprises a first lateral support wall that is adjacent to one of the lateral side portions of the longitudinally movable flexible firing beam and a second lateral support wall that is adjacent to another one of the lateral side portions of the longitudinally movable flexible firing beam.

Example 72—The surgical instrument of Example 71, wherein the first lateral support wall includes a first arcuate surface that faces one of the lateral side portions of the longitudinally movable flexible firing beam and wherein the second lateral support wall includes a second arcuate surface that faces another one of the another lateral side portions of the longitudinally movable flexible firing beam.

Example 73—The surgical instrument of Examples 71 or 72, further comprising a first compression band that extends between the one lateral side portion of the longitudinally movable flexible firing beam and the first lateral support wall. The first compression band comprises a first distal end that is supported on the surgical end effector and a first proximal end that is movably supported on the elongate shaft assembly. A second compression band extends between the another lateral side portion of the longitudinally movable flexible firing beam and the second lateral support wall. The second compression band comprises a second distal end that is supported on the surgical end effector and a second proximal end that is movably supported on the elongate shaft assembly.

Example 74—The surgical instrument of Example 73, further comprising a third compression band that extends between the one lateral side portion of the longitudinally movable flexible firing beam and the first compression band. The third compression band comprises a third distal end that is supported on the surgical end effector and a third proximal end that is movably supported on the elongate shaft assembly. A fourth compression band extends between the another lateral side portion of the longitudinally movable flexible firing beam and the second compression band. The fourth compression band comprises a fourth distal end that is supported on the surgical end effector and a fourth proximal end that is movably supported on the elongate shaft assembly.

Example 75—A surgical instrument comprising an elongate shaft assembly that defines a shaft axis. A surgical end effector is operably coupled to the elongate shaft assembly by an articulation joint such that the surgical end effector is selectively articulatable relative to the elongate shaft assembly about an articulation axis that is transverse to the shaft axis. A longitudinally movable flexible firing beam is configured to flexibly traverse the articulation joint and is selectively axially movable from a starting position to an ending position within the surgical end effector. A middle support member is movably coupled to the elongate shaft assembly for axial and pivotal travel relative thereto and is pivotally coupled to the surgical end effector. The surgical instrument further comprises a U-shaped proximal support link comprises a proximal top member and two proximal side members. The U-shaped proximal support link extends over a proximal portion of the longitudinally movable flexible firing beam such that one of the proximal side members is adjacent one lateral side of the proximal portion of the longitudinally movable flexible firing beam and another one of the proximal side members is adjacent another lateral side of the proximal portion of the longitudinally movable flexible firing beam. The proximal top member movably interfaces with the middle support member. The surgical instrument further comprises a U-shaped distal support link that comprises a distal top member and two distal side members. The U-shaped distal support link extends over a distal portion of the longitudinally movable flexible firing beam such that one of the distal side members is adjacent one lateral side of the distal portion of the longitudinally movable flexible firing beam and another one of the distal side members is adjacent another lateral side of the distal portion of the longitudinally movable flexible firing beam. The distal top member movably interfaces with the middle support member.

Example 76—The surgical instrument of Example 75, wherein the proximal top member movably interfaces with the elongate shaft assembly and wherein the distal top member movably interfaces with a portion of the surgical end effector.

Example 77—The surgical instrument of Examples 75 or 76, wherein the proximal top member comprises a first proximally protruding proximal nose portion that movably extends into a distal pocket formed in the elongate shaft assembly and a first distally protruding distal nose portion that movably extends into a proximal pocket in the middle support member. The distal top member comprises a second proximally protruding proximal nose portion that movably extends into a distal pocket in the middle support member and a second distally protruding distal nose portion that movably extends into a channel pocket in the surgical end effector.

Example 78—The surgical instrument of Examples 75, 76 or 77, wherein one of the two proximal side members comprises a proximal arcuate surface that faces the one lateral side of the proximal portion of the longitudinally movable flexible firing beam. The another one of the proximal side members includes another proximal arcuate surface that faces the another lateral side of the proximal portion of the longitudinally movable flexible firing beam. One of the two distal side members comprises a distal arcuate surface that faces the one lateral side of the distal portion of the longitudinally movable flexible firing beam. Another one of the distal side members comprises another distal arcuate surface that faces the another distal side of the distal portion of the longitudinally movable flexible firing beam.

Example 79—The surgical instrument of Examples 75, 76, 77 or 78, wherein the middle support member is movably coupled to an elongate channel of the surgical end effector that is configured to operably support a surgical staple cartridge therein.

Example 80—A surgical instrument, comprising an elongate shaft assembly that defines a shaft axis. A surgical end effector is operably coupled to the elongate shaft assembly by an articulation joint such that the surgical end effector is selectively articulatable relative to the elongate shaft assembly about an articulation axis that is transverse to the shaft axis. A central firing beam support member extends across the articulation joint and comprises a distal end that is coupled to the surgical end effector and a proximal end that is attached to the elongate shaft assembly. A longitudinally movable flexible firing beam assembly is configured to flexibly traverse the articulation joint and is selectively axially movable from a starting position to an ending position within the surgical end effector. The longitudinally movable flexible firing beam assembly comprises a plurality of beam layers that are supported relative to each other such that at least one of the beam layers is configured to movably pass on one lateral side of the central firing beam support member and at least one other of the beam layers is configured to movably pass on another lateral side of the central firing beam support member. A plurality of lateral load carrying members correspond to the central firing beam support and are supported on portions of the least one of the beam layers that are configured to movably pass on the one lateral side of the central firing beam support member and the at least one other of the beam layers that are configured to movably pass on the another lateral side of the central firing beam support member.

Example 81—The surgical instrument of Example 80, wherein at least one of the beam layers that is configured to movably pass on the one lateral side of the central firing beam support member comprises two of the beam layers and wherein the at least one other of the beam layers that is configured to pass on the another lateral side of the central firing beam support member comprises two of the other beam layers.

Example 82—The surgical instrument of Examples 80 or 81, wherein the lateral load carrying members are movable relative to each other.

Example 83—The surgical instrument of Examples 80, 81 or 82, wherein each of the lateral load carrying members comprises an axial passage for movably receiving the portions of the least one of the beam layers that are configured to movably pass on the one lateral side of the central firing beam support member and the at least one other of the beam layers that are configured to movably pass on the another lateral side of the central firing beam support member.

Example 84—The surgical instrument of Examples 80, 81, 82 or 83, wherein a portion of the surgical end effector that is coupled to the elongate shaft assembly by the articulation joint comprises an elongate channel that is configured to operably support a surgical staple cartridge therein.

Example 85—The surgical instrument of Example 84, further comprising an anvil that is supported relative to the elongate channel such that one of the anvil and the elongate channel is selectively movable relative to the other one of the anvil and the elongate channel between open and closed positions.

Example 86—The surgical instrument of Examples 80, 81, 82, 83, 84 or 85, wherein the distal end of the central firing beam support member protrudes below a bottom surface of the longitudinally movable flexible firing beam assembly to be attached to the surgical end effector and the proximal end of the central firing beam support member protrudes above an upper surface of the longitudinally movable flexible firing beam assembly to be attached to the elongate shaft assembly.

Example 87—The surgical instrument of Example 86, wherein the distal end of the central firing beam support member is pinned to an elongate channel of the surgical end effector and wherein the proximal end of the central firing beam support member is pinned to a spine portion of the elongate shaft assembly.

Example 88—The surgical instrument of Examples 80, 81, 82, 83, 84, 85, 86 or 87, wherein at least two of the plurality of the lateral load carrying members each include arcuate end surfaces and are arranged on the portions of the least one of the beam layers that are configured to movably pass on the one lateral side of the central firing beam support member and the at least one other of the beam layers that are configured to movably pass on the another lateral side of the central firing beam support member such that one of the arcuate end surfaces on one of the at least two lateral load carrying members is adjacent another one of the arcuate end surfaces on another one of the at least two lateral load carrying members.

Example 89—The surgical instrument of Example 83, wherein each axial passage comprises a pair of spaced internal arcuate surfaces that are configured to facilitate pivotal movement of each of the lateral load carrying members on the longitudinally movable flexible firing beam.

Example 90—A surgical instrument, comprising an elongate shaft assembly that defines a shaft axis. A surgical end effector is operably coupled to the elongate shaft assembly by an articulation joint such that the surgical end effector is selectively articulatable relative to the elongate shaft assembly about an articulation axis that is transverse to the shaft axis. A central firing beam support member is axially aligned along the shaft axis and extends across the articulation joint. The central firing beam support member comprises a distal end that is coupled to the surgical end effector and a proximal end that is attached to the elongate shaft assembly. The surgical instrument further comprises a longitudinally movable flexible firing beam assembly that comprises a plurality of beam layers that are configured to axially pass the central firing beam support member such that at least one of the beam layers passes on each lateral side of the central firing beam support member as the longitudinally movable flexible firing beam assembly traverses the articulation joint. Means are movably supported on the longitudinally movable flexible firing beam for laterally supporting a portion of the longitudinally movable flexible firing beam traversing the articulation joint when the surgical end effector is articulated about the articulation axis.

Example 91—The surgical instrument of Example 90, wherein the distal end of the central firing beam support member protrudes below a bottom surface of the longitudinally movable flexible firing beam assembly to be attached to the surgical end effector. The proximal end of the central firing beam support member protrudes above an upper surface of the longitudinally movable flexible firing beam assembly to be attached to the elongate shaft assembly.

Example 92—The surgical instrument of Examples 90 or 91, wherein a portion of the surgical end effector that is coupled to the elongate shaft assembly by the articulation joint comprises an elongate channel that is configured to operably support a surgical staple cartridge therein.

Example 93—The surgical instrument of Example 92, further comprising an anvil that is supported relative to the elongate channel such that one of the anvil and the elongate channel is selectively movable relative to the other one of the anvil and the elongate channel between open and closed positions.

Example 94—The surgical instrument of Examples 90, 91, 92 or 93 further comprising a firing member attached to a distal end of the longitudinally movable flexible firing beam assembly.

Example 95—A surgical instrument, comprising an elongate shaft assembly that defines a shaft axis. A surgical end effector is operably coupled to the elongate shaft assembly by an articulation joint such that the surgical end effector is selectively articulatable relative to the elongate shaft assembly about an articulation axis that is transverse to the shaft axis. A central firing beam support member is axially aligned along the shaft axis and extends across the articulation joint. The central firing beam support member comprises a distal end that is coupled to the surgical end effector and a proximal end that is attached to the elongate shaft assembly. The surgical instrument further comprises a longitudinally movable flexible firing beam assembly that comprises a plurality of beam layers such that as the longitudinally movable flexible firing beam assembly is distally advanced, the longitudinally movable flexible firing beam assembly is bifurcated by the central firing beam support member so that portions of the longitudinally movable flexible firing beam assembly pass adjacent to each lateral side of the central firing beam support member Example 96—The surgical instrument of Example 95, further comprising means that are movably supported on the longitudinally movable flexible firing beam assembly for laterally supporting a portion of the longitudinally movable flexible firing beam assembly traversing the articulation joint when the surgical end effector is articulated about the articulation axis.

Example 97—The surgical instrument of Example 95, wherein means for laterally supporting comprises a plurality of lateral load carrying members that are supported on the longitudinally movable flexible firing beam assembly. Each of the lateral load carrying members is independently movable on the longitudinally movable flexible firing beam assembly.

Example 98—The surgical instrument of Examples 95, 96 or 97, wherein a distal end of the central firing beam support member protrudes below a bottom surface of the longitudinally movable flexible firing beam assembly to be attached to the surgical end effector and the proximal end of the central firing beam support member protrudes above an upper surface of the longitudinally movable flexible firing beam assembly to be attached to the elongate shaft assembly.

Example 99—The surgical instrument of Example 97, wherein each of the lateral load carrying members includes an axial passage therethrough that comprises a pair of spaced internal arcuate surfaces to facilitate pivotal movement of each lateral load carrying member on the longitudinally movable flexible firing beam assembly.

Example 100—A surgical instrument comprising an elongate shaft assembly that defines a shaft axis. A surgical end effector is pivotally coupled to the elongate shaft assembly for selective articulation relative to the elongate shaft assembly about an articulation axis that is transverse to the shaft axis. The surgical instrument further comprises an articulation system that comprises a first distal articulation driver that is supported for selective longitudinal travel in a distal direction and a proximal direction in response to corresponding articulation motions applied thereto. The first distal articulation driver is operably coupled to the surgical end effector. The articulation system further comprises a second distal articulation driver that is supported for longitudinal travel in the distal and proximal directions. The second distal articulation driver is operably coupled to the surgical end effector. At least one pinion gear is in meshing engagement with the first distal articulation driver and the second distal articulation driver such that when the first distal articulation driver is moved in the distal direction, the at least one pinion gear is configured to drive the second distal articulation driver in the proximal direction to articulate the surgical end effector about the articulation axis in a first articulation direction and when the first distal articulation driver is moved in the proximal direction, the at least one pinion gear drives the second distal articulation driver in the distal direction to articulate the surgical end effector about the articulation axis in a second articulation direction that is opposite to the first articulation direction.

Example 101—The surgical instrument of Example 100, wherein the first distal articulation driver is pivotally coupled to the surgical end effector and, wherein the second distal articulation driver is pivotally attached to the surgical end effector.

Example 102—The surgical instrument of Examples 100 or 101, wherein the first distal articulation driver is attached to the surgical end effector by a first movable coupler and wherein the second distal articulation driver is attached to the surgical end effector by a second movable coupler.

Example 103—The surgical instrument of Example 102, wherein the first movable coupler is attached to the first distal articulation driver by a first ball joint and, wherein the second distal articulation driver is attached to the second movable coupler by a second ball joint.

Example 104—The surgical instrument of Examples 100, 101, 102, or 103, further comprising means for selectively locking the surgical end effector in a plurality of articulated positions relative to the elongate shaft assembly.

Example 105—The surgical instrument of Example 104, wherein the means for selectively locking comprises means for selectively preventing the distal articulation driver from longitudinally moving in the proximal and distal directions.

Example 106—The surgical instrument of Examples 104 or 105, further comprising a proximal articulation driver that operably interfaces with a source of proximal and distal articulation motions. The proximal articulation driver operably interfaces with the means for selectively preventing to selectively unlock the means for selectively preventing and cause the means for selectively preventing to apply the proximal and distal articulation motions to the first distal articulation driver.

Example 107—The surgical instrument of Examples 100, 101, 102, 103, 104, 105 or 106, wherein a portion of the surgical end effector that is pivotally coupled to the elongate shaft assembly comprises an elongate channel that is configured to operably support a surgical staple cartridge therein.

Example 108—The surgical stapling instrument of Example 107, further comprising an anvil that is supported relative to the elongate channel such that one of the anvil and the elongate channel is selectively movable relative to the other one of the anvil and the elongate channel between open and closed positions.

Example 109—A surgical instrument, comprising an elongate shaft assembly that defines a shaft axis. A surgical end effector is pivotally coupled to the elongate shaft assembly for selective articulation relative to the elongate shaft assembly about an articulation axis that is transverse to the shaft axis. The surgical instrument further comprises an articulation system that comprises a first distal articulation driver that is supported for selective longitudinal travel in a distal direction and in a proximal direction in response to corresponding articulation motions applied thereto. The first distal articulation driver is operably coupled to the surgical end effector. The articulation system further comprises a second distal articulation driver that comprises an endless member that operably interfaces with the first distal articulation driver and the surgical end effector. The endless member is supported on the elongate shaft assembly for selective rotational travel in response to a longitudinal travel of the first distal articulation driver such that when the first distal articulation driver is moved in the distal direction, the endless member causes the surgical end effector to articulate about the articulation axis in a first articulation direction and when the first distal articulation driver is moved in the proximal direction, the endless member causes the surgical end effector to articulate about the articulation axis in a second articulation direction that is opposite to the first articulation direction.

Example 110—The surgical instrument of Example 109, wherein the endless member is rotatably supported on a proximal pulley mounted to the elongate shaft assembly and a distal pulley on the surgical end effector.

Example 111—The surgical instrument of Examples 110 wherein the endless member is operably attached to the distal pulley by an attachment lug attached to the endless member and configured to be received in an attachment pocket in the distal pulley.

Example 112—The surgical instrument of Examples 109, 110 or 111, wherein the endless member comprises a length of cable including a first lug attached to a first cable end and a second lug attached to a second cable end. The second lug is also attached to the first lug to form the endless member.

Example 113—The surgical instrument of Example 112, wherein the distal articulation driver comprises first and second cradles for receiving the first and second lugs therein.

Example 114—The surgical instrument of Examples 110 or 111, wherein the distal pulley is formed on an elongate channel of the surgical end effector. The elongate channel being configured to operably support a surgical staple cartridge therein.

Example 115—The surgical instrument of Examples 110 or 111, wherein the distal pulley is formed on an end effector mounting assembly that is attached to an elongate channel portion of the surgical end effector. The elongate channel is configured to operably support a surgical staple cartridge therein.

Example 116—The surgical instrument of Examples 114 or 115, further comprising an anvil supported relative to the elongate channel such that one of the anvil and the elongate channel is selectively movable relative to the other one of the anvil and the elongate channel between open and closed positions.

Example 117—A surgical instrument, comprising an elongate shaft assembly that defines a shaft axis. A surgical end effector is pivotally coupled to the elongate shaft assembly for selective articulation relative to the elongate shaft assembly about an articulation axis that is transverse to the shaft axis. The surgical instrument further comprises an articulation system comprising a first distal articulation driver that is supported for selective longitudinal travel in a distal direction and in a proximal direction in response to corresponding articulation motions applied thereto. The first distal articulation driver is operably coupled to the surgical end effector. The articulation system further comprises a second distal articulation driver that is supported for longitudinal travel in the distal and proximal directions. The second distal articulation driver is operably coupled to the surgical end effector. The articulation system further comprises drive means that interfaces with the first distal articulation driver and the second distal articulation driver such that when the first distal articulation driver is moved in the distal direction, the drive means drives the second distal articulation driver in the proximal direction to articulate the surgical end effector about the articulation axis in a first articulation direction and when the first distal articulation driver is moved in the proximal direction, the drive means drives the second distal articulation driver in the distal direction to articulate the surgical end effector about the articulation axis in a second articulation direction that is opposite to the first articulation direction.

Example 118—The surgical instrument of Example 117, wherein the surgical end effector comprises an elongate channel that is configured to operably support a surgical staple cartridge therein. An anvil is supported relative to the elongate channel such that one of the anvil and the elongate channel is selectively movable relative to the other one of the anvil and the elongate channel between open and closed positions.

Example 119—A surgical instrument, comprising an elongate shaft assembly that defines a shaft axis. A surgical end effector is pivotally coupled to the elongate shaft assembly for selective articulation relative to the elongate shaft assembly about an articulation axis that is transverse to the shaft axis. The surgical instrument further comprises an articulation system that comprises a rotary articulation member that is supported for rotational travel about a rotary axis that is transverse to the shaft axis. A first distal articulation driver assembly operably interfaces with the rotary articulation member and is supported for selective longitudinal travel in a distal direction and in a proximal direction in response to corresponding articulation motions applied thereto by the rotary articulation member. The first distal articulation driver assembly operably interfaces with the surgical end effector. A second distal articulation driver assembly operably interfaces with the rotary articulation member and is supported for longitudinal travel in the distal and proximal directions. The second distal articulation driver assembly operably interfaces with the surgical end effector. The articulation system further comprises means for selectively rotating the rotary articulation member in first and second rotary directions about the rotary axis such that when the rotary articulation member is rotated in the first rotary direction by the means for selectively rotating, the first distal articulation driver assembly is longitudinally driven in the distal direction and the second distal articulation driver is simultaneously moved in the proximal direction to articulate the surgical end effector about the articulation axis in a first articulation direction and when the rotary articulation member is rotated in the second rotary direction by the means for selectively rotating, the first distal articulation driver assembly is longitudinally driven in the proximal direction and the second distal articulation driver assembly is simultaneously moved in the distal direction to articulate the surgical end effector about the articulation axis in a second articulation direction about the articulation axis that is opposite to the first articulation direction.

Example 120—The surgical instrument of Example 119, wherein the rotary articulation member comprises a rotary articulation disc and wherein the first distal articulation driver assembly comprises a first articulation driver portion that is movably supported within a first articulation slot in the rotary articulation disc and wherein the second distal articulation driver assembly comprises a second articulation driver portion movably supported within a second articulation slot in the rotary articulation disc.

Example 121—The surgical instrument of Examples 119 or 120, further comprising a first biasing member that interacts with the first articulation driver portion to bias the first distal articulation driver assembly into a first neutral articulation position when the means for selectively rotated is unactuated. A second biasing member interacts with the second articulation driver portion to bias the second distal articulation driver assembly into a second neutral articulation position when the means for selectively rotated is unactuated.

Example 122—The surgical instrument of Examples 119, 120 or 121, wherein the first distal articulation driver assembly comprises a first articulation link that movably interfacing with the rotary articulation member. A first articulation connector is pivotally coupled to the first articulation link. The first articulation connector operably interfaces with the surgical end effector. The second distal articulation assembly comprises a second articulation link that movably interfaces with the rotary articulation member and a second articulation member is pivotally coupled to the second articulation link and operably interfaces with the surgical end effector.

Example 123—The surgical instrument of Example 122, wherein the first distal articulation driver assembly further comprises an articulation lock assembly that operably interfaces with the first articulation connector and the surgical end effector and is configured to selectively lock the surgical end effector in a plurality of articulated positions relative to the elongate shaft assembly.

Example 124—The surgical instrument of Example 123, further comprising a first articulation member that operably interfaces with the articulation lock assembly and the surgical end effector.

Example 125—The surgical instrument of Example 124 wherein the first articulation member is coupled to the surgical end effector by a first movable coupler and wherein the second articulation member is coupled to the surgical end effector by a second movable coupler.

Example 126—The surgical instrument of Example 126, wherein the first articulation member is coupled to the first movable coupler by a first ball joint and wherein the second articulation member is coupled to the second movable coupler by a second ball joint.

Example 127—The surgical instrument of Examples 119, 120, 121, 122, 123, 124, 125 or 126, wherein the means for selectively rotating comprises a motor in meshing engagement with the rotary articulation member.

Example 128—The surgical instrument of Examples 119, 120, 121, 122, 123, 124, 125 or 126, further comprising a longitudinally movable firing member and wherein the means for selectively rotating comprises a motor that is configured to generate rotary output motions and a switching arrangement that operably interfaces with the motor and the longitudinally movable firing member and an articulation drive link that is in operable engagement with the rotary articulation member. The switching arrangement is configured to move between a first position wherein actuation of the motor results in applications of axial articulation motions to the articulation drive link to thereby cause the rotary articulation member to rotate about the rotary axis and a second position wherein actuation of the motor results in applications of axial firing motions to the longitudinally movable firing member Example 129—A surgical instrument, comprising an elongate shaft assembly that defines a shaft axis. A surgical end effector is pivotally coupled to the elongate shaft assembly for selective articulation relative to the elongate shaft assembly about an articulation axis that is transverse to the shaft axis. The surgical instrument further comprises an articulation system that comprises a rotary driver member that is supported for rotation travel about a rotary axis that is transverse to the shaft axis. A rotary driven member is supported for rotational travel relative to the rotary driver member about the rotary axis. The rotary driven member operably interfaces with the rotary drive member such that application of articulation control motions to the rotary driver member causes the rotary driven member to rotate about the rotary axis. A first distal articulation driver assembly operably interfaces with at least the rotary driven member and is supported for selective longitudinal travel in a distal direction and a proximal direction in response to rotation of at least the first rotary driven member. The first distal articulation driver assembly operably interfaces with the surgical end effector. The articulation system further comprises a second distal articulation driver assembly that operably interfaces with at least the rotary driven member and is supported for longitudinal travel in the distal and proximal directions. The second distal articulation driver assembly operably interfaces with the surgical end effector. The articulation system further comprises means for selectively applying the articulation control motions to the rotary driver member to cause the rotary driver member to rotate about the rotary axis and to thereby cause the rotary driven member to rotate about the rotary axis such that when the rotary driven member rotates in a first rotary direction, the first distal articulation driver assembly is longitudinally driven in the distal direction and the second distal articulation driver is simultaneously moved in the proximal direction to articulate the surgical end effector about the articulation axis in a first articulation direction and when the rotary driven member is rotated in a second rotary direction, the first distal articulation driver assembly is longitudinally driven in the proximal direction and the second distal articulation driver assembly is simultaneously moved in the distal direction to articulate the surgical end effector about the articulation axis in a second articulation direction about the articulation axis that is opposite to the first articulation direction.

Example 130—The surgical instrument of Example 129, wherein the rotary driver member comprises a rotary driver articulation disc and wherein the second rotary driven member comprises a rotary driven articulation disc and wherein the first distal articulation driver assembly comprises a first articulation driver portion that is movably supported within corresponding first articulation slots in each of the rotary driver articulation disc and the rotary driven articulation disc and wherein the second distal articulation driver assembly comprises a second articulation driver portion movably supported within corresponding second articulation slots in each of the rotary driver articulation disc and the rotary driven articulation disc.

Example 131—The surgical instrument of Examples 129 or 130 wherein the first distal articulation driver assembly comprises a first articulation link that movably interfaces with the rotary driver member and the rotary driven member and a first articulation member that is pivotally coupled to the first articulation link. The first articulation member operably interfaces with the surgical end effector. The second distal articulation assembly comprises a second articulation link that movably interfaces with the rotary drive member and the rotary driven member and a second articulation member is pivotally coupled to the second articulation link and operably interfaces with the surgical end effector.

Example 132—The surgical instrument of Example 131, wherein the first articulation member is coupled to the surgical end effector by a first movable coupler and the second articulation member is coupled to the surgical end effector by a second movable coupler.

Example 133—The surgical instrument of Example 132, wherein the first articulation member is coupled to the first movable coupler by a first ball joint and wherein the second articulation member is coupled to the second movable coupler by a second ball joint.

Example 134—The surgical instrument of Examples 129, 130, 131, 132 or 133, wherein the means for selectively applying comprises a motor in meshing engagement with the rotary driver member.

Example 135—The surgical instrument of Examples 129, 130, 131, 132 or 133, further comprising a longitudinally movable firing member and wherein the means for selectively applying comprises a motor that is configured to generate rotary output motions. The means for selectively applying further comprising a switching arrangement that operably interfaces with the motor and the longitudinally movable firing member and an articulation drive link that is in operable engagement with the rotary driver member. The switching arrangement is configured to move between a first position wherein actuation of the motor results in applications of axial articulation motions to the articulation drive link to thereby cause the rotary driver member to rotate about the rotary axis and a second position wherein actuation of the motor results in applications of axial firing motions to the longitudinally movable firing member.

Example 136—A surgical instrument, comprising an elongate shaft assembly that defines a shaft axis. A surgical end effector is pivotally coupled to the elongate shaft assembly for selective articulation relative to the elongate shaft assembly about an articulation axis that is transverse to the shaft axis. The surgical instrument further comprises an articulation system that comprises means that is operably coupled to the surgical end effector for articulating the surgical end effector about the articulation axis and means for selectively generating rotary motions. The articulation system further comprises a rotary member that operably interfaces with the means for generating a rotary motion and the means for articulating such that application of the rotary motions by the means for selectively generating to the rotary member causes the means for articulating to simultaneously apply opposed axial articulation motions to the surgical end effector wherein one of the opposed axial motions is applied to at a point of attachment on the surgical end effector that is laterally offset to one lateral side of the articulation axis and wherein the other opposed axial motion is applied to another point of attachment on the surgical end effector that is laterally offset on another lateral side of the articulation axis.

The entire disclosures of:
U.S. Pat. No. 5,403,312, entitled ELECTROSURGICAL HEMOSTATIC DEVICE, which issued on Apr. 4, 1995;
U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
U.S. Pat. No. 7,670,334, entitled SURGICAL INSTRUMENT HAVING AN ARTICULATING END EFFECTOR, which issued on Mar. 2, 2010;
U.S. Pat. No. 7,753,245, entitled SURGICAL STAPLING INSTRUMENTS, which issued on Jul. 13, 2010;
U.S. Pat. No. 8,393,514, entitled SELECTIVELY ORIENTABLE IMPLANTABLE FASTENER CARTRIDGE, which issued on Mar. 12, 2013;
U.S. patent application Ser. No. 11/343,803, entitled SURGICAL INSTRUMENT HAVING RECORDING CAPABILITIES; now U.S. Pat. No. 7,845,537;
U.S. patent application Ser. No. 12/031,573, entitled SURGICAL CUTTING AND FASTENING INSTRUMENT HAVING RF ELECTRODES, filed Feb. 14, 2008;
U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;
U.S. patent application Ser. No. 12/235,782, entitled MOTOR-DRIVEN SURGICAL CUTTING INSTRUMENT, now U.S. Pat. No. 8,210,411;
U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;
U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;
U.S. patent application Ser. No. 12/893,461, entitled STAPLE CARTRIDGE, filed Sep. 29, 2012, now U.S. Pat. No. 8,733,613;
U.S. patent application Ser. No. 13/036,647, entitled SURGICAL STAPLING INSTRUMENT, filed Feb. 28, 2011, now U.S. Pat. No. 8,561,870;
U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;
U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;
U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;
U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;
U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and
U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, plasma peroxide, or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
    an elongate shaft defining a longitudinal axis, wherein said elongate shaft comprises a shaft frame;
    an end effector extending from said elongate shaft, wherein said end effector comprises an elongate channel pivotally coupled to said shaft frame of said elongate shaft, wherein said elongate channel is configured for pivotal travel relative to said elongate shaft about an articulation axis that is transverse to said longitudinal axis;
    a first articulation driver positioned on a first side of said longitudinal axis, wherein said first articulation driver comprises a first drive rack and a first articulation rod extending from said first drive rack, wherein said first drive rack comprises a plurality of first teeth, and wherein said first articulation rod is pivotally coupled directly to a proximal end of said elongate channel;
    a second articulation driver positioned on a second side of said longitudinal axis opposite said first side, wherein said second articulation driver comprises a second drive rack and a second articulation rod extending from said second drive rack, wherein said second drive rack comprises a plurality of second teeth, and wherein said second articulation rod is pivotally coupled directly to said proximal end of said elongate channel;
    a pinion gear rotatably supported by said shaft frame and positioned intermediate said first drive rack and said second drive rack, wherein said pinion gear is in meshing engagement with said plurality of first teeth and said plurality of second teeth; and
    a proximal articulation driver translatable longitudinally to apply a linear articulation motion to said first articulation driver to translate said first articulation driver, wherein said proximal articulation driver is translatable relative to said first articulation driver, wherein said pinion gear operably couples said first articulation driver and said second articulation driver such that said first articulation driver and said second articulation driver move in opposite directions when said first articulation driver is translated by said proximal articulation driver, and wherein said elongate channel is articulated about said articulation axis when said first articulation driver and said second articulation driver move in opposite directions.

2. The surgical instrument of claim 1, wherein said elongate channel is configured to receive a staple cartridge.

3. The surgical instrument of claim 1, wherein said first articulation driver comprises a first movable coupler connecting said first articulation rod to said proximal end of said elongate channel, and wherein said first movable coupler comprises a first ball joint.

4. The surgical instrument of claim 3, wherein said second articulation driver comprises a second movable coupler connecting said second articulation rod to said proximal end of said elongate channel, and wherein said second movable coupler comprises a second ball joint.

5. The surgical instrument of claim 1, wherein said first articulation rod is pivotally coupled directly to said proximal end of said elongate channel by a first pin positioned on the first side of said longitudinal axis, and wherein said second articulation rod is pivotally coupled directly to said proximal end of said elongate channel by a second pin positioned on the second side of said longitudinal axis.

6. The surgical instrument of claim 1, wherein said pinion gear is housed within said elongate shaft.

7. The surgical instrument of claim 1, wherein said pinion gear is rotatably supported in said shaft frame for free rotation relative to said shaft frame.

8. The surgical instrument of claim 1, further comprising a proximal housing and an electric motor positioned within said proximal housing.

9. A surgical instrument, comprising:
    an elongate shaft defining a longitudinal axis, wherein said elongate shaft comprises a shaft frame;
    an end effector extending from said elongate shaft, wherein said end effector comprises an elongate channel pivotally coupled to said shaft frame of said elongate shaft, wherein said elongate channel is configured for pivotal travel relative to said elongate shaft about an articulation axis that is transverse to said longitudinal axis;
    a first articulation driver positioned on a first side of said longitudinal axis, wherein said first articulation driver comprises a first drive rack and a first articulation rod extending from said first drive rack, wherein said first drive rack comprises a plurality of first teeth, and wherein said first articulation rod is pivotally coupled to a proximal end of said elongate channel;
    a second articulation driver positioned on a second side of said longitudinal axis opposite said first side, wherein said second articulation driver comprises a second drive rack and a second articulation rod extending from said second drive rack, wherein said second drive rack comprises a plurality of second teeth, and wherein said second articulation rod is pivotally coupled to said proximal end of said elongate channel;
a pinion gear rotatably supported by said shaft frame and positioned intermediate said first drive rack and said second drive rack, wherein said pinion gear is in meshing engagement with said plurality of first teeth and said plurality of second teeth; and
a proximal articulation driver translatable longitudinally to apply a linear articulation motion to said first articulation driver to translate said first articulation driver, wherein said proximal articulation driver is translatable relative to said first articulation driver, wherein said pinion gear operably couples said first articulation driver and said second articulation driver such that said first articulation driver and said second articulation driver move in opposite directions when said first articulation driver is translated by said proximal articulation driver, and wherein said elongate channel is articulated about said articulation axis when said first articulation driver and said second articulation driver move in opposite directions; and
a laminate firing member extending from said elongate shaft into said end effector.

10. A surgical instrument, comprising:
an elongate shaft defining a longitudinal axis;
an end effector extending from said elongate shaft;
an articulation joint, wherein said end effector is rotatable relative to said elongate shaft about an articulation axis defined by said articulation joint;
a first articulation driver positioned on a first side of said longitudinal axis, wherein said first articulation driver is pivotally coupled directly to a proximal end of said end effector;
a second articulation driver positioned on a second side of said longitudinal axis opposite said first side, wherein said second articulation driver is pivotally coupled directly to said proximal end of said end effector; and
a rotary articulation member positioned in said elongate shaft intermediate said first articulation driver and said second articulation driver; and
a proximal articulation driver translatable longitudinally to apply linear articulation motions to said first articulation driver to translate said first articulation driver, wherein said proximal articulation driver is translatable relative to said first articulation driver, wherein said rotary articulation member operably couples said first articulation driver to said second articulation driver such that when said first articulation driver is translated proximally by said proximal articulation driver, said second articulation driver is translated distally to rotate said end effector about said articulation axis in a first direction, and wherein said rotary articulation member operably couples said first articulation driver to said second articulation driver such that when said first articulation driver is translated distally by said proximal articulation driver, said second articulation driver is translated proximally to rotate said end effector about said articulation axis in a second direction opposite said first direction.

11. The surgical instrument of claim 10, wherein said end effector comprises an elongate channel configured to receive a staple cartridge.

12. The surgical instrument of claim 11, further comprising a flexible firing driver extending through said articulation joint and into said end effector, wherein said flexible firing driver comprises a plurality of layers.

13. The surgical instrument of claim 12, further comprising a proximal housing and an electric motor positioned within said proximal housing, wherein said flexible firing driver is configured to receive a firing motion generated by said electric motor.

14. The surgical instrument of claim 10, wherein said first articulation driver comprises a first movable coupler connecting said first articulation driver to said proximal end of said end effector, and wherein said first movable coupler comprises a first ball joint.

15. The surgical instrument of claim 14, wherein said second articulation driver comprises a second movable coupler connecting said second articulation driver to said proximal end of said end effector, and wherein said second movable coupler comprises a second ball joint.

16. The surgical instrument of claim 10, wherein said rotary articulation member comprises a gear, and wherein said gear is housed within said elongate shaft.

17. The surgical instrument of claim 16, wherein said gear is meshingly engaged with at least one of said first articulation driver and said second articulation driver.

18. The surgical instrument of claim 17, wherein said first articulation driver comprises a first drive rack, and wherein said second articulation driver comprises a second drive rack.

19. The surgical instrument of claim 18, wherein said first articulation driver is pivotally coupled directly to said proximal end of said end effector by a first pin positioned on the first side of said longitudinal axis, and wherein said second articulation driver is pivotally coupled directly to said proximal end of said end effector by a second pin positioned on the second side of said longitudinal axis.

20. A surgical instrument, comprising:
an elongate shaft defining a longitudinal axis;
an end effector extending from said elongate shaft;
an articulation joint, wherein said end effector is rotatable relative to said elongate shaft about an articulation axis defined by said articulation joint;
a first articulation driver positioned on a first side of said longitudinal axis, wherein said first articulation driver is pivotally coupled to a proximal end of said end effector;
a second articulation driver positioned on a second side of said longitudinal axis opposite said first side, wherein said second articulation driver is pivotally coupled to said proximal end of said end effector;
a rotary articulation member positioned in said elongate shaft intermediate said first articulation driver and said second articulation driver;
a proximal articulation driver translatable longitudinally to apply linear articulation motions to said first articulation driver to translate said first articulation driver, wherein said proximal articulation driver is translatable relative to said first articulation driver, wherein said rotary articulation member operably couples said first articulation driver to said second articulation driver such that when said first articulation driver is translated proximally by said proximal articulation driver, said second articulation driver is translated distally to rotate said end effector about said articulation axis in a first direction, and wherein said rotary articulation member operably couples said first articulation driver to said second articulation driver such that when said first articulation driver is translated distally by said proximal articulation driver, said second articulation driver is translated proximally to rotate said end effector about said articulation axis in a second direction opposite said first direction; and a laminate firing member extending through said articulation joint and into said end effector.

\* \* \* \* \*